(12) United States Patent
Ronin et al.

(10) Patent No.: US 8,993,297 B2
(45) Date of Patent: Mar. 31, 2015

(54) PREPARATION AND USES OF GENE SEQUENCES ENCODING CHIMERICAL GLYCOSYLTRANSFERASES WITH OPTIMIZED GLYCOSYLATION ACTIVITY

(75) Inventors: Catherine Ronin, Sausset les Pins (FR); Gaelle Guiraudie-Capraz, Lancon de Provence (FR)

(73) Assignees: Universite de Provence (Aix Marseille I), Marseilles (FR); Centre National de la Recherche Scientifique, Paris (FR)

( * ) Notice: Subject to any disclaimer, the term of this patent is extended or adjusted under 35 U.S.C. 154(b) by 1334 days.

(21) Appl. No.: 12/301,914

(22) PCT Filed: May 24, 2007

(86) PCT No.: PCT/EP2007/055070
§ 371 (c)(1),
(2), (4) Date: May 5, 2009

(87) PCT Pub. No.: WO2007/135194
PCT Pub. Date: Nov. 29, 2007

(65) Prior Publication Data
US 2010/0105106 A1    Apr. 29, 2010

(30) Foreign Application Priority Data
May 24, 2006    (EP) ..................................... 06290843

(51) Int. Cl.
| | |
|---|---|
| C12N 9/10 | (2006.01) |
| C12P 21/06 | (2006.01) |
| C12P 21/04 | (2006.01) |
| C12N 9/24 | (2006.01) |
| C12N 5/00 | (2006.01) |
| C12N 15/00 | (2006.01) |
| C07H 21/04 | (2006.01) |

(52) U.S. Cl.
CPC ............ *C12N 9/1048* (2013.01); *C12N 9/1051* (2013.01); *C12N 9/1081* (2013.01); *C12Y 204/01087* (2013.01); *C12Y 204/01133* (2013.01); *C12Y 204/99001* (2013.01); *C07K 2319/05* (2013.01)
USPC ......... 435/193; 435/200; 435/69.1; 435/69.7; 435/320.1; 435/252.3; 435/325; 435/366; 536/23.2

(58) Field of Classification Search
None
See application file for complete search history.

(56) References Cited

U.S. PATENT DOCUMENTS

| | | |
|---|---|---|
| 2002/0137134 A1 | 9/2002 | Gerngross |
| 2003/0186414 A1 * | 10/2003 | Gilbert et al. ................. 435/193 |

FOREIGN PATENT DOCUMENTS

| | | | |
|---|---|---|---|
| WO | 98/05768 | | 2/1998 |
| WO | WO 03/052088 | * | 6/2003 |
| WO | 03/093448 A2 | | 11/2003 |
| WO | 2004/074461 A2 | | 9/2004 |

OTHER PUBLICATIONS

Vallejo-Ruiz et al. Biochimica Biophysica Acta 1549 (2001), 161-173.*
International Search Report dated Feb. 5, 2008.
European Search Report dated Sep. 1, 2006.
W. Hansen et al., "Generation of serum-stabilized retroviruses: Reduction of . . . glycosyltransferases", Metabolic Engineering, vol. 7, No. 3, May 2005, pp. 221-228.
E. Grabenhorst et al., "Genetic engineering of recombinant glycoproteins . . . host cells", Glycoconjugate Journal, vol. 16, No. 2, Feb. 1999, pp. 81-97.
E. Grabenhorst et al., "Cytoplasmic, Transmembrane, and Stem . . . in the Golgi", Journal of Biological Chemistry, vol. 274, No. 51, Dec. 17, 1999, pp. 36107-36116.
P. Legaigneur et al., "Exploring the Acceptor Substrate . . . of the human beta-Galactoside", Journal of Biological Chemistry, vol. 276, No. 24, Jun. 15, 2001, pp. 21608-21617.
A. Masibay et al., "Mutational Analysis of the Golgi Retention . . . of Bovine beta-1, 4-galactosyltransferase", Journal of Biological Chemistry, May 5, 1993, vol. 268, No. 13, pp. 9908-9916.
S. Donadio et al., "Recognition of cell surface acceptors by two human . . . in CHO cells", Biochimie, vol. 85, No. 3-4, 2003, pp. 311-321.
A. Bragonzi et al., "A new Chinese hamster ovary cell line expressing . . . sialylated recombinant glycoproteins", BBA—General Subjects, Elsevier Science Publishers, NL, vol. 1474, No. 3, May 1, 2000, pp. 273-282.
A. Harduin-Lepers et al., "The animal sialyltransferases and . . . genes: a phylogenetic approach", Glycobiology, Aug. 2005, vol. 15, No. 8, pp. 805-817.

* cited by examiner

*Primary Examiner* — Iqbal H Chowdhury
(74) *Attorney, Agent, or Firm* — Young & Thompson

(57) ABSTRACT

The present invention relates to the production of gene sequences encoding chimerical membrane glycosyltransferases presenting an optimized glycosylation activity in cells transformed with the sequences, the gene sequences corresponding to the fusion: of a first nucleic acid coding for a C-terminal minimal fragment of the catalytic domain (CD) of the native full length glycosyltransferase, to a second nucleic acid coding for a transmembrane peptide comprising in its N-terminal region a cytoplasmic tail (CT) region located upstream from a transmembrane domain (TMD), itself located upstream of a stem region (SR), provided that at least one of these CT, TMD, SR peptides being different from the primary structure of the naturally occurring peptide counterparts present in the native glycosyltransferase from which is derived the CD fragment with optimal glycosyltransferase activity as defined above.

9 Claims, 25 Drawing Sheets

PREPARATION AND USES OF GENE SEQUENCES ENCODING CHIMERICAL GLYCOSYLTRANSFERASES WITH OPTIMIZED GLYCOSYLATION ACTIVITY

The present invention relates to the production of gene sequences encoding chimerical glycosyltransferases presenting optimized glycosylation activity, and to their uses in the frame of the preparation of recombinant proteins of interest by cells transformed with said sequences and sequences encoding said recombinant proteins.

Glycosylation of Proteins and Lipids

Proteins and lipids are major components of cell membranes. Membrane associated carbohydrates are exclusively in the form of oligosaccharides covalently attached to proteins forming glycoproteins, and to lipids forming glycolipids. Glycoconjugates (including glycolipids and glycoproteins) are most often key cell surface molecules which are considered to be involved in cell-cell interactions and cell adhesion (Feizi, 1993; Crocker & Feizi, 1996).

The predominant monosaccharides found in eukaryotic glycoproteins are glucose (Glc), galactose (Gal), mannose (Man), fucose (Fuc), N-Acetylgalactosamine (GalNAc), N-acetylglucosamine (GlcNAc) and sialic acid (Sia) most often as neuraminic acid (NeuAc) which may be N-acetylated or N-glycolylated in mammals but only N-acetylated in humans. Carbohydrate chains also designated as glycans are linked to the polypeptide backbone through either O-glycosidic or N-glycosidic bonds. The N-glycosidic linkage is through the amide group of asparagine. The O-glycosidic linkage is to the hydroxyl of serine, threonine or hydroxylysine. In ser- or thr-type O-linked glycoproteins, the monosaccharide directly attached to the protein is frequently GalNAc while in N-linked glycoproteins, only GlcNAc is found.

The N-glycosidic linkage is conserved throughout the eukaryotic kingdom including yeast; plants, insects, mammals and humans. The site of N-linked glycosylation occurs within a consensus sequence of amino acids, Asn-X-Ser/Thr (N-X-S(T)), where X is any amino acid except proline. When a protein analysis in the public databases is carried out, it can be shown that approximately 65% of all the proteins contain at least one such consensus sequence. N-linked glycoproteins all contain a common (invariant) pentasaccharide attached to the polypeptide. This core consists of three Man and two GlcNAc residues. Antennae of variable sequence are completing the glycan and allowing the classification into three major N-linked subclasses:
1. Mannose-rich glycans contain only mannose as terminal sugars.
2. Hybrid glycans contains at least a GlcNAc-Gal antenna.
3. Complex glycans contain from 2 to 5 of those antennae terminated in GlcNAc, Gal or sialic acid.

In all eukaryotic cells, N-linked glycoproteins are synthesized co-transitionally from polyribosomes bound to the endoplasmic reticulum (ER). Processing of N-linked glycans occurs early in the lumen of the ER and continues in the golgi apparatus and transgolgi network where glycoproteins achieved their final and functional polymorphism. Attachment of O-linked glycans occurs post-translationally in the golgi apparatus where glycosylation of lipids also occurs. Sugars used for both N- and O-glycosylation are activated by coupling to specific nucleotides in the cytoplasm and are imported within the lumen of organelles through specific transporters.

Glycosylation is the most sophisticated set of post-translational modifications which may occur in proteins. They aimed to: i) control the biological activity of proteins, ii) signal proteins for binding lectin-like receptors and/or degradation systems, iii) address proteins to the cell surface (secretion), iv) target proteins to cellular compartments, v) define an immunological identity (blood groups). As a result, glycosylated proteins exist as a mixture of glycoforms whose physico-chemical and biological properties differ from the product directly coded by the relevant gene. It is widely admitted that post-translational modifications of proteins allow a better adaptation the protein to its biological function (Helenius & Aebi, 2001).

Many human glycoproteins are of high clinical relevance. For example, on cell surfaces, they are important for communication between cells, for maintaining cell structure and for self-recognition by the immune system.

Glycoproteins are most abundant in soluble forms in biological fluids such as milk and blood. In this case, glycans protect the proteins against proteases, increase their solubility govern their plasmatic clearance and address them to target organs.

Glycosylation Enzymes

Glycosylation reactions are of major biological importance to both prokaryotes and eukaryotes and require the coordinated action of a large number of enzymes designated as Glycosyltransferases (GTs) (Breton & Imberty, 1999).

Glycosyltransferases (GTs) constitute a large family of enzymes involved in the biosynthesis of polysaccharides and glycoconjugates in the prokaryotic and eukaryotic kingdoms respectively. Sequences of the prokaryotic enzymes are not homologous to mammalian glycosyltransferases while enzymes from human, mammals and drosophila often share significant homology. So far, more than a thousand of GTs are known to mediate a wide array of biological functions. Developments in the molecular biology of these enzymes have revealed an unexpected diversity suggesting that glycosylation process probably require the involvement of about 250 genes in a single human living cell (Breton et al., 2001). About 500 glycosyltransferases including 160 human enzymes have been cloned to date. The number of cloned enzymes is increasing in human and may reach 200 shortly (Narimatsu, 2004). GTs are classified according to the stereochemistry of the reaction substrates and products as either retaining or inverting enzymes (Sinnott, 1990). A classification of glycosyltransferases using nucleotide diphospho-sugar, nucleotide monophospho-sugars and sugar phosphates and related proteins into distinct sequence-based families has been established. It shows that human GTs distribute so far into 42 structural families.

Glycosyltransferases catalyze the transfer of sugar residues from a nucleotide-sugar (activated donor substrate) to an acceptor (lipid, protein or growing carbohydrate chain). In addition to the official classification of enzymes, they can be grouped into functional families based on their sequence similarities, which may reflect enzymatic characteristics such as donor specificity, acceptor specificity, and linkage specificity between donor and acceptor. Based on the sugar they transfer, GTs are named according to the sugar they transfer such as N-Acetylglucosaminyltransferase (GlcNAcT), galactosyltransferases (GalT), and, fucosyltransferases (FucT) or sialyltransferases (SiaT or STs). Owing to the accumulation of glycosyltransferase gene data, it is thought that glycosyltransferases have high specificity for the type of linkage in either the donor and acceptor substrates as well as for the nature of the glycoconjugate acceptor (N-/O-linked glycoproteins or lipids).

Structure of Glycosyltransferases:

All GTs cloned, so far in vertebrates display the same topology. They are type II membrane proteins (N-terminal cytoplasmic domain) composed of four main domains: a short cytoplamic tail (CT) at the N-terminal end, a membrane anchor region (TMD) of 10 to 20 amino acids, a stem region (SR) and a large C-terminal catalytic domain (CD) (FIG. 1) (Paulson et al., 1987). The anchor region acts as a non cleavable signal peptide and also as a transmembrane domain (Wickner & Lodisch, 1985), orientating the catalytic domain of GTs in the lumenal part of the golgi apparatus. The SR is widely considered as a flexible region allowing also the orientation of the CD in the lumenal part of the golgi apparatus. On a general way, the CD is reasonably conserved within GTs of various species whereas the SR constitutes an hypervariable portion of the transferase. Some of these enzymes may be cleaved at their SR by an endogenous protease, or proteases, and secreted out of the cell (Paulson & Colley, 1989) to produce milk or blood enzymes. It has been well documented that the proteolytic cleavage and secretion of glycosyltransferases are affected by various pathological conditions such as malignant transformation and inflammation but the molecular mechanisms underlying the cleavage and secretion have not yet been clarified.

GTs and neoglycosylated proteins/lipids have been localized inside the ER and the subcompartments of Golgi using both subcellular fractionation of cellular membranes and immunoelectron microscopy (Roth, 1987). Early studies suggest that the compartmentalization of GTs may reflect the sequence of the oligosaccharide chain modification (Kornfeld & Kornfeld, 1985). It was thought that this strict localization ensure an optimal biosynthesis of the glycan chains by providing an efficient vicinity between enzyme, substrate and sugar nucleotide donor. Further studies showed that many of glycosylation enzymes overlap in localization and demonstrated cell-type specific golgi subcompartmentation (Colley, 1997). GTs are spread out in the golgi stacks and this can differ between cell types for a given protein (Roth, 1991).

Generally, it has been demonstrated that the transmembrane domain (TMD) of proteins is a determinant key to confer golgi localization essential for at least GalNAcTs, GlcNAcTs, GalT, FucT and SiaT to find their acceptors. It was demonstrated that the flanking region of TMD and/or the lumenal portion contribute to localize as well (Munro, 1998; Yang et al., 1996). Moreover, the CT and the SR of GTs specify their in vivo functional sublocalisation and stability in the golgi apparatus. Substituting either of the three domains (CT, TMD and SR) does not change the catalytic activity of the enzyme but contribute to alter its distribution in the golgi compartments (Grabenhorst & Conradt, 1999). No clear specific targeting sequences have been found over the last decade and only critical regions of the GTs have been identified for their compartmentalization (Opat et al., 2001). More recently, the inventors have found that the soluble catalytic domain of ST6Gal followed a different subcellular route than the full-length enzyme (Ronin, Biochimie 2003).

Among the large number of GTs, the families which are of greatest interest are those which are in charge of terminal glycosylation because these sugars play an important role in phenomenons of recognition and signalization in humans. Those essentially include sialyltransferases (SiaTs), fucosyltransferases (FucTs) and galactosyltransferases (GalTs). Galactose and fucose are involved in recognition of blood group (ABH/Lewis) antigens. Sialylated oligosaccharides of glycoproteins and glycolipids are implicated in many biological processes such as cell adhesion and receptor recognition in inflammation and cancer (sialyLewis antigen) as well as neuronal outgrowth (Polysialic antigen) (Paulson, 1989). The structural diversity and regulated expression of sialylglycoconjugates appear to be well correlated with their functions (Sasaki, 1996).

Sialyltransferases:

The sialic acid family is composed of more than a hundred of derivatives among which neuraminic acid is the most frequent in mammals and humans. Sialyltransferases (STs) catalyze the transfer of a sialic acid residue from its activated form, cytidyl-monophospho-N-acetyl-neuraminic acid (CMP-Neu5Ac), to a non-reducing terminal position on a glycan acceptor in glycoproteins or glycolipids. The catalyzed reaction is as follows:

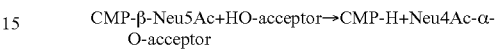

Each ST is classified according to the type of linkage established between the sialic acid residue and the acceptor substrate specificity (which can be either a protein or a lipid). Thus, three groups are distinguished: α2,3-sialyltransferases (α2,3-STs), α2,6-sialyltransferases (α2,6-STs), and α2,8-sialyltransferases (α2,8-STs). α2,6-STs transfer a sialic acid residue at an alpha2,6 position (ST6Gal) to a galactose residue, or to a N-Acetyl-D-galactosamine (ST6GalNAc), or to a N-acetyl-D-glucosamine (ST6GlcNAc). However, the enzyme involved in the formation of this last type of linkage is still unknown. The α2,3-STs transfer a sialic acid to the carbon 3 of galactose (ST3Gal), and the α2,8-STs to the carbon 8 of an other acid sialic residue (ST8Sia).

STs have also been identified in all animals (from birds to humans), in bacterial cells and in viruses (Sujino et al., 2000). The family of human STs is composed of 20 different genes cloned as shown in table 1 (Sasaki, 1996, Ronin 2003). Their substrates specificities are as follows.

1) α2,6-STs

ST6Gal:

ST6Gal I transfers a sialic acid residue on the disaccharide Galβ1-4GlcNAc of N-glycans almost (van den Eijnden et al., 1980; Weinstein et al., 1982). It is expressed in an ubiquitous manner in human tissues except in testis and brain where it is expressed a lower levels (Table 2) (Kitagawa & Paulson, 1994a).

ST6Gal II, identified recently (Krzewinski-Recchi et al., 2003; Takashima et al., 2002), recognizes the disaccharide Galβ1-4GlcNAc as acceptor substrate particularly when it is on a free oligosaccharide (unknown protein or lipid). The expression pattern of ST6Gal II is restricted to the brain and shows a low expression level in testis, thyroid, lymphatic ganglia and some fetal tissues (Table 2).

ST6GalNAc:

The second subfamily of α2,6-STs is represented by the group of ST6GalNAc, which transfer a sialic acid residue on an N-acetyl galactosamine residue. Six members have been identified in human (Table 2).

ST6GalNAc I and ST6GalNAc II possess the broadest substrate specificity as they are able to transfer a sialic acid on the following O-glycan structures: Galβ1-3GalNAc, GalNAcα-O-Ser/Thr, Siaα2-3 Galβ1-3GalNAcα-O-Ser/Thr (Ikehara et al., 1999; Kono et al., 2000; Kurosawa et al., 1994; Kurosawa et al., 1996; Harduin-Lepers et al., 2001). Their expression pattern is different, ST6GalNAc I is expressed in submaxillary and mammary glands, spleen and colon whereas ST6GalNAc II is expressed in many tissues such as testis and lactating mammary glands (Kurosawa et al., 1996; Kurosawa et al., 2000).

ST6GalNAc III, IV, V and VI possess a reduced substrate specificity: they recognize only the trisaccharide Siaα2, 3Galβ1-3GalNAc. However, it is now established that ST6GalNAc III, V and VI catalyze preferentially the formation of the GM1b glycolipid (Sjoberg et al., 1996; Lee et al., 1999) whereas ST6GalNAc IV catalyzes the transfer of sialic acid on O-glycans (Harduin-Lepers et al., 2000, Ikehara et al., 1999; Lee et al., 1999, Okajima et al., 2000). ST6GalNAc IV shows restricted substrate specificity using only the trisaccharide sequence Siaα2,3Galβ1-3GalNAc and does not discriminate between α- and β-linked GalNAc. Two different isoforms have been found. Northern-blot analysis detected a 2.2 kb transcript in various adult tissues and lower levels of expression of an additional transcript in brain, heart and skeletal muscle (Harduin-Lepers et al., 2000).

2) α2,3-STs

They all are ST3Gal transferring sialic acid of a galactose residue in protein or lipid acceptor.

ST3Gal I was cloned from submaxillary glands cDNA library and its ubiquitous expression (Table 2) was confirmed by Northern-blot (Chang et al., 1995). It synthesizes Siaα2,3Galβ1-3-GalNAc, a structure common to many O-linked oligosaccharides. It differs from other STs in its ability to use glycolipid acceptor substrates in vitro (Kitagawa & Paulson, 1994b).

ST3Gal II was cloned by Kim et al. (1996) from a liver cDNA library and the Northern-blot analysis revealed high levels expression in heart, liver and skeletal muscle, intermediate levels in thymus, lymph node, appendix and spleen, and lower levels in lung peripheral blood lymphocytes (Table 2). ST3Gal II can transfer sialic acid residues on Galβ1-3-GalNAc or on the gangliosides (lipid) GM1 or asialo-GM1 as acceptor substrates (Giordanengo et al., 1997).

ST3Gal III has been cloned by screening a human placental cDNA library with a probe based on sialylmotif, the cDNA encoding ST3Gal III was isolated (Kitagawa & Paulson, 1993). Transcript is abundantly expressed in skeletal muscle and fetal tissue and lower expressed in placenta. This enzyme catalyzes the transfer of sialic acid to galactose-containing substrates (Table 2).

ST3Gal IV is involved in sialylation of O-linked Galβ1-3GalNAc (Table 2) (Tetteroo et al., 1987). There are 5 different mRNAs expressed, and they encode for identical protein sequences except at the 5'-ends. These transcripts are produced by a combination of alternative splicing. Northern-blot analysis showed that one of them is specifically expressed in placenta, testis and ovary, indicating that its expression is independently regulated from the others (Kitagawa et al., 1996).

ST3Gal V has been isolated from a human cell library of cDNA and called GM3 synthase. A major 2.4 kb transcript is expressed in many tissues particularly in brain, skeletal muscle, placenta and testis. It is widely distributed in human brain with slightly elevated expression in the cerebral cortex, temporal lobe and putamen. The substrate specificity of this enzyme is highly restricted to lacosylceramide as the acceptor (Table 2) (Ishii et al., 1998).

ST3Gal VI was cloned from a human melanoma cDNA library. This ST exhibits restricted substrate specificity: it is involved in the synthesis of sialyl-paragloboside, a precursor of the sialyl-Lewis X determinant (Okajima et al., 1999). There are 2 forms of ST3Gal VI mRNA (called type 1 and 2), differing only in the 5'-untranslated region. This enzyme is expressed at similar levels in most tissues (Table 2) (Taniguchi et al., 2001).

3) α2,8-STs

ST8Sia I is also called ganglioside GD3 synthase and catalyzes the transfer of a sialic acid molecule to the terminal sialic acid of GM3 via an α2,8 linkage (Sasaki et al., 1994). It has been shown that this enzyme can also use GM1b, GD1a and GT1b as acceptor substrate (Table 2) (Nakayama et al., 1996; Nara et al., 1996; Watanabe et al., 1996).

ST8Sia II is also called STX, Scheidegger et al. (1995) used sequences of rodent STX to clone the human cDNA from a fetal heart library. STX is primarily expressed in embryonic tissues and modestly in adult heart, brain and thymus (Angata et al., 1997). This enzyme regulates the linkage between neural cell adhesion molecule (NCAM) and polysialic acid (PSA) and modulates by this way the adhesive properties of NCAM. STX catalyzes the transfer of the first sialic acid via an α2,8 linkage on an other sialic acid linked in α2,3 or α2,6 (Table 2) (Angata et al., 1997) on a N-Glycan, then it is involved in the elongation process making successive α2,8-linkage over the previous residues.

ST8Sia III transfers a sialic acid on Siaα2-3Galβ1-4GlcNAc structures inside N-glycans and glycolipids such as GM3 (Table 2) (Lee et al., 1998; Yoshida et al., 1995a; Yoshida et al., 1995b).

ST8Sia IV, also called PST (Polysialyltransferase), was cloned by Nakayama et al. (1995). Northern-blot analysis revealed that PST is expressed in many fetal tissues and in adult heart, spleen, thymus and at lower levels in other organs and tissues (Table 2). This enzyme also regulates the linkage between neural cell adhesion molecule (NCAM) and polysialic acid (PSA). In addition, it is shown that it catalyzes the same reaction as the STX (Angata et al., 2000; Nakayam et al., 1995).

ST8Sia V presents a transfer activity towards the gangliosides GM1b, GD1a, GT1b and GD3 (Table 2) (Kono et al., 1996).

ST8Sia VI has been cloned quite recently in human and little is known about it. The mouse ST8Sia VI possesses a transfer activity of sialic acid on the NeuAcα2,3(6)Galβ structure found at the non reduced end of O-glycans, N-glycans and free oligosaccharides such as the sialyllactose (Table 2) (Takashima et al., 2002).

4) Structural Organization Needed for Promoting Sialyltransferase Activity

All members of the STs family possess three conserved region in their CD named Sialylmotifs: motif L for Large, S for Small and VS for very small (Datta & Paulson, 1995; Geremia et al., 1997) based on the comparison of their primary sequences A survey of the animal genomes has been published lately (Harduin-Lepers, 2005) to find out unknown sequences possessing the sialylmotifs and thus potentially new STs.

The sialylmotif L consisted of 44 or 45 amino acids and contained between 5 invariant residues among all the human enzymes as shown in FIG. 2. This region is in the center of the CD. The second sialylmotif S, in the COOH-terminal portion, consisted of 23 amino acids residues, two of which residues being identical among all the STs (Drickamer, 1993). The third sialylmotif VS, at the terminal part of the enzyme, consisted of 13 amino acids with two conserved residues (histidine and glutamate).

It has been demonstrated that the sialylmotif L is involved in the binding of the donor substrate CMP-sialic acid (Datta & paulson, 1995). Some amino acids of this motif can also participate in the catalytic activity of enzymes (Sasaki, 1996). It has been proposed that the sialylmotif S participate to both donor and acceptor binding (Datta et al., 1998). The precise role of VS is still unclear but recent studies on STX and PST examined the functional rule of the conserved His in this motif (Kitazume-Kawaguchi et al., 2001). The change of the Histidine by a Lysine reside affect their catalytic activity showing that the motif VS is involved in catalysis. The sialylmotif VS is necessary for optimal catalytic efficiency and it is part of the active site, mainly on the acceptor site or at the vicinity of both donor and acceptor sugar substrates (Jeanneau et al., 2004). From previous work, it is now clear that the C-terminal part of the CD (part of sialylmotif S, motif 3 and sialylmotif VS) is primarily dedicated to the recognition of acceptor substrates whereas the N-terminal part (sialylmotifs L and part of S) is mostly involved in nucleotide sugar binding (Datta & Paulson, 1995; Datta et al., 1998; Laroy et al., 2001; Kitazume-Kawaguchi et al., 2001; Jeanneau et al., 2004). However, it cannot been excluded that the Sialylmotif L could also be involved in acceptor recognition (Legaigneur et al., 2001).

As mentioned above, the amino acid sequences deduced from the cloned human sialyltransferase cDNA show the same organization in four domains shared by many GTs: i) a short N-terminal cytoplasmic tail (CT; around 10 amino-acids), ii) a transmembrane domain (TMD; around 20 amino acids), iii) a stem region (SR), highly variable in length and iv) a catalytic domain (CD; around 300 amino acids.

The SR is defined as the peptide region between the TMD and the CD which can be removed without altering the enzymatic activity (Paulson 1989, Ronin, 2001, Vallejo-Ruiz et al., 2001; Jeanneau et al., 2004). However, the inventors have shown that this hypervariable region may be essential to define a fine recognition of the glycan acceptor (tri>bi>tetraantennary) and proposed that it may be involved in a conformational change to open the catalytic site (Ronin, 2001). As a result, the catalytic efficiency is increased by a factor 35 and the recognition of glycan acceptor is broadened.

The CD is crucial for STs to display enzymatic activity. It contains at least three highly conserved sequences maintaining identical amino acids positions found in all mammalian STs cloned. Those domains are L-, S- and VS-sialylmotifs (Livingston & Paulson, 1993; Geremia et al., 1997). An additional domain (motif 3) has also been recently isolated between the sialylmotifs S and VS, it contains four highly conserved residues, with the following consensus sequence: (H/y)Y(Y/F/W/h)(E/D/q/g). (Capital letters and lowercase letters indicate a strong or a low occurrence of the amino acid, respectively.) (Jeanneau et al., 2004). Many studies described in the literature aim to get insight into structure/function relationships in the large STs family and thus particularly to define a minimal catalytic domain inside. The minimal CD has been so defined experimentally by site-directed mutagenesis or alternatively by sequence alignment and comparison for a few STs (Vallejo-Ruiz et al., 2001; Chen & Colley, 2000, Ronin 2003).

Despite the broad definition of the CD and the catalytic activity, delineating a minimal CD of STs is still uneasy. ST6Gal I is the most studied enzyme among STs and most of the research has been realised on it to define both minimal catalytic domain and catalytic activity. This is due to the absence of ST6Gal in all cells used to produce human recombinant proteins. This lack is a technological bottleneck for heterologous systems using non animal cells (yeast, insects and plants) since they do not contain any sialic acid. In CHO cells alternatively, only a ST3 activity is expressed.

The delineation between the SR and the CD has never been well defined except experimentally. Based on bioinformatics, the inventors have designed a strategy of identifying the end of the SR for the 3 ST families (Ronin., 2003).

The CD generally coincides with the end of the hypervariable region in the N-terminal half of the enzymes (Ronin., 2003). The catalytic domain is therefore assumed to start around 70-90 residues upstream from the sialylmotif L and around 40-45 residues for ST6GalNAc III to VI. The average size of the CD is estimated around 300 (±20) amino acids, including the sialylmotifs (Jeanneau et al., 2004) (Table 3). The minimal CD has been defined for a few STs—either by truncation experiments or sequence comparison—(Legaigneur et al., 2001; Vallejo-Ruiz et al., 2001; Chen & Colley, 2000), such as for hST3Gal I (minimal CD consisting in amino acids 57-340; Vallejo-Ruiz et al., 2001) and hST8Sia IV (minimal CD consisting in amino acids 62-359; Angata et al., 2004).

When transfected in CHO cells, the soluble CD of hST6Gal I (amino acids 90-406) was found to display an enlarged specificity towards endogenous acceptors as it follows the intracellular secretory pathway within the Golgi apparatus. It has thus been possible to delineate a minimal CD for hST6Gal I containing a critical sequence capable of displacing the acceptor recognition from intracellular resident acceptors to cell surface glycoconjugates (Donadio et al., 2003). In addition, the soluble secreted CD of hST6Gal I showed increased transfer efficiency, irrespectively of the branching pattern of the glycan acceptor (Legaigneur et al., 2001).

Glycosylation of Protein (Drugs) Produced in Heterologous Expression Systems

Proteins of therapeutic interest were first extracted from natural sources such as blood, placenta, human or animal tissues. However, this approach is limited by the source, amount and availability of human tissues and may contain life threatening contaminants (prions, oncogenes, viruses . . . ) as well as potential allergens generated by proteins from animals. With the rise drug-approved proteins and clinical needs, new approaches have been developed to produce proteins using different expression systems.

In most instances, intensive work is currently aiming at humanizing the glycosylation pattern of the recombinant proteins to approach the pattern found in the natural glycoproteins as closely as possible to improve pharmacokinetics and lower immunogenicity of the product.

The machinery required for the synthesis, the activation and the introduction of sialyl residues is poorly expressed in the various existing recombinant proteins expression systems. The recombinant human proteins produced are therefore often under or even not-sialylated compared to their native counterparts.

One of the most used systems is the bacteria *Escherichia coli* (*E. coli*) (Swartz, 2001; Baneyx, 1999), but its main inconvenient is that the human post-traductionnal modifications, particularly protein glycosylations are not carried out by this prokaryote because no such glycosyltranferases are expressed in *E. coli*. This can lead to the reject of the therapeutic proteins of interest by the immune system, the reduction of their circulatory half-life and/or of their biological activity. The protein produced can eventually be misfolded and aggregate as inclusion bodies.

Yeasts and filamentous fungi are also well-known eukaryote expression systems and they possess cellular machinery similar to those of human cells. The yeast produces complex proteins and is able to carry out several post-traductional modifications such as simple glycosylations. However, although the N-glycosylation process performed by yeast and fungi is the same as the mammalian process for the initial steps in the endoplasmic reticulum, no complex oligosaccharide containing sialic acid, galactose, fucose and N-acetylgalactosamine have been found inside the glycoproteins produced by these organisms (Blanchard, 2004); both yeast and fungi typically produce mannose-rich glycans by adding up to 100 mannose residues (in the case of yeast) on the pentasaccharidic core (Tanner & Lehele, 1987; Herscovics &

Orlean, 1993) in the golgi apparatus. Those hypermannosylation foster an immune response in human.

Engineering glycosylation in yeast (Hamilton et al., 2003; Roy et al., 2000) has first allowed the reduction of the mannoses residues number added. Then, enzymes which are necessary to peripheral N-acetylglucosaminylation and galactosylation and have been added in these systems (Maras et al., 1999; Bretthauer, 2003; Vervecken et al., 2004). However, the addition of the terminal sialic acid is still difficult to achieve, due to the large number of enzymes involved in this terminal step.

Proteins expressed in insect cells are properly folded, may undergo post-traductional modifications and be secreted. Early N-linked glycosylation carried out by these cells are similar to those performed by mammalian cells. However, the glycan structures obtained in this case are of the paucimannosidic type i.e. truncated-due to the presence of an undesirable N-acetylhexosaminidase activity which degrades the neoglycoproteins expressed during Baculovirus expression (Blanchard, 2004). In addition, in some insect cells lines, α1,3/fucose residues may be found and these residues generally trigger an undesirable immune response in human. Thus, the use of this system is restricted to the production vaccinal antigens.

In insect cells, the GTs catalyzing the transfer of immunogenic sugars have been deleted and sialylation could be achieved by adding 3 genes encoding for the N-acetylglucosamine 2-epimerase, N-acetylneuraminyl lyase and CMP-Neu5Ac synthase (Jarvis et al., 1998; Aumiller et al., 2003). A new insect cell line (SfSWT-3) designed to synthesize its own CMP-sialic acid has been created The resulting cells express all the 7 mammalian genes, can produce CMP-sialic acid and sialylate an heterologous protein when cultured in a serum-free growth medium (Aumiller et al., 2003).

As eukaryotic cells, plants exhibit a complex and sophisticated cellular machinery which may be used to produce therapeutic proteins. Recombinant proteins possess a very good pharmacological quality because plants have many of the enzymes required for the maturation of the proteins. However, the glycosylation pathway needs major adjustments not to produce allergenic proteins. Indeed, the N-glycosylations in plants (Lerouge et al., 2000) are similar to those performed in humans as far as core glycosylation is concerned. However, glycans are still lacking sialylated antennae and contain inner β1,2-xylose and α1,3-fucose. Both residues are highly immunogenic for human and currently compromise the approval of transgenic plants as expression systems for therapeutics.

In plants, the first strategy used aimed at preventing the addition of allergenic sugars by preventing proteins to exit the endoplasmic reticulum. As a result, N-linked glycans can not mature to complex type. Another strategy was based on the inhibition of several GTs inside the golgi apparatus. This inhibition can not be complete and/or can enter in competition with the endogenous machinery for maturation.

Mammalian cell expression system, namely CHO cells, is currently the only drug-approved system to produce recombinant therapeutics. These cells show a major advantage because they are able to synthesize complex N-linked glycoproteins of high molecular weight and/or multimeric. Mammalian cells naturally express, not only the enzymes involved in the synthesis and the transport of the nucleotide-sugars, but also the glycosyltransferases required to achieve complex glycosylation of the recombinant proteins with a satisfactory content in 3-linked sialic acid. However, there is a lack of some enzymes such as the α1,3/4-fucosyltransferases and α2,6-sialyltransferases, which realize terminal O-linked and N-linked glycosylation. Moreover, in mammalian cells, the sialylation occurs through N-glycolyneuraminic acid (NeuGc) which significantly differs also from the N-Acetylated derivative (NeuAc) found in human cells In the case of mammalian cells, work has been performed through the over-expression of an α2,3-ST and a β1,4GalT (Weikert et al., 1999); both enzymes are present in the genome but their activities are highly variable upon cell culture conditions. This led to a wide variability concerning the presence of the terminal Gal and sialic acid and to an extensive microheterogeneity in glycosylated proteins. Work has also been oriented towards the optimization of the galactosylation and sialylation (Granbenhorst et al., 1999) by introducing an α2,6-ST (Bragonzi et al., 2000) in mammalian cells. A CHO cell line stably expressing native rat α2,6-ST has been established. The glycoproteins produced by these CHO cells display both α2,6 and α2,3-linked terminal sialic acid residues, similar to human; the ratio observed between α2,6 and α2,3-linked terminal sialic acid residues carried was of 40.4% of α2,6- and 59.6% α2,3-sialic acid residues, which improved pharmacokinetics in clearance studies (Bragonzi et al., 2000). Despite these improvements in humanization of cells, the ratio between α2,6 and α2,3-linked terminal sialic acid residues cannot be controlled and has never been found even favorable to the 6-activity. It thus appears that first, sialylation is a critical step to control glycan structures and secondly, the difficulty resides also in expressing the heterologous ST in a specific compartment of the cell (addressing), in optimizing its activity provided that the donor substrate for this enzyme is present (carrier).

It is therefore worth noting that terminal sialylation of approved glycoprotein drugs is the most difficult step to obtain in all expression systems available so far.

GOAL OF THE INVENTION

The goal of the present invention is to provide a process for generating a panel of new gene sequences encoding chimerical membrane enzymes with glycosyltransferase activity, and in particular for designing gene sequences encoding innovative chimerical sialyltransferases to equip cells with a needed sialylating activity and improve the quality and yield of recombinant glycosylated proteins.

The invention relates to a process for producing gene sequences encoding chimerical membrane glycosyltransferases presenting an optimized glycosylation activity in cells transformed with said sequences, when compared with the glycosylation activity of the corresponding native glycosyltransferases, i.e. a glycosylation less selective and/or more efficient (up to at least 30-fold higher than the initial activity of the native full length glycosyltransferases) towards the acceptor substrate, said process comprising the fusion:

of a first nucleic acid sequence coding for a C-terminal minimal fragment of the catalytic domain (CD) of the native full length glycosyltransferase, said C-terminal minimal CD fragment displaying a transferase activity (which can be enhanced up to at least 30-fold higher than the initial activity of to the native CD), said first nucleic sequence being obtained by removing nucleotides coding for one or several contiguous amino acids extending from the first amino acid of the N-terminal end of said CD, and selection of the nucleic acid encoding said C-terminal minimal CD fragment which is such that if n represents the number of contiguous amino acids as defined above which has been deleted, then the fragment obtained when deleting at least n+1 contiguous amino acids as defined above, has no substantial transferase activity, to a second nucleic acid of variable sequence coding for a transmembrane peptide chain specifying the anchorage of the glycosyltransferases in intracellular compartments, and comprising (or consisting of) in its N-terminal region a cytoplasmic tail (CT) region located upstream from a transmembrane domain (TMD), itself located upstream of a stem region (SR) or of a fragment of at least 3 contiguous amino acids of the SR, said SR or part thereof being linked to said catalytic domain, optionally via a linker or connection peptide of at least 2 amino acids encoded by a restriction site which does not exist in the nucleotide sequence coding for the native CD mentioned above, provided that at least one of these CT, TMD, SR peptides being different from the primary structure of the native corresponding peptides in the native glycosyltransferase from which is derived the CD fragment with optimal glycosyltransferase activity as defined above, this fusion being carried out in such way that the first nucleic acid is located downstream from the second nucleic acid and provides a protein product in which the CD is in the C-terminal half.

By chimerical membrane glycosyltransferases presenting an optimized glycosylation activity in cells transformed with said sequences, when compared with the glycosylation activity of the corresponding native glycosyltransferases, one should understand that said chimerical membrane glycosyltransferases:

have a sugar transfer activity less selective towards acceptor substrates than the corresponding native glycosyltransferases when tested in vitro with exogeneous/commercially available acceptor glycoproteins having known bi-, tri- or tetraantennary glycans, i.e. have a in vivo glycosylation activity in cells towards all cell glycoprotein acceptors, said glycosylation activity being measurable preferably in intracellular and cell surface compartments according to the following general procedure using lectin SNA binding, and/or have a more efficient sugar transfer activity towards their acceptor substrates than the corresponding native glycosyltransferases, i.e. show a glycosylation activity up to at least 30-fold higher than the initial activity of the native full length glycosyltransferases, said glycosylation activity being measurable according to the general in vitro procedure with exogeneous/commercially available acceptor glycoproteins having known bi-, tri- or tetraantennary glycans.

The expression "chimerical glycosyltransferases" used above corresponds to a glycosyltransferase whose full length sequence is not the direct product of a native gene or a transcript but has been designed using sequences from other glycosyltransferases exclusively.

The expression "native glycosyltransferases" used above corresponds to the sequence of the full length enzyme as represented by a naturally occurring coding sequence.

The expression "glycosylation activity" used above corresponds to the catalytic reaction of transferring a sugar from a nucleotide donor to an acceptor substrate.

The expression "minimal catalytic domain (CD)" used above corresponds to the C-terminal peptide domain of a glycosyltransferase sequence which cannot be deleted further without loss of transfer activity.

The expression "transmembrane domain (TMD)" used above corresponds to a peptide portion composed of a stretch of 17-24 essentially hydrophobic amino acids The expression "cytoplasmic tail (CT)" used above corresponds to the N-terminal peptide of a glycosyltransferase which may encompass at least more than 3 amino acids upstream from the TMD.

The expression "stem region (SR)" used above corresponds to a stretch of at most 246 amino acids downstream the TMD/upstream from the CD.

The invention relates more particularly to a process as defined above, characterized in that the first and second nucleic acids are derived from nucleotide sequences encoding CD domains, or CT, TMD, and SR regions, respectively, in glycosyltransferases from eukaryotic origin, preferably mammals and humans, said glycosyltransferases being involved in:

O-glycosylation of the proteins in cells, such as N-acetylgalactosaminyl-, N-acetylglucosaminyl-, glucosyl-, galactosyl-, or sialyltransferases, N-glycosylation of the proteins in cells such as N-acetylglucosaminyl-, galactosyl-, fucosyl-, or sialyltransferases, Glycosylation of lipids such as the N-acetylgalactosaminyl-, N-acetylglucosaminyl-, fucosyl-, galactosyl-, or sialyltransferases.

The expression "O-glycosylation" used above corresponds to the biosynthetic pathway elaborating monosaccharides or oligosaccharides covalently attached to amino acids which are not asparagine residues but can be preferably hydroxy amino acids such as serine, threonine or hydroxylysine residues.

The expression "N-glycosylation" used above corresponds to the biosynthetic pathway elaborating oligosaccharides attached to asparagine residues within the consensus tripeptide Asn-X-Ser/Thr (X being not Proline).

The expression "galactosyltransferases" used above corresponds to a glycosyltransferase which transfers a galactose residue from UDP-Gal to an N-/O-linked protein or glycolipid acceptor.

The expression "sialyltransferases" used above corresponds to a glycosyltransferase which transfers a sialic acid residue, preferably a derivative of neuraminic acid from CMP-NeuAc to a N-/O-linked protein or glycolipid acceptor.

The invention concerns more particularly a process as defined above, characterized in that the first and second nucleic acids are derived from nucleotide sequences encoding CD domains, or CT, TMD, and SR regions, respectively in N-acetylgalactosaminyltransferases, N-acetylglucosaminyltransferases, glucosyltransferases, galactosyltransferases, fucosyltransferases, or sialyltransferases.

The invention concerns more particularly a process as defined above, characterized in that the first and second nucleic acids are derived from nucleotide sequences encoding CD domains, or CT, TMD, and SR regions, respectively in alpha 6 fucosyltransferases (core glycosylation), beta 2/4/6 N-acetylglucosaminyltransferases (branching), beta 4 galactosyltransferases, and alpha 3/6/8 sialyltransferases (terminal glycosylation).

Advantageously, the first and second nucleic acids are derived from nucleotide sequences encoding CD domains, or CT, TMD, and SR regions, of enzymes implicated in the N-glycosylation pathway.

The invention relates more particularly to a process as defined above, characterized in that the first and second nucleic acids are derived from nucleotide sequences encoding CD domains, or CT, TMD, and SR regions, respectively, in sialyltransferases.

The invention concerns more particularly a process as defined above, characterized in that the first and second nucleic acids are derived from nucleotide sequences encoding CD domains, or CT, TMD, and SR regions, respectively, in α2,6-sialyltransferases, α2,3-sialyltransferases, or α2,8-sialyltransferases.

Advantageously, nucleotide sequences encoding CT, TMD and/or SR or SR fragment mentioned above are preferably from synthetic origin.

The expression "α2,6-sialyltransferases" used above corresponds to a glycosyltransferase able to transfer a sialic acid residue, preferably a derivative of neuraminic acid from CMP-NeuAc to the 6-position of a carbohydrate acceptor from the N-/O-linked protein or glycolipid type.

The expression "α2,3-sialyltransferases" used above corresponds to a glycosyltransferase able to transfer a sialic acid residue, preferably a derivative of neuraminic acid from CMP-NeuAc to the 3-position of an carbohydrate acceptor from the N-/O-linked protein or glycolipid type.

The expression "α2,8-sialyltransferases" used above corresponds to a glycosyltransferase able to transfer a sialic acid residue, preferably a derivative of neuraminic acid from CMP-NeuAc to the 8-position of a sialylated acceptor from the N-/O-linked protein or glycolipid type.

The invention relates more particularly to a process as defined above, characterized in that the first and second nucleic acids are derived from nucleotide sequences encoding CD domains, or CT, TMD, and SR regions, respectively, in:
α2,6-sialyltransferases chosen among:
the human β1,4-galactoside α2,6-sialyltransferases I and II (hST6Gal I, and hST6Gal II) represented by SEQ ID NO: 2, and SEQ ID NO: 4, respectively, encoded by the nucleotide sequences SEQ ID NO: 1, and SEQ ID NO: 3, respectively, or
the human N-acetylgalactosaminide-α2,6-sialyltransferases I to VI (hST6GalNAc I to VI) represented by SEQ ID NO: 6, SEQ ID NO: 8, SEQ ID NO: 10, SEQ ID NO: 12, SEQ ID NO: 14, and SEQ ID NO: 16, respectively, encoded by the nucleotide sequences SEQ ID NO: 5, SEQ ID NO: 7, SEQ ID NO: 9, SEQ ID NO: 11, SEQ ID NO: 13, and SEQ ID NO: 15, respectively,
α2,3-sialyltransferases chosen among the human galactoside-α2,3-sialyltransferases I to VI (hST3Gal I to VI) represented by SEQ ID NO: 18, SEQ ID NO: 20, SEQ ID NO: 22, SEQ ID NO: 24, SEQ ID NO: 26, and SEQ ID NO: 28, respectively, encoded by the nucleotide sequences SEQ ID NO: 17, SEQ ID NO: 19, SEQ ID NO: 21, SEQ ID NO: 23, SEQ ID NO: 25, and SEQ ID NO: 27, respectively, or the rat galactoside-α2,3-sialyltransferases I to VI (rST3Gal I to VI), such as the rST3Gal III represented by SEQ ID NO: 30 encoded by the nucleotide sequence SEQ ID NO: 29, or any ST from other animal origin provided that it shares at least 85% homology with the human enzyme,
α2,8-sialyltransferases chosen among the human sialic acid-α2,8-sialyltransferases I to VI (hST8Sia I to VI) represented by SEQ ID NO: 32, SEQ ID NO: 34, SEQ ID NO: 36, SEQ ID NO: 38, SEQ ID NO: 40, and SEQ ID NO: 42, respectively, encoded by the nucleotide sequences SEQ ID NO: 31, SEQ ID NO: 33, SEQ ID NO: 35, SEQ ID NO: 37, SEQ ID NO: 39, and SEQ ID NO: 41, respectively.

The expression "galactoside-α2,6-sialyltransferases" used above corresponds to a glycosyltransferase which transfers a sialic acid residue, preferably a derivative of neuraminic acid from CMP-NeuAc to the 6-position of a galactosylated acceptor from the N-/O-linked protein or lipid type.

The expression "N-acetylgalactosaminide α2,6-sialyltransferases" used above corresponds to a glycosyltransferase which transfers a sialic acid residue, preferably a derivative of neuraminic acid from CMP-NeuAc to the 6-position of a N-acetylgalactosaminyl residue of a N-/O-linked protein or glycolipid acceptor.

The expression "galactoside α2,3-sialyltransferases" used above corresponds to a glycosyltransferase which transfers a sialic acid residue, preferably a derivative of neuraminic acid from CMP-NeuAc to the 3-position of a galactosylated N-/O-linked protein or lipid acceptor.

The expression "sialic acid α2,8-sialyltransferases" used above corresponds to a glycosyltransferase which transfers a sialic acid residue, preferably a derivative of neuraminic acid from CMP-NeuAc to a sialylated N-/O-linked protein or glycolipid acceptor.

The invention concerns more particularly a process as defined above, characterized in that the nucleotide sequence encoding the CD domain comprised in the first nucleic acid is chosen among the sequences constituted of, or comprising:
the nucleotide sequence delimited in its 5' end by the nucleotide located in position 268 to 330 and in its 3' end by the nucleotide located in position 1218 of SEQ ID NO: 1, said nucleotide sequence encoding the polypeptide sequence corresponding to the CD domain of hST6Gal I delimited in its N-terminal end by the amino acid located in position 90 to 110 and in its C-terminal end by the amino acid located in position 406 of SEQ ID NO: 2, the nucleotide sequence delimited in its 5' end by the nucleotide located in position 307 to 369 and in its 3' end by the nucleotide located in position 1587 of SEQ ID NO: 3, said nucleotide sequence encoding the polypeptide sequence corresponding to the CD domain of hST6Gal II delimited in its N-terminal end by the amino acid located in position 103 to 123 and in its C-terminal end by the amino acid located in position 529 of SEQ ID NO: 4, the nucleotide sequence delimited in its 5' end by the nucleotide located in position 814 to 876 and in its 3' end by the nucleotide located in position 1800 of SEQ ID NO: 5, said nucleotide sequence encoding the polypeptide sequence corresponding to the CD domain of hST6GalNac I delimited in its N-terminal end by the amino acid located in position 272 to 292 and in its C-terminal end by the amino acid located in position 600 of SEQ ID NO: 6, the nucleotide sequence delimited in its 5' end by the nucleotide located in position 172 to 234 and in its 3' end by the nucleotide located in position 1122 of SEQ ID NO: 7, said nucleotide sequence encoding the polypeptide sequence corresponding to the CD domain of hST6GalNac II delimited in its N-terminal end by the amino acid located in position 58 to 78 and in its C-terminal end by the amino acid located in position 374 of SEQ ID NO: 8, the nucleotide sequence delimited in its 5' end by the nucleotide located in position 73 to 135 and in its 3' end by the nucleotide located in position 915 of SEQ ID NO: 9, said nucleotide sequence encoding the polypeptide sequence corresponding to the CD domain of hST6GalNac III delimited in its N-terminal end by the amino acid located in position 25 to 45 and in its C-terminal end by the amino acid located in position 305 of SEQ ID NO: 10, the nucleotide sequence delimited in its 5' end by the nucleotide located in position 61 to 123 and in its 3' end by the nucleotide located in position 906 of SEQ ID NO: 11, said nucleotide sequence encoding the polypeptide sequence corresponding to the CD domain of hST6GalNac IV delimited in its N-terminal end by the amino acid located in position 21 to 41 and in its C-terminal end by the amino acid located in position 302 of SEQ ID NO: 12, the nucleotide sequence delimited in its 5' end by the nucleotide located in position 121 to 183 and in its 3' end by the nucleotide located in position 1008 of SEQ ID NO: 13, said nucleotide sequence encoding the polypeptide sequence corresponding to the CD domain of hST6GalNac V delimited in its N-terminal end by the amino acid located in position 41 to 61 and in its C-terminal end by the amino acid located in position 336 of SEQ ID NO: 14, the nucleotide sequence delimited in its 5' end by the nucleotide located in position 154 to 216 and in its 3' end by the nucleotide located in position 999 of SEQ ID NO: 15, said nucleotide sequence encoding the polypeptide sequence corresponding to the CD domain of hST6GalNac VI delimited in its N-terminal end by the amino acid located in position 52 to 72 and in its C-terminal end by the amino acid located in position 333 of SEQ ID NO: 16, the nucleotide sequence delimited in its 5' end by the nucleotide located in position 145 to 207 and in its 3' end by the nucleotide located in position 1020 of SEQ ID NO: 17, said nucleotide sequence encoding the polypeptide sequence corresponding to the CD domain of hST3Gal I delimited in its N-terminal end by the amino acid located in position 49 to 69 and in its C-terminal end by the amino acid located in position 340 of SEQ ID NO: 18, the nucleotide sequence delimited in its 5' end by the nucleotide located in position 175 to 237 and in its 3' end by the nucleotide located in position 1050 of SEQ ID NO: 19, said nucleotide sequence encoding the polypeptide sequence corresponding to the CD domain of hST3Gal II delimited in its N-terminal end by the amino acid located in position 59 to 79 and in its C-terminal end by the amino acid located in position 350 of SEQ ID NO: 20, the nucleotide sequence delimited in its 5' end by the nucleotide located in position 199 to 261 and in its 3' end by the nucleotide located in position 1332 of SEQ ID NO: 21, said nucleotide sequence encoding the polypeptide sequence corresponding to the CD domain of hST3Gal III delimited in its N-terminal end by the amino acid located in position 67 to 87 and in its C-terminal end by the amino acid located in position 444 of SEQ ID NO: 22, the nucleotide sequence delimited in its 5' end by the nucleotide located in position 79 to 141 and in its 3' end by the nucleotide located in position 987 of SEQ ID NO: 23, said nucleotide sequence encoding the polypeptide sequence corresponding to the CD domain of hST3Gal IV delimited in its N-terminal end by the amino acid located in position 27 to 47 and in its C-terminal end by the amino acid located in position 329 of SEQ ID NO: 24, the nucleotide sequence delimited in its 5' end by the nucleotide located in position 136 to 198 and in its 3' end by the nucleotide located in position 1086 of SEQ ID NO: 25, said nucleotide sequence encoding the polypeptide sequence corresponding to the CD domain of hST3Gal V delimited in its N-terminal end by the amino acid located in position 46 to 66 and in its C-terminal end by the amino acid located in position 362 of SEQ ID NO: 26, the nucleotide sequence delimited in its 5' end by the nucleotide located in position 73 to 135 and in its 3' end by the nucleotide located in position 993 of SEQ ID NO: 27, said nucleotide sequence encoding the polypeptide sequence corresponding to the CD domain of hST3Gal VI delimited in its N-terminal end by the amino acid located in position 25 to 45 and in its C-terminal end by the amino acid located in position 331 of SEQ ID NO: 28, the nucleotide sequence delimited in its 5' end by the nucleotide located in position 103 to 165 and in its 3' end by the nucleotide located in position 1122 of SEQ ID NO: 29, said nucleotide sequence encoding the polypeptide sequence corresponding to the CD domain of rat ST3Gal III delimited in its N-terminal end by the amino acid located in position 35 to 55 and in its C-terminal end by the amino acid located in position 374 of SEQ ID NO: 30, the nucleotide sequence delimited in its 5' end by the nucleotide located in position 133 to 195 and in its 3' end by the nucleotide located in position 1068 of SEQ ID NO: 31, said nucleotide sequence encoding the polypeptide sequence corresponding to the CD domain of hST8Sia I delimited in its N-terminal end by the amino acid located in position 45 to 65 and in its C-terminal end by the amino acid located in position 356 of SEQ ID NO: 32, the nucleotide sequence delimited in its 5' end by the nucleotide located in position 190 to 252 and in its 3' end by the nucleotide located in position 1125 of SEQ ID NO: 33, said nucleotide sequence encoding the polypeptide sequence corresponding to the CD domain of hST8Sia II delimited in its N-terminal end by the amino acid located in position 64 to 84 and in its C-terminal end by the amino acid located in position 375 of SEQ ID NO: 34, the nucleotide sequence delimited in its 5' end by the nucleotide located in position 205 to 267 and in its 3' end by the nucleotide located in position 1140 of SEQ ID NO: 35, said nucleotide sequence encoding the polypeptide sequence corresponding to the CD domain of hST8Sia III delimited in its N-terminal end by the amino acid located in position 69 to 89 and in its C-terminal end by the amino acid located in position 380 of SEQ ID NO: 36, the nucleotide sequence delimited in its 5' end by the nucleotide located in position 145 to 207 and in its 3' end by the nucleotide located in position 1077 of SEQ ID NO: 37, said nucleotide sequence encoding the polypeptide sequence corresponding to the CD domain of hST8Sia IV delimited in its N-terminal end by the amino acid located in position 49 to 69 and in its C-terminal end by the amino acid located in position 359 of SEQ ID NO: 38, the nucleotide sequence delimited in its 5' end by the nucleotide located in position 211 to 273 and in its 3' end by the nucleotide located in position 1128 of SEQ ID NO: 39, said nucleotide sequence encoding the polypeptide sequence corresponding to the CD domain of hST8Sia V delimited in its N-terminal end by the amino acid located in position 71 to 91 and in its C-terminal end by the amino acid located in position 376 of SEQ ID NO: 40, the nucleotide sequence delimited in its 5' end by the nucleotide located in position 277 to 339 and in its 3' end by the nucleotide located in position 1194 of SEQ ID NO: 41, said nucleotide sequence encoding the polypeptide sequence corresponding to the CD domain of hST8Sia VI delimited in its N-terminal end by the amino acid located in position 93 to 113 and in its C-terminal end by the amino acid located in position 398 of SEQ ID NO: 42.

The invention relates more particularly to a process as defined above, characterized in that the first nucleic acid is the nucleotide sequence SEQ ID NO: 43 corresponding to the sequence delimited by the nucleotides located in position 268 and 1218 of SEQ ID NO: 1, said nucleotide sequence SEQ ID NO: 43 encoding the polypeptide sequence SEQ ID NO: 44 corresponding to the C-terminal minimal fragment of the CD domain of hST6Gal I delimited by the amino acids located in positions 90 to 406 of SEQ ID NO: 2.

The invention concerns more particularly a process as defined above, characterized in that:
the nucleotide sequence encoding the CT region comprised in the second nucleic acid is chosen among:
  the nucleotide sequence SEQ ID NO: 45 corresponding to the nucleotide sequence delimited by the nucleotides located in positions 1 and 27 of SEQ ID NO: 1, said nucleotide sequence SEQ ID NO: 45 encoding the polypeptide sequence SEQ ID NO: 46 corresponding to the CT region of hST6Gal I delimited by the amino acids located in positions 1 to 9 of SEQ ID NO: 2,
  the nucleotide sequence SEQ ID NO: 47 corresponding to the nucleotide sequence delimited by the nucleotides located in positions 1 and 30 of SEQ ID NO: 3, said nucleotide sequence SEQ ID NO: 47 encoding the polypeptide sequence SEQ ID NO: 48 corresponding to the CT region of hST6Gal II delimited by the amino acids located in positions 1 to 10 of SEQ ID NO: 4, the nucleotide sequence SEQ ID NO: 49 corresponding to the nucleotide sequence delimited by the nucleotides located in positions 1 and 42 of SEQ ID NO: 5, said nucleotide sequence SEQ ID NO: 49 encoding the polypeptide sequence SEQ ID NO: 50 corresponding to the CT region of hST6GalNAc I delimited by the amino acids located in positions 1 to 14 of SEQ ID NO: 6, the nucleotide sequence SEQ ID NO: 51 corresponding to the nucleotide sequence delimited by the nucleotides located in positions 1 and 21 of SEQ ID NO: 7, said nucleotide sequence SEQ ID NO: 51 encoding the polypeptide sequence SEQ ID NO: 52 corresponding to the CT region of hST6GalNac II delimited by the amino acids located in positions 1 to 7 of SEQ ID NO: 8, the nucleotide sequence SEQ ID NO: 53 corresponding to the nucleotide sequence delimited by the nucleotides located in positions 1 and 24 of SEQ ID NO: 9, said nucleotide sequence SEQ ID NO: 53 encoding the polypeptide sequence SEQ ID NO: 54 corresponding to the CT region of hST6GalNAc III delimited by the amino acids located in positions 1 to 8 of SEQ ID NO: 10, the nucleotide sequence SEQ ID NO: 55 corresponding to the nucleotide sequence delimited by the nucleotides located in positions 1 and 18 of SEQ ID NO: 11, said nucleotide sequence SEQ ID NO: 55 encoding the polypeptide sequence SEQ ID NO: 56 corresponding to the CT region of hST6GalNAc IV delimited by the amino acids located in positions 1 to 6 of SEQ ID NO: 12, the nucleotide sequence SEQ ID NO: 57 corresponding to the nucleotide sequence delimited by the nucleotides located in positions 1 and 24 of SEQ ID NO: 13, said nucleotide sequence SEQ ID NO: 57 encoding the polypeptide sequence SEQ ID NO: 58 corresponding to the CT region of hST6GalNAc V delimited by the amino acids located in positions 1 to 8 of SEQ ID NO: 14, the nucleotide sequence SEQ ID NO: 59 corresponding to the nucleotide sequence delimited by the nucleotides located in positions 1 and 129 of SEQ ID NO: 15, said nucleotide sequence SEQ ID NO: 59 encoding the polypeptide sequence SEQ ID NO: 60 corresponding to the CT region of hST6GalNAc VI delimited by the amino acids located in positions 1 to 43 of SEQ ID NO: 16, the nucleotide sequence SEQ ID NO: 61 corresponding to the nucleotide sequence delimited by the nucleotides located in positions 1 and 39 of SEQ ID NO: 17, said nucleotide sequence SEQ ID NO: 61 encoding the polypeptide sequence SEQ ID NO: 62 corresponding to the CT region of hST3Gal I delimited by the amino acids located in positions 1 to 13 of SEQ ID NO: 18, the nucleotide sequence SEQ ID NO: 63 corresponding to the nucleotide sequence delimited by the nucleotides located in positions 1 and 18 of SEQ ID NO: 19, said nucleotide sequence SEQ ID NO: 63 encoding the polypeptide sequence SEQ ID NO: 64 corresponding to the CT region of hST3Gal II delimited by the amino acids located in positions 1 to 6 of SEQ ID NO: 20, the nucleotide sequence SEQ ID NO: 65 corresponding to the nucleotide sequence delimited by the nucleotides located in positions 1 and 24 of SEQ ID NO: 21, said nucleotide sequence SEQ ID NO: 65 encoding the polypeptide sequence SEQ ID NO: 66 corresponding to the CT region of hST3Gal III delimited by the amino acids located in positions 1 to 8 of SEQ ID NO: 22, the nucleotide sequence SEQ ID NO: 67 corresponding to the nucleotide sequence delimited by the nucleotides located in positions 1 and 24 of SEQ ID NO: 23, said nucleotide sequence SEQ ID NO: 67 encoding the polypeptide sequence SEQ ID NO: 68 corresponding to the CT region of hST3Gal IV delimited by the amino acids located in positions 1 to 8 of SEQ ID NO: 24, the nucleotide sequence SEQ ID NO: 69 corresponding to the nucleotide sequence delimited by the nucleotides located in positions 1 and 15 of SEQ ID NO: 25, said nucleotide sequence SEQ ID NO: 69 encoding the polypeptide sequence SEQ ID NO: 70 corresponding to the CT region of hST3Gal V delimited by the amino acids located in positions 1 to 5 of SEQ ID NO: 26, the nucleotide sequence SEQ ID NO: 71 corresponding to the nucleotide sequence delimited by the nucleotides located in positions 1 and 12 of SEQ ID NO: 27, said nucleotide sequence SEQ ID NO: 71 encoding the polypeptide sequence SEQ ID NO: 72 corresponding to the CT region of hST3Gal VI delimited by the amino acids located in positions 1 to 4 of SEQ ID NO: 28, the nucleotide sequence SEQ ID NO: 73 corresponding to the nucleotide sequence delimited by the nucleotides located in positions 1 and 24 of SEQ ID NO: 29, said nucleotide sequence SEQ ID NO: 73 encoding the polypeptide sequence SEQ ID NO: 74 corresponding to the CT region of ratST3Gal III delimited by the amino acids located in positions 1 to 8 of SEQ ID NO: 30, the nucleotide sequence SEQ ID NO: 75 corresponding to the nucleotide sequence delimited by the nucleotides located in positions 1 and 87 of SEQ ID NO: 31, said nucleotide sequence SEQ ID NO: 75 encoding the polypeptide sequence SEQ ID NO: 76 corresponding to the CT region of hST8Sia I delimited by the amino acids located in positions 1 to 29 of SEQ ID NO: 32, the nucleotide sequence SEQ ID NO: 77 corresponding to the nucleotide sequence delimited by the nucleotides located in positions 1 and 18 of SEQ ID NO: 33, said nucleotide sequence SEQ ID NO: 77 encoding the polypeptide sequence SEQ ID NO: 78 corresponding to the CT region of hST8Sia II delimited by the amino acids located in positions 1 to 6 of SEQ ID NO: 34, the nucleotide sequence SEQ ID NO: 79 corresponding to the nucleotide sequence delimited by the nucleotides located in positions 1 and 27 of SEQ ID NO: 35, said nucleotide sequence SEQ ID NO: 79 encoding the polypeptide sequence SEQ ID NO: 80 corresponding to the CT region of hST8Sia III delimited by the amino acids located in positions 1 to 9 of SEQ ID NO: 36, the nucleotide sequence SEQ ID NO: 81 corresponding to the nucleotide sequence delimited by the nucleotides located in positions 1 and 21 of SEQ ID NO: 37, said nucleotide sequence SEQ ID NO: 81 encoding the polypeptide sequence SEQ ID NO: 82 corresponding to the CT region of hST8Sia IV delimited by the amino acids located in positions 1 to 7 of SEQ ID NO: 38, the nucleotide sequence SEQ ID NO: 83 corresponding to the nucleotide sequence delimited by the nucleotides located in positions 1 and 51 of SEQ ID NO: 39, said nucleotide sequence SEQ ID NO: 83 encoding the polypeptide sequence SEQ ID NO: 84 corresponding to the CT region of hST8Sia V delimited by the amino acids located in positions 1 to 17 of SEQ ID NO: 40, the nucleotide sequence SEQ ID NO: 85 corresponding to the nucleotide sequence delimited by the nucleotides located in positions 1 and 9 of SEQ ID NO: 41, said nucleotide sequence SEQ ID NO: 85 encoding the polypeptide sequence SEQ ID NO: 86 corresponding to the CT region of hST8Sia VI delimited by the amino acids located in positions 1 to 3 of SEQ ID NO: 42, the nucleotide sequence encoding the TMD region comprised in the second nucleic acid is chosen among:

the nucleotide sequence SEQ ID NO: 87 corresponding to the nucleotide sequence delimited by the nucleotides located in positions 28 and 78 of SEQ ID NO: 1, said nucleotide sequence SEQ ID NO: 87 encoding the polypeptide sequence SEQ ID NO: 88 corresponding to the TMD region of hST6Gal I delimited by the amino acids located in positions 10 to 26 of SEQ ID NO: 2, the nucleotide sequence SEQ ID NO: 89 corresponding to the nucleotide sequence delimited by the nucleotides located in positions 31 and 90 of SEQ ID NO: 3, said nucleotide sequence SEQ ID NO: 89 encoding the polypeptide sequence SEQ ID NO: 90 corresponding to the TMD region of hST6Gal II delimited by the amino acids located in positions 11 to 30 of SEQ ID NO: 4, the nucleotide sequence SEQ ID NO: 91 corresponding to the nucleotide sequence delimited by the nucleotides located in positions 43 and 105 of SEQ ID NO: 5, said nucleotide sequence SEQ ID NO: 91 encoding the polypeptide sequence SEQ ID NO: 92 corresponding to the TMD region of hST6GalNAc I delimited by the amino acids located in positions 15 to 35 of SEQ ID NO: 6, the nucleotide sequence SEQ ID NO: 93 corresponding to the nucleotide sequence delimited by the nucleotides located in positions 22 and 84 of SEQ ID NO: 7, said nucleotide sequence SEQ ID NO: 93 encoding the polypeptide sequence SEQ ID NO: 94 corresponding to the TMD region of hST6GalNAc II delimited by the amino acids located in positions 8 to 28 of SEQ ID NO: 8, the nucleotide sequence SEQ ID NO: 95 corresponding to the nucleotide sequence delimited by the nucleotides located in positions 25 and 84 of SEQ ID NO: 9, said nucleotide sequence SEQ ID NO: 95 encoding the polypeptide sequence SEQ ID NO: 96 corresponding to the TMD region of hST6GalNAc III delimited by the amino acids located in positions 9 to 28 of SEQ ID NO: 10, the nucleotide sequence SEQ ID NO: 97 corresponding to the nucleotide sequence delimited by the nucleotides located in positions 19 and 81 of SEQ ID NO: 11, said nucleotide sequence SEQ ID NO: 97 encoding the polypeptide sequence SEQ ID NO: 98 corresponding to the TMD region of hST6GalNAc IV delimited by the amino acids located in positions 7 to 27 of SEQ ID NO: 12, the nucleotide sequence SEQ ID NO: 99 corresponding to the nucleotide sequence delimited by the nucleotides located in positions 25 and 87 of SEQ ID NO: 13, said nucleotide sequence SEQ ID NO: 99 encoding the polypeptide sequence SEQ ID NO: 100 corresponding to the TMD region of hST6GalNAc V delimited by the amino acids located in positions 9 to 29 of SEQ ID NO: 14, the nucleotide sequence SEQ ID NO: 101 corresponding to the nucleotide sequence delimited by the nucleotides located in positions 130 and 177 of SEQ ID NO: 15, said nucleotide sequence SEQ ID NO: 101 encoding the polypeptide sequence SEQ ID NO: 102 corresponding to the TMD region of hST6GalNAc VI delimited by the amino acids located in positions 44 to 59 of SEQ ID NO: 16, the nucleotide sequence SEQ ID NO: 103 corresponding to the nucleotide sequence delimited by the nucleotides located in positions 40 and 102 of SEQ ID NO: 17, said nucleotide sequence SEQ ID NO: 103 encoding the polypeptide sequence SEQ ID NO: 104 corresponding to the TMD region of hST3Gal I delimited by the amino acids located in positions 14 to 34 of SEQ ID NO: 18, the nucleotide sequence SEQ ID NO: 105 corresponding to the nucleotide sequence delimited by the nucleotides located in positions 19 and 81 of SEQ ID NO: 19, said nucleotide sequence SEQ ID NO: 105 encoding the polypeptide sequence SEQ ID NO: 106 corresponding to the TMD region of hST3Gal II delimited by the amino acids located in positions 7 to 27 of SEQ ID NO: 20, the nucleotide sequence SEQ ID NO: 107 corresponding to the nucleotide sequence delimited by the nucleotides located in positions 25 and 84 of SEQ ID NO: 21, said nucleotide sequence SEQ ID NO: 107 encoding the polypeptide sequence SEQ ID NO: 108 corresponding to the TMD region of hST3Gal III delimited by the amino acids located in positions 9 to 28 of SEQ ID NO: 22, the nucleotide sequence SEQ ID NO: 109 corresponding to the nucleotide sequence delimited by the nucleotides located in positions 25 and 78 of SEQ ID NO: 23, said nucleotide sequence SEQ ID NO: 109 encoding the polypeptide sequence SEQ ID NO: 110 corresponding to the TMD region of hST3Gal IV delimited by the amino acids located in positions 9 to 26 of SEQ ID NO: 24, the nucleotide sequence SEQ ID NO: 111 corresponding to the nucleotide sequence delimited by the nucleotides located in positions 16 and 78 of SEQ ID NO: 25, said nucleotide sequence SEQ ID NO: 111 encoding the polypeptide sequence SEQ ID NO: 112 corresponding to the TMD region of hST3Gal V delimited by the amino acids located in positions 6 to 26 of SEQ ID NO: 26, the nucleotide sequence SEQ ID NO: 113 corresponding to the nucleotide sequence delimited by the nucleotides located in positions 13 and 75 of SEQ ID NO: 27, said nucleotide sequence SEQ ID NO: 113 encoding the polypeptide sequence SEQ ID NO: 114 corresponding to the TMD region of hST3Gal VI delimited by the amino acids located in positions 5 to 25 of SEQ ID NO: 28, the nucleotide sequence SEQ ID NO: 115 corresponding to the nucleotide sequence delimited by the nucleotides located in positions 25 and 84 of SEQ ID NO: 29, said nucleotide sequence SEQ ID NO: 115 encoding the polypeptide sequence SEQ ID NO: 116 corresponding to the TMD region of rat ST3Gal III delimited by the amino acids located in positions 9 to 28 of SEQ ID NO: 30, the nucleotide sequence SEQ ID NO: 117 corresponding to the nucleotide sequence delimited by the nucleotides located in positions 88 and 144 of SEQ ID NO: 31, said nucleotide sequence SEQ ID NO: 117 encoding the polypeptide sequence SEQ ID NO: 118 corresponding to the TMD region of hST8Sia I delimited by the amino acids located in positions 30 to 48 of SEQ ID NO: 32, the nucleotide sequence SEQ ID NO: 119 corresponding to the nucleotide sequence delimited by the nucleotides located in positions 19 and 69 of SEQ ID NO: 33, said nucleotide sequence SEQ ID NO: 119 encoding the polypeptide sequence SEQ ID NO: 120 corresponding to the TMD region of hST8Sia II delimited by the amino acids located in positions 7 to 23 of SEQ ID NO: 34, the nucleotide sequence SEQ ID NO: 121 corresponding to the nucleotide sequence delimited by the nucleotides located in positions 28 and 99 of SEQ ID NO: 35, said nucleotide sequence SEQ ID NO: 121 encoding the polypeptide sequence SEQ ID NO: 122 corresponding to the TMD region of hST8Sia III delimited by the amino acids located in positions 10 to 33 of SEQ ID NO: 36, the nucleotide sequence SEQ ID NO: 123 corresponding to the nucleotide sequence delimited by the nucleotides located in positions 22 and 60 of SEQ ID NO: 37, said nucleotide sequence SEQ ID NO: 123 encoding the polypeptide sequence SEQ ID NO: 124 corresponding to the TMD region of hST8Sia IV delimited by the amino acids located in positions 8 to 20 of SEQ ID NO: 38, the nucleotide sequence SEQ ID NO: 125 corresponding to the nucleotide sequence delimited by the nucleotides located in positions 52 and 114 of SEQ ID NO: 39, said nucleotide sequence SEQ ID NO: 125 encoding the polypeptide sequence SEQ ID NO: 126 corresponding to the TMD region of hST8Sia V delimited by the amino acids located in positions 18 to 38 of SEQ ID NO: 40, the nucleotide sequence SEQ ID NO: 127 corresponding to the nucleotide sequence delimited by the nucleotides located in positions 10 and 72 of SEQ ID NO: 41, said nucleotide sequence SEQ ID NO: 127 encoding the polypeptide sequence SEQ ID NO: 128 corresponding to the TMD region of hST8Sia VI delimited by the amino acids located in positions 4 to 24 of SEQ ID NO: 42, the nucleotide sequence encoding the SR region comprised in the second nucleic acid, or encoding a fragment of at least 2 amino acids thereof, is chosen among sequences constituted of, or comprising:

the nucleotide sequence delimited in its 5' end by the nucleotide located in position 79 and in its 3' end by the nucleotide located in position 267 to 327 of SEQ ID NO: 1, said nucleotide sequence encoding the polypeptide sequence corresponding to the SR region of hST6Gal I delimited in its N-terminal end by the amino acid located in position 27 and in its C-terminal end by the amino acid located in position 89 to 109 of SEQ ID NO: 2, the nucleotide sequence delimited in its 5' end by the nucleotide located in position 91 and in its 3' end by the nucleotide located in position 306 to 336 of SEQ ID NO: 3, said nucleotide sequence encoding the polypeptide sequence corresponding to the SR region of hST6Gal II delimited in its N-terminal end by the amino acid located in position 31 and in its C-terminal end by the amino acid located in position 102 to 112 of SEQ ID NO: 4, the nucleotide sequence delimited in its 5' end by the nucleotide located in position 106 and in its 3' end by the nucleotide located in position 813 to 873 of SEQ ID NO: 5, said nucleotide sequence encoding the polypeptide sequence corresponding to the SR region of hST6GalNAc I delimited in its N-terminal end by the amino acid located in position 36 and in its C-terminal end by the amino acid located in position 271 to 291 of SEQ ID NO: 6, the nucleotide sequence delimited in its 5' end by the nucleotide located in position 85 and in its 3' end by the nucleotide located in position 171 to 231 of SEQ ID NO: 7, said nucleotide sequence encoding the polypeptide sequence corresponding to the SR region of hST6GalNAc II delimited in its N-terminal end by the amino acid located in position 29 and in its C-terminal end by the amino acid located in position 57 to 77 of SEQ ID NO: 8, the nucleotide sequence delimited in its 5' end by the nucleotide located in position 85 and in its 3' end by the nucleotide located in position 102 to 132 of SEQ ID NO: 9, said nucleotide sequence encoding the polypeptide sequence corresponding to the SR region of hST6GalNAc III delimited in its N-terminal end by the amino acid located in position 29 and in its C-terminal end by the amino acid located in position 34 to 44 of SEQ ID NO: 10, the nucleotide sequence delimited in its 5' end by the nucleotide located in position 82 and in its 3' end by the nucleotide located in position 90 to 120 of SEQ ID NO: 11, said nucleotide sequence encoding the polypeptide sequence corresponding to the SR region of hST6GalNAc IV delimited in its N-terminal end by the amino acid located in position 28 and in its C-terminal end by the amino acid located in position 30 to 40 of SEQ ID NO: 12, the nucleotide sequence delimited in its 5' end by the nucleotide located in position 88 and in its 3' end by the nucleotide located in position 120 to 180 of SEQ ID NO: 13, said nucleotide sequence encoding the polypeptide sequence corresponding to the SR region of hST6GalNAc V delimited in its N-terminal end by the amino acid located in position 30 and in its C-terminal end by the amino acid located in position 40 to 60 of SEQ ID NO: 14, the nucleotide sequence delimited in its 5' end by the nucleotide located in position 178 and in its 3' end by the nucleotide located in position 183 of SEQ ID NO: 15, said nucleotide sequence encoding the polypeptide sequence corresponding to the SR region of hST6GalNAc VI delimited in its N-terminal end by the amino acid located in position 60 and in its C-terminal end by the amino acid located in position 61 of SEQ ID NO: 16, the nucleotide sequence delimited in its 5' end by the nucleotide located in position 103 and in its 3' end by the nucleotide located in position 144 to 204 of SEQ ID NO: 17, said nucleotide sequence encoding the polypeptide sequence corresponding to the SR region of hST3Gal I delimited in its N-terminal end by the amino acid located in position 35 and in its C-terminal end by the amino acid located in position 48 to 68 of SEQ ID NO: 18, the nucleotide sequence delimited in its 5' end by the nucleotide located in position 82 and in its 3' end by the nucleotide located in position 174 to 234 of SEQ ID NO: 19, said nucleotide sequence encoding the polypeptide sequence corresponding to the SR region of hST3Gal II delimited in its N-terminal end by the amino acid located in position 28 and in its C-terminal end by the amino acid located in position 58 to 78 of SEQ ID NO: 20, the nucleotide sequence delimited in its 5' end by the nucleotide located in position 85 and in its 3' end by the nucleotide located in position 198 to 258 of SEQ ID NO: 21, said nucleotide sequence encoding the polypeptide sequence corresponding to the SR region of hST3Gal III delimited in its N-terminal end by the amino acid located in position 29 and in its C-terminal end by the amino acid located in position 66 to 86 of SEQ ID NO: 22, the nucleotide sequence delimited in its 5' end by the nucleotide located in position 79 and in its 3' end by the nucleotide located in position 108 to 138 of SEQ ID NO: 23, said nucleotide sequence encoding the polypeptide sequence corresponding to the SR region of hST3Gal IV delimited in its N-terminal end by the amino acid located in position 27 and in its C-terminal end by the amino acid located in position 36 to 46 of SEQ ID NO: 24, the nucleotide sequence delimited in its 5' end by the nucleotide located in position 79 and in its 3' end by the nucleotide located in position 135 to 195 of SEQ ID NO: 25, said nucleotide sequence encoding the polypeptide sequence corresponding to the SR region of hST3Gal V delimited in its N-terminal end by the amino acid located in position 27 and in its C-terminal end by the amino acid located in position 45 to 65 of SEQ ID NO: 26, the nucleotide sequence delimited in its 5' end by the nucleotide located in position 76 and in its 3' end by the nucleotide located in position 102 to 132 of SEQ ID NO: 27, said nucleotide sequence encoding the polypeptide sequence corresponding to the SR region of hST3Gal VI delimited in its N-terminal end by the amino acid located in position 26 and in its C-terminal end by the amino acid located in position 34 to 44 of SEQ ID NO: 28, the nucleotide sequence delimited in its 5' end by the nucleotide located in position 85 and in its 3' end by the nucleotide located in position 105 to 165 of SEQ ID NO: 29, said nucleotide sequence encoding the polypeptide sequence corresponding to the SR region of rST3Gal III delimited in its N-terminal end by the amino acid located in position 29 and in its C-terminal end by the amino acid located in position 35 to 55 of SEQ ID NO: 30, the nucleotide sequence delimited in its 5' end by the nucleotide located in position 145 and in its 3' end by the nucleotide located in position 162 to 192 of SEQ ID NO: 31, said nucleotide sequence encoding the polypeptide sequence corresponding to the SR region of hST8Sia I delimited in its N-terminal end by the amino acid located in position 49 and in its C-terminal end by the amino acid located in position 54 to 64 of SEQ ID NO: 32, the nucleotide sequence delimited in its 5' end by the nucleotide located in position 70 and in its 3' end by the nucleotide located in position 189 to 249 of SEQ ID NO: 33, said nucleotide sequence encoding the polypeptide sequence corresponding to the SR region of hST8Sia II delimited in its N-terminal end by the amino acid located in position 24 and in its C-terminal end by the amino acid located in position 63 to 83 of SEQ ID NO: 34, the nucleotide sequence delimited in its 5' end by the nucleotide located in position 100 and in its 3' end by the nucleotide located in position 204 to 264 of SEQ ID NO: 35, said nucleotide sequence encoding the polypeptide sequence corresponding to the SR region of hST8Sia III delimited in its N-terminal end by the amino acid located in position 34 and in its C-terminal end by the amino acid located in position 68 to 88 of SEQ ID NO: 36, the nucleotide sequence delimited in its 5' end by the nucleotide located in position 61 and in its 3' end by the nucleotide located in position 144 to 204 of SEQ ID NO: 37, said nucleotide sequence encoding the polypeptide sequence corresponding to the SR region of hST8Sia IV delimited in its N-terminal end by the amino acid located in position 21 and in its C-terminal end by the amino acid located in position 48 to 68 of SEQ ID NO: 38, the nucleotide sequence delimited in its 5' end by the nucleotide located in position 115 and in its 3' end by the nucleotide located in position 210 to 270 of SEQ ID NO: 39, said nucleotide sequence encoding the polypeptide sequence corresponding to the SR region of hST8Sia V delimited in its N-terminal end by the amino acid located in position 39 and in its C-terminal end by the amino acid located in position 70 to 90 of SEQ ID NO: 40, the nucleotide sequence delimited in its 5' end by the nucleotide located in position 73 and in its 3' end by the nucleotide located in position 276 to 336 of SEQ ID NO: 41, said nucleotide sequence encoding the polypeptide sequence corresponding to the SR region of hST8Sia VI delimited in its N-terminal end by the amino acid located in position 25 and in its C-terminal end by the amino acid located in position 92 to 112 of SEQ ID NO: 42, or any fragment of at least 6 nucleotides of the nucleotide sequences encoding polypeptides sequence corresponding to SR regions mentioned above, and encoding at least 2 contiguous amino acids of said SR regions, such as:

the fragment SEQ ID NO: 129 delimited by the nucleotides located in positions 106 to 222 of SEQ ID NO: 5, encoding the polypeptide sequence SEQ ID NO: 130 corresponding to the fragment of the SR region of hST6GalNAc I delimited by the amino acids located in positions 36 to 74 of SEQ ID NO: 6, the fragment SEQ ID NO: 131 delimited by the nucleotides located in positions 109 to 222 of SEQ ID NO: 5, encoding the polypeptide sequence SEQ ID NO: 132 corresponding to the fragment of the SR region of hST6GalNAc I delimited by the amino acids located in positions 37 to 74 of SEQ ID NO: 6, the fragment SEQ ID NO: 133 delimited by the nucleotides located in positions 106 to 420 of SEQ ID NO: 5, encoding the polypeptide sequence SEQ ID NO: 134 corresponding to the fragment of the SR region of hST6GalNAc I delimited by the amino acids located in positions 36 to 140 of SEQ ID NO: 6, the fragment SEQ ID NO: 135 delimited by the nucleotides located in positions 106 to 774 of SEQ ID NO: 5, encoding the polypeptide sequence SEQ ID NO: 136 corresponding to the fragment of the SR region of hST6GalNAc I delimited by the amino acids located in positions 36 to 258 of SEQ ID NO: 6, the fragment SEQ ID NO: 137 delimited by the nucleotides located in positions 85 to 138 of SEQ ID NO: 21, encoding the polypeptide sequence SEQ ID NO: 138 corresponding to the fragment of the SR region of hST3Gal III delimited by the amino acids located in positions 29 to 46 of SEQ ID NO: 22, the fragment SEQ ID NO: 139 delimited by the nucleotides located in positions 85 to 138 of SEQ ID NO: 29, encoding the polypeptide sequence SEQ ID NO: 140 corresponding to the fragment of the SR region of ratST3Gal III delimited by the amino acids located in positions 29 to 46 of SEQ ID NO: 30, the fragment SEQ ID NO: 141 delimited by the nucleotides located in positions 70 to 237 of SEQ ID NO: 33, encoding the polypeptide sequence SEQ ID NO: 142 corresponding to the fragment of the SR region of hST8Sia II delimited by the amino acids located in positions 24 to 79 of SEQ ID NO: 34, the fragment SEQ ID NO: 143 delimited by the nucleotides located in positions 61 to 201 of SEQ ID NO: 37, encoding the polypeptide sequence SEQ ID NO: 144 corresponding to the fragment of the SR region of hST8Sia IV delimited by the amino acids located in positions 21 to 67 of SEQ ID NO: 38.

The invention relates more particularly to a process as defined above, characterized in that:

the nucleotide sequence encoding the CT region comprised in the second nucleic acid is chosen among:

the nucleotide sequence SEQ ID NO: 49 corresponding to the nucleotide sequence delimited by the nucleotides located in positions 1 and 42 of SEQ ID NO: 5, said nucleotide sequence SEQ ID NO: 49 encoding the polypeptide sequence SEQ ID NO: 50 corresponding to the CT region of hST6GalNAc I delimited by the amino acids located in positions 1 to 14 of SEQ ID NO: 6, the nucleotide sequence SEQ ID NO: 65 corresponding to the nucleotide sequence delimited by the nucleotides located in positions 1 and 24 of SEQ ID NO: 21, said nucleotide sequence SEQ ID NO: 65 encoding the polypeptide sequence SEQ ID NO: 66 corresponding to the CT region of hST3Gal III delimited by the amino acids located in positions 1 to 8 of SEQ ID NO: 22, the nucleotide sequence SEQ ID NO: 73 corresponding to the nucleotide sequence delimited by the nucleotides located in positions 1 and 24 of SEQ ID NO: 29, said nucleotide sequence SEQ ID NO: 73 encoding the polypeptide sequence SEQ ID NO: 74 corresponding to the CT region of ratST3Gal III delimited by the amino acids located in positions 1 to 8 of SEQ ID NO: 30, the nucleotide sequence SEQ ID NO: 77 corresponding to the nucleotide sequence delimited by the nucleotides located in positions 1 and 18 of SEQ ID NO: 33, said nucleotide sequence SEQ ID NO: 77 encoding the polypeptide sequence SEQ ID NO: 78 corresponding to the CT region of hST8Sia II delimited by the amino acids located in positions 1 to 6 of SEQ ID NO: 34, the nucleotide sequence SEQ ID NO: 81 corresponding to the nucleotide sequence delimited by the nucleotides located in positions 1 and 21 of SEQ ID NO: 37, said nucleotide sequence SEQ ID NO: 81 encoding the polypeptide sequence SEQ ID NO: 82 corresponding to the CT region of hST8Sia IV delimited by the amino acids located in positions 1 to 7 of SEQ ID NO: 38, the nucleotide sequence encoding the TMD region comprised in the second nucleic acid is chosen among:

the nucleotide sequence SEQ ID NO: 91 corresponding to the nucleotide sequence delimited by the nucleotides located in positions 43 and 105 of SEQ ID NO: 5, said nucleotide sequence SEQ ID NO: 91 encoding the polypeptide sequence SEQ ID NO: 92 corresponding to the TMD region of hST6GalNAc I delimited by the amino acids located in positions 15 to 35 of SEQ ID NO: 6, the nucleotide sequence SEQ ID NO: 107 corresponding to the nucleotide sequence delimited by the nucleotides located in positions 25 and 84 of SEQ ID NO: 21, said nucleotide sequence SEQ ID NO: 107 encoding the polypeptide sequence SEQ ID NO: 108 corresponding to the TMD region of hST3Gal III delimited by the amino acids located in positions 9 to 28 of SEQ ID NO: 22, the nucleotide sequence SEQ ID NO: 115 corresponding to the nucleotide sequence delimited by the nucleotides located in positions 25 and 84 of SEQ ID NO: 29, said nucleotide sequence SEQ ID NO: 115 encoding the polypeptide sequence SEQ ID NO: 116 corresponding to the TMD region of rST3Gal III delimited by the amino acids located in positions 9 to 28 of SEQ ID NO: 30, the nucleotide sequence SEQ ID NO: 119 corresponding to the nucleotide sequence delimited by the nucleotides located in positions 19 and 69 of SEQ ID NO: 33, said nucleotide sequence SEQ ID NO: 119 encoding the polypeptide sequence SEQ ID NO: 120 corresponding to the TMD region of hST8Sia II delimited by the amino acids located in positions 7 to 23 of SEQ ID NO: 34, the nucleotide sequence SEQ ID NO: 123 corresponding to the nucleotide sequence delimited by the nucleotides located in positions 22 and 60 of SEQ ID NO: 37, said nucleotide sequence SEQ ID NO: 123 encoding the polypeptide sequence SEQ ID NO: 124 corresponding to the TMD region of hST8Sia IV delimited by the amino acids located in positions 8 to 20 of SEQ ID NO: 38, the nucleotide sequence encoding the SR region or fragment thereof comprised in the second nucleic acid, is chosen among:

the sequence SEQ ID NO: 129 delimited by the nucleotides located in positions 106 to 222 of SEQ ID NO: 5, encoding the polypeptide sequence SEQ ID NO: 130 corresponding to the fragment of the SR region of hST6GalNAc I delimited by the amino acids located in positions 36 to 74 of SEQ ID NO: 6, the sequence SEQ ID NO: 131 delimited by the nucleotides located in positions 109 to 222 of SEQ ID NO: 5, encoding the polypeptide sequence SEQ ID NO: 132 corresponding to the fragment of the SR region of hST6GalNAc I delimited by the amino acids located in positions 37 to 74 of SEQ ID NO: 6, the sequence SEQ ID NO: 133 delimited by the nucleotides located in positions 106 to 420 of SEQ ID NO: 5, encoding the polypeptide sequence SEQ ID NO: 134 corresponding to the fragment of the SR region of hST6GalNAc I delimited by the amino acids located in positions 36 to 140 of SEQ ID NO: 6, the sequence SEQ ID NO: 135 delimited by the nucleotides located in positions 106 to 774 of SEQ ID NO: 5, encoding the polypeptide sequence SEQ ID NO: 136 corresponding to the fragment of the SR region of hST6GalNAc I delimited by the amino acids located in positions 36 to 258 of SEQ ID NO: 6, the sequence SEQ ID NO: 137 delimited by the nucleotides located in positions 85 to 138 of SEQ ID NO: 21, encoding the polypeptide sequence SEQ ID NO: 138 corresponding to the fragment of the SR region of hST3Gal III delimited by the amino acids located in positions 29 to 46 of SEQ ID NO: 22, the sequence SEQ ID NO: 139 delimited by the nucleotides located in positions 85 to 138 of SEQ ID NO: 29, encoding the polypeptide sequence SEQ ID NO: 140 corresponding to the fragment of the SR region of ratST3Gal III delimited by the amino acids located in positions 29 to 46 of SEQ ID NO: 30, the sequence SEQ ID NO: 141 delimited by the nucleotides located in positions 70 to 237 of SEQ ID NO: 33, encoding the polypeptide sequence SEQ ID NO: 142 corresponding to the fragment of the SR region of hST8Sia II delimited by the amino acids located in positions 24 to 79 of SEQ ID NO: 34, the sequence SEQ ID NO: 143 delimited by the nucleotides located in positions 61 to 201 of SEQ ID NO: 37, encoding the polypeptide sequence SEQ ID NO: 144 corresponding to the fragment of the SR region of hST8Sia IV delimited by the amino acids located in positions 21 to 67 of SEQ ID NO: 38.

The invention concerns more particularly a process as defined above, characterized in that the CT, TMD, SR, or SR fragment peptides comprised in the second nucleic acid, are homologous sequences deriving from the same native glycosyltransferase, this latter being different from peptides in the native glycosyltransferase from which is derived the CD fragment with optimal glycosyltransferase activity as defined above.

The invention relates more particularly to a process as defined above, characterized in that the second nucleic acid is chosen among the following sequences:

the sequence SEQ ID NO: 145 delimited by the nucleotides located in positions 1 to 222 of SEQ ID NO: 5, containing SEQ ID NO: 49, 91, and 129, and encoding the polypeptide sequence SEQ ID NO: 146 corresponding to the fragment of hST6GalNAc I delimited by the amino acids located in positions 1 to 74 of SEQ ID NO: 6, and containing the CT, TMD and SR fragment regions of hST6GalNAc I corresponding to SEQ ID NO: 50, 92, and 130, respectively, the sequence SEQ ID NO: 147 delimited by the nucleotides located in positions 1 to 420 of SEQ ID NO: 5, containing SEQ ID NO: 49, 91, and 133, and encoding the polypeptide sequence SEQ ID NO: 148 corresponding to the fragment of the SR region of hST6GalNac I delimited by the amino acids located in positions 1 to 140 of SEQ ID NO: 6, and containing the CT, TMD and SR fragment regions of hST6GalNAc I corresponding to SEQ ID NO: 50, 92, and 134, respectively, the sequence SEQ ID NO: 149 delimited by the nucleotides located in positions 1 to 774 of SEQ ID NO: 5, containing SEQ ID NO: 49, 91, and 135, and encoding the polypeptide sequence SEQ ID NO: 150 corresponding to the fragment of the SR region of hST6GalNAc I delimited by the amino acids located in positions 1 to 258 of SEQ ID NO: 6, and containing the CT, TMD and SR fragment regions of hST6GalNAc I corresponding to SEQ ID NO: 50, 92, and 136, respectively, the sequence SEQ ID NO: 151 delimited by the nucleotides located in positions 1 to 138 of SEQ ID NO: 21, containing SEQ ID NO: 65, 107, and 137, and encoding the polypeptide sequence SEQ ID NO: 152 corresponding to the fragment of the SR region of hST3Gal III delimited by the amino acids located in positions 1 to 46 of SEQ ID NO: 22, and containing the CT, TMD and SR fragment regions of hST3Gal III corresponding to SEQ ID NO: 66, 108, and 138, respectively, the sequence SEQ ID NO: 153 delimited by the nucleotides located in positions 1 to 138 of SEQ ID NO: 29, containing SEQ ID NO: 73, 115, and 139, and encoding the polypeptide sequence SEQ ID NO: 154 corresponding to the fragment of the SR region of rST3Gal III delimited by the amino acids located in positions 1 to 46 of SEQ ID NO: 30, and containing the CT, TMD and SR fragment regions of hST3Gal III corresponding to SEQ ID NO: 74, 116, and 140, respectively, the sequence SEQ ID NO: 155 delimited by the nucleotides located in positions 1 to 237 of SEQ ID NO: 33, containing SEQ ID NO: 77, 119, and 141, and encoding the polypeptide sequence SEQ ID NO: 156 corresponding to the fragment of the SR region of hST8Sia II delimited by the amino acids located in positions 1 to 79 of SEQ ID NO: 34, and containing the CT, TMD and SR regions of hST8Sia II corresponding to SEQ ID NO: 78, 120, and 142, respectively, the sequence SEQ ID NO: 157 delimited by the nucleotides located in positions 1 to 201 of SEQ ID NO: 37, containing SEQ ID NO: 81, 123, and 143, and encoding the polypeptide sequence SEQ ID NO: 158 corresponding to the fragment of the SR region of hST8Sia IV delimited by the amino acids located in positions 1 to 67 of SEQ ID NO: 38, and containing the CT, TMD and SR regions of hST8Sia IV corresponding to SEQ ID NO: 82, 124, and 144, respectively, The invention concerns more particularly a process as defined above, characterized in that the CT, TMD, SR, or SR fragment peptides comprised in the second nucleic acid, are heterologous sequences deriving from different natural glycosyltransferase gene or transcript.

The invention relates more particularly to a process as defined above, characterized in that the second nucleic acid is the sequence SEQ ID NO: 159 corresponding the fusion of the nucleotide sequence SEQ ID NO: 177 containing SEQ ID NO: 65 and 107 encoding the CT and TMD regions of hST3Gal III corresponding to SEQ ID NO: 66 and 108 respectively, with the nucleotide sequence SEQ ID NO: 131 encoding the polypeptide sequence SEQ ID NO: 132 corresponding to the fragment of the SR region of hST6GalNAc I delimited by the amino acids located in positions 37 to 74 of SEQ ID NO: 6, said sequence SEQ ID NO: 159 encoding the fusion polypeptide SEQ ID NO: 160 between the CT and TMD regions of hST3Gal III, on the one hand, and the 37-74 fragment of the SR region of hST6GalNAc I, on the other hand.

The invention relates more particularly to a process as defined above, characterized in that the second nucleic acid is the sequence SEQ ID NO: 179 corresponding the fusion of the nucleotide sequence SEQ ID NO: 65 encoding the CT of hST3Gal III corresponding to SEQ ID NO: 66, with the nucleotide sequence SEQ ID NO: 119 encoding the TMD region of hST8Sia II corresponding to SEQ ID. NO: 120, and with the nucleotide sequence SEQ ID NO: 129 encoding the polypeptide sequence SEQ ID NO: 130 corresponding to the fragment of the SR region of hST6GalNAc I delimited by the amino acids located in positions 36 to 74 of SEQ ID NO: 6, said sequence SEQ ID NO: 179 encoding the fusion polypeptide SEQ ID NO: 180 between the CT region of hST3Gal III, the TMD region of hST8Sia II, and the 36-74 fragment of the SR region of hST6GalNAc I.

The invention concerns more particularly a process as defined above, characterized in that it comprises the fusion of the sequence SEQ ID NO: 43 as the first nucleic acid, with a second acid nucleic chosen among:

the sequence SEQ ID NO: 145, leading to the nucleotide sequence SEQ ID NO: 161 encoding the fusion protein SEQ ID NO: 162 containing the CT, TMD and SR fragment regions of hST6GalNAc I corresponding to SEQ ID NO: 50, 92, and 130, respectively, linked via a GS linker to the 90-406 C-terminal minimal fragment of the CD domain of hST6Gal I, the sequence SEQ ID NO: 147, leading to the nucleotide sequence SEQ ID NO: 163 encoding the fusion protein SEQ ID NO: 164 containing the CT, TMD and SR fragment regions of hST6GalNAc I corresponding to SEQ ID NO: 50, 92, and 134, respectively, linked via a GS linker to the 90-406 C-terminal minimal fragment of the CD domain of hST6Gal I, the sequence SEQ ID NO: 149, leading to the nucleotide sequence SEQ ID NO: 165 encoding the fusion protein SEQ ID NO: 166 containing the CT, TMD and SR fragment regions of hST6GalNAc I corresponding to SEQ ID NO: 50, 92, and 136, respectively, linked via a SR linker to the 90-406 C-terminal minimal fragment of the CD domain of hST6Gal I, the sequence SEQ ID NO: 151, leading to the nucleotide sequence SEQ ID NO: 167 encoding the fusion protein SEQ ID NO: 168 containing the CT, TMD and SR fragment regions of hST3Gal III corresponding to SEQ ID NO: 66, 108, and 138, respectively, linked via a GS linker to the 90-406 C-terminal minimal fragment of the CD domain of hST6Gal I, the sequence SEQ ID NO: 153, leading to the nucleotide sequence SEQ ID NO: 169 encoding the fusion protein SEQ ID NO: 170 containing the CT, TMD and SR fragment regions of ratST3Gal III corresponding to SEQ ID NO: 74, 116, and 140, respectively, linked via a SR linker to the 90-406 C-terminal minimal fragment of the CD domain of hST6Gal I, the sequence SEQ ID NO: 155, leading to the nucleotide sequence SEQ ID NO: 171 encoding the fusion protein SEQ ID NO: 172 containing the CT, TMD and SR regions of hST8Sia II corresponding to SEQ ID NO: 78, 120, and 142, respectively, linked via a KL linker to the 90-406 C-terminal minimal fragment of the CD domain of hST6Gal I, the sequence SEQ ID NO: 157, leading to the nucleotide sequence SEQ ID NO: 173 encoding the fusion protein SEQ ID NO: 174 containing the CT, TMD and SR regions of hST8Sia IV corresponding to SEQ ID NO: 82, 124, and 144, respectively, linked via a KL linker to the 90-406 C-terminal minimal fragment of the CD domain of hST6Gal I, the sequence SEQ ID NO: 159, leading to the nucleotide sequence SEQ ID NO: 175 encoding the fusion protein SEQ ID NO: 176 containing the CT and TMD regions of hST3Gal III corresponding to SEQ ID NO: 66 and 108 respectively, and the 37-74 fragment of the SR region of hST6GalNac I corresponding to SEQ ID NO: 132, linked via a GS linker to the 90-406 C-terminal minimal fragment of the CD domain of hST6Gal I, the sequence SEQ ID NO: 179, leading to the nucleotide sequence SEQ ID NO: 181 encoding the fusion protein SEQ ID NO: 182 containing the CT region of hST3Gal III, the TMD region of hST8Sia II, and the 36-74 fragment of the SR region of hST6GalNAc I, corresponding to SEQ ID NO: 66, 120, and 130 respectively, linked via a GS linker to the 90-406 C-terminal minimal fragment of the CD domain of hST6Gal I.

The invention also relates to gene sequences encoding chimerical glycosyltransferases such as obtained according to the process as defined above.

The invention concerns more particularly gene sequences as defined above, chosen among:

the sequence SEQ ID NO: 161 encoding the fusion protein SEQ ID NO: 162 containing the CT, TMD and SR fragment regions of hST6GalNAc I corresponding to SEQ ID NO: 50, 92, and 130, respectively, linked via a GS linker to the 90-406 C-terminal minimal fragment of the CD domain of hST6Gal I, said sequence SEQ ID NO: 161 corresponding to the fusion of the sequence SEQ ID NO: 43 and the sequence SEQ ID NO: 145, the sequence SEQ ID NO: 163 encoding the fusion protein SEQ ID NO: 164 containing the CT, TMD and SR fragment regions of hST6GalNAc I corresponding to SEQ ID NO: 50, 92, and 134, respectively, linked via a GS linker to the 90-406 C-terminal minimal fragment of the CD domain of hST6Gal I, said sequence SEQ ID NO: 163 corresponding to the fusion of the sequence SEQ ID NO: 43 and the sequence SEQ ID NO: 147, the sequence SEQ ID NO: 165 encoding the fusion protein SEQ ID NO: 166 containing the CT, TMD and SR fragment regions of hST6GalNac I corresponding to SEQ ID NO: 50, 92, and 136, respectively, linked via a SR linker to the 90-406 C-terminal minimal fragment of the CD domain of hST6Gal I, said sequence SEQ ID NO: 165 corresponding to the fusion of the sequence SEQ ID NO: 43 and the sequence SEQ ID NO: 149, the sequence SEQ ID NO: 167 encoding the fusion protein SEQ ID NO: 168 containing the CT, TMD and SR fragment regions of hST3Gal III corresponding to SEQ ID NO: 66, 108, and 138, respectively, linked via a GS linker to the 90-406 C-terminal minimal fragment of the CD domain of hST6Gal I, said sequence SEQ ID NO: 167 corresponding to the fusion of the sequence SEQ ID NO: 43 and the sequence SEQ ID NO: 151, the sequence SEQ ID NO: 169 encoding the fusion protein SEQ ID NO: 170 containing the CT, TMD and SR fragment regions of ratST3Gal III corresponding to SEQ ID NO: 74, 116, and 140, respectively, linked via a SR linker to the 90-406 C-terminal minimal fragment of the CD domain of hST6Gal I, said sequence SEQ ID NO: 169 corresponding to the fusion of the sequence SEQ ID NO: 43 and the sequence SEQ ID NO: 153, the sequence SEQ ID NO: 171 encoding the fusion protein SEQ ID NO: 172 containing the CT, TMD and SR regions of hST8Sia II corresponding to SEQ ID NO: 78, 120, and 142, respectively, linked via a KL linker to the 90-406 C-terminal minimal fragment of the CD domain of hST6Gal I, said sequence SEQ ID NO: 171 corresponding to the fusion of the sequence SEQ ID NO: 43 and the sequence SEQ ID NO: 155, the sequence SEQ ID NO: 173 encoding the fusion protein SEQ ID NO: 174 containing the CT, TMD and SR regions of hST8Sia IV corresponding to SEQ ID NO: 82, 124, and 144, respectively, linked via a KL linker to the 90-406 C-terminal minimal fragment of the CD domain of hST6Gal I, said sequence SEQ ID NO: 173 corresponding to the fusion of the sequence SEQ ID NO: 43 and the sequence SEQ ID NO: 157, the sequence SEQ ID NO: 175 encoding the fusion protein SEQ ID NO: 176 containing the CT and TMD regions of hST3Gal III corresponding to SEQ ID NO: 66 and 108 respectively, and the 37-74 fragment of the SR region of hST6GalNAc I corresponding to SEQ ID NO: 132, linked via a GS linker to the 90-406 C-terminal minimal fragment of the CD domain of hST6Gal I, said sequence SEQ ID NO: 175 corresponding to the fusion of the sequence SEQ ID NO: 43 and the sequence SEQ ID NO: 159, the sequence SEQ ID NO: 181 encoding the fusion protein SEQ ID NO: 182 containing the CT region of hST3Gal III, the TMD region of hST8Sia II, and the 36-74 fragment of the SR region of hST6GalNAc I, corresponding to SEQ ID NO: 66, 120, and 130 respectively, linked via a GS linker to the 90-406 C-terminal minimal fragment of the CD domain of hST6Gal I, said sequence SEQ ID NO: 181 corresponding to the fusion of the sequence SEQ ID NO: 43 and sequence SEQ ID NO: 179.

The invention also concerns vectors, such as plasmids, viral or bacterial constructs, comprising at least one gene sequence as defined above.

The invention also relates to host eukaryotic cells from yeast, fungi, insect, plants, mammalian or human origin, transformed with at least one gene sequence as defined above, using at least one vector as mentioned above.

The invention also concerns the use of at least one gene sequence as defined above, or of a vector as mentioned above, for the transformation of cells as defined above, or the use of transgenic animals obtained from such transformed cells, in the frame of the production of recombinant proteins of interest.

The invention also relates to a method for the preparation of recombinant proteins of interest comprising the transformation of cells as defined above, with a vector containing at least one nucleotide sequence encoding said recombinant proteins of interest.

Preferred recombinant proteins of interest which can be prepared according to a method as mentioned above according to the invention are chosen among hormones, enzymes, clotting factors, carbohydrate antigens/serum biomarkers, cytokines, growth factors, antibodies or receptors.

Preferred host cells for the preparation of recombinant proteins of interest as mentioned above, are chosen among drug-approved cells or organisms, preferably rodent, mammalian or human cells.

DESCRIPTION OF THE FIGURES

Figure 2:
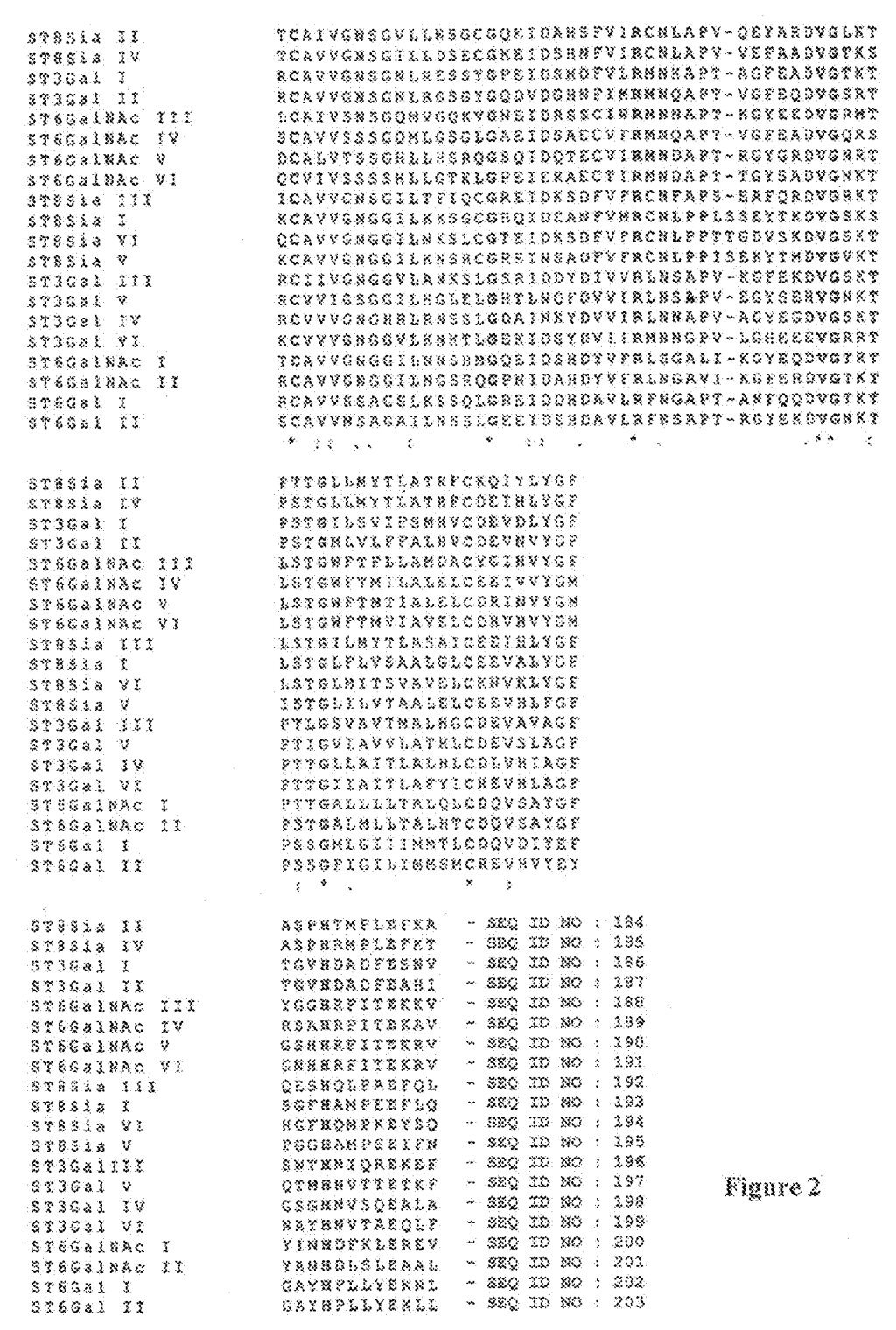

FIG. 2 Amino acid sequence of sialylmotif L, S, and VS in 20 human sialyltransferases. Consensus amino acid residues in the all sialyltransferases are shown by bold letters.

FIG. 5 represents sequence alignment of the rat and the human ST6Gal I. It can be noticed that the N-terminal sequence comprising the CT (1-9), TMD (10-26) is fully conserved while the juxtamebrane SR portion (27-89) is more variable although the juxtamembrane peptide and especially positively lysine and cysteine residues are wellconserved.

Of note, the sialic acid derivative shown in this diagram, namely "Neu5Ac," is widely considered as the 'human' form of sialic acid. In all other animals, with the exception of chickens, there is an additional step in the pathway (shown in this diagram) where CMP-Neu5Ac is further hydroxylated and converted to CMP-Neu5Gc by the enzymatic action of CMP-N-Acetylneuraminic Acid Hydroxylase.

Figure 7:
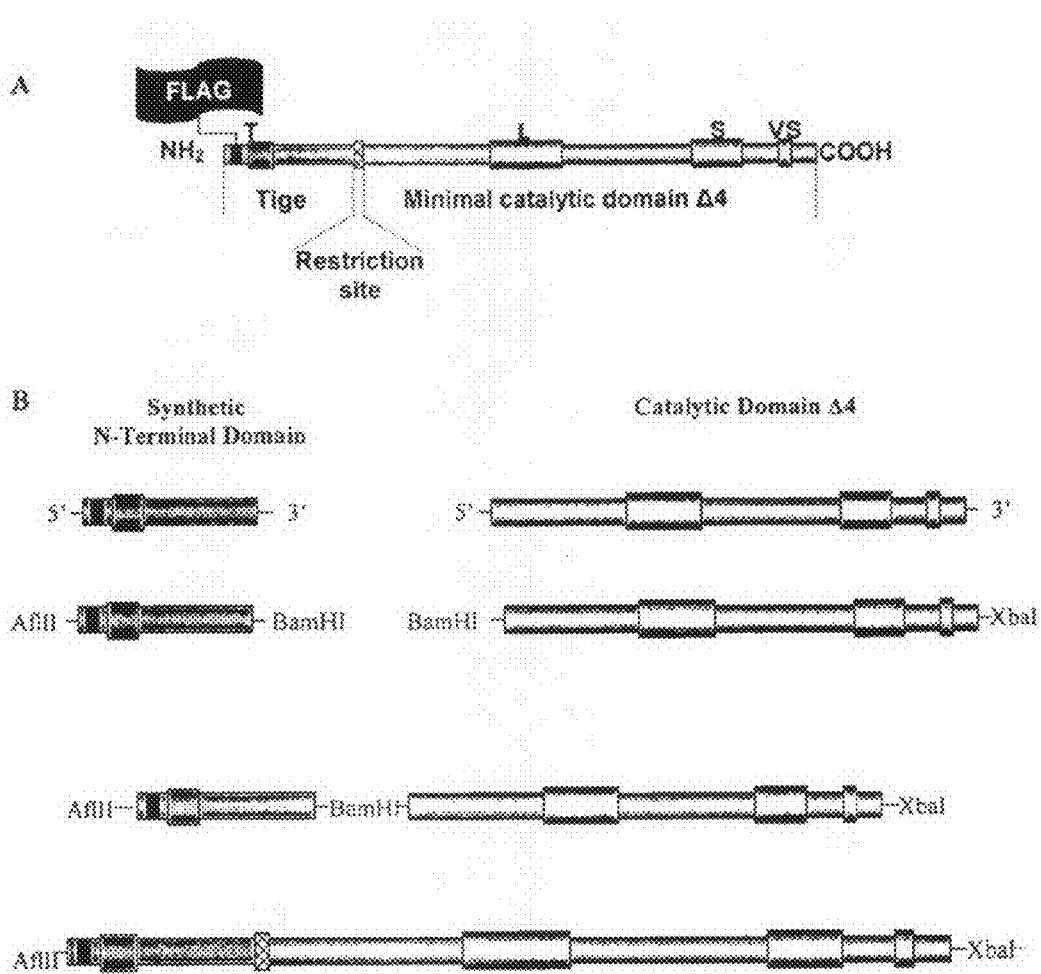

FIG. 7 represents a schematical overview of the various synthetic chimerical constructs generated by the invention.

FIG. 7A represents the general construction of a synthetic chimera including the N-terminal synthetic domain tagged with the FLAG epitope fused to the minimal catalytic domain (CD) through the addition of a restriction site.

FIG. 7B shows the ligation between the N-terminal synthetic and the catalytic domains using a BamHI restriction site. Note that the constructs are introduced into the vector using restriction sites, namely AflII and XbaI distinct from the ligation site.

Figure 8:
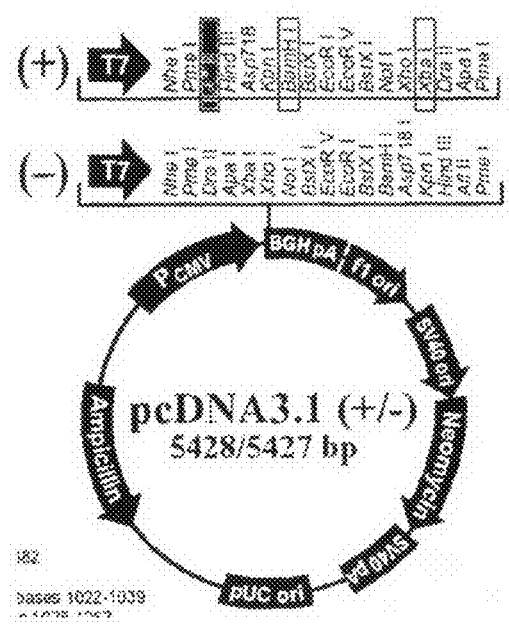

FIG. 8 shows the topology and characteristic of the pcDNA3.1 (+) vector (Invitrogen).

Figure 9:
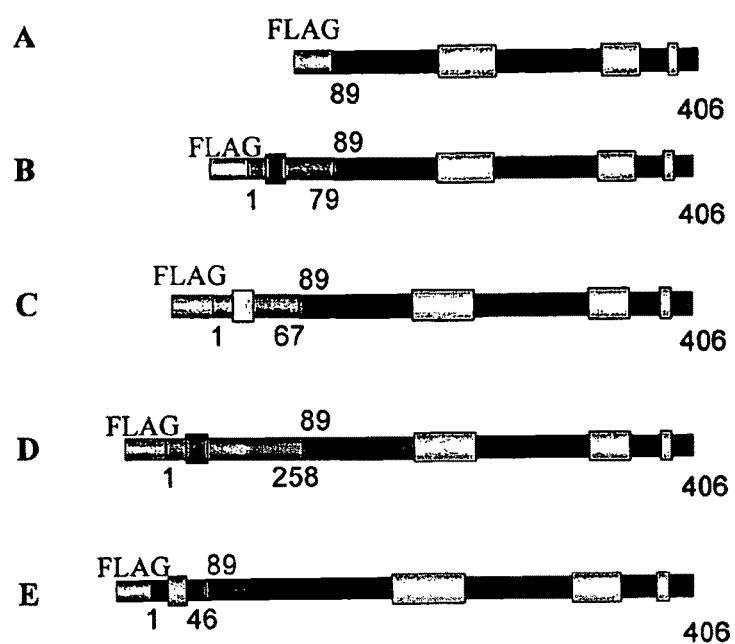

FIG. 9 represents the constructions of the FLAG-hST6Gal I CD and of the chimeric forms of this CD fused to several N-Terminal fragments of other sialyltransferases of variable length.

FIG. 9A corresponds to FLAG-CD.
FIG. 9B corresponds to hST8SiaII-79/CD.
FIG. 9C corresponds to hST8SiaIV-67/CD.
FIG. 9D corresponds to hST6GalNAc I-258/CD.
FIG. 9E corresponds to r/hST3Gal III-46/CD.

Figure 10:
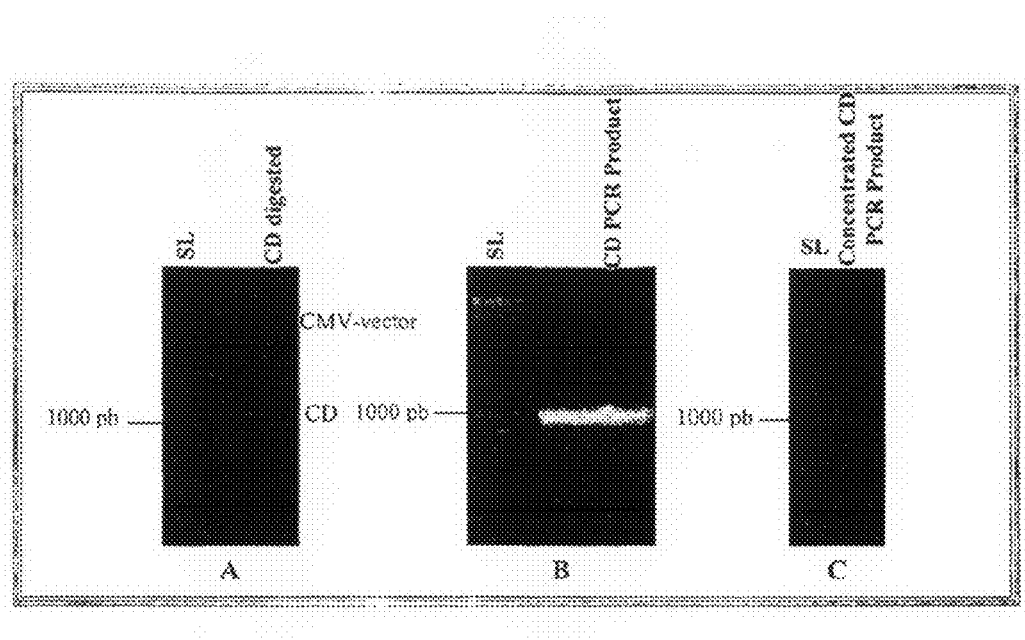

FIG. 10 represents the digested minimum catalytic domain of hST6Gal I and its amplified PCR product to be used in each construction of the synthetic chimera. Samples were loaded on a 1.5% agarose gel with the SmartLadder (SL) nucleic marker.

FIG. 10A shows the digested hST6Gal I catalytic domain from CMV-vector, issued from the cloning in the laboratory.

FIG. 10B shows the PCR product of the minimum catalytic domain at 966 pb.

FIG. 10C shows the concentrated PCR product of the minimum catalytic domain of hST6Gal I with 5 μL loaded on the gel.

Figure 11:
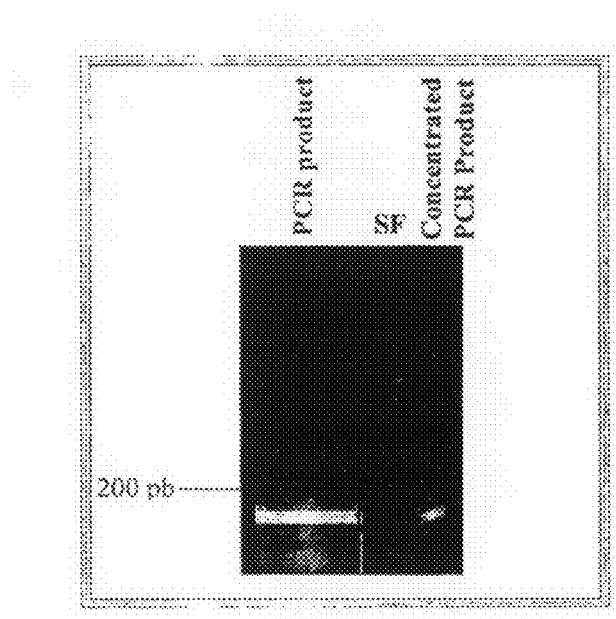

FIG. 11 shows an agarose gel (2%) showing the DNA band of the reconstituted synthetic N-terminal region of hST3Gal III. Lane 1 corresponds to a PCR product of 174 pb; lane 2 corresponds to the SmartLadder SF; lane 3 corresponds to 5 μL of the concentrated PCR product of 174 pb size.

Figure 12:
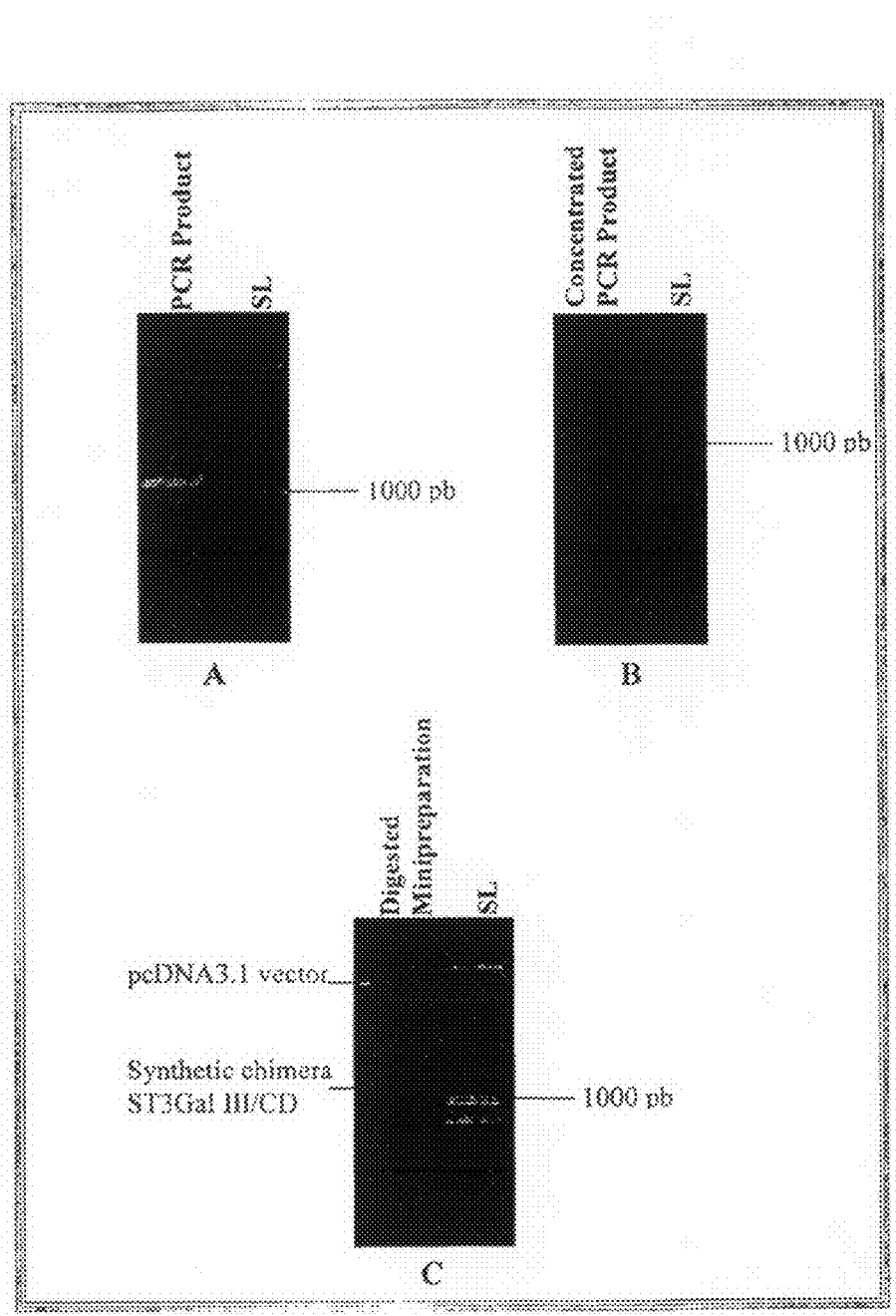

FIG. 12 represents the total reconstructed enzyme gene of hST3Gal III/CD.

In FIG. 12A, an agarose gel (1.5%) shows the DNA band of the reconstituted synthetic hST3Gal III/CD amplified by PCR.

FIG. 12B corresponds to 5 μL of the concentrated PCR products of around 1200 pb in size.

FIG. 12C represents the product of the digestion of the recombinant vector by the restriction enzymes AflII and XbaI, showing the insertion of the chimera gene (expected size 1200 pb).

Figure 13:
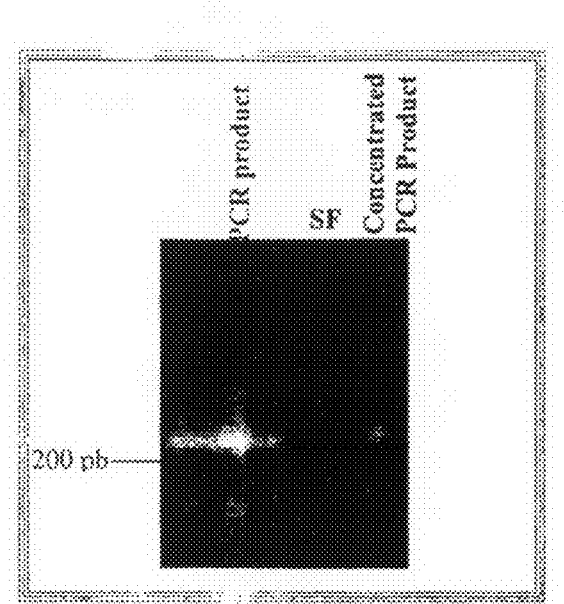

FIG. 13 shows an agarose gel (2%) showing the DNA band of the reconstituted synthetic N-terminal region of hST6GalNAc I-74. Lane 1 corresponds to a PCR product of 270 pb; lane 2 corresponds to the SmartLadder SF; lane 3 corresponds to 5 μL of the concentrated PCR products of 270 pb size.

Figure 14:
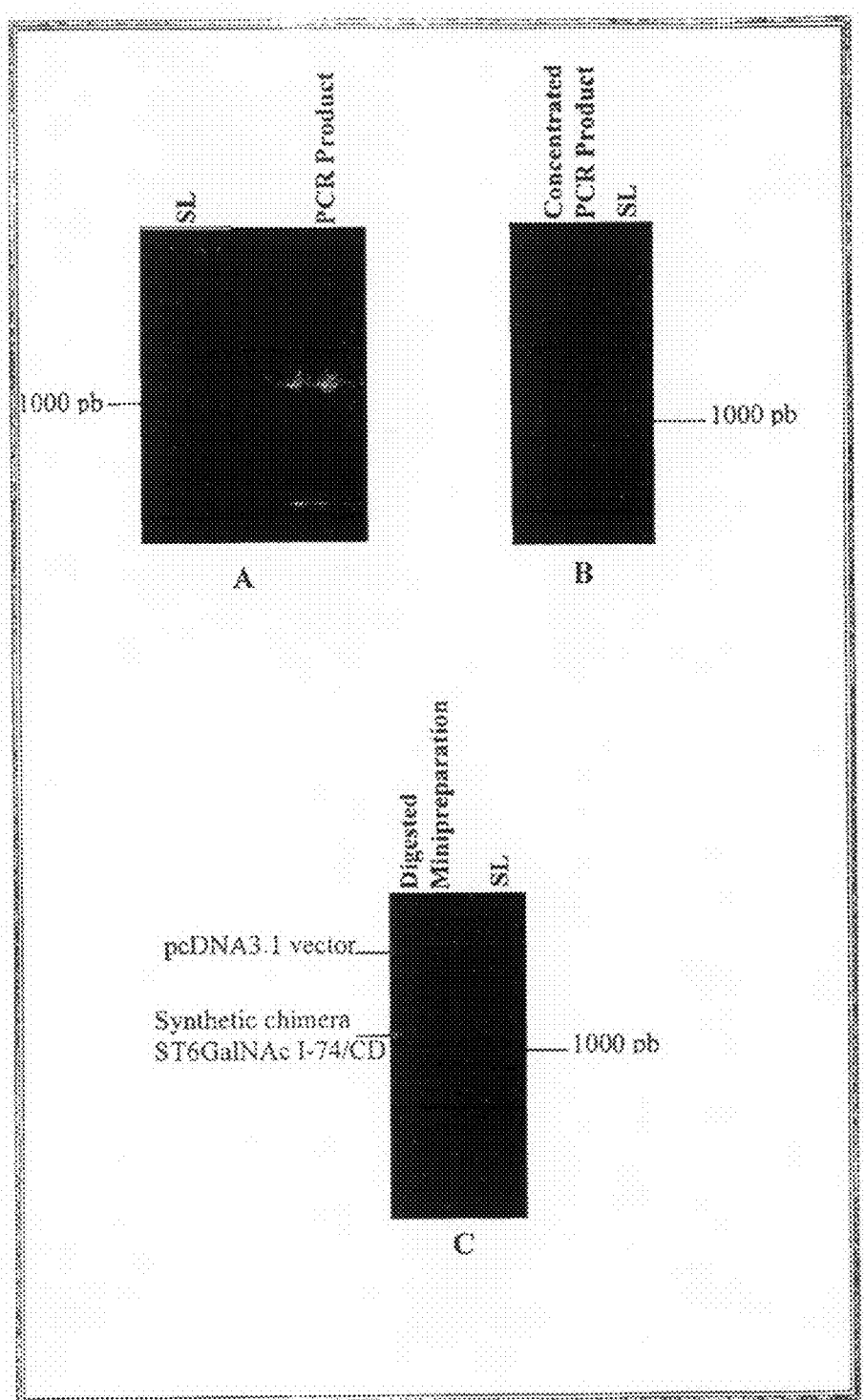

FIG. 14 represents the complete reconstructed synthetic gene of hST6GalNAc I-74/CD.

FIG. 14A shows an agarose gel (1.5%) with the DNA band of the reconstituted synthetic hST6GalNAc I-74/CD amplified by PCR.

FIG. 14B shows 5 μL of the concentrated PCR products of the chimera of around 1200 pb in size.

FIG. 14C shows the product of the digestion of the recombinant vector by the restriction enzymes AflII and XbaI, showing the insertion of the chimera gene (expected size 1225 pb).

Figure 15:
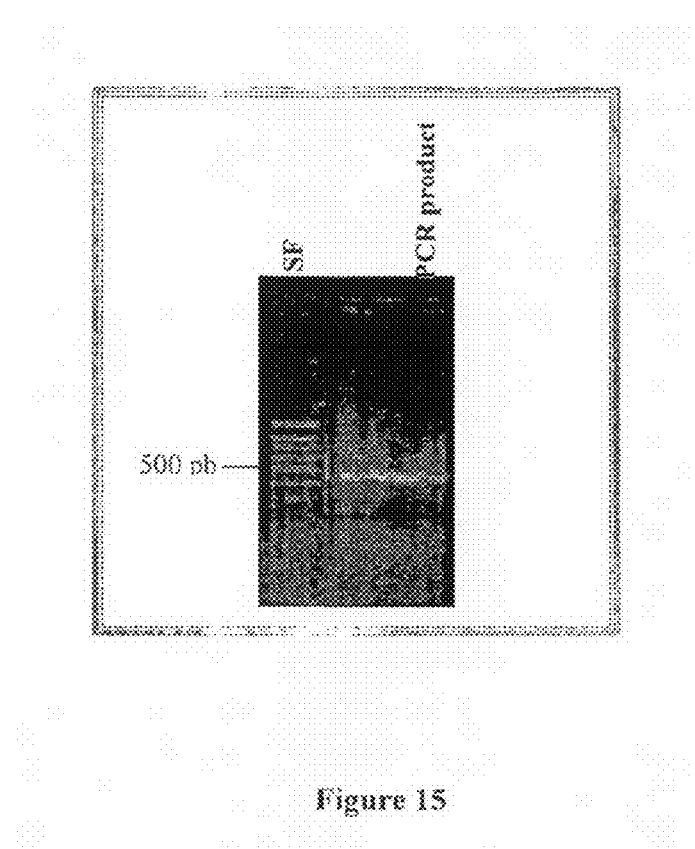

FIG. 15 shows an agarose gel (1.5%) showing the DNA band of the reconstituted synthetic N-terminal region of hST6GalNAc I-140. Lane 1: SmartLadder SF; lane 2: PCR product of 468 pb.

Figure 16:
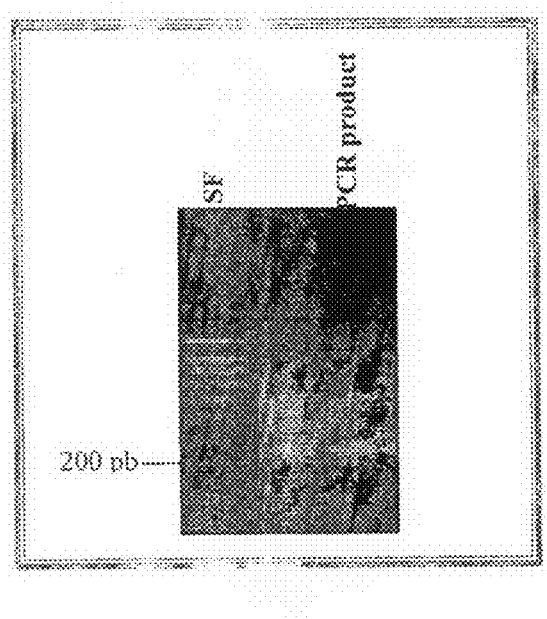

FIG. 16 shows an agarose gel (1.5%) showing the DNA band of the reconstituted synthetic hybrid gene composed of hST3Gal III-29/37-hST6GalNAc I-74. Lane 1 corresponds to the SmartLadder SF; lane 2 corresponds to a PCR product of 249 pb.

Figure 17:
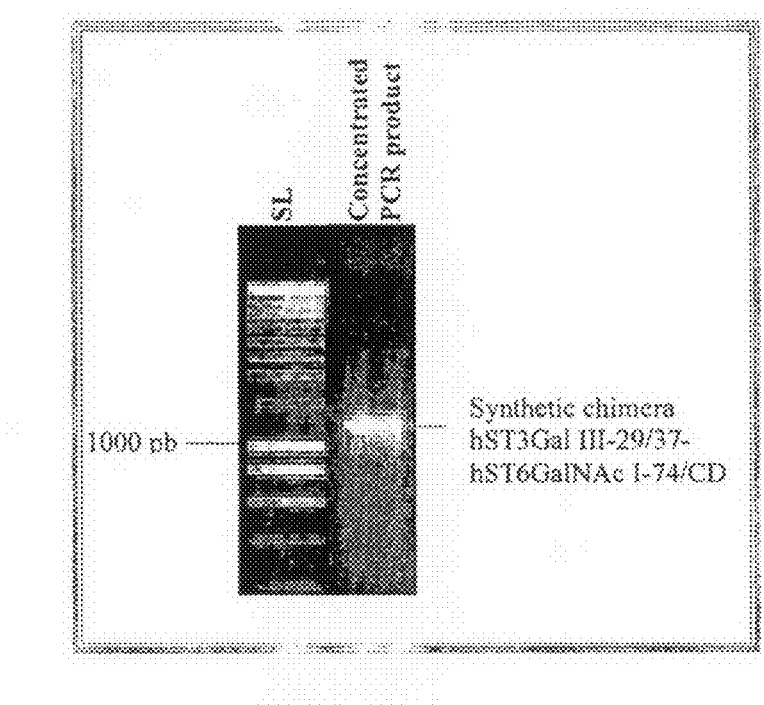

FIG. 17 shows an agarose gel (1.5%) showing the DNA band of the reconstituted synthetic hybrid gene composed of hST3Gal III-29/37-hST6GalNAc I-74 ligated with the CD.

Lane 1 corresponds to the SmartLadder SF; lane 2 corresponds to a PCR product of 1197 pb.

Figure 18:
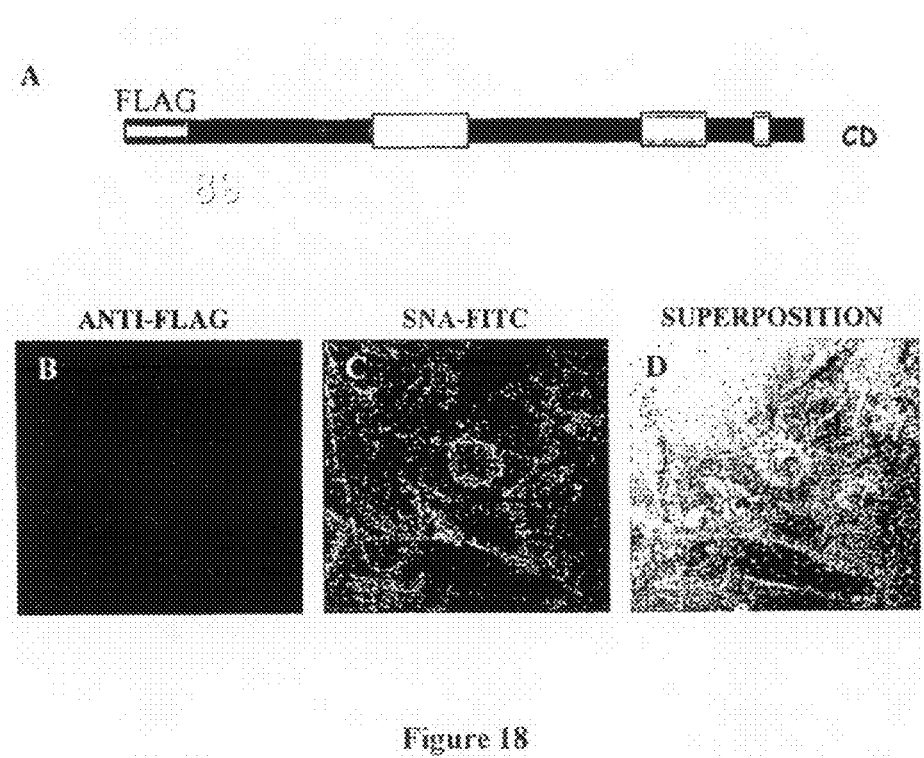

FIG. 18 represents the expression of the minimal catalytic domain (CD) (Panel A) of hST6Gal I in CHO cells, based on a double labelling with FITC-SNA binding 6-linked sialic acid and with an anti-FLAG mAb and using confocal microscopy. Transient expression of the CD was analysed by anti-FLAG labelling (Panel B) and for SNA-FITC binding (Panel C). Panel D shows the superposition of the signal from panels B and C (Donadio et al., 2003)

Figure 19:
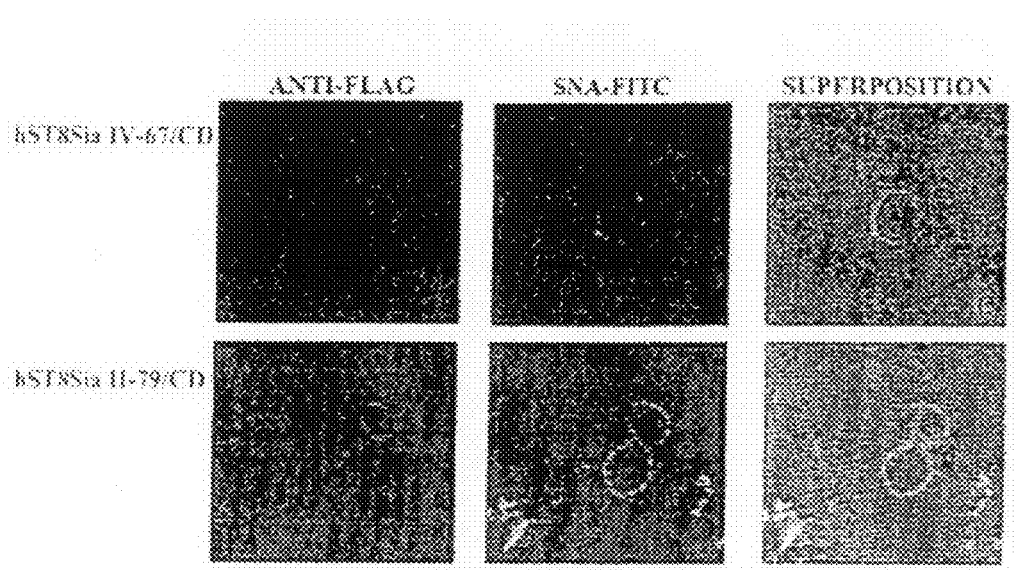

FIG. 19 shows the expression of two chimeric enzymes, hST8SiaIV-67/CD, hST8SiaII-79/CD in CHO cells. Transfected cells were double-labelled with an anti-FLAG mAb (A and D) and with FITC-SNA (B and E). Overlays are represented in C and F.

Figure 20:
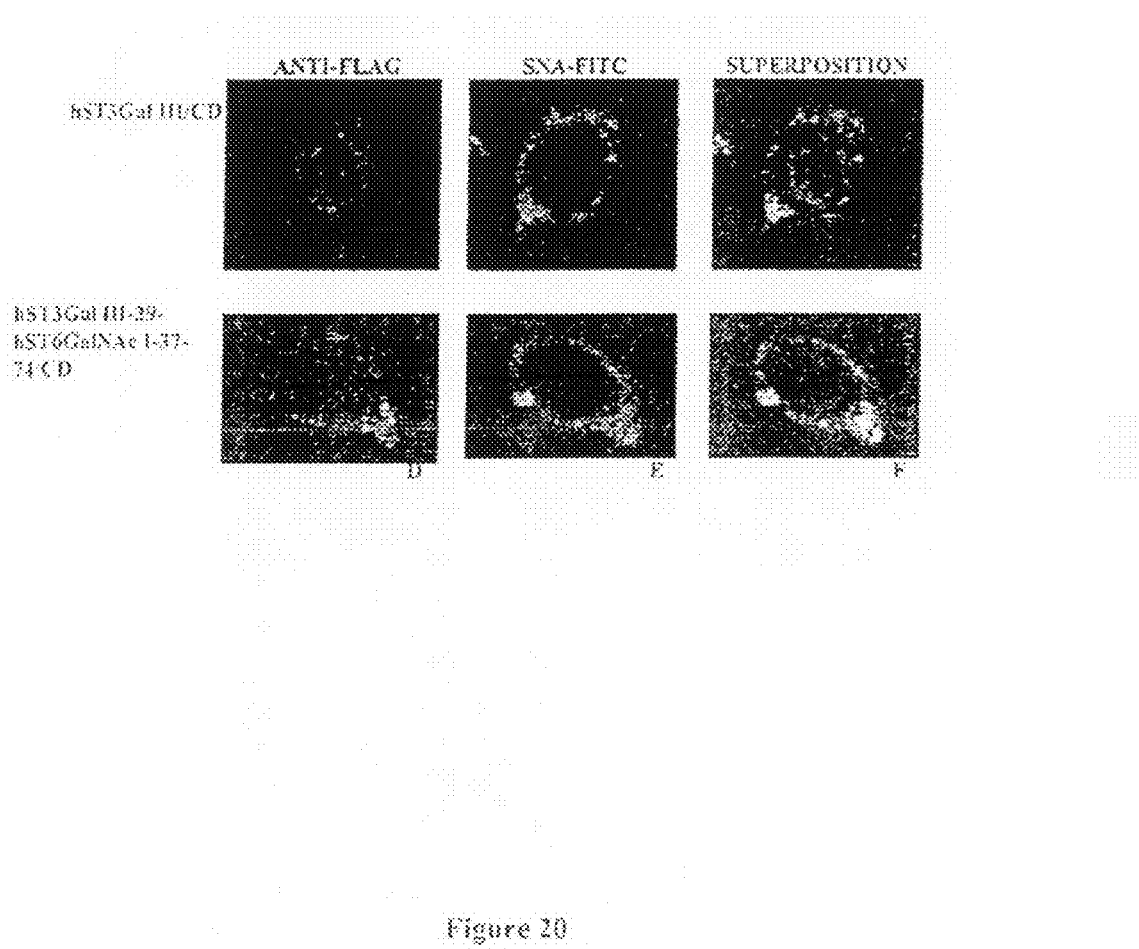

FIG. 20 shows the expression of ST3GalIII/CD and ST3GalIII-hST6GalNAc I-74/CD in CHO cells. Transfected cells were double-labelled with an anti-FLAG mAb (A and D) and with FITC-SNA (B and E). Overlays are represented in C and F.

Figure 21:
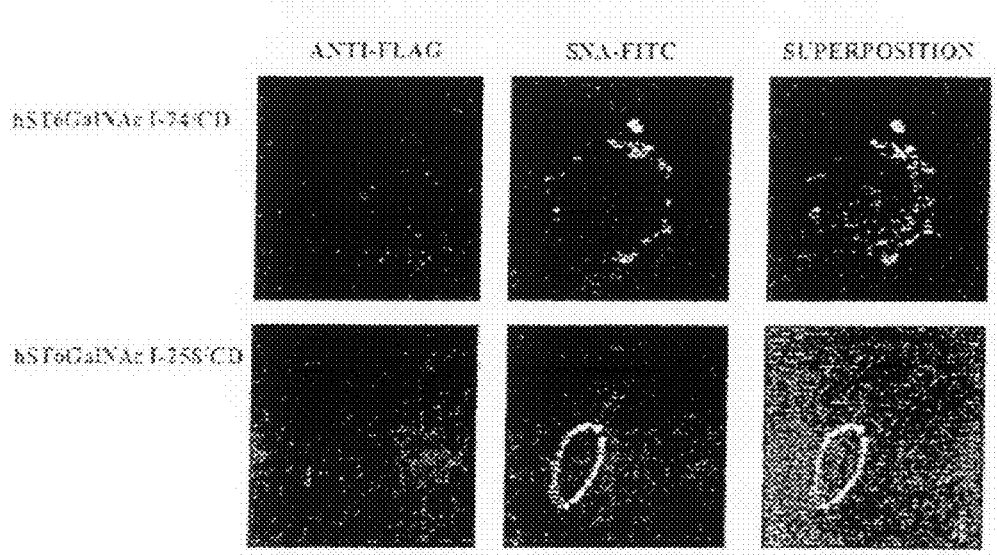

FIG. 21 shows the expression of hST6GalNAc I-74/CD, and 258/CD in CHO cells. Transfected cells were double-labelled with an anti-FLAG mAb (A and D) and with FITC-SNA (B and E). Overlays are represented in C and F.

Figure 22:
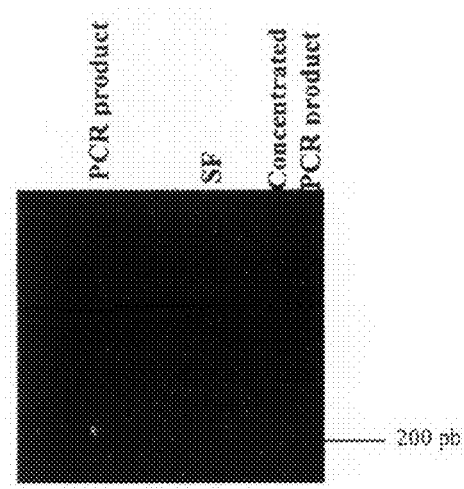

FIG. 22 shows an agarose gel (2%) showing the DNA band of the reconstituted synthetic N-terminal region of hST3Gal III/hST8Sia II/hST6GalNAc I. Lane 1 corresponds to a PCR product of 240 pb; lane 2 corresponds to the SmartLadder SF; lane 3 corresponds to 3 μL of the 240 pb concentrated PCR product.

Figure 23:
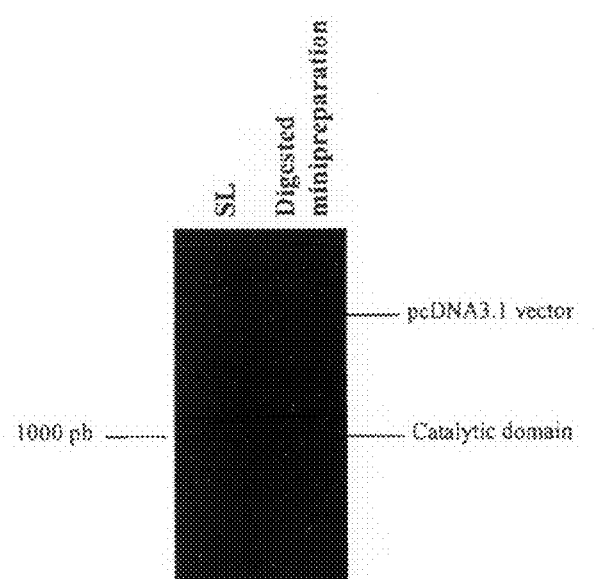

FIG. 23 represents the product of the digestion of the recombinant vector by the restriction enzymes XbaI and BamHI, showing the insertion of the catalytic domain gene (expected size 960 pb). Sample was loaded on a 1.5% agarose gel with the SL nucleic marker.

Figure 24:
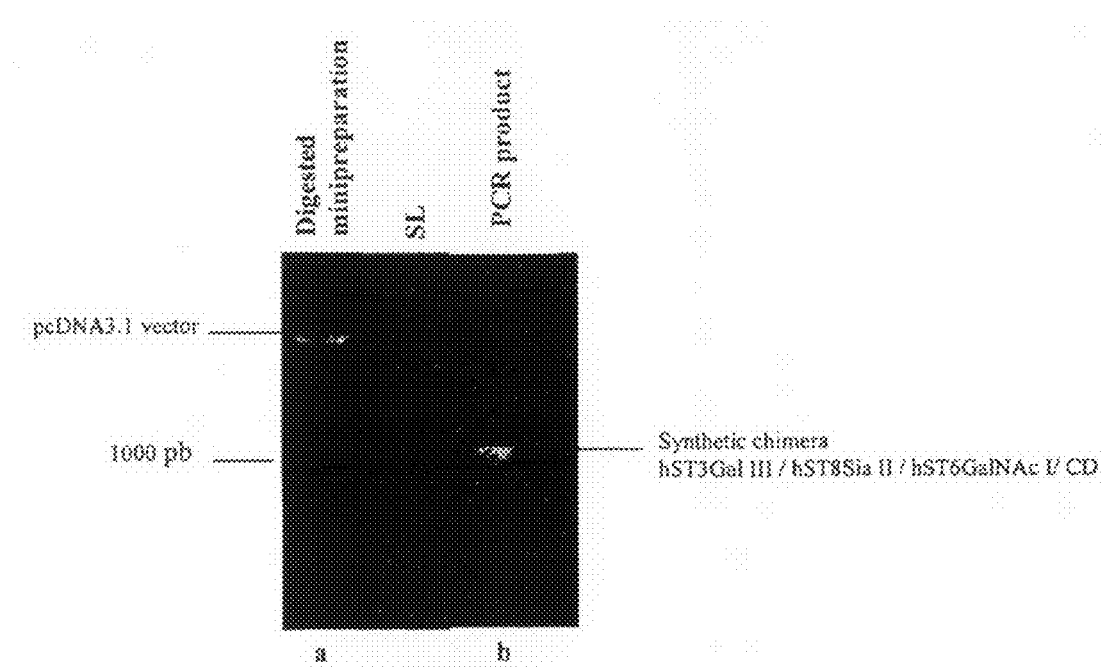

FIG. 24 represents the reconstructed enzyme gene of hST3Gal III/hST8Sia II/hST6GalNAc I/CD.

In FIG. 24a, an agarose gel (1.5%) shows the product of the digestion of the recombinant vector by the restriction enzymes XbaI and AflIII, showing the insertion of the chimera gene (expected size 1200 pb).

FIG. 24b represents the PCR product obtained after the amplification of a minipreparation sample, confirming the insertion of the chimera gene.

Figure 25:
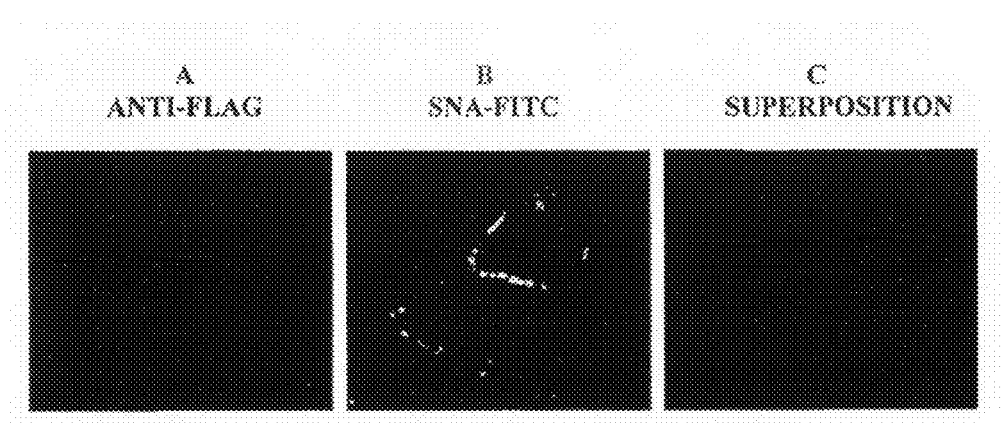

FIG. 25 shows the expression of the chimeric enzyme hST3Gal III/hST8Sia II/hST6GalNAc I/CD in CHO cells. Transfected cells were double-labelled with an anti-FLAG mAb (A) and with FITC-SNA (B). Overlay is represented in C.

LEGENDS OF TABLES 1 TO 5

Table 1: Sequences and accession numbers of the 20 sialyltransferases known in human.

Table 2: Acceptor substrates and expression sites of human sialyltransferases as described in Harduin-Lepers et al., 2001 and Jeanneau et al, 2003.

Table 3: Distribution of the 4 peptide domains shared by human STs. A short N-terminal cytoplasmic tail (CT; around 10 amino-acids), a transmembrane domain (TMD; around 20 amino acids), a stem region (SR), highly variable in length and a catalytic domain (CD; around 300 amino acids), including the sialylmotifs L, S and VS.

Table 4: Proposed conserved peptides of around 31-85 amino acids identified within the hypervariable SR region. 5 motifs were found: motif A common to ST6Gal and ST6GalNAc I, motif B common to ST6GalNAc I and ST6GalNAc II, motifs C and D common to all ST8Sia and motif E present in ST3Gal except the ST3Gal I and II (Donadio et al., 2003).

Table 5: Design of the four primer pairs used for PCR amplification.

TABLE 1

| HUMAN SIALYLTRANSFERASES | ACCESSION N° GenBank | ACCESSION N° Swiss Prot |
|---|---|---|
| ST6Gal I | A17362 | P15907 |
| ST6Gal II | NM_032528 | Q8IUG7 |
| ST6GalNAc I | NM_018414 | Q9NSC7 |
| ST6GalNAc II | NM_006456 | Q9UJ37 |
| ST6GalNAc III | NM_152996 | Q8NDV1 |
| ST6GalNAc IV | NM_014403 | Q9H4F1 |
| ST6GalNAc V | NM_030965 | Q9BVH7 |
| ST6GalNAc VI | AB035173 | Q969X2 |
| ST3Gal I | L29555 | Q11201 |
| ST3Gal II | U63090 | Q16842 |
| ST3Gal III | L23768 | Q11203 |
| ST3Gal IV | L23767 | Q11206 |
| ST3Gal V | AF105026 | Q9UNP4 |
| ST3Gal VI | AF119391 | Q9Y274 |
| ST8Sia I | L32867 | Q92185 |
| ST8Sia II | U33551 | Q92186 |
| ST8Sia III | AF004668 | O43173 |
| ST8Sia IV | L41680 | Q92187 |
| ST8Sia V | U91641 | O15466 |
| ST8Sia VI | AJ621583 | P61647 |

TABLE 2

| HUMAN SIALYLTRANSFERASES | Acceptor | Expression |
|---|---|---|
| ST6Gal I | Galβ1-4GlcNAc | Ubiquitous |
| ST6Gal II | Galβ1-4GlcNAc | Brain, testicules, thyroid, fetal tissue, lymphatic ganglia |
| ST6GalNAc I | Galβ1-3GalNAc | Submaxillary and mammary glands, spleen, colon |
| | GalNAcα-O-Ser/Thr | |
| | Siaα2-3 Galβ1-3GalNAcα-O-Ser/Thr | |
| ST6GalNAc II | Galβ1-3GalNAcα-O-Ser/Thr | Lacting mammary glands, testis |
| | Siaα2-3Galβ1-3GalNAcα-O-Ser/Thr | |
| ST6GalNAc III | Siaα2-3Galβ1-3GalNAc | |
| ST6GalNAc IV | Siaα2-3Galβ1-3GalNAc, GM1b | Ubiquitous |

TABLE 2-continued

| HUMAN SIALYLTRANSFERASES | Acceptor | Expression |
|---|---|---|
| ST6GalNAc V | Siaα2-3Galβ1-3GalNAc, GM1b | |
| ST6GalNAc VI | GM1b, GT1b | |
| ST3Gal I | Galβ1-3GalNAc | Ubiquitous |
| ST3Gal II | Galβ1-3GalNAc, GM1, asialo-GM1 | Heart, liver, skeletal muscle, thymus, lymph node, appendix, salivary glands, spleen |
| ST3Gal III | Galβ1-3GlcNAc Galβ1-4GlcNAc | Skeletal muscle, fetal tissue |
| ST3Gal IV | Galβ1-4GlcNAc-O Galβ1-3GalNAc-O | Placenta, testis, ovary |
| ST3Gal V | Galβ1-4Glcβ-Cer | Ubiquitous |
| ST3Gal VI | Galβ1-4GlcNAc | Heart, placenta, liver and most other tissues. |
| ST8Sia I | Siaα2-3Galβ1-4Glcβ1-O-Cer, GM3 | |
| ST8Sia II | SiaGalβ1-4GalNAc | Embryonic tissues, brain |
| ST8Sia III | Sia2-3Galβ1-4GlcNAc | |
| ST8Sia IV | SiaGalβ1-4GalNAc | Brain, fetal tissues, adult heart, spleen, thymus |
| ST8Sia V | GM1b, GD1a, GT1b, GD3 | |
| ST8Sia VI | NeuAcα2,3(6)Galβ | |

TABLE 3

ESTIMATION OF LENGTH OF DOMAINS

| Human Sialyltransferases | Total | Cytoplasmic Tail (CT) | Transmembrane Domain (TMD) | Stem Region (SR; +/−10 AA) | Catalytic Domain (CD; +/−10 AA) | Sialylmotif L (47 AA) | Sialylmotif S (24 AA) | Sialylmotif VS (12 AA) |
|---|---|---|---|---|---|---|---|---|
| ST6Gal I | 406 | 1-9 (9 AA) | 10-26 (17 AA) | 27-100 (74 AA) | 101-406 (306 AA) | 181-227 | 320-343 | 366-378 |
| ST6Gal II | 529 | 1-10 (10 AA) | 11-30 (20 AA) | 31-112 (82 AA) | 113-529 (417 AA) | 293-339 | 433-456 | 479-491 |
| ST6GalNAc I | 600 | 1-14 (14 AA) | 15-35 (41 AA) | 36-281 (246 AA) | 282-600 (319 AA) | 362-408 | 518-541 | 563-575 |
| ST6GalNAc II | 374 | 1-7 (7 AA) | 8-28 (21 AA) | 29-67 (39 AA) | 68-374 (307 AA) | 148-194 | 302-325 | 347-359 |
| ST6GalNAc III | 305 | 1-8 (8 AA) | 9-28 (20 AA) | 29-34 (6 AA) | 35-305 (271 AA) | 77-123 | 214-237 | 273-285 |
| ST6GalNAc IV | 302 | 1-6 (6 AA) | 7-27 (21 AA) | 28-30 (3 AA) | 31-302 (272 AA) | 73-119 | 210-233 | 270-282 |
| ST6GalNAc V | 336 | 1-8 (8 AA) | 9-29 (21 AA) | 30-50 (21 AA) | 51-336 (286 AA) | 93-139 | 230-253 | 291-303 |
| ST6GalNAc VI | 333 | 1-43 (43 AA) | 44-59 (16 AA) | 60-61 (2 AA) | 62-333 (272 AA) | 105-151 | 241-264 | 303-315 |
| ST3Gal I | 340 | 1-13 (13 AA) | 14-34 (21 AA) | 35-58 (24 AA) | 59-340 (282 AA) | 139-185 | 266-289 | 312-324 |
| ST3Gal II | 350 | 1-6 (6 AA) | 7-27 (21 AA) | 28-68 (41 AA) | 69-350 (282 AA) | 149-195 | 276-299 | 322-334 |
| ST3Gal III | 444 | 1-8 (8 AA) | 9-28 (20 AA) | 29-76 (48 AA) | 77-444 (368 AA) | 157-203 | 299-322 | 346-358 |
| ST3Gal IV | 329 | 1-8 (8 AA) | 9-26 (18 AA) | 27-36 (10 AA) | 37-329 (293 AA) | 117-163 | 258-281 | 307-319 |
| ST3Gal V | 362 | 1-5 (5 AA) | 6-26 (21 AA) | 27-55 (29 AA) | 56-362 (307 AA) | 136-182 | 282-305 | 329-341 |
| ST3Gal VI | 331 | 1-4 (4 AA) | 5-25 (21 AA) | 26-34 (9 AA) | 35-331 (297 AA) | 115-161 | 256-279 | 303-315 |
| ST8Sia 1 | 356 | 1-29 (29 AA) | 30-48 (19 AA) | 49-54 (6 AA) | 55-356 (302 AA) | 135-182 | 272-295 | 318-330 |
| ST8Sia II | 375 | 1-6 (6 AA) | 7-23 (17 AA) | 24-73 (50 AA) | 74-375 (302 AA) | 157-200 | 292-315 | 342-354 |
| ST8Sia III | 380 | 1-9 (9 AA) | 10-33 (24 AA) | 34-78 (45 AA) | 79-380 (302 AA) | 159-205 | 298-321 | 350-362 |
| ST8Sia IV | 359 | 1-7 (7 AA) | 8-20 (13 AA) | 21-58 (38 AA) | 59-359 (301 AA) | 139-185 | 277-300 | 327-339 |
| ST8Sia V | 376 | 1-17 (17 AA) | 18-38 (21 AA) | 39-80 (42 AA) | 81-376 (296 AA) | 93-208 | 298-321 | 344-350 |
| ST8Sia VI | 398 | 1-3 (3 AA) | 4-24 (21 AA) | 25-102 (78 AA) | 103-398 (296 AA) | 183-230 | 320-343 | 360-378 |

TABLE 4

| ENZYMES | conserved region | Motif A | Motif B | Motif C | Motif D | Motif E |
|---|---|---|---|---|---|---|
| hST6Gal I | 93-165 | 159-165 | X | X | X | X |
| hST6GalNAc I | 259-331 | 310-315 | 324-331 | X | X | X |
| hST8Sia IV | 71-133 | X | X | 71-90 | 119-133 | X |
| hST3Gal IV | 75-106 | X | X | X | X | 84-91 |

TABLE 5

| Amplified fragments | Primers set | PCR product size (Pb) |
|---|---|---|
| hST3Gal III | 5' AflII-ST3 3'ST3-BamHI | 186 |
| hST6GalNAc I-74 | 5' AflII-ST6 3"ST6-BamHI | 270 |
| hST6GalNAc I-140 | 5' AflII-ST6 3'ST6-BamHIn°2 | 468 |
| hST3Gal III-29/37-hST6GalNAc-74 | 5' AflII-ST3 3'ST6-BamHI | 246 |

DESCRIPTION OF THE INVENTION

The invention will be further described in the detailed description which follows.

I—Introduction

Bases of the Invention:

The inventors have focused on the study of hST6Gal I because this enzyme activity is missing in all host cells used so far for heterologous protein production, especially in drug-approved cell systems. The human enzyme has been cloned by the inventors in Ronin, 2001.

In contrast to the literature, the inventors were initially able to show that the full-length enzyme can differentially sialylate acceptor glycoproteins of bi-, tri- and/or tetraantennary glycan structure (Ronin 2001) and at that time, the inventors hypothesized that within the transferase structure, a steric control located in the hypervariable SR region should be exerted on the CD to regulate and naturally constrain enzymatic specificity. For the purpose of producing sialylated proteins of biomedical interest, this regulatory control should be abolished and as a result, the specificity may be enlarged. Inside the conserved region (93-165) of hST6Gal I, an hydrophobic sequence has been noticed: 93-QVWxKDS-100. The importance of this sequence has been studied by progessively deleting hST6Gal I of its N-terminal part within the conserved region newly identified. The Δ35, Δ48, Δ60 and Δ82 deleted mutants show an increasing transfer efficiency. Deletions carried out before and after the conserved domain (93-165 of ST6GalI) showed that the Δ100 mutant lose its catalytic activity, whereas the Δ89 (containing the hydrophobic sequence QVWxKDS) possesses an optimal catalytic activity. The results clearly indicate that this short sequence is crucial to promote activity. This hydrophobic sequence may contribute to local conformational changes essential for the active site to promote sialic acid transfer.

A second study has been realized by the inventors aimed at elucidating the molecular and cellular basis that govern the acceptor preference of STs (Ronin 2003). As it was difficult to delineate the CD from the hypervariable region of the SR, they hypothesized that the SR of STs should contain structural features related to an acceptor preference. 53 animal and human enzymes of known specificity were analyzed by bioinformatics to determine if STs may share a peptidic portion to restrict the acceptor recognition to an enzyme subfamily. A highly conserved region of around 31-85 amino acids has been identified and inside this region, 5 motifs were found: motif A common to ST6Gal and ST6GalNAc I, motif B common to ST6GalNAc I and ST6GalNAc II, motifs C and D common to all ST8Sia and motif E present in ST3Gal except the ST3Gal I and II (Table 4).

Those 5 motifs are typical of a STs subgroup sharing a similar catalytic activity and thus involved in the same way to transfer sialic acid. They are located at the end of the SR closed to the sialylmotif L and can be considered as part of the CD as key feature for acceptor recognition.

Of special interest also, was also the finding that the Δ89 mutant is extremely efficient in CHO cells and that it follows the intracellular pathway from the early golgi to the trans golgi/trans golgi network. Δ89 is expressed along the intracellular routing of the glycoproteins and glycolipids in the entire stacks of the golgi apparatus (Ronin, 2003). This work made it possible to delineate the minimum CD for hST6Gal I containing the crucial hydrophobic sequence (QVWxKDS) and displacing the acceptor recognition from intracellular resident acceptors to cell surface glycoconjugates. These findings gave the ground of designing novel membrane-anchored chimera which may display a similar intracellular trafficking to encounter neosynthesized glycoproteins within the secretory pathway as they are packed in engineered host cells when produced as drugs.

The minimum CD of hST6Gal I Δ89 have been used in the invention as an "optimized CD" of enlarged specificity and increased transfer efficiency and will be further named CD.

The Distribution of the Sialyltransferases in the Golgi Apparatus

Golgi localization of GTs is not strictly organized, enzymes are not distributed and isolated in a single compartment of the golgi apparatus, most of them overlap and co-compartmentalized (Colley, 1997; Berger et al., 1998; Berger, 2002). No clear retention signals have been identified yet but enzymes form overlapping gradients across the stacks (Opat et al., 2001), and only crucial regions have been identified.

There are two hypothesis concerning retention mechanisms in the golgi: i) the length of the TMD drives the golgi retention (bilayer thickness model; Bretscher & Munro, 1993; Colley, 1997; Munro, 1998) and ii) the proteins oligomerization leeds to golgi retention (Oligomerization/kin recognition hypothesis; Machamer, 1991; Colley, 1997), in which authors postulate that enzymes interact in golgi cisterna to form too large structures to enter in transport vesicules (Munro, 1998).

The length of the TMD seems also crucial as a retention signal. TMD represents a key factor in the retention process, in most of cases it is sufficient to promote a golgi localization i.e. throughout the cis-, medial and trans compartments. Lengthening the TMD of STs results in reduced retention and synthetic TMD (creates by mutagenesis) of 17 leucine gives golgi retention whereas one of 23 leucines does not (Munro, 1991, 1995, 1998). Concerning the retention signals of the STs, several regions are involved in an independent manner to retain enzymes in the golgi apparatus. The TMD with its flanking regions are sufficient for golgi retention (Colley, 1997). Other work suggest that no specific sequence in the TMD are required for golgi retention, especially in the presence of appropriate spaced cytoplasmic and luminal flanking sequences and/or SR (Colley, 1997). The presence of negatively charged amino acid sequences on STs, particularly close to the membrane anchor, was found to mislocalize the proteins in the golgi apparatus. The presence of FLAG or MYC epitope, in the CT, disturbs the golgi localization of ST6Gal I, whereas using an additional spacer sequence, to space out the negative charges from the TMD, reveals strong advantage for golgi retention (Yang et al., 1996). The SR sequences alone appear to function as an other type of golgi retention (Colley, 1997).

There is probably more than one retention mechanism, explaining the colocalization of the STs inside the trans golgi and the trans golgi network. Moreover the localization of the enzymes also depends of the cell type where they are expressed (Colley, 1997). The TMD of STs alone may be sufficient for golgi retention in MDCK cells but the same TMD and its flanking sequences are clearly required for golgi retention in CHO cells (Colley, 1997). Of interest, available data reveal that changing the CT, the TMD and the SR does not disturb the catalytic activity of STs, but allow to delocalize them inside the golgi apparatus (Grabenhorst et Conradt, 1999).

Figure 1:
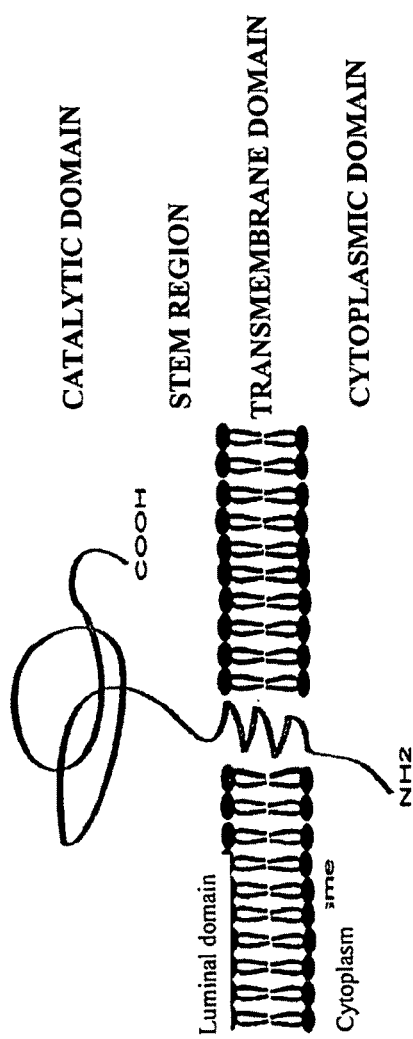
FIG. 1 represents the membrane topology of glycosyltransferases. Glycosyltransferases are type II membrane proteins including a cytoplasmic N-terminal tail (CT), a transmembrane (TMD) anchor signal followed by a stem region (SR) and a large C-terminal catalytic domain (CD).
Figure 3:
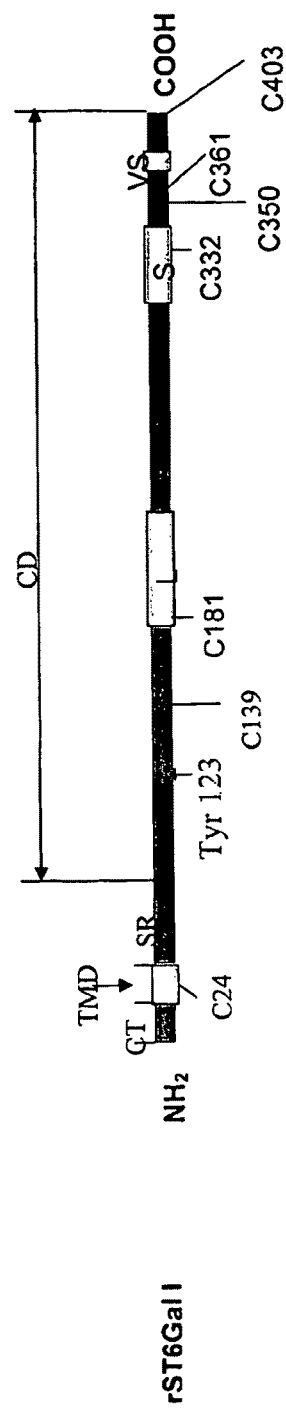
FIG. 3 represents schematic distribution of CT, TMD, SR and CD of the rat ST6Gal I showing key residues which are tyr123 and 7 conserved cys. CT: cytoplasmic tail (9 amino acids); TMD: transmembrane domain (17 aa); SR: stem region (70 aa); CD: catalytic domain (307 aa); L: sialylmotif L; S: sialylmotif L and VS sialylmotif VS

The most studied enzyme for the golgi retention signal, is the ratST6Gal I (rST6Gal I), that has been localized in the trans golgi and the trans golgi network of hepatocytes (Roth et al., 1985; Opat et al., 2001) and in post golgi compartments in other cells (Colley, 1997). Two natural isoforms of rST6Gal I exist, they differ only by one amino acid at position 123 in the CD. This is due to a single A to G nucleotide change, resulting of Tyr to Cys amino acid change. No catalytic activity differences were found between the two isoforms of the enzyme (Chen et al., 2003). The STcys form is found in the golgi in moderately expressing cells and never at the cell surfaces or cleaved or secreted into the media of COS-1 or HeLa cells, whereas the STtyr isoform is found in the golgi, at low levels on the cell surface and is cleaved and secreted from COS-1 and HeLa cells (Ma et al., 1997). To explain the two different localizations of the proteins, authors have proposed two hypothesis on the retention mechanism: bilayer thickness and oligomerization. First, analysis of lengthening TMD of STcys and tyr suggests that the bilayer thickness is not a predominant process for the golgi retention for ST6Gal I. Second, analysis of oligomers reveals that 100% and 13% of STcys and STtyr respectively are insoluble at pH 6.3 (late golgi pH), but at pH 8.0 both isoforms are soluble. The results suggest that conformational changes and disulfide bounds formation in the CD represent the basis for the increased ability for STcys to form oligomers and its stable localization in the golgi apparatus. The nature of the amino acid 123 influences the oligomers formations (Chen et al., 2000). Moreover, the oligomerization process and the catalytic activity depend also on the other seven conserved cystein residues (C24, 139, 181, 332, 359, 361 and 403). The Cys24, inside the TMD is required for dimerization, while the cystein residues present in the CD are required for trafficking and catalytic activity. Cys181 and Cys332 (in sialylmotif L and S, respectively) enzymes are retained in the endoplasmic reticulum and are minimally active or inactive respectively. Cys359 and 361 (between sialylmotifs S and VS) are inactive enzymes without compromising their localization and trafficking. Cys139 or Cys403 mutated enzymes produce no change of the catalytic activity and of the golgi localization. The replacement of these two cystein residues decreases cleavage and secretion suggesting that they are necessary for signal cleavage (Qian et al., 2001) (FIG. 3).

Mutants of STtyr enzymes, sharing deletion in the SR have been characterized: STtyrΔ4 and STtyrΔ5 (deleted of amino acids 32 to 104 and 86 to 104, respectively) are not active and/or secreted, STtyrΔ1, Δ2 and Δ3 (deleted between amino acids 32 to 86) represent not cleavable forms and show an increasing cell surface expression (Kitazume et al., 1999).

Figure 4:
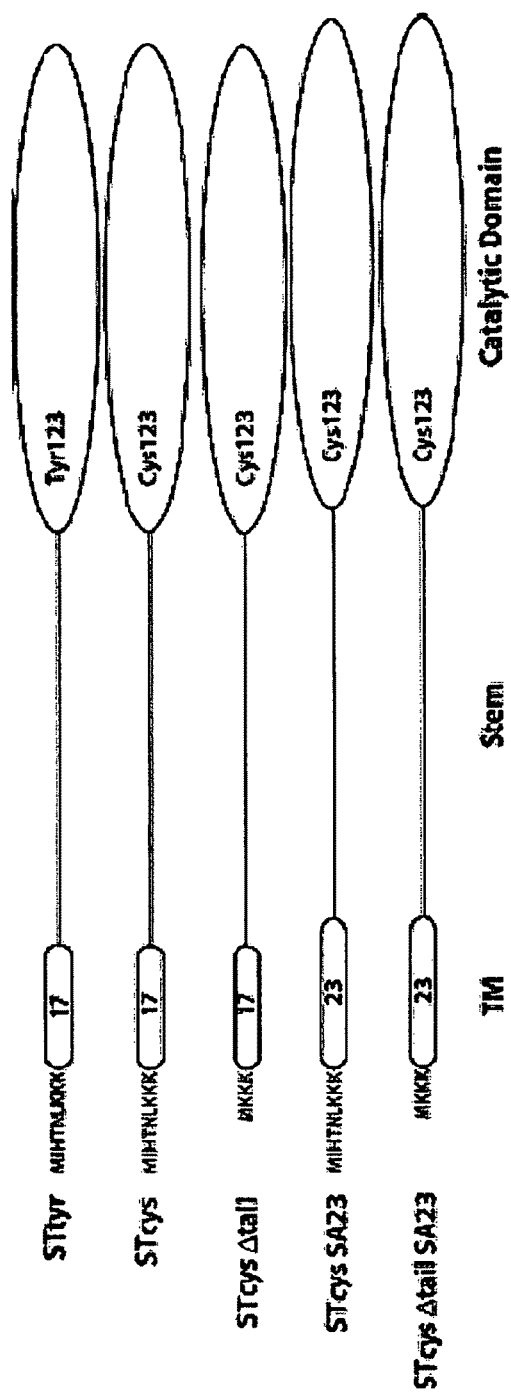
FIG. 4 represents DNA constructs to produce chimera and evaluate the role of the cytoplasmic tail, the transmembrane domain in two enzyme isoforms (rST6Gal I Tyr or Cys 123 respectively) (Fenteany & Colley, 2005).

A recent work (Fenteany & Colley, 2005) show that multiple signals are indeed required for rST6Gal I oligomerization and for the golgi localization. Authors aimed at reevaluating the role of the CT, the TMD of the two enzyme isoforms (Tyr or Cys 123). They realised several DNA constructs to produce chimera as represented in FIG. 4. Lengthening the transmembrane domain (with more than 17 amino acids) does not enhance the golgi exit, it does not change trafficking or golgi localization. Concerning the role of the CT and the TMD in the STcys isoform, there is a signal composed of 3 Lysine residues in the CT that are recognized as export signal out of the ER. Authors show that altering both CT and TMD disturb the routing of the enzyme. The only difference between the isoforms of rST6Gal I is their capacity to form oligomers according to the pH. For STcys, the oligomers formation, according to the pH, is compromised only when CT and TMD are altered. For STtyr, it increases slightly the rate of golgi exit (Fenteany & Colley, 2005).

Figure 5:
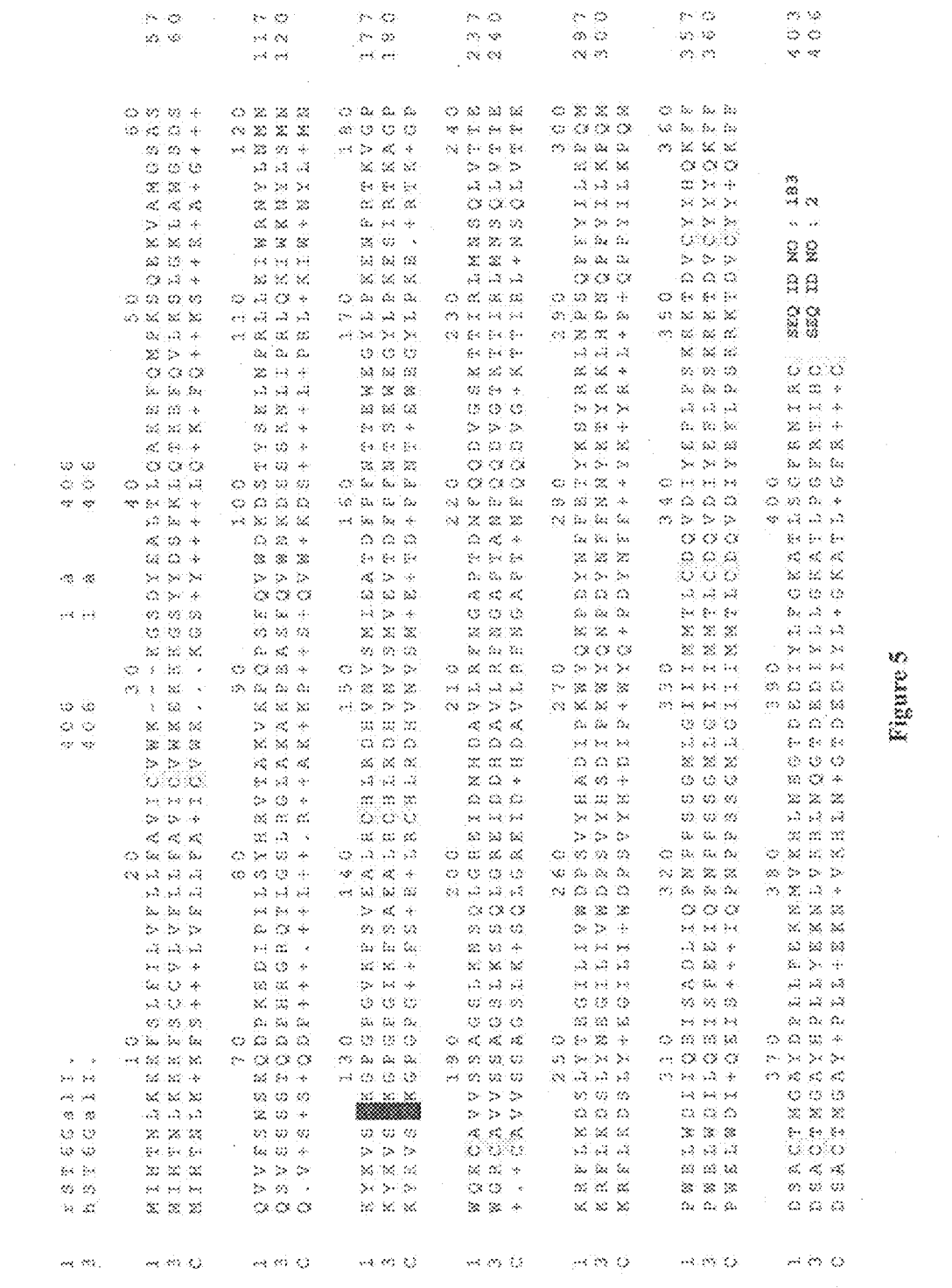

All these recent findings concerning the rST6Gal I can be considered applicable to the human ST6Gal I since both enzymes share 85% homology and that both CDs are virtually identical. Indeed, the two sequences alignment (FIG. 5) clearly show that the seven cysteins previously described are conserved in the hST6Gal I, and the Tyrosine 123 is also present.

Despite considerable efforts from scientists, no signal in the sequence of STs or FuTs could be demonstrated. It is believed that a multifactorial process may slow down the enzymes in their way to the surface to target them in appropriate compartments which are the Trans Golgi Network for ST6Gal. Accordingly, the inventors hypothesized that CT, TMD and SR may be alternatively exchanged to anchor a defined CD in host cells which lack the relevant gene and fail to express the relevant transferase activity. Thus, it is therefore possible to generate a wide array of combination as these 3 portions can be selected out of 55 animal known genes. Each of them can be potentially fused to 20 known distinct catalytic domains to display the ability of transferring sialic acid. This is of definite interest for the humanisation of yeast (*Pichia pastoris* or *Shyzosaccharomyces piombae*), plant and insects which do not express these activities and yet are used to produce recombinant drugs. Although not tested, this reasoning may also well apply to FuTs, GalTs, GalNAcTs and GlcNAcs as they govern the biosynthesis of glycotopes of high clinical relevance.

Importance of Several Residues

As previously described, a fourth motif (motif 3) has been identified in the ST family, between the S and the VS motifs. It is composed of four highly conserved amino acids with the following consensus sequence: (H/y)Y(Y/F/W/h)(E/D/q/g). Site directed mutagenesis on the hST3Gal I showed the functional importance of two amino acids in this motif: His299 and Tyr300. Results suggest the importance of aromatic residues, their possible involvement in acceptor recognition and their contribution for an optimal catalytic efficiency. Particularly the invariant Tyr300 plays a major conformational role. Mutational analysis showed that mutants H299A and Y300A display no catalytic activities, whereas mutant Y300F restore partially the activity (Jeanneau et al., 2004). This motif is also present in the catalytic domain of hST6Gal I. Moreover several cystein residues are of major importance in dimerization and catalytic activity as previously evoked (Qian et al., 2001). At least one disulfide bound has been evidenced between two conserved cystein residues inside the sialylmotifs L and S. This link is essential to maintain the protein conformation. The same observations revealed the existence of this binding in the PST (Angata et al., 2001), moreover, a second disulfide bound exists between sialylmotifs and the C-terminal region. Dimerization of the ST6Gal I, via disulfide bound, has been demonstrated. This enzyme inside the golgi apparatus is for around 20 to 30% in dimer form which has a lower activity because its affinity is reduced for the CMP-NeuAc (Jeanneau, 2003).

"Autoglycosylations"

GTs are often themselves glycosylated. Few data are available concerning the state of STs glycosylation and its importance on the biological function of the enzymes. It seems that the N-glycosylation on the ST6Gal I is not required for the biological activity of the enzyme in vivo. On the other hand, when tested in vitro on mutant, enzymatic activity is only observed for the the protein mutated on the first glycosylation site. These results suggest the existence of two N-glycans (Asn 146 and Asn 158) that can stabilise and/or prevent the protein against degradation. The mutation on the second glycosylation site may leading to aggregation or degradation of the protein (Chen & Colley, 2000; Chen et al., 2000). However, the N-glycosylation on the ST8Sia I can affect its activity and its subcellular localization (Martina et al., 1998). The elimination of the N-glycans reduced its in vivo activity with less than 10% of the initial activity. It has been recently shown that ST8SiaII and ST8SiaIV possess, in addition to their classical activity, an autopolysialylation activity (Muhlenhoff et al., 2001). This autopolysialylation occurs on the N-glycans at the position Asn 74 in the PST and at the positions Asn 69 and 219 in the STX. Site directed mutagenesis on these sites inactive the enzyme both in vivo and in vitro. As a result, care has been taken to maintain the Asn 74 and Asn 69 glycosylation sites when using SR of ST8SiaIV and ST8SiaII respectively to construct chimerical genes.

II—Use of the Sequences of the Invention for Introducing New Transferase Activity in Expression Systems IIa—The Role of Glycans, their Importance in the Immune System Glycans are recognition signals in most living organisms but they are also structural key determinants for protein biopotency.

They play a pivotal role in protein folding oligomerization, quality control, sorting and transport (Helenius & Aebi, 2001). Glycans represent oligosidic epitopes that can be considered as carbohydrate antigens. The nature of the glycans modifies the immunoreactivity. Several families of oligosidic antigens exist: ABH blood groups determinants, Lewis tissue groups, antigens members of the T family and antigens specific of the polysialylated or sulfated cellular adhesion (Legaigneur et al., 1999). Glycans have multiple roles: they are also involved in mechanisms of interactions between cells and between cells and matrix. Some cell proteins named Lectins specifically recognize glycanic structures and act as specific receptors (Gabius et al., 2004). In most cases, they are components of cell surface glycoconjugates.

The carbohydrate moieties act as recognition signals in the immune system and influence the immune recognition in at least two ways: i) the conformation of the protein is altered and it modulates their biological function; ii) the oligosaccharides serve as recognition determinants. Particularly, sialic acids contribute greatly to both of these effects because their highly electronegative and hydrophilic nature may influence the conformation of sialylated macromolecules, and this is particularly relevant for glycoproteins. Sialic acids possess the ability to act as biological masks to prevent or reduce the accessibility and play a significant role on the cell surface in the recognition process of self/non self discrimination (Pilatte et al., 1993, Glycobiology 2006 to be added).

Since N-glycans are well represented in serum glycoproteins and many other tissue proteins of human body, it is highly desirable that they should not be antigenic when present in recombinant glycosylated drugs. However since HuEPO produced in CHO cells has been developed as 1st approved drug, it appeared that several terminal sugars may be antigenic in humans: polyLacNAc, alpha1,3 Gal and N-Glycolylneuraminic acid. According to the most recent regulatory bodies, they should not be present any further in recombinant therapeutics.

IIb—The Clearance

Aside from their influence on the physico-chemical properties and the biological functions of proteins, glycans also possess a prevailing role on duration of glycoproteins in blood. This phenomenon is named metabolic clearance and represents the rate at which a natural compound or a drug is removed from the body by the liver or the kidney. It is defined as the plasmatic volume purified according to time (mL/min). This mechanism allows the organism to eliminate drugs.

Most of the circulating plasmatic proteins belong to the glycoproteins family sharing N-linked oligosaccharides and all of them are terminated in sialic acid, particularly in humans. Removal of sialic acid by a neuraminidase drastically decreases the plasmatic lifespan of the serum glycoproteins to minutes and promotes their uptake by the liver (van den Hamer et al., 1970; Morell et al., 1971). For example, when the pregnancy hormone (more recently recombinant HuEPO) is lacking sialic acid, its half-life is reduced to 2 minutes, whereas usually, its lifespan is around 48 hours. It is widely known at present that sialic acid is required to keep glycoproteins in blood because they prevent the circulating proteins from elimination by a sialoglycoprotein receptor (ASGPR or hepatic Lectin) composed of two subunits and included in the membranes of hepatocytes (Hudgin et al., 1974; Kawasaki & Ashwell, 1976; Bianucci & Chiellini, 2000). This receptor binds galactose or N-acetylglucosamine residues of the desialylated N-glycans (Meier et al., 2000). The recognized glycoproteins are then internalized in endocytic vesicles covered of clathrin and redirected into lysosomes where they are degraded (Ashwell & Hardford, 1982).

This step appeared crucial for pharmacokinetic properties of therapeutic recombinant glycoproteins as lower organisms are not capable of sialylating proteins and in CHO cells, the addition of sialic acid is extremely sensitive to the energetic status of the cells in culture (NeuAc is synthesized by condensation of pyruvate and lactic acid) and is barely complete. All the sialylated blockbusters (EPO, IFN, GM-CSF, FSH, Ab . . . ) should be purified for the manufacturer to present a high sialic acid content and be controlled for batch-to-batch consistency.

IIc—Control of Glycosylation & Allergenicity

Sialic acid residues at the terminal position of N-glycans are of major importance for therapeutic proteins as the sialylation of the proteins confers important properties to glycoproteins. The machinery required for the synthesis, the activation and the introduction of sialylated residues is poorly represented in the different recombinant proteins expression systems. Then, the recombinant human proteins produced are most often under or even not-sialylated compared to their native counterparts. Moreover, if they are expressed in mammalian cells, the sialylation may occur through N-glycolylneuraminic acid (NeuGc) which significantly differs from the N-Acetylated derivative (NeuAc) as it is present in mammalian cells but not in human cells.

Because there is an important issue with sialic acid in the market of recombinant drugs, many research teams are working on the modification of the N-glycosylation process in the different existing expression systems. Intensive work is aiming at humanizing the glycosylation pattern of the recombinant proteins to approach the pattern found in the natural glycoproteins as closely as possible and improve pharmacokinetics as well as safety of the product. Meanwhile, the procedure will tend to reduce the presence of immunogenic determinants. In this respect, a very recent study confirmed that 6-linked sialic acid and 3-linked sialic acid prevent glycoproteins to bind receptors of the immune system and generate activation (Glycobiology 2006). Adding 6-linked sialic acid to recombinant glycosylated proteins would therefore largely benefit to the safety of the drug and be major advance in the field.

Proteins of therapeutic interest were first extracted from natural sources such as blood, placenta, human or animal tissues. However, this approach is limited by the quantity of human tissues available and may bring in important risks of contamination (viruses, prions, oncogenes) and/or generate allergic reactions due to traces of animal proteins or toxins. With the rise of molecular biology, new approaches have been developed to produce proteins using quite different expression systems. A large range of heterologous expression systems are available (Andersen & Krummen, 2002) and each of them possess advantages and disadvantages with a particular attention given to the N-glycosylation pattern of the recombinant proteins produced in these systems.

IId—Biosynthesis of N-Glycans in Known Expression Systems: Needs for Humanization of the Glycosylation Pathway Bacteria One of the most used system is the bacteria *Escherichia coli* (*E. coli*) (Swartz, 2001; Baneyx, 1999), but its main inconvenient is that the human post-traductionnal modifications, particularly glycosylations, are not realised by this prokaryote because no such glycosyltranferases are expressed in *E. coli*. This can lead to misfolding and subsequent reject of the therapeutic proteins of interest by the immune system, reduction in their lifespan and biological activity.

No N-glycosylation of the human type has been found so far in this microorganism.

Yeasts and Filamentous Fungi

Yeasts and filamentous fungi are also well-established eukaryote expression systems and they possess a cellular machinery approaching those of human cells. Yeast produces complex proteins and realizes several post-traductional modifications including glycosylations. Both yeasts and mushrooms typically produce mannose-rich glycans by adding until 100 mannose residues (concerning yeast) on top of the pentasaccharidic core (Tanner & Lehele, 1987; Herscovics & Orlean, 1993). Those hypermannosylation definitely foster immune response in human. Moreover, until now, no complex oligosaccharide containing sialic acid, galactose, fucose and N-acetylgalactosamine has been found inside the glycoproteins produced by these organisms (Blanchard, 2004).

The N-glycosylation process realized by yeasts and mushrooms is similar to the mammalian process with respect to the initial steps in the ER but the presence of polymannans added in the golgi apparatus prevent them to get approval from regulatory bodies.

Insect Cells

Proteins expressed in insect cells are properly folded, secreted and may receive post-traductional modifications. The post-traductional modifications carry out by these cells are similar to those realised by mammalian cells, in particular concerning the N-glycosylation of the protein. The glycan structures obtained in this case, are however incomplete and designated as paucimannose due to the presence of an undesirable N-acetylglucosaminidase activity which degrades the neoglycoproteins expressed during Baculovirus expression (Blanchard, 2004).

The lack of neuraminic acid in insects is still actively debated (Marchal et al., 2001, Lerouge et al 2005). In some insect cells lines, α1,3 linked fucose residues are found and this may trigger off an immune responds in human. At present, the use of this system is therefore restricted to produce vaccinal antigens.

Transgenic Plants

As other eukaryotic cells, plants exhibit a complex and sophisticated cellular machinery which may be used to produce therapeutic proteins. Recombinant proteins possess a very good pharmacological quality because plants express the enzymes required for the maturation of the proteins.

However, the glycosylation process needs several adjustments not to produced allergenic proteins. Indeed, N-glycosylations in plants (Lerouge et al., 2000) are similar to those realized in humans as far as core glycosylation is concerned. The glycosylations are still lacking sialylated antennae and there is an addition of β1,2-xylose and α1,3-fucose. Both residues are highly immunogenic for human and currently considerably compromise the approval of transgenic plants as expression systems for therapeutics.

Mammalian Cells

Mammalian cells expression system, namely CHO cells, is currently the only drug-approved system to produce recombinant therapeutics. Such cells show a major advantage because they are able to synthesis complex proteins, achieve complex type N-glycosylation of high molecular mass. Mammalian cells naturally use, not only the enzymes involved in the synthesis and the transport of the nucleotides-sugars, but also the glycosyltransferases required to guarantee a complex glycosylation of heterologous recombinant proteins with a high level of α2,3-sialylation. However, there is lack of other enzymes such as the α1,3/4-fucosyltransferases and α2,6-sialytransferases, that transfer glycosidic motifs specific of the N-glycans of human tissues. In rodents, N-glycolylneuraminic acid is substantially preferred in N-glycans, O-acetylation of N-Acetyl neuraminic acid at position 4, 7, 8 and most often 9 also occurs frequently and each of these derivatives may be potentially immunogenic in human. This represents a limitation for the use of mouse cells or lactating mice/rabbits to express recombinant proteins (Blanchard, 2004).

IIe—Glycoengineering

Figure 6:
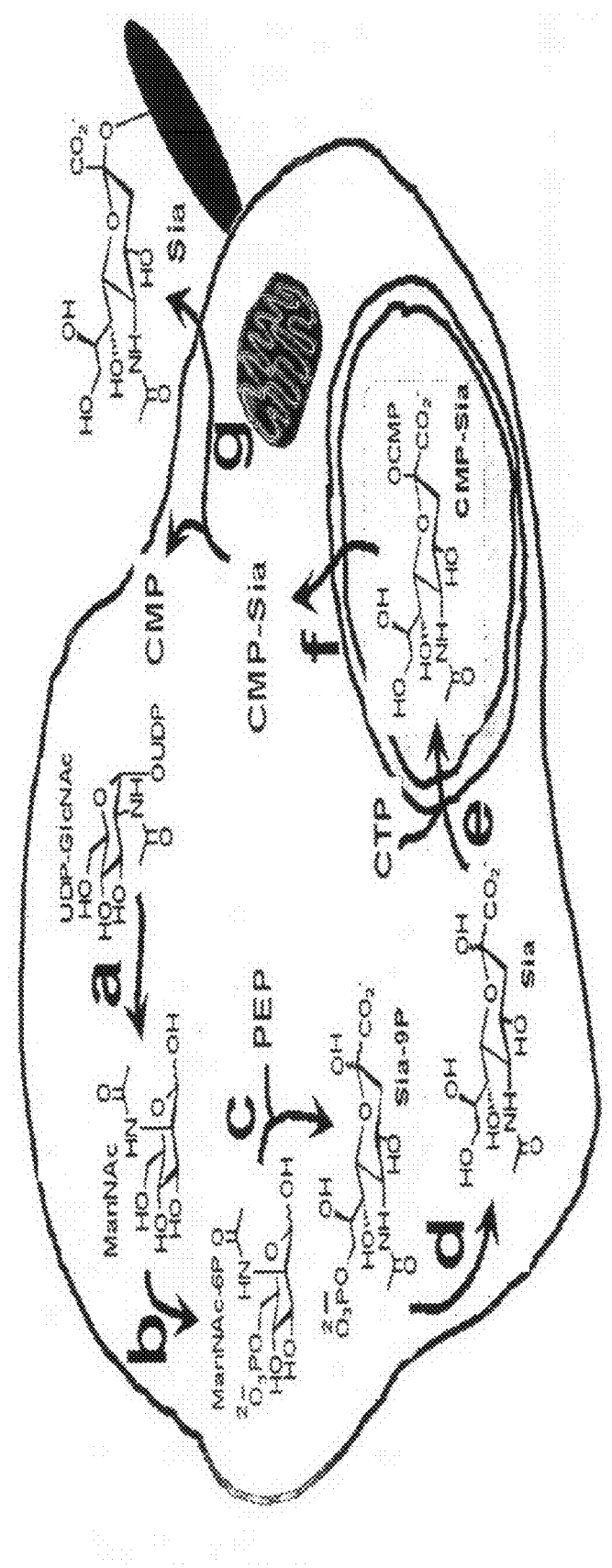
FIG. 6 represents the sialic acid pathway in human cells in the context of overall cellular glycosylation. The enzymes involved in this sequential process are: (a and b) UDP-N-acetylglucosamine/2-epimerase/N-acetylmannosamine kinase (UDP-GlcNAc 2-epimerase/ManNAc 6-kinase)—Reactions: (a) epimerase and (b) kinase, (c) N-acetylneuraminic acid phosphate synthase; (NANS SAS; N-acetylneuraminic acid phosphate synthase)—Reaction and Homo sapiens N-acetylneuraminate pyruvate lyase (NPL; N-acetylneuraminate pyruvate lyase)—Reaction, (d) NeuAc 9-phosphatase, (e) Cytidine 5'-monophosphate N-acetylneuraminic acid synthetase, (CMP-NeuAc synthetase), (f) Cytidine monophosphate-sialic acid transporter (Golgi CMP-NeuAc transporter), and (g) sialyltransferases.

As discussed above, terminal sialylation of approved glycoproteins is the most difficult step to obtain in all the expression systems available so far. As an example, no α2,6-liked sialic acid could be added while it is the prevalent linkage in human blood. In all organisms, the enzymatic machinery required is simply missing (FIG. 6).

The ultimate goal of research in this field is improving the glycosylation process, the yield of production and the quality of the recombinant proteins. The use of expression systems genetically modified for glycosylation would allow to produce glycoproteins with an exceptional homogeneity in their glycanic structures. Such systems could be then used to develop a high level production for proteins of biomedical interest of well-defined structures. The glycosylation engineering in yeast (Hamilton et al., 2003; Roy et al., 2000) has first prevented the addition of polymannosidic chains. Then, enzymes which are necessary to galactosylation and N-acetylglucosaminylation have been added in the systems (Maras et al., 1999; Bretthauer, 2003; Vervecken et al., 2004). However, the addition of the terminal sialic acid is still difficult to realise, due to the number and location enzymes involved in this process but is currently being done in Japan (FIG. 6).

In insect cells, the GTs catalyzing the transfer of immunogenic sugars have been removed and the sialylation has been realised by adding 3 genes encoding for the N-acetylglucosamine 2-epimerase, N-acetylneuraminyl lyase and CMP-Neu5Ac synthase (Jarvis et al., 1998; Aumiller et al., 2003). Authors have created new insect cell lines (SfSWT-3) designed to synthesize their own CMP-sialic acid. The resulting cells express all the 7 mammalian genes necessary to form an N-glycan, produce CMP-sialic acid and sialylated a recombinant protein when cultured in a serum-free growth medium (Aumiller et al., 2003). This work has been patented.

In plants, the first strategy used aimed to prevent the addition of allergenic sugars by stocking proteins in the ER. But in this case, the glycans can not be of the complex type. An other strategy was based on the inhibition of several GTs inside the golgi apparatus. This inhibition can be completed and/or can enter in competition with the endogeneous machinery for maturation. The addition of the sialyl machinery is also in process.

In the case of mammalian cells, work has been realized through the over-expression of an α2,3-ST and a β1,4Gal (Weikert et al., 1999), these enzymes are both present in the genome but their activities vary upon culture conditions. This leads to a wide variability concerning the presence of the terminal Gal and sialic acid and also to extensive microheterogeneity in glycan structures of secretory proteins.

Researches have been mostly oriented in the optimization of the galactosylation and sialylation (Granbenhorst et al., 1999) by introducing an α2,6-ST (Bragonzi et al., 2000). A CHO cell line stably expressing full length α2,6-ST has been established long ago and has also been disappointing. The ratio observed between α2,6 and α2,3-linked terminal sialic acid residues carried was of 40.4% of α2,6- and 59.6% α2,3-sialic acid residues improving pharmacokinetics in clearance studies (Bragonzi et al., 2000). Despite improvement in humanization of cells, the ratio between α2,6 and α2,3-linked terminal sialic acid residues cannot be controlled and is not even favorable to the 6-activity.

In summary, the sialylation is a critical step to control glycan structures in proteins produced by genetic engineering. The main difficulty resides not so much in expressing the lacking activity but in getting the heterologous production system to work successfully. Indeed, 3 main objectives should be met to humanize glycosylation of current expression systems: 1) getting the donor substrate and the relevant transporter needed for this enzyme to work within the Golgi. 2) getting the enzyme properly compartmentalized to eventually compete with endogenous sialyltransferase activity. 3) getting the enzyme able to catalyze sialic transfer to any relevant acceptor substrate.

IIf—Background of the Invention:

The strategy of the inventors is based on the consideration that the full length ST6 enzyme has been so far unable to meet the above objectives, especially the competition with the endogenous ST3 activity existing in most mammalian cells, probably because the gene product is not inserted in intracellular compartments involved with the secretory pathway. The inventors thus developed a procedure which may afford the best opportunity for a transferase CD to reach the golgi compartments where the neoglycoproteins are sorted into secretory vesicles and/or where they meet the engineered ST before/instead of the existing ST3

III—Design of Synthetic Membrane STs

The present invention consists in a procedure which delivers a panel of chimeric STs of known catalytic activity, possessing a membrane anchor to target them to the Golgi apparatus of eukaryotic cells. None of them exist in living cells and are considered as "synthetic STs" because their construction does not need any of the DNA sequence coding for CT, TMD or SR. The relevant oligonucleotides are within 200 pb (60 amino acids) in length and could be designed by informatics and obtain commercially. Using PCR methods, a tagged synthetic anchor is constructed to code for the N-terminal half of the ST protein and fused to the optimized catalytic domain of the hST6GalI.

The invention describes various molecular methods to construct 3 types of membrane chimeric STs:

homologous construct: ST anchor fused to the CD Δ89 of ST6Gal. Synthetic or eventually copied by PCR. In this case, CT+TMD+SR portions are from the same ST: ST3Gal/ST6GalNAc/ST8Sia. The example describes a 200 pb sequence hybrid construct: CT+TMD are from a ST and the SR from another ST. Here too, the minimal size is 200 pb.

Heterologous construct: CT, TMD and SR fragments are from different STs. Here too, the minimal size is 200 pb.

long construct: a CT+TMD+SR1 construct of 200 pb is prepared and fused to a second SR2 construct of at most 200 pb in such a way that SR2 is downstream from SR1. The duplicated constructed can be further ligated at the 3' end to any other SR construct as as repeatedly as needed.

The size of 200 pb has been based on the observation that the shortest N-terminal portion of all human STs is ST6GalNAcIII with CT+TMD+SR=200 pb. This enzyme has virtually no stem.

At present, the inventors have validated a method to construct synthetic fragment of DNA and fuse them to a minimal catalytic domain to generate a novel transferase enzyme of desired activity. Several representative constructs are available for further expression. The synthetic chimeras are active and are being studied in CHO cells using transient expression and confocal microscopy.

Examples

Example 1

Producing the Minimal Catalytic Domain (CD) of hST6Gal I (SEQ ID NO: 43 Coding for SEQ ID NO: 44)

The human ST6Gal I (hST6Gal I) cloned by Legaigneur et al., 2001 was used to amplify the minimal CD cloned into the pFLAG-CMV-vector (Sigma) (Donadio et al., 2003) that was used in all the chimera constructs.

The recombinant vector was first digested to verify the presence of the CD of hST6Gal I. The running agarose gel reveals the presence of a nucleotidic band at around 1000 pb, corresponding to the expected size for the minimal catalytic domain (FIG. 10A-C).

The CD corresponding to the amino acids 90 to 406 of hST6Gal I was obtained by PCR using the following primers:

```
5'BamHI-Δ4:  5'-GAGCCCGGATCCGAG     (SEQ ID NO: 204)
GCCTCCTTC-3'  and

3'Δ4-XbaI:  5'TAACCCTCTAGATTAGC    (SEQ ID NO: 205)
AGTGAATGGTCCGGAAGC-3'.
```

These primers contain BamH1 (5'BamHI-Δ4) and XbaI (3'Δ4-XbaI) restriction sites and the natural stop codon of the sequence. The BamH1 restriction site was used to ligate the CD of hST6Gal 90-406 to the synthetic N-terminal part of other STs to form chimeric enzymes. The XbaI restriction site at the 3' end was used to introduce the chimera inside the pcDNA3.1 vector (Invitrogen) (FIG. 11).

PCR was performed on an I-Cycler apparatus (Biorad), using 2.5 units of ProofStart DNA polymerase (Qiagen), 300 µM of each dNTP (Sigma Aldrich), 1 µM each primer, 1× of ProofStart manufacturer buffer (Qiagen), 1× of manufacturer Q-Solution (Qiagen) and 1.5 mM of $Mg^{2+}$ in a final volume of 50 µl with 200 ng of pFlag-CMV-hST6Gal I-90-406. The reaction was performed as follows: 95° C. for 5 min, followed by 40 cycles of 30 s at 94° C., 30 s at 55° C. and 1 min at 72° C. The amplified PCR product was analyzed by electrophoresis on a 1.5% agarose gel (amplification of one PCR product at the expected size of 1000 pb; FIG. 17B) and purified using the Gel Extraction kit Qiagen according manufacturers' instructions.

Several PCR amplification products were pooled and concentrated to estimate the amount of DNA in an agarose gel (FIG. 10C). Purified PCR products were kept at −20° C. until used.

Example 2

Assembling Synthetic N-Terminal Domains

To create a wide array of STs as sorted by bioinformatic analysis, CT, TMD and SR from distinct STs were synthesized and assembled.

All the selected N-terminal parts of the chimera contain the 3 typical regions of the ST family: the CT, the TMD and the SR. Of note, the SR may be of variable length and could originate from synthetic gene duplication. All of these fragments i.e. CT+TMD+SR have been entirely reconstituted using complementary hybridization and phosphorylation steps as described below.

a—Construction of the Non-Catalytic Domain of hST3Gal III (SEQ ID NO: 151 Encoding SEQ ID NO: 152)

Six sense oligonucleotides and five antisense oligonucleotides corresponding to part of the N-terminal region (1 to 138 pb) sequence of hST3Gal III were designed and synthesized (Eurogentec). This example shows the method of synthesizing a naturally occurring sequence of interest. A FLAG epitope (in Bold and underlined) was added between the initiating codon ATG and the second codon (GGA) of the hST3Gal III sequence:

ATG GACTACAAAGACGATGACGACAAG GGA (SEQ ID NO: 206).

One microgram of each internal nucleotide was phosphorylated using 1 unit of polynucleotide kinase (Eurogentec) in a kinase buffer containing 2 mM of ATP (Sigma). Reaction was performed for 60 min at 37° C., and the incubation finally inactivated for 10 min at 65° C. All the oligonucleotides were separately denatured for 10 min at 80° C. and then mixed for matching. Matching was performed overnight with a decreasing temperature gradient from 80° C. to 20° C. The resulting fragment was then subjected to PCR.

b—Construction of the Non-Catalytic Domain of hST6GalNAc I-74 (SEQ ID NO: 145 Encoding SEQ ID NO: 146)

One of the shortest stem within the ST family is the stem of the hST6GalNAc III, which is composed of around 6 amino acids. A possible N-terminal domain of this ST is of 74 amino acids (CT, TMD and SR) which correspond to 222 pb. Therefore to delineate a construct with the shortest SR, a synthetic N-terminal domain of 222 pb corresponding to the 74 first amino acids of the hST6GalNAc I was reconstituted.

Nine sense oligonucleotides and eight antisense oligonucleotides corresponding to the complete N-terminal region (1 to 222 pb) sequence of hST6GalNAcI were designed and synthesized (Eurogentec). A FLAG sequence (in Bold and underined) was added between the initiating codon ATG and the second codon (GGA) of the hST6GalNAc I sequence:

ATG GACTACAAAGACGATGACGACAAG GGA (SEQ ID NO: 206).

The phosphorylation and the matching reactions were performed as previously described.

c—Synthetic Oligonucleotide Duplication to Assemble the Non Catalytic Domain hST6GalNAc I1-140 (SEQ ID NO: 148)

hST6GalNAc I was selected as the sialyltransferase exhibiting the longest SR (246 aas). In this example, the length of the synthetically reconstituted CT+TMD+SR portion (1- to 35 amino acids residues) was joint to another SR stretch (36-140 amino acids residues) to duplicate the length and be able to add a membrane anchor of 140 amino acids residues as reported in Donadio et al., 2003.

d—Construction of a Hybrid Synthetic Domain: hST3Gal III 1-28-hST6GalNAc I 37-74 (SEQ ID NO: 160)

An hybrid N-terminal region containing first the CT and the TMD of the hST3Gal III (1 to 28 amino acids residues) and second the begin of the SR of hST6GalNAc I (amino acids 37 to 74) was constructed.

The total length of this synthetic hybrid is of 66 amino acids corresponding to 198 nucleotides (SEQ ID NO: 159). Nine sense oligonucleotides and eight antisense oligonucleotides corresponding to the hybride N-terminal region described above (1 to 225 pb), using the sequences of hST3Gal III/hST6GalNAc I, were designed and synthesized (Eurogentec). A FLAG epitope (in Bold) was added between the initiating codon ATG and the second codon (GGA) of the hST3Gal III sequence:

```
                                    (SEQ ID NO: 206)
5'-ATG GACTACAAAGACGATGACGACAAG GGA-3'.
```

The phosphorylation and the matching reaction were performed as previously described.

e—PCR Amplification of the Synthetic Constructs

After the synthetic reconstitution step, the product was amplified by PCR technique using specific primers that bring in the desired restriction sites at each end of the reconstituted DNA fragment in order to ligate them first with the selected CD and then into the vector pcDNA3.1.

The following primers were designated:

```
5'AflII-ST3:  5'-GAGCCCCTTAAGAT    (SEQ ID NO: 207)
GGACTACAAAGACGACGATGACG-3' and

3'ST3-BamHI:  5'-TAAGGGGATCCGC     (SEQ ID NO: 208)
TAGAGTGACTATACTTACTGGA-3;

5'AflII-ST6:  5'-GAGCCCCTTAAGAT    (SEQ ID NO: 209)
GGACTACAAAGACGACGATGACG-3' and

3'ST6-BamHI:  5'-TAAGGGGATCCGG     (SEQ ID NO: 210)
TTGTGGAGGAACGGGA-3';

3'ST6-BamHIn°2:  5'-TAAGGGGATC     (SEQ ID NO: 211)
CTCTGGGTGACAGTGTGTTCAC-3'.
```

These primers contain AflII (5'AflII-ST3 and 5'AflII-ST6) and BamHI (3' ST3-BamHI, 3' ST6-BamHI and 3' ST6-BamHI no. 2) restriction sites to ensure the further ligations.

PCRs were carried out with the primer pairs set described in Table 5. They were performed on a PCR apparatus (I-Cycler, Biorad) with 5 µL of the each synthetic fragments in a solution containing 2.5 units of ProofStart DNA polymerase (Qiagen), 300 µM of each dNTP (Sigma Aldrich), 1 µM each primer, 1× of ProofStart manufacturer buffer (Qiagen), 1× of manufacturer Q-Solution (Qiagen) and 1.5 mM of $Mg^{2+}$ in a final volume of 50 µL. a The reaction was performed as follows: 95° C. for 5 min, followed by 40 cycles of 30 s at 94° C., 30 s at 55° C., 53° C., 53° C. and 55° C. respectively for hST3Gal III (SEQ ID NO: 151), hST6GalNAc I-74 (SEQ ID NO: 145), hST6GalNAc I-140 (SEQ ID NO: 147) and hST3Gal III-28/37-hST6GalNAc I-74 (SEQ ID NO: 159), and 1 min at 72° C. The amplified PCR product was analyzed by electrophoresis on a 2% agarose gel, according to the PCR product size (Table 5):

hST3 Gal III: only one PCR product was amplified at an estimated size of 170 pb, which corresponds to the expected size of 174 pb (FIG. 11).

hST6 Gal NAc I: FIG. 13 shows one amplified PCR product with an estimated size of 270 pb, which corresponds to the expected size of 270 pb.

hST6GalNAc I-140: a 468 pb nucleotidic sequence was amplified (FIG. 15).

hST3Gal III-28-hST6GalNAc I37-74: a 249 pb nucleotide sequence (FIG. 17) was amplified.

The PCR products were purified using the Gel Extraction kit Qiagen according manufacturers' instructions.

The PCR product of hST6GalNAc I-140 was submitted to direct both strand DNA sequencing by Genome Express (Meylan, France).

The PCR product of hST3Gal III and hST6GalNAc I-74 were ligated to the CD (SEQ ID NO: 43) before being introduced in the pcDNA3.1 vector (Invitrogen) to be also further sequenced by Genome Express (Meylan, France).

The hST3Gal III-28-hST6GalNAc I37-74 synthetic fragment was ligated with the CD (SEQ ID NO: 43) and directly sequenced in both strand prior its introduction into the pcDNA3.1 vector (Invitrogen).

f—Quantification of the PCR Products

All the PCR products were pooled and concentrated according to each synthetic construct. Two volumes ethanol and 0.1 volume of 3 M sodium acetate, pH 5.2 were added to PCR product samples. The mix was incubated for 30 min at −20° C. and centrifuged 20 min at 10000 g at 4° C. The pellets were washed with 100 µL of 70% ethanol and a centrifugation was run for 10 min at 10000 g at 4° C. Then supernatants were removed and the pellets dried and resuspended in 50 µL of purified water. Samples were conserved at −20° C. until use. Five microliters of the four concentrated synthetic fragments were loaded on a 2% agarose gel to estimate their quantity (FIGS. 11, 12, 13 and 14).

Example 3

Assembling Non-Catalytic N Terminal Membrane Domains with a Sialyltransferase Activity a—Digestions and Purification All the PCR products (either the synthetic N-terminal constructs or the catalytic domain) were digested by the BamHI restriction enzyme.

200 nanograms of the synthetic N-terminal constructs were digested in a solution containing 3 units of the BamHI restriction enzyme, 0.1 µg.µL$^{-1}$ of Bovin Serum Albumin and 1× of the appropriate manufacturer's buffer E (Promega) in a final volume of 20 µL.

500 nanograms of the CD were digested with 5 units of BamHI, 0.1 µg.µL$^{-1}$ of Bovin Serum Albumin and 1× of buffer E (Promega) in a final volume of 20 µL.

Digestions were performed for 90 min at 37° C. and the incubation was finally inactivated for 15 min at 65° C. Digested DNA was purified using the PCR purification kit (Qiagen).

b—Ligation

Each of the N-terminal fragments were ligated to the CD fragment in a solution containing 1.5 units of T4 DNA ligase, 1× of the ligation buffer, both commercialized (Promega), 62.5 ng, 78.2 ng and 75 ng, respectively for hST3Gal III, hST6GalNAc I-74, and the hybrid hST3Gal III-28-hST6GalNAc I37-74 fragment and 100 ng of CD in a final volume of 20 µL. The mix was incubated at 15° C. overnight and followed by an inactivation step for 10 min at 70° C. (FIG. 17).

c—Amplification of the Tagged Synthetic Insert

To verify the proper ligation, the ligation products were directly submitted to PCR using the following primers pairs: 5'AflII-ST3/3'Δ4-XbaI, 5'AflII-ST6/3'Δ4-XbaI and 5'AflII-ST3/3'Δ4-XbaI respectively for the ST3/CD, the ST6GalNAc-74/CD and the hybrid/CD.

Reactions were carried out using 2.5 units of ProofStart DNA polymerase (Qiagen), 300 µM of each dNTP (Sigma Aldrich), 1 µM each primer, 1× of ProofStart manufacturer buffer (Qiagen), 1× of manufacturer Q-Solution (Qiagen) and 3 mM of Mg$^{2+}$ in a final volume of 50 µL. The reaction was performed as follows: 95° C. for 5 min, followed by 40 cycles of 1 min at 94° C., 1 min at 57° C., and 1 min 30 s at 72° C.

The amplified PCR products were analyzed by electrophoresis on a 1.5% agarose gel:

hST3Gal III/CD synthetic insert (SEQ ID NO: 167): a 1200 pb PCR product was amplified (FIG. 12), which corresponds to the expected size of the ligated DNA fragment: ST3Gal III plus CD.

hST6GalNAc I-74/CD insert (SEQ ID NO: 161): a 1200 pb PCR product was amplified (FIG. 14), which corresponds to the expected size of the ligated DNA fragment: ST6GalNAc I plus CD that is of 1225 pb exactly.

hST3GalIII-28/37hST6GalNAc-74/CD insert (SEQ ID NO: 175): a 1200 pb PCR product was amplified (FIG. 17) which corresponds to the expected size of the ligated DNA fragment hST3GalIII-29/hST6GalNAc37-74 plus CD.

The amplified PCR products were purified using the Gel Extraction kit Qiagen according manufacturers' instructions.

Amplified PCR products of the same synthetic ST were pooled, concentrated and quantified on a 1.5% agarose gel (FIGS. 12, 13 and 16), as previously described above, to obtained enough quantity of DNA to ligate the chimera into the pcDNA3.1 vector.

d—Cloning the Synthetic ST Insert into an Expression Vector

1—Digestion and Purification

Synthetic inserts such as the hST3Gal III/CD or hST6GalNAc I-74/CD insert were ligated into the pcDNA3.1 vector into AflII and XbaI restriction sites.

The synthetic insert and the pcDNA3.1 vector (FIG. 12) (Invitrogen) were first digested by the restriction enzyme XbaI:

for each construction, 500 ng of vector were digested using 2.5 units of XbaI (Promega), 0.1 µg.µL$^{-1}$ of BSA and 1× of the appropriate buffer D, supplied by manufacturer (Promega), in a final volume of 20 µL, following the manufacturer's instructions;

the insert was digested with 2 to 2.5 units of XbaI (Promega), depending on the quantity of insert available after PCR (e.g. 200 ng hST3Gal III/CD, hST3Gal III-28/hST6GalNAc I 37-74/CD and 500 ng of hST6GalNAc I-74/CD were respectively digested with 2 and 2.5 units of XbaI), 0.1 µg.µL$^{-1}$ of BSA and 1× of Buffer D (Promega), in a final volume of 20 µL.

The digestions were performed at 37° C. during 60 min and inactivated at 65° C. for 15 min.

The digested products were then submitted to a digestion by the restriction enzyme AflII following the manufacturer's instructions (Biolabs): using the appropriate number enzyme units, depending on the DNA quantity (2, 2, 2.5 and 2.5 units, respectively for hST3Gal III/CD, hST3Gal III-28/hST6GalNAc I 37-74/CD, hST6GalNAc I-74/CD and pcDNA3.1), 0.1 µg.µL$^{-1}$ of BSA and 1× of buffer 2 (Biolabs) in a final volume of 50 µL. The digestions were carried out at 37° C. for 60 min and inactivated at 65° C. for 20 min. The digestions were purified with the PCR purification kit (Qiagen).

2—Ligation

The ligation conditions were calculated according to the following formula:

$$X \text{ ng insert} = \frac{(Y \text{ pb insert})(x \text{ ng } vecteur \text{ pcDNA3.1})}{\text{size in } pb \text{ } vecteur \text{ pcDNA3.1} \approx 5428} \times \text{molar ratio } \frac{\text{Insert}}{\text{Vecteur}}$$

where the size of the insert is around 1200 pb for the synthetic construct (e.g. hST3Gal III/CD, hST3Gal III-28/hST6GalNAc I 37-74/CD or hST6GalNAc I-74/CD), the size of the vector pcDNA3.1 is of 5428 pb, the quantity of vector used is of 50 ng or 100 ng, and finally the molar ratio of Insert/Vector is of 3/1.

Construction of pcDNA3.1/ST3/CD recombinant vector was performed using 33 ng of the digested chimera hST3Gal III/CD (SEQ ID NO: 167), 50 ng of pcDNA3.1 digested vector, 3 units of T4 DNA ligase enzyme (Promega) and 1× of the ligation buffer in a final volume of 15 µL. The mix was incubated overnight at 4° C. and the reaction was inactivated for 10 min at 70° C.

The second construction of pcDNA3.1/ST6/CD recombinant vector was performed using 66.5 ng of the digested chimera hST6GalNAc I-74/CD (SEQ ID NO: 161), 100 ng of pcDNA3.1 digested vector, 3 units of T4 DNA ligase enzyme (Promega) and 1× of the ligation buffer in a final volume of 15 µL. The mix was incubated overnight at 15° C. and the reaction was inactivated for 10 min at 70° C.

The third construction of pCDNA3.1/HYB/CD recombinant vector was performed using 66.5 ng of the digested chimera hST3Gal III-28/hST6GalNAc I 37-74/CD (SEQ ID NO: 175), 100 ng of pCDNA3.1 vector, 3 units of T4DNA ligase enzyme (Promega) and 1× of ligation buffer in a final volume of 15 µL. The mix was incubated overnight at 15° C. and the reaction was inactivated for 10 min at 70° C.

3—Cloning

Competent Cells Chemical Transformation

One Shot® TOP10 chemically competent *E. coli* (Invitrogen) were transformed with the recombinant vector following the manufacturer's instructions. Two microliters of each ligation reaction were added to 25 µL of chemical competent cells and mixed by taping gently. The vials were incubated on ice for 30 min. The chemical transformations were performed for exactly 40 s in a 42° C. water bath. Vials were removed from the 42° C. bath and place on ice during 2 min. Two hundred and fifty microliters of pre-warmed S.O.C. medium, provided by Invitrogen, were added into each vial under sterile conditions. Then, the mixtures were shaked at 37° C. for exactly 1 h at 225 rpm in a shaking incubator. Each transformations were spread on LB agar plates (10 g of bacto-tryptone, 5 g of bacto-yeast extract, 10 g of NaCl and 15 g of agar per liter of solution from GibcoBRL) containing 50 µg/mL of ampicillin under sterile conditions. Plates were inverted, incubated at 37° C. overnight and maintained at 4° C. the next day until the transformants selection.

Amplification

At the end of the day, single colonies were isolated and inoculated into 3 mL of LB (10 g of bacto-tryptone, 5 g of bacto-yeast extract, 10 g of NaCl from Difco) containing 50 µg/mL of ampicillin. The growth was ensured at 37° C. in a shaking incubator overnight. The next day, glycerol stocks of cultures were prepared by mixing 0.85 mL of cultures with 0.15 mL of sterile glycerol and transferred to a cryovial. Glycerol stocks were stored at −80° C. until sequence verification and further use.

Minipreparation of Plasmids

The recombinant vectors were purified by Minipreparation procedure (Maniatis), 1.5 mL of cultures were isolated and centrifuged for 5 min at 10000 g to pellet the bacteria. Cold Solution I (5 mM glucose, 25 mM Tris-HCl pH 8.0, 10 mM EDTA pH 8.0) was added (100 µL) to resuspend the pellet, 200 µL of Solution II (0.2 N NaOH and 1% SDS) and 150 µL of Solution III (3 M potassium and 5 M acetate) were also added. The mixtures were gently mixed by vortexing, placed on ice 5 min, and centrifuged at 4° C., 5 min at 15000 g. The supernatants were taken and 1 volume of isopropanol was added. The minipreparations were incubated 5 min at room temperature and centrifuged at 4° C., 5 min at 15000 g. Then, the supernatants were removed. The DNA pellet was dried and resuspended into 50 µL of water. The quantity of DNA was measured using a spectrophotometer DO apparatus (Biophotometer, Eppendorf). At least 30 minipreparations are performed to screen the presence of the interest insert for each construction.

One microgram of each of the 30 minipreparations was double digested using AflII and XbaI restriction enzyme in order to verify the presence of the insert. First, the digestion solution contained 10 units of XbaI (Promega), 0.1 µg.µL$^{-1}$ of BSA and 1× of the appropriate manufacturer buffer D (Promega) in a final solution of 20 µL. Digestions were performed in a 37° C. water bath for 1 h and inactivated at 65° C. for 15 min. Samples were secondly digested using 10 units of AflII restriction enzyme (Biolabs), 0.1× of BSA and 1× of Buffer 2 (Biolabs) in a final volume of 50 µL. Reactions were carried out in a 37° C. water bath for 1 h and inactivated at 65° C. for 20 min. The digested samples were all purified using the PCR purification kit (Qiagen). The digestion products were loaded on a 1.5% agarose gel to detect the presence of the chimeric insert. The electrophoresis was run at 100 V during around 35 min.

In the case of the pcDNA3.1/ST3/CD and pcDNA3.1/ST6/CD, an insert of 1200 pb was detected (FIG. 19C or 23C). The size of this insert corresponds exactly to the expected size of the reconstituted chimera ST3Gal III/CD or ST6GalNAc I-74/CD.

The positive clones were fully sequenced to assess the expected inserted DNA sequence.

Sequencing

The cloning steps were verified by both strands DNA sequencing by Genome Express (Meylan, France) using universal primers present inside the vector: T7 Promoter and BGH Reverse.

The final expected sequences of the three chimeras ST3Gal III/CD (SEQ ID NO: 167), hST3Gal III-28/hST6GalNAc I 37-74/CD (SEQ ID NO: 175), and ST6GalNAc I-74/CD (SEQ ID NO: 161). The nucleotidic sequence obtained was aligned to the expected sequence and the alignment revealed 100% identity between these three sequences. The deduced amino acid sequence was also aligned with the expected sequence of the chimera (http://www.infobiogen.fr/services/analyseq/cgi-bin/alignp_in.pl) and it shows 100% identity between two of theses amino acid sequences.

The nucleotide sequence obtained for hST6GalNAc I-140 showed 84% identity with the theoretical sequence. The missing parts of the sequence are the 36 first and the 39 last nucleotides, they both correspond to the primers designed to sequence the DNA fragment in both strands. Moreover the amino acids alignment between the expected and the resulting sequences showed 76.9% identity. The 12 first and the 24 last amino acids are not found due to their correspondences with the specific primers used for the sequencing.

Minipreparation

After the DNA insert sequence verification, the recombinant plasmids were amplified in 100 mL cultures to obtain high quantity of each construction (pcDNA3.1/ST3/CD and pcDNA3.1/ST6/CD and pcDNA3.1/HYB/CD). A single colony of each plasmid from a freshly streaked selective plate was picked and inoculated into a starter 3 mL culture of LB medium containing the selective antibiotic (ampicillin 50 µg.µL$^{-1}$). The cultures were incubated overnight at 37° C. with vigorous shaking. The started cultures were diluted into 100 mL of selective LB medium and incubated once again overnight at 37° C. with vigorous shaking. The bacterial cells were harvested and the recombinant vectors were purified using the QIAGEN® Plasmid Midi Kit (Qiagen) following the manufacturer's instructions. The yield was determined with an UV spectrophotometry to quantify the DNA concentration (biophotometer, Eppendorf). Each construct was stored at −20° C. until used.

Example 4

Functional Expression of the Synthetic Constructs in CHO Cells

The expressed inserts are represented in FIG. 15.

A—Transient Expression of Synthetic ST6s in CHO Cells

The CHO-K1 cell line was used to express constructions as described by Donadio et al. (2003). Briefly, cells were grown in Ham medium supplemented with 10% of Fetal Calf Serum (FCS), fungizone (2.5 µg/mL) and gentamicin (50 µg/mL) at 37° C. in a 5% $CO_2$ incubator. Transfections with FLAG-CMV vector constructs were carried out using the LipoFectamine reagent following the recommended procedure of manufacturer, with 3 µg of recombinant plasmid DNA. Immunofluorescence experiments were run after 36-48 h of transfection.

Double labelling with FITC-SNA and anti-FLAG mAb was performed as described by Donadio et al. (2003). Cells were fixed in a 1% para-formaldehyde (PFA solution, saturated with 1% BSA, washed with phosphatase-buffered saline (PBS) and incubated with FITC-SNA. Cells expressing a ST6 activity are labeled in green. Samples were washed twice with PBS and fixed in 1% PFA, further washed with PBS, incubated in 0.05 M $NH_4Cl$ and washed with PBS. Cells were permeabilized with 0.1% Triton in PBS and further incubated in PBS containing 10% goat serum. Anti-FLAG labeling was carried out using the M2 anti-FLAG mAb (1:600) in PBS containing 5% inactivated goat or horse serum followed by incubation with a secondary anti-mouse IgG antibody labeled with Alexa Fluor 568 (1:200) in the same buffer. Cells expressing the FLAG-tagged sialyltransferase are labeled in red. After washings, cells were mounted in Mowiol and kept at −20° C. in dark. Confocal microscopy was performed with an Olympus or Leica instrument. Confocal images were processed with a Metamorph Imaging System. Volumes were originally traced as 24-bit TrueColor Images and transferred to Adobe Photoshop as RGB TIFF or JPG files. Under such conditions, untransfected CHO-K1 cells are not labeled with either of the above reagents.

B—Enzymatic Activity of Synthetic ST6s in CHO Cells

B1 Activity of the Optimized Catalytic Domain of hST6Gal I

The hST6Gal I CD, was cloned into the pFLAG-cytomegalovirus vector (pFLAG-CMV1) from Sigma, using a pre-protrypsinogen signal peptide. This construction and these plasmids were previously characterized in vitro by Legaigneur et al. (2001) and shown to give an enzymatic protein of the expected size released into the cell medium. This soluble CD was found equally active on known exogenous glycoprotein acceptors of various degree of branching.

To generate the minimal CD soluble form of hST6Gal I, a PCR fragment encoded between the 5' (5'-TAATA<u>AAGCTT</u>GAGGCCTCCTTCCAG-3') (SEQ ID NO: 212) introducing a HindIII restriction site and the 3' (5'-CTATT<u>GGATCC</u>TTAGCAGTGAATGGT-3') (SEQ ID NO: 213) encoding a BamHI site was generated. The fragment was then HindIII/BamHI digested and inserted into the pFLAg-CMV1 mammalian expression vector and subcloned into the pBluescript II KS vector (Stratagene) for further constructions.

The minimal ST6Gal I CD (SEQ ID NO: 44) tagged with the FLAG epitope (FIG. 18) is expressed at a high level in CHO cells (FIG. 18B, D). Its activity and localization was characterized using double labeling with anti-FLAG monoclonal Antibody and FITC-SNA. Interestingly, the mutant FLAG-CD was highly efficient in sialylating cell surface acceptors as shown in FIGS. 18C and D.

B2—Functional Expression of ST8/CD

CHO-K1 cells were transiently transfected with chimeric forms of hST8SiaIV (1-67)/CD (SEQ ID NO: 173), hST8SiaII (1-79)/CD (SEQ ID NO: 171). Their activity and localization were characterized using double labeling with anti-FLAG monoclonal Antibody and FITC-SNA, as shown in FIG. 19.

Both hST8SiaIV (1-67)/CD (SEQ ID NO: 174) and hST8SiaII (1-79)/CD (SEQ ID NO: 172) chimeras were found active on endogeneous cell acceptors as the SNA lectin reveals an intense cell surface labeling (FIGS. 19B, C, E and F), indicating that the CD is active independently of the origin of N-Terminal part fused to the catalytic domain. The α2,6-sialyltransferase activity is maintained for the both chimeras, indicating that in the chimerical enzyme, the information contained in the minimal CD is necessary and sufficient for acceptor recognition and transfer efficiency.

B3—Functional Expression of ST3/CD and Hybrid ST3-ST6GalNAc/CD

CHO-K1 cells were transiently transfected with chimeric constructs of hST3Gal III/CD (SEQ ID NO: 167), and ST3 1-28-ST6GalNAc37-74/CD (SEQ ID NO: 175). Their activity and localization were characterized using double labeling with anti-FLAG monoclonal Antibody and FITC-SNA, as shown in FIG. 19.

Again, both chimeras were found active on endogeneous acceptors as SNA binding reveals an intense cell surface labeling (FIGS. 19B, C, E and F). This indicates that the CD is active independently of the origin of CT+TMD+SR added. Since α2,6-sialyltransferase activity is maintained for both chimeras, it can be also concluded that the information contained in the minimal CD is necessary and sufficient for full transfer efficiency.

Therefore, fusing ST3/8 sequences upstream from the CD, does not alter the expression of a ST6 catalytic activity. Since rat and human ST3 GalIII and more generally rodent and mammalian ST3Gal lIII are identical in their N-terminal (CT+TMD+juxtamembrane SR) portion, it also appears that exchanging any of this peptide portion with non-human heterologous has no effect on ST6 catalytic activity. Furthermore, substitution of CT, TMD and SR with heterologous portions selected among enzymes of O-glycosylation like ST GalNAcI does not alter recognition of intracellular acceptors nor enzymatic activity.

B4—Functional Expression of hST6GalNAc I-74/CD and hST6GalNAc 258/CD

A similar approach was used to estimate the expression and activity of hST6GalNAc I (1-74)/CD (SEQ ID NO: 162) and hST6GalNAc I-258/CD (SEQ ID NO: 166) enzymes. Both chimeric transferases are active: SNA binding revealed a similar intense cell surface sialylation and the FLAG labeling shows identical localization within the Golgi (FIGS. 21G, H and I).

It can thus be concluded that the length of the SR region can be widely variable and extended up to 258 residues without affecting the functional expression and intracellular localization of a chimerical ST6Gal catalytic activity. This also further confirms that the length of the heterologous N-terminal membrane anchor does not affect the biological active conformation of the newly designed sialyltransferase.

Based on the above examples, it can be stated that the process described in the invention can abolish the regulatory control of the SR region over the CD activity. As a result, any possible combination of CT+TMD+SR among glycosyltransferases (sialyltransferases) of the N- or O-glycosylation pathway can be selected to equip host cells with a needed transferase activity through a relevant CD. Furthermore, the process described in the invention is also able to target a needed activity in intracellular compartments in which neosynthesized glycoproteins migrate to the cell surface. This finding is of crucial importance for properly sorting and secreting sialylated proteins of therapeutic interest in cells (from yeast to human) engineered as described in the invention.

Example 5

Construction of a Hybrid Synthetic Domain: hST3Gal III/hST8Sia II/hST6GalNAc I, and Fusion to the CD of hST6Gal I An hybrid N-terminal region (SEQ ID NO: 180) containing first the CT of hST3Gal III (1 to 8 amino acids residues; SEQ ID NO: 66), then the TMD of hST8Sia II (7 to 23 amino acids residues; SEQ ID NO: 120) and finally the SR of hST6GalNAc I (amino acids 36 to 74; SEQ ID NO: 130) was constructed. A FLAG epitope (in Bold) was added between the initiating codon ATG and the second codon (GGA) of the hST3Gal III sequence:

```
                                         (SEQ ID NO: 206)
5'-ATG GACTACAAAGACGATGACGACAAGGGA-3'
```

The total length of this hybrid is 72 amino acids (SEQ ID NO: 180) corresponding to 216 nucleotides (SEQ ID NO: 179). Eight sense oligonucleotides and seven anti-sense oligonucleotides corresponding to the hybrid N-terminal region described above (1 to 216 nucleotides), using the sequences of hST3Gal III/hST8Sia II/hST6GalNAc I, were designed and synthesized (Eurogentec).

The phosphorylation and the matching reaction were performed as previously described.

PCR Amplification of the Synthetic Construct

After the synthetic reconstitution step, the product was amplified by a high fidelity PCR using specific primers that bring in the desired restriction sites at each end of the reconstituted DNA fragment in order to ligate it into the pcDNA3.1 vector. The AflII and BamHI restriction sites were respectively introduced on the 5' and the 3' extremities.

The following primers were designated:

```
                                         (SEQ ID NO: 207)
5'AflII-ST3:  5'-GAGCCCCTTAAGATGGACTACAAA
GACGATGACG-3' and (SEQ ID NO: 214)
3'ST6-BamHIn°3:  5'-TAAGGGGGATCCGGTTGTC
CTCCTTGCCCT-3'
```

The PCR was performed on a PCR apparatus (I-cycler, Biorad) with 5 µL, of the synthetic fragment in a solution containing 1× of ProofStart manufacturer buffer and 1× of manufacturer Q-Solution, 1.5 mM of $Mg^{2+}$, 300 µM of each dNTP (Sigma Aldrich), 1 µM forward primer AflII-ST3, 1 µM reverse primer ST6-BamHI no. 3, 2.5 units of ProofStart DNA polymerase (Qiagen) in a final volume of 50 µL. The thermocycling profile used was: 95° C. for 5 minutes, followed by 40 cycles of 30 seconds at 94° C., 30 seconds at 55° C. and 1 minute at 72° C.

The amplified PCR products were analysed by electrophoresis on a 2% agarose gel. A 240 pb nucleotidic sequence was amplified which corresponds to the expected size of the fragment (FIG. 22 lane 1). The PCR products were purified using the Gel Extraction Kit (QIA GEN) according to manufacturer's instructions.

Quantification of the PCR Product

All PCR products were pooled and concentrated. Two volumes of ethanol and 0.1 volume of 3 M sodium acetate, pH 5.2, were added to the PCR products. The mix was incubated for 30 min at −20° C. and centrifuged 20 min at 10000 g at 4° C. The pellet was washed with 100 µL of 70% ethanol, centrifuged again 10 min at 10000 g at 4° C. Then, the supernatant was removed and the pellet dried and resuspended in 30 µL double distilled water. DNA sample was conserved at −20° C. until use.

Three microliters of the concentrated fragment was loaded on a 2% agarose gel to estimate its quantity (FIG. 22 lane 3). Ligation of the Catalytic Domain into an Expression Vector, pcDNA3.1(+)

1—Digestions and Purifications

The nucleotide sequence of the catalytic domain CD of hST6Gal I (SEQ ID NO: 43) was ligated into the pcDNA3.1 vector into BamHI and XbaI restriction sites.

Both pcDNA3.1(+) vector and CD were first digested by the BamHI restriction enzyme:

500 ng of the CD were digested with 5 units of BamHI (Promega), 0.1 µg.µL$^{-1}$ of Bovin Serum Albumin and 1× of buffer E (Promega) in a final volume of 20 µL.

1 µg of the pcDNA3.1 vector was digested with 10 units of BamHI (Promega), 0.1 µg.µL$^{-1}$ of Bovin Serum Albumin and 1× of buffer E (Promega) in a final volume of 20 µL.

Digestions were performed for 60 min at 37° C. and the incubations were finally inactivated for 15 min at 65° C. Digested products were purified using the PCR purification Kit (QIAGEN).

The digested products were then submitted to a digestion by the restriction enzyme XbaI (Promega), following the manufacturer's instructions: using the appropriate enzyme units number, depending on DNA quantity (5 and 6, respectively for CD and pcDNA3.1), 0.1 µg.µL$^{-1}$ of BSA and 1× of buffer D (Promega) in a final volume of 50 µL. The digestions were carried out at 37° C. for 60 min. The digestions were purified using the PCR purification Kit (QIAGEN).

2—Ligation

The ligation conditions were calculated according to the formula previously mentioned. The size of the insert CD is around 960 pb, the size of the vector pcDNA3.1 is 5428 pb, the quantity of vector used is 100 ng, and finally the molar ratio of Insert/Vector is 3/1.

The construction of pcDNA3.1/CD recombinant vector was performed using 53 ng of the double digested CD, 100 ng of pcDNA3.1 double digested vector, 6 units of T4 DNA ligase enzyme (Promega) and 1× ligation buffer in a final volume of 20 μL. The mix was incubated overnight at 15° C. and the reaction was inactivated for 10 min at 70° C.

3—Cloning

Competent Cells Chemical Transformation

One Shot® TOP10 Chemically Competent *E. coli* (Invitrogen, Life Technologies) were transformed with the recombinant vector following manufacturer's instructions. Five microliters of the ligation product were added to 50 μL aliquot of TOP 10 cells and mixed by tapping gently. The mix was incubated on ice for 30 minutes, then heat-shocked for exactly 30 seconds in a 42° C. water bath and placed on ice for 2 min. Two hundred and fifty microliters of preheated SOC medium (Invitrogen) were added to the transformation reaction and incubated at 37° C. for one hour with shaking at 250 rpm. The transformation reaction was spread on LB agar plates (composition mentioned previously) containing 50 $\mu g.\mu ml^{-1}$ of ampicillin. Plates were incubated overnight at 37° C.

Amplification

At the end of the next day, single colonies were picked and incubated, with 3 ml of LB broth (composition mentioned previously) containing 50 $\mu g.ml^{-1}$ of ampicillin, overnight at 37° C. with shaking at 250 rpm.

Minipreparation of Plamsids

The recombinant vectors were purified from 1.5 mL aliquots of the previous cultures using the QIAprep Spin Miniprep Kit provided by QIAGEN and following manufacturer's instructions. Twenty-four minipreparations were performed to screen the presence of the insert.

Five microliters of each of the 24 minipreparations were double digested using XbaI and BamHI restriction enzymes in order to verify the presence of the insert.

First, the digestion solution contained 12 units of XbaI (Promega), 0.1 $\mu g.\mu L^{-1}$ of BSA and 1× of buffer D (Promega) in a final volume of 10 μL. Digestions were performed for 2 hours at 37° C. Samples were secondly digested using 20 units of BamHI (Promega) and 1× of buffer E (Promega) in a final volume of 20 μL. Reactions were carried out overnight at 37° C. The digestion products were loaded on a 1.5% agarose gel to detect the presence of the CD. An insert of around 1000 pb was detected (FIG. 23) which corresponds to the expected size of the CD (960 pb).

One positive clone has been selected for the next steps of the construction.

Ligation of the N-Terminal Region into pcDNA3.1/CD Recombinant Vector

1—Digestions and Purifications

The nucleotide sequence of the N-terminal region (SEQ ID NO: 179) was ligated into the pcDNA3.1/CD recombinant vector into BamHI and AflII restrictions sites. Both N-terminal fragment and pcDNA3.1/CD recombinant vector were first digested by the BamHI restriction enzyme:

300 ng of the N-terminal fragment were digested with 5 units of BamHI (Promega), 0.1 $\mu g.\mu L^{-1}$ of BSA and 1× of buffer E (Promega) in a final volume of 20 μL.

2 μg of pcDNA3.1/CD recombinant vector were digested with 20 units of BamHI (Promega), 0.1 $\mu g.\mu L^{-1}$ of BSA and 1× of buffer E (Promega) in a final volume of 20 μL.

Digestions were performed for 100 min at 37° C. and the incubations were finally inactivated for 15 min at 65° C. Digested products were purified using the PCR purification Kit (QIAGEN).

The digested products were then submitted to a digestion by the restriction enzyme AflII (New England BIOLABS), following the manufacturer's instructions: using the appropriate enzyme units number, depending on DNA quantity (10 and 20, respectively for N-terminal fragment and pcDNA3.1/CD recombinant vector), 1× of BSA and 1× of buffer 2 (New England BIOLABS) in a final volume of 50 μL. The digestions were carried out at 37° C. for 60 min and the incubations were finally inactivated for 20 min at 65° C. The digestions were purified using the PCR purification Kit (QIAGEN).

2—Ligation

The ligation conditions were calculated according to the formula previously mentioned. The size of the insert N-terminal fragment is 240 pb, the size of the pcDNA3.1/CD recombinant vector is 6388 pb, the quantity of vector used is 100 ng, and finally the molar ratio of Insert/Vector is 1/1.

The construction of pcDNA3.1/N-terminal fragment/CD recombinant vector was performed using 5 ng of the digested N-terminal fragment, 100 ng of pcDNA3.1/CD digested recombinant vector, 6 units of T4 DNA ligase enzyme (Promega) and 1× of ligation buffer in a final volume of 20 μL. The mix was incubated overnight at 15° C. and the reaction was inactivated for 10 min at 70° C.

3—Cloning

Competent Cells Chemical Transformation

One Shot® TOP10 Chemically Competent *E. coli* (Invitrogen) were transformed with the ligation product following manufacturer's instructions and as previously described.

Amplification

At the end of the next day, single colonies were picked and incubated, with 3 ml of LB broth (composition mentioned previously) containing 50 $\mu g.ml^{-1}$ of ampicillin, overnight at 37° C. with shaking at 250 rpm.

Minipreparation of Plasmids

The recombinant vectors were purified from 1.5 mL aliquots of the previous cultures using the QIAprep Spin Miniprep Kit provided by QIAGEN following manufacturer's instructions. Twenty four minipreparations were performed to screen the presence of the insert.

Five microliters of each of the 24 minipreparations were double digested using XbaI and AflII restriction enzymes in order to verify the presence of the insert (N-terminal fragment+CD; SEQ ID NO: 181).

The digestion solution contained 20 units of XbaI (BIOLABS), 20 units of AflII (BIOLABS), 1× of BSA (BIOLABS) and 1× of buffer 2 (BIOLABS) in a final volume of 20 μL. Digestions were performed for 2 hours and 30 min at 37° C. The digestion products were loaded on a 1.5% agarose gel to detect the presence of both N-terminal region and CD. An insert of around 1200 pb was detected (FIG. 24*a*) which corresponds to the expected size of the insert.

A PCR was finally performed on five minipreparation samples to verify the presence of the insert DNA (N-terminal fragment followed by the CD: SEQ ID NO: 181). The PCR was performed on a PCR apparatus (I-cycler, Biorad) with 1 μL of each of the minipreparation samples in a solution containing 1× of ProofStart manufacturer buffer and 1× of manufacturer Q-Solution, 3 mM of $Mg^{2+}$, 300 μM of each dNTP (Sigma Aldrich), 1 μM forward primer AflII-ST3, 1 μM reverse primer Δ4-XbaI, 2.5 units of ProofStart DNA polymerase (Qiagen) in a final volume of 50 μL.

The oligonucleotides included in the reaction were as follows:

(SEQ ID NO: 207)
5'AflII-ST3: 5'-GAGCCCCTTAAGATGGACTACAAA
GACGATGACG-3' and (SEQ ID NO: 205)
3'Δ4-XbaI: 5'-TAACCCTCTAGATTAGCAGTGAATGG
TCCGGAAGC-3'

The thermocycling profile used was: 95° C. for 5 minutes, followed by 40 cycles of 1 min at 94° C., 1 min at 57° C. and 1 minute 30 s at 72° C. The amplified PCR products were analysed by electrophoresis on a 1.5% agarose gel: a 1200 pb nucleotidic sequence was amplified for each minipreparation sample which corresponds to the expected size of the total insert (FIG. 24b).

Sequencing

The cloning steps were verified by both strands DNA sequencing by GENOME express (Meylan, France) using universal primers present inside the vector: T7 promoter and BGH reverse.

The nucleotidic sequence obtained was aligned to the expected sequence and the alignment revealed 100% identity. The deduced amino acid sequence was also aligned with the expected sequence SEQ ID NO: 181 of the chimera and it shows 100% identity.

Midipreparation

After the DNA insert sequence verification, the recombinant plasmid was amplified in 100 mL culture to obtain high quantity of the construction. Four hundred microliters of the corresponding 3 mL LB broth culture mentioned previously were inoculated into 100 mL LB broth containing 50 μg.ml$^{-1}$ of ampicillin, and incubated overnight at 37° C. with shaking at 250 rpm. The bacterial cells were harvested and the recombinant vectors were purified using the QIAGEN Plasmid Midi Kit (Qiagen) following manufacturer's instructions. The yield was determined with an UV spectrophotometer to quantify the DNA concentration. The construct was stored at –20° C.

Cell Culture: Expression of the Chimeric Enzyme hST3Gal III/hST8Sia II/hST6GalNAc I/CD (SEQ ID NO: 182) in CHO Cells CHO-K1 cells were routinely cultured at 37° C. with 5% of $CO_2$ in DMEM supplemented with 10% FBS, 2.5 μg/mL fungizone and 50 μg/mL gentamicin. The day before transfection, cells were seeded at a density of 100 000 cells/mL in a 6-well plate containing 3 glass coverslips per well. CHO-K1 cells were transiently transfected with FuGENE 6 transfection reagent (Roche) using a 3:1 ratio.

Following one day of culture, cells were fixed with 1% paraformaldehyde for 15 minutes at room temperature (RT). Cells were washed three times with PBS, blocked for 30 minutes at RT with 1% BSA and then incubated with 10 μg/mL of SNA-FITC (vector laboratories) for one hour at 4° C. Cells were successively washed three times with PBS, fixed with 3% paraformaldehyde for 20 minutes at RT, further washed with PBS and incubated with 0.05 M $NH_4Cl$ for 10 minutes at RT. After washings with PBS, cells were permeabilized with 0.25% Triton X-100 for 5 minutes at RT and blocked with 10% inactivated goat serum and 1% BSA for 30 minutes at RT. Cells were incubated for one hour at RT with 1 μg/mL monoclonal anti-FLAG M2 antibody (Sigma) in PBS containing 5% inactivated goat serum and 0.5% BSA. Cells were washed three times with PBS and incubated for 45 minutes with 5.7 μg/mL of Alexa Fluor® 594-coupled secondary goat anti-mouse antibody (Molecular Probes) in PBS containing 5% inactivated goat serum and 0.5% BSA. After washings with PBS, cells were mounted in Mowiol and analysed using an Olympus microscope (FIG. 25).

REFERENCES

Andersen D. C. & Krummen L. (2002) Recombinant protein expression for therapeutic applications. *Curr. Opin. Biotechnol.*, 13(2):117-23.

Angata K., Nakayama J., Fredette B., Chong K., Ranscht B. & Fukuda M. (1997) Human STX polysialyltransferase forms the embryonic form of the neural cell adhesion molecule. Tissue-specific expression, neurite outgrowth, and chromosomal localization in comparison with another polysialyltransferase, PST. *J. Biol. Chem.*, 272(11):7182-90.

Angata K., Suzuki M., McAuliffe J., Ding Y., Hindsgaul O. & Fukuda M. (2000) Differential biosynthesis of polysialic acid on neural cell adhesion molecule (NCAM) and oligosaccharide acceptors by three distinct alpha 2,8-sialyltransferases, ST8Sia IV (PST), ST8Sia II (STX), and ST8Sia III. *J. Biol. Chem.*, 275(24):18594-601.

Angata K., Yen T. Y., El-Battari A., Macher B. A. & Fukuda M. (2001) Unique disulfide bond structures found in ST8Sia IV polysialyltransferase are required for its activity. *J. Biol. Chem.*, 276(18):15369-77.

Ashwell G. & Harford J. (1982) Carbohydrate-specific receptors of the liver. *Annu. Rev. Biochem.*, 51:531-54.

Aumiller J. J., Hollister J. R., & Jarvis D. L. (2003) A transgenic insect cell line engineered to produce CMP-sialic acid and sialylated glycoproteins. *Glycobiology*, 13(6):497-507.

Baneyx F. (1999) Recombinant protein expression in *Escherichia coli*. *Curr. Opin. Biotechnol.*, 10(5):411-21.

Berger E. G. (2002) Ectopic localizations of Golgi glycosyltransferases. *Glycobiology*, 12(2):29R-36R.

Berger E. G., Burger P., Borsig L., Malissard M., Felner K. M., Zeng S., Dinter A. (1998) Immunodetection of glycosyltransferases: prospects and pitfalls. *Adv. Exp. Med. Biol.*, 435:119-32.

Blanchard S. (2004) Ingénierie de glicoside hydrolases pour la glycosylation des protéines recombinantes. *Thèse de l'université Joseph Fourier*, 272p.

Bragonzi A., Distefano G., Buckberry L. D., Acerbis G., Foglieni C., Lamotte D., Campi G., Marc A., Soria M. R., Jenkins N., Monaco L. (2000) A new Chinese hamster ovary cell line expressing alpha2,6-sialyltransferase used as universal host for the production of human-like sialylated recombinant glycoproteins. *Biochim. Biophys. Acta*, 1474(3):273-82.

Breton C. & Imberty A. (1999) Structure/function studies of glycosyltransferases. *Curr. Opin. Struct. Biol.*, 9(5):563-71.

Breton C., Mucha J. & Jeanneau C. (2001) Structural and functional features of glycosyltransferases. *Biochimie.*, 83(8):713-8.

Bretscher M. S. & Munro S. (1993) Cholesterol and the Golgi apparatus. *Science*, 261(5126):1280-1.

Bretthauer R. K. (2003) Genetic engineering of *Pichia pastoris* to humanize N-glycosylation of proteins. *Trends Biotechnol.*, 21(11):459-62.

Bianucci A. M. & Chiellini F. (2000) A 3D model for the human hepatic asialoglycoprotein receptor (ASGP-R). *J. Biomol. Struct. Dyn.*, 18(3):435-51.

Chang M. L., Eddy R. L., Shows T. B., Lau J. T. (1995) Three genes that encode human beta-galactoside alpha 2,3-sialyltransferases. Structural analysis and chromosomal mapping studies. *Glycobiology*, 5(3):319-25.

Chen C. & Colley K. J. (2000) Minimal structural and glycosylation requirements for ST6Gal I activity and trafficking. *Glycobiology*, 10(5):531-83.

Chen C., Ma J., Lazic A., Backovic M., Colley K. J. (2000) Formation of insoluble oligomers correlates with ST6Gal I stable localization in the golgi. *J. Biol. Chem.*, 275(18):13819-26.

Chen T. L., Chen C., Bergeron N. Q., Close B. E., Bohrer T. J., Vertel B. M. & Colley K. J. (2003) The two rat alpha 2,6-sialyltransferase (ST6Gal I) isoforms: evaluation of catalytic activity and intra-Golgi localization. *Glycobiology*, 13(2):109-17.

Colley K. J. (1997) Golgi localization of glycosyltransferases: more questions than answers. *Glycobiology*, 7(1):1-13.

Crocker P. R. & Feizi T. (1996) Carbohydrate recognition systems: functional triads in cell-cell interactions. *Curr. Opin. Struct. Biol.*, 6(5):679-91.

Datta A. K., Sinha A. & Paulson J. C. (1998) Mutation of the sialyltransferase S-sialylmotif alters the kinetics of the donor and acceptor substrates. *J. Biol. Chem.*, 273(16):9608-14.

Datta A. K. & Paulson J. C. (1995) Sialylmotifs of sialyltransferases. *Indian J. Biochem. Biophys.*, 34(1-2): 157-65.

Donadio S., Dubois C., Fichant G., Roybon L., Guillemot J. C., Breton C. & Ronin C. (2003) Recognition of cell surface acceptors by two human alpha-2,6-sialyltransferases produced in CHO cells. *Biochimie*, 85(3-4):311-21.

Drickamer K. (1993) A conserved disulphide bond in sialyltransferases. *Glycobiology*, 3(1):2-3.

Feizi T. (1993) Carbohydrate—protein interactions in capillary morphogenesis? *Glycobiology*, 3(6):547-8.

Fenteany F. H. & Colley K. J. (2005) Multiple signals are required for alpha2,6-sialyltransferase (ST6Gal I) oligomerization and Golgi localization. *J. Biol. Chem.*, (7):5423-9.

Gabius H. J., Siebert H. C., Andre S., Jimenez-Barbero J. & Rudiger H. (2004) Chemical biology of the sugar code. *Chembiochem.*, 5(6):740-64.

Geremia R. A., Harduin-Lepers A. & Delannoy P. (1997) Identification of two novel conserved amino acid residues in eukaryotic sialyltransferases: implications for their mechanism of action. Glycobiology, 7(2):v-vii.

Giordanengo V., Bannwarth S., Laffont C., Van Miegem V., Harduin-Lepers A., Delannoy P. & Lefebvre J. C. (1997) Cloning and expression of cDNA for a human Gal(beta1-3)GalNAc alpha2,3-sialyltransferase from the CEM T-cell line. *Eur. J. Biochem.*, 247(2):558-66.

Grabenhorst E. & Conradt H. S. (1999) The cytoplasmic, transmembrane, and stem regions of glycosyltransferases specify their in vivo functional sublocalization and stability in the Golgi. *J. Biol. Chem.*, 274(51):36107-16.

Grabenhorst E., Schlenke P., Pohl S., Nimtz M. & Conradt H. S. (1999) Genetic engineering of recombinant glycoproteins and the glycosylation pathway in mammalian host cells. *Glycoconj. J.*, 16(2):81-97.

Hamilton S. R., Bobrowicz P., Bobrowicz B., Davidson R. C., Li H., Mitchell T., Nett J. H., Rausch S., Stadheim T. A., Wischnewski H., Wildt S. & Gerngross, T. U. (2003) Production of complex human glycoproteins in yeast. *Science*, 301, 1244-1246.

Harduin-Lepers A., Stokes D. C., Steelant W. F., Samyn-Petit B., Krzewinski-Recchi M. A., Vallejo-Ruiz V., Zanetta J. P., Auge C. & Delannoy P. (2000) Cloning, expression and gene organization of a human Neu5Ac alpha 2-3Gal beta 1-3GalNAc alpha 2,6-sialyltransferase: hST6GalNAcIV. *Biochem. J.*, 352(Pt 1):37-48.

Harduin-Lepers A., Vallejo-Ruiz V., Krzewinski-Recchi M. A., Samyn-Petit B., Julien S. & Delannoy P. (2001) The human sialyltransferase family. *Biochimie*, 83(8):727-37.

Helenius A. & Aebi M. (2001) Intracellular functions of N-linked glycans. *Science*, 291(5512):2364-9.

Herscovics A. & Orlean P. (1993) Glycoprotein biosynthesis in yeast. *FASEB J.*, 7(6):540-50.

Hudgin R. L., Pricer W. E. Jr, Ashwell G., Stockert R. J. & Morell A. G. (1974) The isolation and properties of a rabbit liver binding protein specific for asialoglycoproteins. *J. Biol. Chem.*, 249(17):5536-43.

Ikehara Y., Shimizu N., Kono M., Nishihara S., Nakanishi H., Kitamura T., Narimatsu H., Tsuji S. & Tatematsu M. (1999) A novel glycosyltransferase with a polyglutamine repeat; a new candidate for GD1alpha synthase (ST6GalNAc V) (1). *FEBS Lett.*, 463(1-2):92-6.

Ishii A., Ohta M., Watanabe Y., Matsuda K., Ishiyama K., Sakoe K., Nakamura M., Inokuchi J., Sanai Y. & Saito M. (1998) Expression cloning and functional characterization of human cDNA for ganglioside GM3 synthase. *J. Biol. Chem.*, 273(48):31652-5.

Jarvis D. L., Kawar Z. S. & Hollister J. R. (1998) Engineering N-glycosylation pathways in the baculovirus-insect cell system. *Curr. Opin. Biotechnol.*, 9(5):528-33.

Jeanneau C. (2003) Bioanalyse et ingénierie de glycosyltransferase. *Thèse de l'université de Paris* 7, 179p.

Jeanneau C., Chazalet V., Auge C., Soumpasis D. M., Harduin-Lepers A., Delannoy P., Imberty A. & Breton C. (2004) Structure-function analysis of the human sialyltransferase ST3Gal I: role of n-glycosylation and a novel conserved sialylmotif. *J. Biol. Chem.*, 279(14):13461-8.

Kawasaki G. & Ashwell T. (1976) Carbohydrate structure of glycopeptides isolated from an hepatic membrane-binding protein specific for asialoglycoproteins. *J. Biol. Chem.*, 251(17):5292-9.

Kim Y. J., Kim K. S., Kim S. H., Kim C. H., Ko J. H., Choe I. S., Tsuji S. & Lee Y. C. (1996) Molecular cloning and expression of human Gal beta 1,3GalNAc alpha 2,3-sialytransferase (hST3Gal II). *Biochem. Biophys. Res. Commun.*, 228(2):324-7.

Kitagawa H. & Paulson J. C. (1993) Cloning and expression of human Gal beta 1,3(4)GlcNAc alpha 2,3-sialyltransferase. *Biochem. Biophys. Res. Commun.*, 194(1):375-82.

Kitagawa H. & Paulson J. C. (1994a) Differential expression of five sialyltransferase genes in human tissues. *J. Biol. Chem.*, 269(27):17872-8.

Kitagawa H. & Paulson J. C. (1994b) Cloning of a novel alpha 2,3-sialyltransferase that sialylates glycoprotein and glycolipid carbohydrate groups. *J. Biol. Chem.*, 269(2):1394-401.

Kitagawa H., Mattei M. G. & Paulson J. C. (1996) Genomic organization and chromosomal mapping of the Gal beta 1,3GalNAc/Gal beta 1,4GlcNAc alpha 2,3-sialyltransferase. *J. Biol. Chem.*, 271(2):931-8.

Kitazume-Kawaguchi S., Dohmae N., Takio K., Tsuji S. & Colley K. J. (1999) The relationship between ST6Gal I Golgi retention and its cleavage-secretion. *Glycobiology*, 9(12):1397-406.

Kitazume-Kawaguchi S., Kabata S. & Arita M. (2001) Differential biosynthesis of polysialic or disialic acid Structure by ST8Sia II and ST8Sia IV. *J. Biol. Chem.*, 276(19): 15696-703.

Kono M., Yoshida Y., Kojima N. & Tsuji S. (1996) Molecular cloning and expression of a fifth type of alpha2,8-sialyltransferase (ST8Sia V). Its substrate specificity is similar to that of SAT-V/III, which synthesize GD1c, GT1a, GQ1b and GT3. *J. Biol. Chem.*, 271(46):29366-71.

Kono M., Tsuda T., Ogata S., Takashima S., Liu H., Hamamoto T., Itzkowitz S. H., Nishimura S. & Tsuji S. (2000) Redefined substrate specificity of ST6GalNAc II: a second candidate sialyl-Tn synthase. *Biochem. Biophys. Res. Commun.*, 272(1):94-7.

Kornfeld R. & Kornfeld S. (1985) Assembly of asparagine-linked oligosaccharides. *Annu. Rev. Biochem.*, 1985;54: 631-64.

Krzewinski-Recchi M. A., Julien S., Juliant S., Teintenier-Lelievre M., Samyn-Petit B., Montiel M. D., Mir A. M., Cerutti M., Harduin-Lepers A. & Delannoy P. (2003) Identification and functional expression of a second human beta-galactoside alpha2,6-sialyltransferase, ST6Gal II. *Eur. J. Biochem.*, 270(5):950-61.

Kurosawa N., Kojima N., Inoue M., Hamamoto T. & Tsuji S. (1994) Cloning and expression of Gal beta 1,3GalNAc-specific GalNAc alpha 2,6-sialyltransferase. *J. Biol. Chem.*, 269(29):19048-53.

Kurosawa N., Inoue M., Yoshida Y. & Tsuji S. (1996) Molecular cloning and genomic analysis of mouse Galbeta1,3GalNAc-specific GalNAc alpha2,6-sialyltransferase. *J. Biol. Chem.*, 1996 Jun. 21; 271(25):15109-16.

Kurosawa N., Takashima S., Kono M., Ikehara Y., Inoue M., Tachida Y., Narimatsu H. & Tsuji S. (2000) Molecular cloning and genomic analysis of mouse GalNAc alpha2,6-sialyltransferase (ST6GalNAc I). *J. Biochem.*, 127(5):845-54.

Laroy W., Ameloot P., & Contreras R. (2001) Characterization of sialyltransferase mutants using surface plasmon resonance. *Glycobiology*, 11(3):175-82.

Lee Y. C., Kim Y. J., Lee K. Y., Kim K. S., Kim B. U., Kim H. N., Kim C. H. & Do S. I. (1998) Cloning and expression of cDNA for a human Sia alpha 2,3Gal beta 1,4GlcNA:alpha 2,8-sialyltransferase (hST8Sia III). *Arch. Biochem. Biophys.*, 360(1):41-6.

Lee Y. C., Kaufmann M., Kitazume-Kawaguchi S, Kono M, Takashima S, Kurosawa N, Liu H., Pircher H. & Tsuji S. (1999) Molecular cloning and functional expression of two members of mouse NeuAcalpha2,3Galbeta1,3GalNAc GalNAcalpha2,6-sialyltransferase family, ST6GalNAc III and IV. *J. Biol. Chem.*, 274(17):11958-67.

Legaigneur P., Brioude B. & Ronin C. (1999) Antigenes glycanniques recombinants. *Immunoanal. Biol. Spec.*, 14:297-307.

Legaigneur P., Breton C., El Battari A., Guillemot J. C., Auge C., Malissard M., Berger E. G. & Ronin C. (2001) Exploring the acceptor substrate recognition of the human beta-galactoside alpha 2,6-sialyltransferase. *J. Biol. Chem.*, 276 (24):21608-17.

Lerouge P., Bardor M., Pagny S., Gomord V. & Faye L. (2000) N-glycosylation of recombinant pharmaceutical glycoproteins produced in transgenic plants: towards an humanization of plant N-glycans. *Curr. Pharm. Biotechnol.*, 1(4): 347-54.

Livingston B. D. & Paulson J. C. (1993) Polymerase chain reaction cloning of a developmentally regulated member of the sialyltransferase gene family. *J. Biol. Chem.*, 268(16): 11504-7.

Ma J., Qian R., Rausa F. M. 3$^{rd}$ & Colley K. J. (1997) Two naturally occurring alpha2,6-sialyltransferase forms with a single amino acid change in the catalytic domain differ in their catalytic activity and proteolytic processing. *J. Biol. Chem.*, 272(1):672-9.

Machamer C. E. (1991) Golgi retention signals: do membranes hold the key? *Trends Cell Biol.*, 1(6):141-4.

Maras M., Van Die I., Contreras R. & Van den Hondel C. A. M. J. J. (1999) Filamentous fungi as production organisms for glycoproteins of bio-medical interest. *Glycoconj. J.*, 16:99-107.

Marchal I., Jarvis D. L., Cacan R. & Verbert A. (2001) Glycoproteins from insect cells: sialylated or not? *Biol. Chem.*, 382, 151-159.

Martina J. A., Daniotti J. L. & Maccioni H. J. (1998) Influence of N-glycosylation and N-glycan trimming on the activity and intracellular traffic of GD3 synthase. *J. Biol. Chem.*, 273(6):3725-31.

Meier M., Bider M. D., Malashkevich V. N., Spiess M. & Burkhard P. (2000) Crystal structure of the carbohydrate recognition domain of the H1 subunit of the asialoglycoprotein receptor. *J. Mol. Biol.*, 300(4):857-65.

Morell A. G., Gregoriadis G., Scheinberg I. H., Hickman J. & Ashwell G. (1971) The role of sialic acid in determining the survival of glycoproteins in the circulation. *J. Biol. Chem.*, 246(5):1461-7.

Muhlenhoff M., Manegold A., Windfuhr M., Gotza B. & Gerardy-Schahn R. (2001) The impact of N-glycosylation on the functions of polysialyltransferases. *J. Biol. Chem.*, 276(36):34066-73.

Munro S. (1991) Sequences within and adjacent to the transmembrane segment of alpha-2,6-sialyltransferase specify Golgi retention. *EMBO J.*, 10(12):3577-88.

Bretscher M. S. & Munro S. (1993) Cholesterol and the Golgi apparatus. *Science*, 261(5126):1280-1.

Munro S. (1995) An investigation of the role of transmembrane domains in Golgi protein retention. *EMBO J.*, 14(19):4695-704.

Munro S. (1998) Localization of proteins to the Golgi apparatus. *Trends Cell Biol.*, 8(1):11-5.

Nakayama J., Fukuda M. N., Fredette B., Ranscht B. & Fukuda M. (1995) Expression cloning of a human polysialyltransferase that forms the polysialylated neural cell adhesion molecule present in embryonic brain. *Proc. Natl. Acad. Sci. U.S.A.*, 92(15):7031-5.

Nakayama J., Fukuda M. N., Hirabayashi Y., Kanamori A., Sasaki K., Nishi T. & Fukuda M. (1996) Expression cloning of a human GT3 synthase. GD3 AND GT3 are synthesized by a single enzyme. *J. Biol. Chem.*, 271(7):3684-91.

Nara K., Watanabe Y., Kawashima I., Tai T., Nagai Y. & Sanai Y. (1996) Acceptor substrate specificity of a cloned GD3 synthase that catalyzes the biosynthesis of both GD3 and GD1c/GT1a/GQ1b. *Eur. J. Biochem.*, 238(3):647-52.

Narimatsu H. (2004) Construction of a human glycogene library and comprehensive functional analysis. *Glycoconj. J.*, 21(1-2):17-24.

Okajima T., Fukumoto S., Miyazaki H., Ishida H., Kiso M., Furukawa K., Urano T. & Furukawa K. (1999) Molecular cloning of a novel alpha2,3-sialyltransferase (ST3Gal VI) that sialylates type II lactosamine structures on glycoproteins and glycolipids. *J. Biol. Chem.*, 274(17):11479-86.

Okajima T., Chen H. H., I to H., Kiso M., Tai T., Furukawa K., Urano T. & Furukawa K. (2000) Molecular cloning and expression of mouse GD1alpha/GT1aalpha/GQ1balpha synthase (ST6GalNAc VI) gene. *J. Biol. Chem.*, 275(10): 6717-23.

Opat A. S., van Vliet C. & Gleeson P. A. (2001) Trafficking and localisation of resident Golgi glycosylation enzymes. *Biochimie*, 83(8):763-73.

Paulson J. C. (1989) Glycoproteins: what are the sugar chains for? *Trends Biochem. Sci.*, 14(7):272-6.

Paulson J. C., Weinstein J., Ujita E. L., Riggs K. J. & Lai P H. (1987) The membrane-binding domain of a rat liver Golgi sialyltransferase. *Biochem. Soc. Trans.*, 15(4):618-20.

Paulson J. C. & Colley K. J. (1989) Glycosyltransferases. Structure, localization, and control of cell type-specific glycosylation. *J. Biol. Chem.*, 264(30):17615-8.

Pilatte Y., Bignon J. & Lambre C. R. (1993) Sialic acids as important molecules in the regulation of the immune system: pathophysiological implications of sialidases in immunity. *Glycobiology*, 3(3):201-18.

Qian R., Chen C. & Colley K. J. (2001) Location and mechanism of alpha 2,6-sialyltransferase dimer formation. Role of cysteine residues in enzyme dimerization, localization, activity, and processing. *J. Biol. Chem.*, 276(31):28641-9.

Reid M. E. & Lomas-Francis C. (2002) Molecular approaches to blood group identification. *Curr. Opin. Hematol.*, 9(2):152-9.

Roth J., Taatjes D. J., Lucocq J. M., Weinstein J. & Paulson J. C. (1985) Demonstration of an extensive trans-tubular network continuous with the Golgi apparatus stack that may function in glycosylation. *Cell*, 43(1):287-95.

Roth J. (1987) Subcellular organization of glycosylation in mammalian cells. *Biochim. Biophys. Acta*, 906(3):405-36.

Roth J. (1991) Localization of glycosylation sites in the Golgi apparatus using immunolabeling and cytochemistry. *J. Electron. Microsc. Tech.*, 17(2):121-31.

Roy S. K., Chiba Y. & Jigami, Y. (2000) Production of Therapeutic Glycoproteins through the Engineering of Glycosylation Pathway in Yeast. *Biotechnol. Bioprocess Eng.*, 5, 219-226.

Sasaki K. (1996) Molecular cloning and characterization of sialyltransferases. *Trends Glycosci. Glycotechnol.*, 8:195-215.

Sasaki K., Kurata K., Kojima N., Kurosawa N., Ohta S., Hanai N., Tsuji S. & Nishi T. (1994) Expression cloning of a GM3-specific alpha-2,8-sialyltransferase (GD3 synthase). *J. Biol. Chem.*, 269(22): 15950-6.

Scheidegger E. P., Sternberg L. R., Roth J. & Lowe J B. (1995) A human STX cDNA confers polysialic acid expression in mammalian cells. *J. Biol. Chem.*, 270(39): 22685-8.

Sinnott M. L. (1990) Catalytic mechanism of enzymic glycosyl transfer. *Chem. Rev.*, 90, 1171-1202.

Sjoberg E. R, Kitagawa H., Glushka J., van Halbeek H. & Paulson J. C. (1996) Molecular cloning of a developmentally regulated N-acetylgalactosamine alpha2,6-sialyltransferase specific for sialylated glycoconjugates. *J. Biol. Chem.*, 271(13):7450-9.

Sujino K., Jackson R. J., Chan N. W., Tsuji S. & Palcic M. M. (2000) A novel viral alpha2,3-sialyltransferase (v-ST3Gal I): transfer of sialic acid to fucosylated acceptors. *Glycobiology*, 10(3):313-20.

Swartz J. R. (2001) Advances in *Escherichia coli* production of therapeutic proteins. *Curr. Opin. Biotechnol.*, 12, 195-201.

Takashima S., Ishida H. K., Inazu T., Ando T., Ishida H., Kiso M., Tsuji S. & Tsujimoto M. (2002) Molecular cloning and expression of a sixth type of alpha 2,8-sialyltransferase (ST8Sia VI) that sialylates O-glycans. *J. Biol. Chem.*, 277 (27):24030-8.

Taniguchi A., Kaneta R., Morishita K. & Matsumoto K. (2001) Gene structure and transcriptional regulation of human Gal beta1,4(3) GlcNAc alpha2,3-sialyltransferase VI (hST3Gal VI) gene in prostate cancer cell line. *Biochem. Biophys. Res. Commun.*, (5):1148-56.

Tanner W. & Lehele L. (1987) Protein glycosylation in yeast. *Biochim. Biophys. Acta*, 906(1):81-99.

Tetteroo P. A., de Heij H. T., Van den Eijnden D. H., Visser F. J., Schoenmarker E. & Geurts van Kessel A H. (1987) A GDP-fucose:[Gal beta 1—4]GlcNAc alpha 1—3-fixosyltransferase activity is correlated with the presence of human chromosome 11 and the expression of the Lex, Ley, and sialyl-Lex antigens in human-mouse cell hybrids. *J. Biol. Chem.*, 262(33):15984-9.

Vallejo-Ruiz V., Hague R., Mir A. M., Schwientek T., Mandel U., Cacan R., Delannoy P. & Harduin-Lepers A. (2001) Delineation of the minimal catalytic domain of human Galbeta1-3GalNAc alpha2,3-sialyltransferase (hST3Gal I). *Biochim. Biophys. Acta*, 1549(2):161-73.

van den Eijnden D. H., Joziasse D. H., Dorland L., van Halbeek H., Vliegenthart J. F. & Schmid K. (1980) Specificity in the enzymic transfer of sialic acid to the oligosaccharide branches of b1- and triantennary glycopeptides of alpha 1-acid glycoprotein. *Biochem. Biophys. Res. Commun.*, 92(3):839-45.

Van Den Hamer C. J., Morell A. G., Scheinberg I. H., Hickman J. & Ashwell G. (1970) Physical and chemical studies on ceruloplasmin. IX. The role of galactosyl residues in the clearance of ceruloplasmin from the circulation. *J. Biol. Chem.*, 245(17):4397-402.

Vervecken W., Kaigorodov V., Callewaert N., Geysens S., De Vusser K. & Contreras R. (2004) In vivo synthesis of mammalian-like, hybrid-type N-glycans in Pichia pastoris. *Appl. Environ. Microbiol.*, 70, 2639-2646.

Watanabe Y., Nara K., Takahashi H., Nagai Y. & Sanai Y. (1996) The molecular cloning and expression of alpha 2,8-sialyltransferase (GD3 synthase) in a rat brain. *J. Biochem.*, 120(5):1020-7.

Weikert S., Papac D., Briggs J., Cowfer D., Tom S., Gawlitzek M., Lofgren J., Mehta S., Chisholm V., Modi N., Eppler S., Carroll K., Chamow S., Peers D., Berman P. & Krummen L. (1999) Engineering Chinese hamster ovary cells to maximize sialic acid content of recombinant glycoproteins. *Nat. Biotechnol.*, 17(11):1116-21.

Weinstein J., de Souza-e-Silva U. & Paulson J. C. (1982) Sialylation of glycoprotein oligosaccharides N-linked to asparagine. Enzymatic characterization of a Gal beta 1 to 3(4)GlcNAc alpha 2 to 3 sialyltransferase and a Gal beta 1 to 4GlcNAc alpha 2 to 6 sialyltransferase from rat liver. *J. Biol. Chem.*, 257(22):13845-53.

Wickner W. T. & Lodisch H. F. (1985) Multiple mechanisms of protein insertion into and across membranes. *Science*, 230(4724):400-7.

Yang W., Pepperkok R., Bender P., Kreis T E. & Storrie B. (1996) Modification of the cytoplasmic domain affects the subcellular localization of Golgi glycosyl-transferases. *Eur. J. Cell Biol.*, 71(1):53-61.

Yoshida Y., Kojima N. & Tsuji S. (1995a) Molecular cloning and characterization of a third type of N-glycan alpha 2,8-sialyltransferase from mouse lung. *J. Biochem.*, 118 (3):658-64.

Yoshida Y., Kojima N., Kurosawa N., Hamamoto T. & Tsuji S. (1995b) Molecular cloning of Sia alpha 2,3Gal beta 1,4GlcNAc alpha 2,8-sialyltransferase from mouse brain. *J. Biol. Chem.*, 270(24):14628-33.

SEQUENCE LISTING

<160> NUMBER OF SEQ ID NOS: 214

<210> SEQ ID NO 1
<211> LENGTH: 1221
<212> TYPE: DNA
<213> ORGANISM: Homo sapiens
<220> FEATURE:
<221> NAME/KEY: CDS
<222> LOCATION: (1)..(1221)

<400> SEQUENCE: 1

| | | | | | | | | | | | | | | | | |
|---|---|---|---|---|---|---|---|---|---|---|---|---|---|---|---|---|
| atg | att | cac | acc | aac | ctg | aag | aaa | aag | ttc | agc | tgc | tgc | gtc | ctg | gtc | 48 |
| Met | Ile | His | Thr | Asn | Leu | Lys | Lys | Lys | Phe | Ser | Cys | Cys | Val | Leu | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | ctt | ctg | ttt | gca | gtc | atc | tgt | gtg | tgg | aag | gaa | aag | aag | aaa | ggg | 96 |
| Phe | Leu | Leu | Phe | Ala | Val | Ile | Cys | Val | Trp | Lys | Glu | Lys | Lys | Lys | Gly | |
| | | | 20 | | | | 25 | | | | | 30 | | | | |

| | | | | | | | | | | | | | | | | |
|---|---|---|---|---|---|---|---|---|---|---|---|---|---|---|---|---|
| agt | tac | tat | gat | tcc | ttt | aaa | ttg | caa | acc | aag | gaa | ttc | cag | gtg | tta | 144 |
| Ser | Tyr | Tyr | Asp | Ser | Phe | Lys | Leu | Gln | Thr | Lys | Glu | Phe | Gln | Val | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | agt | ctg | ggg | aaa | ttg | gcc | atg | ggg | tct | gat | tcc | cag | tct | gta | tcc | 192 |
| Lys | Ser | Leu | Gly | Lys | Leu | Ala | Met | Gly | Ser | Asp | Ser | Gln | Ser | Val | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| tca | agc | agc | acc | cag | gac | ccc | cac | agg | ggc | cgc | cag | acc | ctc | ggc | agt | 240 |
| Ser | Ser | Ser | Thr | Gln | Asp | Pro | His | Arg | Gly | Arg | Gln | Thr | Leu | Gly | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctc | aga | ggc | cta | gcc | aag | gcc | aaa | cca | gag | gcc | tcc | ttc | cag | gtg | tgg | 288 |
| Leu | Arg | Gly | Leu | Ala | Lys | Ala | Lys | Pro | Glu | Ala | Ser | Phe | Gln | Val | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| aac | aag | gac | agc | tct | tcc | aaa | aac | ctt | atc | cct | agg | ctg | caa | aag | atc | 336 |
| Asn | Lys | Asp | Ser | Ser | Ser | Lys | Asn | Leu | Ile | Pro | Arg | Leu | Gln | Lys | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| tgg | aag | aat | tac | cta | agc | atg | aac | aag | tac | aaa | gtg | tcc | tac | aag | ggg | 384 |
| Trp | Lys | Asn | Tyr | Leu | Ser | Met | Asn | Lys | Tyr | Lys | Val | Ser | Tyr | Lys | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| cca | gga | cca | ggc | atc | aag | ttc | agt | gca | gag | gcc | ctg | cgc | tgc | cac | ctc | 432 |
| Pro | Gly | Pro | Gly | Ile | Lys | Phe | Ser | Ala | Glu | Ala | Leu | Arg | Cys | His | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| cgg | gac | cat | gtg | aat | gta | tcc | atg | gta | gag | gtc | aca | gat | ttt | ccc | ttc | 480 |
| Arg | Asp | His | Val | Asn | Val | Ser | Met | Val | Glu | Val | Thr | Asp | Phe | Pro | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aat | acc | tct | gaa | tgg | gag | ggt | tat | ctg | ccc | aag | gag | agc | att | agg | acc | 528 |
| Asn | Thr | Ser | Glu | Trp | Glu | Gly | Tyr | Leu | Pro | Lys | Glu | Ser | Ile | Arg | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | gct | ggg | cct | tgg | ggc | agg | tgt | gct | gtt | gtg | tcg | tca | gcg | gga | tct | 576 |
| Lys | Ala | Gly | Pro | Trp | Gly | Arg | Cys | Ala | Val | Val | Ser | Ser | Ala | Gly | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | aag | tcc | tcc | caa | cta | ggc | aga | gaa | atc | gat | gat | cat | gac | gca | gtc | 624 |
| Leu | Lys | Ser | Ser | Gln | Leu | Gly | Arg | Glu | Ile | Asp | Asp | His | Asp | Ala | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| ctg | agg | ttt | aat | ggg | gca | ccc | aca | gcc | aac | ttc | caa | caa | gat | gtg | ggc | 672 |
| Leu | Arg | Phe | Asn | Gly | Ala | Pro | Thr | Ala | Asn | Phe | Gln | Gln | Asp | Val | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| aca | aaa | act | acc | att | cgc | ctg | atg | aac | tct | cag | ttg | gtt | acc | aca | gag | 720 |
| Thr | Lys | Thr | Thr | Ile | Arg | Leu | Met | Asn | Ser | Gln | Leu | Val | Thr | Thr | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | cgc | ttc | ctc | aaa | gac | agt | ttg | tac | aat | gaa | gga | atc | cta | att | gta | 768 |
| Lys | Arg | Phe | Leu | Lys | Asp | Ser | Leu | Tyr | Asn | Glu | Gly | Ile | Leu | Ile | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| tgg | gac | cca | tct | gta | tac | cac | tca | gat | atc | cca | aag | tgg | tac | cag | aat | 816 |
| Trp | Asp | Pro | Ser | Val | Tyr | His | Ser | Asp | Ile | Pro | Lys | Trp | Tyr | Gln | Asn | |

```
                260                 265                 270
ccg gat tat aat ttc ttt aac aac tac aag act tat cgt aag ctg cac         864
Pro Asp Tyr Asn Phe Phe Asn Asn Tyr Lys Thr Tyr Arg Lys Leu His
        275                 280                 285 ccc aat cag ccc ttt tac atc ctc aag ccc cag atg cct tgg gag cta         912
Pro Asn Gln Pro Phe Tyr Ile Leu Lys Pro Gln Met Pro Trp Glu Leu
    290                 295                 300 tgg gac att ctt caa gaa atc tcc cca gaa gag att cag cca aac ccc         960
Trp Asp Ile Leu Gln Glu Ile Ser Pro Glu Glu Ile Gln Pro Asn Pro
305                 310                 315                 320 cca tcc tct ggg atg ctt ggt atc atc atc atg atg acg ctg tgt gac        1008
Pro Ser Ser Gly Met Leu Gly Ile Ile Ile Met Met Thr Leu Cys Asp
                325                 330                 335 cag gtg gat att tat gag ttc ctc cca tcc aag cgc aag act gac gtg        1056
Gln Val Asp Ile Tyr Glu Phe Leu Pro Ser Lys Arg Lys Thr Asp Val
            340                 345                 350 tgc tac tac tac cag aag ttc ttc gat agt gcc tgc acg atg ggt gcc        1104
Cys Tyr Tyr Tyr Gln Lys Phe Phe Asp Ser Ala Cys Thr Met Gly Ala
        355                 360                 365 tac cac ccg ctg ctc tat gag aag aat ttg gtg aag cat ctc aac cag        1152
Tyr His Pro Leu Leu Tyr Glu Lys Asn Leu Val Lys His Leu Asn Gln
    370                 375                 380 ggc aca gat gag gac atc tac ctg ctt gga aaa gcc aca ctg cct ggc        1200
Gly Thr Asp Glu Asp Ile Tyr Leu Leu Gly Lys Ala Thr Leu Pro Gly
385                 390                 395                 400 ttc cgg acc att cac tgc taa                                             1221
Phe Arg Thr Ile His Cys
                405

<210> SEQ ID NO 2
<211> LENGTH: 406
<212> TYPE: PRT
<213> ORGANISM: Homo sapiens

<400> SEQUENCE: 2

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175
```

```
Lys Ala Gly Pro Trp Gly Arg Cys Ala Val Ser Ser Ala Gly Ser
            180                 185                 190
Leu Lys Ser Ser Gln Leu Gly Arg Glu Ile Asp Asp His Asp Ala Val
        195                 200                 205
Leu Arg Phe Asn Gly Ala Pro Thr Ala Asn Phe Gln Gln Asp Val Gly
    210                 215                 220
Thr Lys Thr Thr Ile Arg Leu Met Asn Ser Gln Leu Val Thr Thr Glu
225                 230                 235                 240
Lys Arg Phe Leu Lys Asp Ser Leu Tyr Asn Glu Gly Ile Leu Ile Val
            245                 250                 255
Trp Asp Pro Ser Val Tyr His Ser Asp Ile Pro Lys Trp Tyr Gln Asn
        260                 265                 270
Pro Asp Tyr Asn Phe Phe Asn Asn Tyr Lys Thr Tyr Arg Lys Leu His
    275                 280                 285
Pro Asn Gln Pro Phe Tyr Ile Leu Lys Pro Gln Met Pro Trp Glu Leu
290                 295                 300
Trp Asp Ile Leu Gln Glu Ile Ser Pro Glu Ile Gln Pro Asn Pro
305                 310                 315                 320
Pro Ser Ser Gly Met Leu Gly Ile Ile Ile Met Met Thr Leu Cys Asp
            325                 330                 335
Gln Val Asp Ile Tyr Glu Phe Leu Pro Ser Lys Arg Lys Thr Asp Val
        340                 345                 350
Cys Tyr Tyr Tyr Gln Lys Phe Asp Ser Ala Cys Thr Met Gly Ala
    355                 360                 365
Tyr His Pro Leu Leu Tyr Glu Lys Asn Leu Val Lys His Leu Asn Gln
370                 375                 380
Gly Thr Asp Glu Asp Ile Tyr Leu Leu Gly Lys Ala Thr Leu Pro Gly
385                 390                 395                 400
Phe Arg Thr Ile His Cys
            405

<210> SEQ ID NO 3
<211> LENGTH: 1590
<212> TYPE: DNA
<213> ORGANISM: Homo sapiens
<220> FEATURE:
<221> NAME/KEY: CDS
<222> LOCATION: (1)..(1590)

<400> SEQUENCE: 3 atg aaa cca cac ttg aag caa tgg aga caa cga atg ctt ttc gga ata    48
Met Lys Pro His Leu Lys Gln Trp Arg Gln Arg Met Leu Phe Gly Ile
1               5                  10                  15 ttc gct tgg ggg ctc ctc ttt ttg ctg att ttc atc tac ttc acc gac    96
Phe Ala Trp Gly Leu Leu Phe Leu Leu Ile Phe Ile Tyr Phe Thr Asp
                20                  25                  30 agc aac ccc gct gag cct gta ccc agc tcc ctc tcc ttc ctg gag acc   144
Ser Asn Pro Ala Glu Pro Val Pro Ser Ser Leu Ser Phe Leu Glu Thr
            35                  40                  45 agg agg ctc ctg ccg gtg cag ggg aag cag cgg gcc atc atg ggc gcc   192
Arg Arg Leu Leu Pro Val Gln Gly Lys Gln Arg Ala Ile Met Gly Ala
        50                  55                  60 gca cat gag ccc tcc ccg cct ggg ggc ctg gac gca cgc cag gcg ctg   240
Ala His Glu Pro Ser Pro Pro Gly Gly Leu Asp Ala Arg Gln Ala Leu
65                  70                  75                  80 ccc cgc gcc cac cca gcc ggt tcc ttt cat gcg ggg cct gga gac ctg   288
Pro Arg Ala His Pro Ala Gly Ser Phe His Ala Gly Pro Gly Asp Leu
                85                  90                  95
```

```
cag aaa tgg gcc cag tcc caa gat ggg ttt gaa cat aaa gag ttt ttt      336
Gln Lys Trp Ala Gln Ser Gln Asp Gly Phe Glu His Lys Glu Phe Phe
            100                 105                 110 tca tcc cag gtg ggg aga aaa tct caa agt gct ttc tac ccg gag gat      384
Ser Ser Gln Val Gly Arg Lys Ser Gln Ser Ala Phe Tyr Pro Glu Asp
        115                 120                 125 gac gac tac ttt ttt gct gct ggt cag cca ggg tgg cac agc cac act      432
Asp Asp Tyr Phe Phe Ala Ala Gly Gln Pro Gly Trp His Ser His Thr
130                 135                 140 cag ggg aca ttg gga ttc cct tcc ccc ggg gag cca ggc cca cgg gag      480
Gln Gly Thr Leu Gly Phe Pro Ser Pro Gly Glu Pro Gly Pro Arg Glu
145                 150                 155                 160 ggg gct ttt ccg gct gca cag gtc cag agg agg cgg gtg aag aag agg      528
Gly Ala Phe Pro Ala Ala Gln Val Gln Arg Arg Arg Val Lys Lys Arg
                165                 170                 175 cac cgg agg cag aga agg agc cac gtg ttg gag gag ggc gac gac ggc      576
His Arg Arg Gln Arg Arg Ser His Val Leu Glu Glu Gly Asp Asp Gly
            180                 185                 190 gac agg ctg tac tcc tcc atg tcc agg gcc ttc ctg tac cgg ctc tgg      624
Asp Arg Leu Tyr Ser Ser Met Ser Arg Ala Phe Leu Tyr Arg Leu Trp
        195                 200                 205 aag ggg aac gtc tct tcc aaa atg ctg aac ccg cgc ctg cag aag gcg      672
Lys Gly Asn Val Ser Ser Lys Met Leu Asn Pro Arg Leu Gln Lys Ala
    210                 215                 220 atg aag gat tac ctg acc gcc aac aag cac ggg gtg cgc ttc cgc ggg      720
Met Lys Asp Tyr Leu Thr Ala Asn Lys His Gly Val Arg Phe Arg Gly
225                 230                 235                 240 aag cgg gag gcc ggg ctg agc agg gca cag ctg ctg tgc cag ctg cgg      768
Lys Arg Glu Ala Gly Leu Ser Arg Ala Gln Leu Leu Cys Gln Leu Arg
                245                 250                 255 agc cgc gcg cgc gtg cgg acg ctg gac ggc acc gag gcg ccc ttt tct      816
Ser Arg Ala Arg Val Arg Thr Leu Asp Gly Thr Glu Ala Pro Phe Ser
            260                 265                 270 gcg ctg ggc tgg cgg cgc ctg gtg ccc gcc gtg ccc ctg agc cag ctg      864
Ala Leu Gly Trp Arg Arg Leu Val Pro Ala Val Pro Leu Ser Gln Leu
        275                 280                 285 cac ccc cgc ggc ctg cgc agc tgc gct gtc gtc atg tct gca ggc gca      912
His Pro Arg Gly Leu Arg Ser Cys Ala Val Val Met Ser Ala Gly Ala
    290                 295                 300 atc ctc aac tct tcc ttg ggc gag gaa ata gat tct cat gat gcg gtt      960
Ile Leu Asn Ser Ser Leu Gly Glu Glu Ile Asp Ser His Asp Ala Val
305                 310                 315                 320 ttg aga ttt aac tct gct cct aca cgt ggt tat gag aaa gat gtt ggg     1008
Leu Arg Phe Asn Ser Ala Pro Thr Arg Gly Tyr Glu Lys Asp Val Gly
                325                 330                 335 aat aaa acc acc ata cgc atc att aat tcg cag att ctg acc aac ccc     1056
Asn Lys Thr Thr Ile Arg Ile Ile Asn Ser Gln Ile Leu Thr Asn Pro
            340                 345                 350 agc cat cac ttc att gac agt tca ctg tat aaa gac gtc att ttg gtg     1104
Ser His His Phe Ile Asp Ser Ser Leu Tyr Lys Asp Val Ile Leu Val
        355                 360                 365 gcc tgg gac cct gcc cca tat tcc gca aat ctt aac ctg tgg tac aaa     1152
Ala Trp Asp Pro Ala Pro Tyr Ser Ala Asn Leu Asn Leu Trp Tyr Lys
    370                 375                 380 aaa ccg gat tac aac ctg ttc act cca tat att cag cat cgt cag aga     1200
Lys Pro Asp Tyr Asn Leu Phe Thr Pro Tyr Ile Gln His Arg Gln Arg
385                 390                 395                 400 aac cca aat cag cca ttt tac att ctt cat cct aaa ttt ata tgg cag     1248
Asn Pro Asn Gln Pro Phe Tyr Ile Leu His Pro Lys Phe Ile Trp Gln
```

```
                       405                 410                 415
ctc tgg gat att atc cag gag aac act aaa gag aag att caa cca aac    1296
Leu Trp Asp Ile Ile Gln Glu Asn Thr Lys Glu Lys Ile Gln Pro Asn
        420                 425                 430 cca cca tct tct ggt ttc att gga atc ctc atc atg atg tcc atg tgc    1344
Pro Pro Ser Ser Gly Phe Ile Gly Ile Leu Ile Met Met Ser Met Cys
        435                 440                 445 aga gag gtg cac gtg tat gaa tat atc cca tcc gtg cgg cag acg gag    1392
Arg Glu Val His Val Tyr Glu Tyr Ile Pro Ser Val Arg Gln Thr Glu
450                 455                 460 ctg tgc cac tac cac gag ctg tac tac gac gca gcc tgc acc ctc ggg    1440
Leu Cys His Tyr His Glu Leu Tyr Tyr Asp Ala Ala Cys Thr Leu Gly
465                 470                 475                 480 gcg tac cac cca cta ctc tat gag aag ctc ctg gtg cag cgc ctg aac    1488
Ala Tyr His Pro Leu Leu Tyr Glu Lys Leu Leu Val Gln Arg Leu Asn
                485                 490                 495 atg ggc acg cag ggg gat ttg cat cgc aag ggc aag gtg gtt ctt cct    1536
Met Gly Thr Gln Gly Asp Leu His Arg Lys Gly Lys Val Val Leu Pro
            500                 505                 510 ggc ttc cag gcg gtg cac tgc cct gca cca agt cca gtc att cca cac    1584
Gly Phe Gln Ala Val His Cys Pro Ala Pro Ser Pro Val Ile Pro His
        515                 520                 525 tct taa                                                            1590
Ser
```

<210> SEQ ID NO 4
<211> LENGTH: 529
<212> TYPE: PRT
<213> ORGANISM: Homo sapiens

<400> SEQUENCE: 4

```
Met Lys Pro His Leu Lys Gln Trp Arg Gln Arg Met Leu Phe Gly Ile
1               5                   10                  15

Phe Ala Trp Gly Leu Leu Phe Leu Leu Ile Phe Ile Tyr Phe Thr Asp
            20                  25                  30

Ser Asn Pro Ala Glu Pro Val Pro Ser Ser Leu Ser Phe Leu Glu Thr
        35                  40                  45

Arg Arg Leu Leu Pro Val Gln Gly Lys Gln Arg Ala Ile Met Gly Ala
    50                  55                  60

Ala His Glu Pro Ser Pro Pro Gly Gly Leu Asp Ala Arg Gln Ala Leu
65                  70                  75                  80

Pro Arg Ala His Pro Ala Gly Ser Phe His Ala Gly Pro Gly Asp Leu
                85                  90                  95

Gln Lys Trp Ala Gln Ser Gln Asp Gly Phe Glu His Lys Glu Phe Phe
            100                 105                 110

Ser Ser Gln Val Gly Arg Lys Ser Gln Ser Ala Phe Tyr Pro Glu Asp
        115                 120                 125

Asp Asp Tyr Phe Phe Ala Ala Gly Gln Pro Gly Trp His Ser His Thr
    130                 135                 140

Gln Gly Thr Leu Gly Phe Pro Ser Pro Gly Glu Pro Gly Pro Arg Glu
145                 150                 155                 160

Gly Ala Phe Pro Ala Ala Gln Val Gln Arg Arg Val Lys Lys Arg
                165                 170                 175

His Arg Arg Gln Arg Arg Ser His Val Leu Glu Glu Gly Asp Asp Gly
            180                 185                 190

Asp Arg Leu Tyr Ser Ser Met Ser Arg Ala Phe Leu Tyr Arg Leu Trp
        195                 200                 205
```

```
Lys Gly Asn Val Ser Ser Lys Met Leu Asn Pro Arg Leu Gln Lys Ala
        210                 215                 220

Met Lys Asp Tyr Leu Thr Ala Asn Lys His Gly Val Arg Phe Arg Gly
225                 230                 235                 240

Lys Arg Glu Ala Gly Leu Ser Arg Ala Gln Leu Leu Cys Gln Leu Arg
                245                 250                 255

Ser Arg Ala Arg Val Arg Thr Leu Asp Gly Thr Glu Ala Pro Phe Ser
            260                 265                 270

Ala Leu Gly Trp Arg Arg Leu Val Pro Ala Val Pro Leu Ser Gln Leu
        275                 280                 285

His Pro Arg Gly Leu Arg Ser Cys Ala Val Val Met Ser Ala Gly Ala
290                 295                 300

Ile Leu Asn Ser Ser Leu Gly Glu Glu Ile Asp Ser His Asp Ala Val
305                 310                 315                 320

Leu Arg Phe Asn Ser Ala Pro Thr Arg Gly Tyr Glu Lys Asp Val Gly
                325                 330                 335

Asn Lys Thr Thr Ile Arg Ile Ile Asn Ser Gln Ile Leu Thr Asn Pro
            340                 345                 350

Ser His His Phe Ile Asp Ser Ser Leu Tyr Lys Asp Val Ile Leu Val
        355                 360                 365

Ala Trp Asp Pro Ala Pro Tyr Ser Ala Asn Leu Asn Leu Trp Tyr Lys
370                 375                 380

Lys Pro Asp Tyr Asn Leu Phe Thr Pro Tyr Ile Gln His Arg Gln Arg
385                 390                 395                 400

Asn Pro Asn Gln Pro Phe Tyr Ile Leu His Pro Lys Phe Ile Trp Gln
                405                 410                 415

Leu Trp Asp Ile Ile Gln Glu Asn Thr Lys Glu Lys Ile Gln Pro Asn
            420                 425                 430

Pro Pro Ser Ser Gly Phe Ile Gly Ile Leu Ile Met Met Ser Met Cys
        435                 440                 445

Arg Glu Val His Val Tyr Glu Tyr Ile Pro Ser Val Arg Gln Thr Glu
450                 455                 460

Leu Cys His Tyr His Glu Leu Tyr Tyr Asp Ala Ala Cys Thr Leu Gly
465                 470                 475                 480

Ala Tyr His Pro Leu Leu Tyr Glu Lys Leu Leu Val Gln Arg Leu Asn
                485                 490                 495

Met Gly Thr Gln Gly Asp Leu His Arg Lys Gly Lys Val Val Leu Pro
            500                 505                 510

Gly Phe Gln Ala Val His Cys Pro Ala Pro Ser Pro Val Ile Pro His
        515                 520                 525

Ser

<210> SEQ ID NO 5
<211> LENGTH: 1803
<212> TYPE: DNA
<213> ORGANISM: Homo sapiens
<220> FEATURE:
<221> NAME/KEY: CDS
<222> LOCATION: (1)..(1803)

<400> SEQUENCE: 5 atg agg tcc tgc ctg tgg aga tgc agg cac ctg agc caa ggc gtc cag      48
Met Arg Ser Cys Leu Trp Arg Cys Arg His Leu Ser Gln Gly Val Gln
1               5                   10                  15 tgg tcc ttg ctt ctg gct gtc ctg gtc ttc ttt ctc ttc gcc ttg ccc      96
```

```
                Trp Ser Leu Leu Leu Ala Val Leu Val Phe Phe Leu Phe Ala Leu Pro
                         20                  25                  30 tct ttt att aag gag cct caa aca aag cct tcc agg cat caa cgc aca        144
Ser Phe Ile Lys Glu Pro Gln Thr Lys Pro Ser Arg His Gln Arg Thr
         35                  40                  45 gag aac att aaa gaa agg tct cta cag tcc ctg gca aag cct aag tcc        192
Glu Asn Ile Lys Glu Arg Ser Leu Gln Ser Leu Ala Lys Pro Lys Ser
 50                  55                  60 cag gca ccc aca agg gca agg agg aca acc atc tat gca gag cca gtg        240
Gln Ala Pro Thr Arg Ala Arg Arg Thr Thr Ile Tyr Ala Glu Pro Val
 65                  70                  75                  80 cca gag aac aat gcc ctc aac aca caa acc cag ccc aag gcc cac acc        288
Pro Glu Asn Asn Ala Leu Asn Thr Gln Thr Gln Pro Lys Ala His Thr
                 85                  90                  95 acc gga gac aga gga aag gag gcc aac cag gca ccg ccg gag gag cag        336
Thr Gly Asp Arg Gly Lys Glu Ala Asn Gln Ala Pro Pro Glu Glu Gln
            100                 105                 110 gac aag gtg ccc cac aca gca cag agg gca gca tgg aag agc cca gaa        384
Asp Lys Val Pro His Thr Ala Gln Arg Ala Ala Trp Lys Ser Pro Glu
        115                 120                 125 aaa gag aaa acc atg gtg aac aca ctg tca ccc aga ggg caa gat gca        432
Lys Glu Lys Thr Met Val Asn Thr Leu Ser Pro Arg Gly Gln Asp Ala
130                 135                 140 ggg atg gcc tct ggc agg aca gag gca caa tca tgg aag agc cag gac        480
Gly Met Ala Ser Gly Arg Thr Glu Ala Gln Ser Trp Lys Ser Gln Asp
145                 150                 155                 160 aca aag acg acc caa gga aat ggg ggc cag acc agg aag ctg acg gcc        528
Thr Lys Thr Thr Gln Gly Asn Gly Gly Gln Thr Arg Lys Leu Thr Ala
                165                 170                 175 tcc agg acg gtg tca gag aag cac cag ggc aaa gcg gca acc aca gcc        576
Ser Arg Thr Val Ser Glu Lys His Gln Gly Lys Ala Ala Thr Thr Ala
            180                 185                 190 aag acg ctc att ccc aaa agt cag cac aga atg ctg gct ccc aca gga        624
Lys Thr Leu Ile Pro Lys Ser Gln His Arg Met Leu Ala Pro Thr Gly
        195                 200                 205 gca gtg tca aca agg acg aga cag aaa gga gtg acc aca gca gtc atc        672
Ala Val Ser Thr Arg Thr Arg Gln Lys Gly Val Thr Thr Ala Val Ile
    210                 215                 220 cca cct aag gag aag aaa cct cag gcc acc cca ccc cct gcc cct ttc        720
Pro Pro Lys Glu Lys Lys Pro Gln Ala Thr Pro Pro Pro Ala Pro Phe
225                 230                 235                 240 cag agc ccc acg acg cag aga aac caa aga ctg aag gcc gcc aac ttc        768
Gln Ser Pro Thr Thr Gln Arg Asn Gln Arg Leu Lys Ala Ala Asn Phe
                245                 250                 255 aaa tct gag cct cgg tgg gat ttt gag gaa aaa tac agc ttc gaa ata        816
Lys Ser Glu Pro Arg Trp Asp Phe Glu Glu Lys Tyr Ser Phe Glu Ile
            260                 265                 270 gga ggc ctt cag acg act tgc cct gac tct gtg aag atc aaa gcc tcc        864
Gly Gly Leu Gln Thr Thr Cys Pro Asp Ser Val Lys Ile Lys Ala Ser
        275                 280                 285 aag tcg ctg tgg ctc cag aaa ctc ttt ctg ccc aac ctc act ctc ttc        912
Lys Ser Leu Trp Leu Gln Lys Leu Phe Leu Pro Asn Leu Thr Leu Phe
    290                 295                 300 ctg gac tcc aga cac ttc aac cag agt gag tgg gac cgc ctg gaa cac        960
Leu Asp Ser Arg His Phe Asn Gln Ser Glu Trp Asp Arg Leu Glu His
305                 310                 315                 320 ttt gca cca ccc ttt ggc ttc atg gag ctc aac tac tcc ttg gtg cag       1008
Phe Ala Pro Pro Phe Gly Phe Met Glu Leu Asn Tyr Ser Leu Val Gln
                325                 330                 335
```

| | | |
|---|---|---|
| aag gtc gtg aca cgc ttc cct cca gtg ccc cag cag cag ctg ctc ctg<br>Lys Val Val Thr Arg Phe Pro Pro Val Pro Gln Gln Gln Leu Leu Leu<br>340                         345                        350 | | 1056 |
| gcc agc ctc ccc gct ggg agc ctc cgg tgc atc acc tgt gcc gtg gtg<br>Ala Ser Leu Pro Ala Gly Ser Leu Arg Cys Ile Thr Cys Ala Val Val<br>355                         360                        365 | | 1104 |
| ggc aac ggg ggc atc ctg aac aac tcc cac atg ggc cag gag ata gac<br>Gly Asn Gly Gly Ile Leu Asn Asn Ser His Met Gly Gln Glu Ile Asp<br>370                         375                        380 | | 1152 |
| agt cac gac tac gtg ttc cga ttg agc gga gct ctc att aaa ggc tac<br>Ser His Asp Tyr Val Phe Arg Leu Ser Gly Ala Leu Ile Lys Gly Tyr<br>385                         390                        395                        400 | | 1200 |
| gaa cag gat gtg ggg act cgg aca tcc ttc tac ggc ttt acc gcc ttc<br>Glu Gln Asp Val Gly Thr Arg Thr Ser Phe Tyr Gly Phe Thr Ala Phe<br>405                         410                        415 | | 1248 |
| tcc ctg acc cag tca ctc ctt ata ttg ggc aat cgg ggt ttc aag aac<br>Ser Leu Thr Gln Ser Leu Leu Ile Leu Gly Asn Arg Gly Phe Lys Asn<br>420                         425                        430 | | 1296 |
| gtg cct ctt ggg aag gac gtc cgc tac ttg cac ttc ctg gaa ggc acc<br>Val Pro Leu Gly Lys Asp Val Arg Tyr Leu His Phe Leu Glu Gly Thr<br>435                         440                        445 | | 1344 |
| cgg gac tat gag tgg ctg gaa gca ctg ctt atg aat cag acg gtg atg<br>Arg Asp Tyr Glu Trp Leu Glu Ala Leu Leu Met Asn Gln Thr Val Met<br>450                         455                        460 | | 1392 |
| tca aaa aac ctt ttc tgg ttc agg cac aga ccc cag gaa gct ttt cgg<br>Ser Lys Asn Leu Phe Trp Phe Arg His Arg Pro Gln Glu Ala Phe Arg<br>465                         470                        475                        480 | | 1440 |
| gaa gcc ctg cac atg gac agg tac ctg ttg ctg cac cca gac ttt ctc<br>Glu Ala Leu His Met Asp Arg Tyr Leu Leu Leu His Pro Asp Phe Leu<br>485                         490                        495 | | 1488 |
| cga tac atg aag aac agg ttt ctg agg tct aag acc ctg gat ggt gcc<br>Arg Tyr Met Lys Asn Arg Phe Leu Arg Ser Lys Thr Leu Asp Gly Ala<br>500                         505                        510 | | 1536 |
| cac tgg agg ata tac cgc ccc acc act ggg gcc ctg ctg ctc act<br>His Trp Arg Ile Tyr Arg Pro Thr Thr Gly Ala Leu Leu Leu Thr<br>515                         520                        525 | | 1584 |
| gcc ctt cag ctc tgt gac cag gtg agt gct tat ggc ttc atc act gag<br>Ala Leu Gln Leu Cys Asp Gln Val Ser Ala Tyr Gly Phe Ile Thr Glu<br>530                         535                        540 | | 1632 |
| ggc cat gag cgc ttt tct gat cac tac tat gat aca tca tgg aag cgg<br>Gly His Glu Arg Phe Ser Asp His Tyr Tyr Asp Thr Ser Trp Lys Arg<br>545                         550                        555                        560 | | 1680 |
| ctg atc ttt tac ata aac cat gac ttc aag ctg gag aga gaa gtc tgg<br>Leu Ile Phe Tyr Ile Asn His Asp Phe Lys Leu Glu Arg Glu Val Trp<br>565                         570                        575 | | 1728 |
| aag cgg cta cac gat gaa ggg ata atc cgg ctg tac cag cgt cct ggt<br>Lys Arg Leu His Asp Glu Gly Ile Ile Arg Leu Tyr Gln Arg Pro Gly<br>580                         585                        590 | | 1776 |
| ccc gga act gcc aaa gcc aag aac tga<br>Pro Gly Thr Ala Lys Ala Lys Asn<br>595                         600 | | 1803 |

<210> SEQ ID NO 6
<211> LENGTH: 600
<212> TYPE: PRT
<213> ORGANISM: Homo sapiens

<400> SEQUENCE: 6

Met Arg Ser Cys Leu Trp Arg Cys Arg His Leu Ser Gln Gly Val Gln
1                   5                   10                 15

```
Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
        35                  40                  45

Glu Asn Ile Lys Glu Arg Ser Leu Gln Ser Leu Ala Lys Pro Lys Ser
    50                  55                  60

Gln Ala Pro Thr Arg Ala Arg Arg Thr Thr Ile Tyr Ala Glu Pro Val
65                  70                  75                  80

Pro Glu Asn Asn Ala Leu Asn Thr Gln Thr Gln Pro Lys Ala His Thr
                85                  90                  95

Thr Gly Asp Arg Gly Lys Glu Ala Asn Gln Ala Pro Glu Glu Gln
                100                 105                 110

Asp Lys Val Pro His Thr Ala Gln Arg Ala Ala Trp Lys Ser Pro Glu
            115                 120                 125

Lys Glu Lys Thr Met Val Asn Thr Leu Ser Pro Arg Gly Gln Asp Ala
        130                 135                 140

Gly Met Ala Ser Gly Arg Thr Glu Ala Gln Ser Trp Lys Ser Gln Asp
145                 150                 155                 160

Thr Lys Thr Thr Gln Gly Asn Gly Gln Thr Arg Lys Leu Thr Ala
                165                 170                 175

Ser Arg Thr Val Ser Glu Lys His Gln Gly Lys Ala Ala Thr Thr Ala
            180                 185                 190

Lys Thr Leu Ile Pro Lys Ser Gln His Arg Met Leu Ala Pro Thr Gly
        195                 200                 205

Ala Val Ser Thr Arg Thr Arg Gln Lys Gly Val Thr Thr Ala Val Ile
    210                 215                 220

Pro Pro Lys Glu Lys Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
                245                 250                 255

Lys Ser Glu Pro Arg Trp Asp Phe Glu Glu Lys Tyr Ser Phe Glu Ile
            260                 265                 270

Gly Gly Leu Gln Thr Thr Cys Pro Asp Ser Val Lys Ile Lys Ala Ser
        275                 280                 285

Lys Ser Leu Trp Leu Gln Lys Leu Phe Leu Pro Asn Leu Thr Leu Phe
290                 295                 300

Leu Asp Ser Arg His Phe Asn Gln Ser Glu Trp Asp Arg Leu Glu His
305                 310                 315                 320

Phe Ala Pro Pro Phe Gly Phe Met Glu Leu Asn Tyr Ser Leu Val Gln
                325                 330                 335

Lys Val Val Thr Arg Phe Pro Pro Val Pro Gln Gln Gln Leu Leu Leu
            340                 345                 350

Ala Ser Leu Pro Ala Gly Ser Leu Arg Cys Ile Thr Cys Ala Val Val
        355                 360                 365

Gly Asn Gly Gly Ile Leu Asn Asn Ser His Met Gly Gln Glu Ile Asp
370                 375                 380

Ser His Asp Tyr Val Phe Arg Leu Ser Gly Ala Leu Ile Lys Gly Tyr
385                 390                 395                 400

Glu Gln Asp Val Gly Thr Arg Thr Ser Phe Tyr Gly Phe Thr Ala Phe
                405                 410                 415

Ser Leu Thr Gln Ser Leu Leu Ile Leu Gly Asn Arg Gly Phe Lys Asn
            420                 425                 430

Val Pro Leu Gly Lys Asp Val Arg Tyr Leu His Phe Leu Glu Gly Thr
```

```
                    435                 440                 445
Arg Asp Tyr Glu Trp Leu Glu Ala Leu Leu Met Asn Gln Thr Val Met
450                 455                 460

Ser Lys Asn Leu Phe Trp Phe Arg His Arg Pro Gln Glu Ala Phe Arg
465                 470                 475                 480

Glu Ala Leu His Met Asp Arg Tyr Leu Leu His Pro Asp Phe Leu
                    485                 490                 495

Arg Tyr Met Lys Asn Arg Phe Leu Arg Ser Lys Thr Leu Asp Gly Ala
                500                 505                 510

His Trp Arg Ile Tyr Arg Pro Thr Thr Gly Ala Leu Leu Leu Thr
                515                 520                 525

Ala Leu Gln Leu Cys Asp Gln Val Ser Ala Tyr Gly Phe Ile Thr Glu
530                 535                 540

Gly His Glu Arg Phe Ser Asp His Tyr Tyr Asp Thr Ser Trp Lys Arg
545                 550                 555                 560

Leu Ile Phe Tyr Ile Asn His Asp Phe Lys Leu Glu Arg Glu Val Trp
                565                 570                 575

Lys Arg Leu His Asp Glu Gly Ile Ile Arg Leu Tyr Gln Arg Pro Gly
                580                 585                 590

Pro Gly Thr Ala Lys Ala Lys Asn
                595                 600

<210> SEQ ID NO 7
<211> LENGTH: 1125
<212> TYPE: DNA
<213> ORGANISM: Homo sapiens
<220> FEATURE:
<221> NAME/KEY: CDS
<222> LOCATION: (1)..(1125)

<400> SEQUENCE: 7 atg ggg ctc ccg cgc ggg tcg ttc ttc tgg gtg ctg ctc ctg ctc acg      48
Met Gly Leu Pro Arg Gly Ser Phe Phe Trp Val Leu Leu Leu Leu Thr
1               5                   10                  15 gct gcc tgc tcg ggg ctc ctc ttt gcc ctg tac ttc tcg gcg gtg cag      96
Ala Ala Cys Ser Gly Leu Leu Phe Ala Leu Tyr Phe Ser Ala Val Gln
            20                  25                  30 cgg tac ccg ggg cca gcg gcc gga gcc agg gac aca aca tca ttt gaa     144
Arg Tyr Pro Gly Pro Ala Ala Gly Ala Arg Asp Thr Thr Ser Phe Glu
        35                  40                  45 gca ttc ttt caa tcc aag gca tcg aat tct tgg aca gga aag ggc cag     192
Ala Phe Phe Gln Ser Lys Ala Ser Asn Ser Trp Thr Gly Lys Gly Gln
    50                  55                  60 gcc tgc cga cac ctg ctt cac ctg gcc att cag cgg cac ccc cac ttc     240
Ala Cys Arg His Leu Leu His Leu Ala Ile Gln Arg His Pro His Phe
65                  70                  75                  80 cgt ggc ctg ttc aat ctc tcc att cca gtg ctg ctg tgg ggg gac ctc     288
Arg Gly Leu Phe Asn Leu Ser Ile Pro Val Leu Leu Trp Gly Asp Leu
                85                  90                  95 ttc acc cca gcg ctc tgg gac cgc ctg agc caa cac aaa gcc ccg tat     336
Phe Thr Pro Ala Leu Trp Asp Arg Leu Ser Gln His Lys Ala Pro Tyr
            100                 105                 110 ggc tgg cgg ggg ctc tct cac caa gtc atc gcc tcc acc ctg agc ctt     384
Gly Trp Arg Gly Leu Ser His Gln Val Ile Ala Ser Thr Leu Ser Leu
        115                 120                 125 ctg aac ggc tca gag agt gcc aag ctg ttt gcc ccg ccc agg gac acc     432
Leu Asn Gly Ser Glu Ser Ala Lys Leu Phe Ala Pro Pro Arg Asp Thr
    130                 135                 140
```

```
cct cca aag tgt atc cgg tgt gcc gtg gtg ggc aac gga ggc att ctg      480
Pro Pro Lys Cys Ile Arg Cys Ala Val Val Gly Asn Gly Gly Ile Leu
145                 150                 155                 160 aat ggg tcc cgc cag ggt ccc aac atc gat gcc cat gac tat gta ttc      528
Asn Gly Ser Arg Gln Gly Pro Asn Ile Asp Ala His Asp Tyr Val Phe
                165                 170                 175 aga ctc aat gga gct gtg atc aaa ggc ttc gag cgc gat gtg ggc acc      576
Arg Leu Asn Gly Ala Val Ile Lys Gly Phe Glu Arg Asp Val Gly Thr
            180                 185                 190 aag act tcc ttc tat ggt ttc act gtg aac acg atg aag aac tcc ctc      624
Lys Thr Ser Phe Tyr Gly Phe Thr Val Asn Thr Met Lys Asn Ser Leu
        195                 200                 205 gtc tcc tac tgg aat ctg ggc ttc acc tcc gtg cca caa gga cag gac      672
Val Ser Tyr Trp Asn Leu Gly Phe Thr Ser Val Pro Gln Gly Gln Asp
    210                 215                 220 ctg cag tat atc ttc atc ccc tca gac atc cgc gac tat gtg atg ctg      720
Leu Gln Tyr Ile Phe Ile Pro Ser Asp Ile Arg Asp Tyr Val Met Leu
225                 230                 235                 240 aga tcg gcc att ctg ggc gtg cct gtc cct gag ggc cta gat aaa ggg      768
Arg Ser Ala Ile Leu Gly Val Pro Val Pro Glu Gly Leu Asp Lys Gly
                245                 250                 255 gac agg ccg cac gcc tat ttt gga cca gaa gcc tct gcc agt aaa ttc      816
Asp Arg Pro His Ala Tyr Phe Gly Pro Glu Ala Ser Ala Ser Lys Phe
                260                 265                 270 aag ctg cta cat ccg gac ttc atc agc tac ctg aca gaa agg ttc ttg      864
Lys Leu Leu His Pro Asp Phe Ile Ser Tyr Leu Thr Glu Arg Phe Leu
            275                 280                 285 aaa tca aag ttg att aac aca cat ttt gga gac cta tat atg cct agt      912
Lys Ser Lys Leu Ile Asn Thr His Phe Gly Asp Leu Tyr Met Pro Ser
        290                 295                 300 acc ggg gct ctc atg ctg ctg aca gct ttg cat acc tgt gac cag gtc      960
Thr Gly Ala Leu Met Leu Leu Thr Ala Leu His Thr Cys Asp Gln Val
305                 310                 315                 320 agt gcc tat gga ttc atc aca agc aac tac tgg aaa ttt tcc gac cac     1008
Ser Ala Tyr Gly Phe Ile Thr Ser Asn Tyr Trp Lys Phe Ser Asp His
                325                 330                 335 tat ttc gaa cga aaa atg aag cca ttg ata ttt tat gca aac cac gat     1056
Tyr Phe Glu Arg Lys Met Lys Pro Leu Ile Phe Tyr Ala Asn His Asp
                340                 345                 350 ctg tcc ctg gaa gct gcc ctg tgg agg gac ctg cac aag gcc ggc atc     1104
Leu Ser Leu Glu Ala Ala Leu Trp Arg Asp Leu His Lys Ala Gly Ile
            355                 360                 365 ctt cag ctg tac cag cgc tga                                         1125
Leu Gln Leu Tyr Gln Arg
        370

<210> SEQ ID NO 8
<211> LENGTH: 374
<212> TYPE: PRT
<213> ORGANISM: Homo sapiens

<400> SEQUENCE: 8

Met Gly Leu Pro Arg Gly Ser Phe Phe Trp Val Leu Leu Leu Leu Thr
1               5                   10                  15

Ala Ala Cys Ser Gly Leu Leu Phe Ala Leu Tyr Phe Ser Ala Val Gln
                20                  25                  30

Arg Tyr Pro Gly Pro Ala Ala Gly Ala Arg Asp Thr Thr Ser Phe Glu
            35                  40                  45

Ala Phe Phe Gln Ser Lys Ala Ser Asn Ser Trp Thr Gly Lys Gly Gln
        50                  55                  60
```

```
Ala Cys Arg His Leu Leu His Leu Ala Ile Gln Arg Pro His Phe
 65                  70                  75                  80

Arg Gly Leu Phe Asn Leu Ser Ile Pro Val Leu Leu Trp Gly Asp Leu
             85                  90                  95

Phe Thr Pro Ala Leu Trp Asp Arg Leu Ser Gln His Lys Ala Pro Tyr
            100                 105                 110

Gly Trp Arg Gly Leu Ser His Gln Val Ile Ala Ser Thr Leu Ser Leu
        115                 120                 125

Leu Asn Gly Ser Glu Ser Ala Lys Leu Phe Ala Pro Pro Arg Asp Thr
    130                 135                 140

Pro Pro Lys Cys Ile Arg Cys Ala Val Val Gly Asn Gly Gly Ile Leu
145                 150                 155                 160

Asn Gly Ser Arg Gln Gly Pro Asn Ile Asp Ala His Asp Tyr Val Phe
                165                 170                 175

Arg Leu Asn Gly Ala Val Ile Lys Gly Phe Glu Arg Asp Val Gly Thr
            180                 185                 190

Lys Thr Ser Phe Tyr Gly Phe Thr Val Asn Thr Met Lys Asn Ser Leu
        195                 200                 205

Val Ser Tyr Trp Asn Leu Gly Phe Thr Ser Val Pro Gln Gly Gln Asp
    210                 215                 220

Leu Gln Tyr Ile Phe Ile Pro Ser Asp Ile Arg Asp Tyr Val Met Leu
225                 230                 235                 240

Arg Ser Ala Ile Leu Gly Val Pro Val Pro Glu Gly Leu Asp Lys Gly
                245                 250                 255

Asp Arg Pro His Ala Tyr Phe Gly Pro Glu Ala Ser Ala Ser Lys Phe
            260                 265                 270

Lys Leu Leu His Pro Asp Phe Ile Ser Tyr Leu Thr Glu Arg Phe Leu
        275                 280                 285

Lys Ser Lys Leu Ile Asn Thr His Phe Gly Asp Leu Tyr Met Pro Ser
    290                 295                 300

Thr Gly Ala Leu Met Leu Leu Thr Ala Leu His Thr Cys Asp Gln Val
305                 310                 315                 320

Ser Ala Tyr Gly Phe Ile Thr Ser Asn Tyr Trp Lys Phe Ser Asp His
                325                 330                 335

Tyr Phe Glu Arg Lys Met Lys Pro Leu Ile Phe Tyr Ala Asn His Asp
            340                 345                 350

Leu Ser Leu Glu Ala Ala Leu Trp Arg Asp Leu His Lys Ala Gly Ile
        355                 360                 365

Leu Gln Leu Tyr Gln Arg
    370

<210> SEQ ID NO 9
<211> LENGTH: 918
<212> TYPE: DNA
<213> ORGANISM: Homo sapiens
<220> FEATURE:
<221> NAME/KEY: CDS
<222> LOCATION: (1)..(918)

<400> SEQUENCE: 9 atg gcc tgc atc ctg aag aga aag tct gtg att gct gtg agc ttc ata    48
Met Ala Cys Ile Leu Lys Arg Lys Ser Val Ile Ala Val Ser Phe Ile
 1               5                  10                  15 gca gcg ttc ctt ttc ctg ctg gtt gtg cgt ctt gta aat gaa gtg aat    96
Ala Ala Phe Leu Phe Leu Leu Val Val Arg Leu Val Asn Glu Val Asn
             20                  25                  30
```

| | | |
|---|---|---|
| ttc cca ttg cta cta aac tgc ttt gga caa cct ggt aca aag tgg ata<br>Phe Pro Leu Leu Leu Asn Cys Phe Gly Gln Pro Gly Thr Lys Trp Ile<br>35 40 45 | | 144 |
| cca ttc tcc tac aca tac agg cgg ccc ctt cga act cac tat gga tac<br>Pro Phe Ser Tyr Thr Tyr Arg Arg Pro Leu Arg Thr His Tyr Gly Tyr<br>50 55 60 | | 192 |
| ata aat gtg aag aca caa gag cct ttg caa ctg gac tgt gac ctt tgt<br>Ile Asn Val Lys Thr Gln Glu Pro Leu Gln Leu Asp Cys Asp Leu Cys<br>65 70 75 80 | | 240 |
| gcc ata gtg tca aac tca ggt cag atg gtt ggc cag aag gtg gga aat<br>Ala Ile Val Ser Asn Ser Gly Gln Met Val Gly Gln Lys Val Gly Asn<br>85 90 95 | | 288 |
| gag ata gat cga tcc tcc tgc att tgg aga atg aac aat gcc ccc acc<br>Glu Ile Asp Arg Ser Ser Cys Ile Trp Arg Met Asn Asn Ala Pro Thr<br>100 105 110 | | 336 |
| aaa ggt tat gaa gaa gat gtc ggc cgc atg acc atg att cga gtt gtg<br>Lys Gly Tyr Glu Glu Asp Val Gly Arg Met Thr Met Ile Arg Val Val<br>115 120 125 | | 384 |
| tcc cat acc agc gtt cct ctt ttg cta aaa aac cct gat tat ttt ttc<br>Ser His Thr Ser Val Pro Leu Leu Leu Lys Asn Pro Asp Tyr Phe Phe<br>130 135 140 | | 432 |
| aag gaa gcg aat act act att tat gtt att tgg gga cct ttc cgc aat<br>Lys Glu Ala Asn Thr Thr Ile Tyr Val Ile Trp Gly Pro Phe Arg Asn<br>145 150 155 160 | | 480 |
| atg agg aaa gat ggc aat ggc atc att tac aac atg ttg aaa aag aca<br>Met Arg Lys Asp Gly Asn Gly Ile Ile Tyr Asn Met Leu Lys Lys Thr<br>165 170 175 | | 528 |
| gtt ggt atc tat ccg aat gcc caa ata tac gtg acc aca gag aag cgc<br>Val Gly Ile Tyr Pro Asn Ala Gln Ile Tyr Val Thr Thr Glu Lys Arg<br>180 185 190 | | 576 |
| atg agt tac tgt gat gga gtt ttt aag aag gaa act ggg aag gac aga<br>Met Ser Tyr Cys Asp Gly Val Phe Lys Lys Glu Thr Gly Lys Asp Arg<br>195 200 205 | | 624 |
| gtc cag tct ggc tca tat ctc agc aca ggg tgg ttt acc ttc ctt ctg<br>Val Gln Ser Gly Ser Tyr Leu Ser Thr Gly Trp Phe Thr Phe Leu Leu<br>210 215 220 | | 672 |
| gcc atg gac gcc tgt tat ggc att cac gtc tac ggg atg ata aat gac<br>Ala Met Asp Ala Cys Tyr Gly Ile His Val Tyr Gly Met Ile Asn Asp<br>225 230 235 240 | | 720 |
| acc tac tgc aag aca gaa ggg tat aga aaa gtc ccc tac cat tat tat<br>Thr Tyr Cys Lys Thr Glu Gly Tyr Arg Lys Val Pro Tyr His Tyr Tyr<br>245 250 255 | | 768 |
| gaa caa gga aga gat gag tgt gat gaa tat ttt ctt cat gaa cat gcc<br>Glu Gln Gly Arg Asp Glu Cys Asp Glu Tyr Phe Leu His Glu His Ala<br>260 265 270 | | 816 |
| cca tat ggg ggt cat agg ttt atc act gaa aag aaa gtg ttt gct aaa<br>Pro Tyr Gly Gly His Arg Phe Ile Thr Glu Lys Lys Val Phe Ala Lys<br>275 280 285 | | 864 |
| tgg gcc aag aag cac agg ata ata ttt aca cat cca aac tgg aca ttg<br>Trp Ala Lys Lys His Arg Ile Ile Phe Thr His Pro Asn Trp Thr Leu<br>290 295 300 | | 912 |
| tct tga<br>Ser<br>305 | | 918 |

<210> SEQ ID NO 10
<211> LENGTH: 305
<212> TYPE: PRT
<213> ORGANISM: Homo sapiens -continued

<400> SEQUENCE: 10

Met Ala Cys Ile Leu Lys Arg Lys Ser Val Ile Ala Val Ser Phe Ile
1               5                   10                  15

Ala Ala Phe Leu Phe Leu Leu Val Val Arg Leu Val Asn Glu Val Asn
            20                  25                  30

Phe Pro Leu Leu Leu Asn Cys Phe Gly Gln Pro Gly Thr Lys Trp Ile
        35                  40                  45

Pro Phe Ser Tyr Thr Tyr Arg Arg Pro Leu Arg Thr His Tyr Gly Tyr
    50                  55                  60

Ile Asn Val Lys Thr Gln Glu Pro Leu Gln Leu Asp Cys Asp Leu Cys
65                  70                  75                  80

Ala Ile Val Ser Asn Ser Gly Gln Met Val Gly Gln Lys Val Gly Asn
                85                  90                  95

Glu Ile Asp Arg Ser Ser Cys Ile Trp Arg Met Asn Asn Ala Pro Thr
            100                 105                 110

Lys Gly Tyr Glu Glu Asp Val Gly Arg Met Thr Met Ile Arg Val Val
        115                 120                 125

Ser His Thr Ser Val Pro Leu Leu Lys Asn Pro Asp Tyr Phe Phe
    130                 135                 140

Lys Glu Ala Asn Thr Thr Ile Tyr Val Ile Trp Gly Pro Phe Arg Asn
145                 150                 155                 160

Met Arg Lys Asp Gly Asn Gly Ile Ile Tyr Asn Met Leu Lys Lys Thr
                165                 170                 175

Val Gly Ile Tyr Pro Asn Ala Gln Ile Tyr Val Thr Thr Glu Lys Arg
            180                 185                 190

Met Ser Tyr Cys Asp Gly Val Phe Lys Lys Glu Thr Gly Lys Asp Arg
        195                 200                 205

Val Gln Ser Gly Ser Tyr Leu Ser Thr Gly Trp Phe Thr Phe Leu Leu
    210                 215                 220

Ala Met Asp Ala Cys Tyr Gly Ile His Val Tyr Gly Met Ile Asn Asp
225                 230                 235                 240

Thr Tyr Cys Lys Thr Glu Gly Tyr Arg Lys Val Pro Tyr His Tyr Tyr
                245                 250                 255

Glu Gln Gly Arg Asp Glu Cys Asp Glu Tyr Phe Leu His Glu His Ala
            260                 265                 270

Pro Tyr Gly Gly His Arg Phe Ile Thr Glu Lys Lys Val Phe Ala Lys
        275                 280                 285

Trp Ala Lys Lys His Arg Ile Ile Phe Thr His Pro Asn Trp Thr Leu
    290                 295                 300

Ser
305

<210> SEQ ID NO 11
<211> LENGTH: 909
<212> TYPE: DNA
<213> ORGANISM: Homo sapiens
<220> FEATURE:
<221> NAME/KEY: CDS
<222> LOCATION: (1)..(909)

<400> SEQUENCE: 11 atg aag gct ccg ggt cgg ctc gtg ctc atc atc ctg tgc tcc gtg tcc      48
Met Lys Ala Pro Gly Arg Leu Val Leu Ile Ile Leu Cys Ser Val Val
1               5                   10                  15 ttc tct gcc gtc tac atc ctc ctg tgc tgc tgg gcc ggc ctg ccc ctc      96
Phe Ser Ala Val Tyr Ile Leu Leu Cys Cys Trp Ala Gly Leu Pro Leu

```
                    20                  25                  30
tgc ctg gcc acc tgc ctg gac cac cac ttc ccc aca ggc tcc agg ccc      144
Cys Leu Ala Thr Cys Leu Asp His His Phe Pro Thr Gly Ser Arg Pro
        35                  40                  45 act gtg ccg gga ccc ctg cac ttc agt gga tat agc agt gtg cca gat      192
Thr Val Pro Gly Pro Leu His Phe Ser Gly Tyr Ser Ser Val Pro Asp
 50                  55                  60 ggg aag ccg ctg gtc cgc gag ccc tgc cgc agc tgt gcc gtg gtg tcc      240
Gly Lys Pro Leu Val Arg Glu Pro Cys Arg Ser Cys Ala Val Val Ser
 65                  70                  75                  80 agc tcc ggc caa atg ctg ggc tca ggc ctg ggt gct gag atc gac agt      288
Ser Ser Gly Gln Met Leu Gly Ser Gly Leu Gly Ala Glu Ile Asp Ser
                 85                  90                  95 gcc gag tgc gtg ttc cgc atg aac cag gcg ccc acc gtg ggc ttt gag      336
Ala Glu Cys Val Phe Arg Met Asn Gln Ala Pro Thr Val Gly Phe Glu
            100                 105                 110 gcg gat gtg ggc cag cgc agc acc ctg cgt gtc gtc tca cac aca agc      384
Ala Asp Val Gly Gln Arg Ser Thr Leu Arg Val Val Ser His Thr Ser
        115                 120                 125 gtg ccg ctg ctg ctg cgc aac tat tca cac tac ttc cag aag gcc cga      432
Val Pro Leu Leu Leu Arg Asn Tyr Ser His Tyr Phe Gln Lys Ala Arg
130                 135                 140 gac acg ctc tac atg gtg tgg ggc cag ggc agg cac atg gac cgg gtg      480
Asp Thr Leu Tyr Met Val Trp Gly Gln Gly Arg His Met Asp Arg Val
145                 150                 155                 160 ctc ggc ggc cgc acc tac cgc acg ctg ctg cag ctc acc agg atg tac      528
Leu Gly Gly Arg Thr Tyr Arg Thr Leu Leu Gln Leu Thr Arg Met Tyr
                165                 170                 175 ccc ggc ctg cag gtg tac acc ttc acg gag cgc atg atg gcc tac tgc      576
Pro Gly Leu Gln Val Tyr Thr Phe Thr Glu Arg Met Met Ala Tyr Cys
            180                 185                 190 gac cag atc ttc cag gac gag acg ggc aag aac cgg agg cag tcg ggc      624
Asp Gln Ile Phe Gln Asp Glu Thr Gly Lys Asn Arg Arg Gln Ser Gly
        195                 200                 205 tcc ttc ctc agc acc ggc tgg ttc acc atg atc ctc gcg ctg gag ctg      672
Ser Phe Leu Ser Thr Gly Trp Phe Thr Met Ile Leu Ala Leu Glu Leu
210                 215                 220 tgt gag gag atc gtg gtc tat ggg atg gtc agc gac agc tac tgc agg      720
Cys Glu Glu Ile Val Val Tyr Gly Met Val Ser Asp Ser Tyr Cys Arg
225                 230                 235                 240 gag aag agc cac ccc tca gtg cct tac cac tac ttt gag aag ggc cgg      768
Glu Lys Ser His Pro Ser Val Pro Tyr His Tyr Phe Glu Lys Gly Arg
                245                 250                 255 cta gat gag tgt cag atg tac ctg gca cac gag cag gcg ccc cga agc      816
Leu Asp Glu Cys Gln Met Tyr Leu Ala His Glu Gln Ala Pro Arg Ser
            260                 265                 270 gcc cac cgc ttc atc act gag aag gcg gtc ttc tcc cgc tgg gcc aag      864
Ala His Arg Phe Ile Thr Glu Lys Ala Val Phe Ser Arg Trp Ala Lys
        275                 280                 285 aag agg ccc atc gtg ttc gcc cat ccg tcc tgg agg act gag tag          909
Lys Arg Pro Ile Val Phe Ala His Pro Ser Trp Arg Thr Glu
        290                 295                 300

<210> SEQ ID NO 12
<211> LENGTH: 302
<212> TYPE: PRT
<213> ORGANISM: Homo sapiens

<400> SEQUENCE: 12

Met Lys Ala Pro Gly Arg Leu Val Leu Ile Ile Leu Cys Ser Val Val
```

```
1               5                   10                  15
    Phe Ser Ala Val Tyr Ile Leu Leu Cys Cys Trp Ala Gly Leu Pro Leu
                20                  25                  30
    Cys Leu Ala Thr Cys Leu Asp His His Phe Pro Thr Gly Ser Arg Pro
                35                  40                  45
    Thr Val Pro Gly Pro Leu His Phe Ser Gly Tyr Ser Ser Val Pro Asp
                50                  55                  60
    Gly Lys Pro Leu Val Arg Glu Pro Cys Arg Ser Cys Ala Val Val Ser
    65                  70                  75                  80
    Ser Ser Gly Gln Met Leu Gly Ser Gly Leu Gly Ala Glu Ile Asp Ser
                    85                  90                  95
    Ala Glu Cys Val Phe Arg Met Asn Gln Ala Pro Thr Val Gly Phe Glu
                    100                 105                 110
    Ala Asp Val Gly Gln Arg Ser Thr Leu Arg Val Val Ser His Thr Ser
                    115                 120                 125
    Val Pro Leu Leu Leu Arg Asn Tyr Ser His Tyr Phe Gln Lys Ala Arg
                130                 135                 140
    Asp Thr Leu Tyr Met Val Trp Gly Gln Gly Arg His Met Asp Arg Val
    145                 150                 155                 160
    Leu Gly Gly Arg Thr Tyr Arg Thr Leu Leu Gln Leu Thr Arg Met Tyr
                        165                 170                 175
    Pro Gly Leu Gln Val Tyr Thr Phe Thr Glu Arg Met Met Ala Tyr Cys
                    180                 185                 190
    Asp Gln Ile Phe Gln Asp Glu Thr Gly Lys Asn Arg Arg Gln Ser Gly
                    195                 200                 205
    Ser Phe Leu Ser Thr Gly Trp Phe Thr Met Ile Leu Ala Leu Glu Leu
            210                 215                 220
    Cys Glu Glu Ile Val Val Tyr Gly Met Val Ser Asp Ser Tyr Cys Arg
    225                 230                 235                 240
    Glu Lys Ser His Pro Ser Val Pro Tyr His Tyr Phe Glu Lys Gly Arg
                        245                 250                 255
    Leu Asp Glu Cys Gln Met Tyr Leu Ala His Glu Gln Ala Pro Arg Ser
                    260                 265                 270
    Ala His Arg Phe Ile Thr Glu Lys Ala Val Phe Ser Arg Trp Ala Lys
                    275                 280                 285
    Lys Arg Pro Ile Val Phe Ala His Pro Ser Trp Arg Thr Glu
            290                 295                 300

<210> SEQ ID NO 13
<211> LENGTH: 1011
<212> TYPE: DNA
<213> ORGANISM: Homo sapiens
<220> FEATURE:
<221> NAME/KEY: CDS
<222> LOCATION: (1)..(1011)

<400> SEQUENCE: 13 atg aag acc ctg atg cgc cat ggt ctg gca gtg tgt tta gcg ctc acc        48
Met Lys Thr Leu Met Arg His Gly Leu Ala Val Cys Leu Ala Leu Thr
1               5                   10                  15 acc atg tgc acc agc ttg ttg cta gtg tac agc agc ctc ggc ggc cag        96
Thr Met Cys Thr Ser Leu Leu Leu Val Tyr Ser Ser Leu Gly Gly Gln
                20                  25                  30 aag gag cgg ccc ccg cag cag cag cag cag cag caa cag cag cag           144
Lys Glu Arg Pro Pro Gln Gln Gln Gln Gln Gln Gln Gln Gln Gln
            35                  40                  45
```

```
cag gcg tcg gcc acc ggc agc tcg cag ccg gcg gcg gag agc agc acc      192
Gln Ala Ser Ala Thr Gly Ser Ser Gln Pro Ala Ala Glu Ser Ser Thr
     50                  55                  60 cag cag cgc ccc ggg gtc ccc gcg gga ccg cgg cca ctg gac gga tac      240
Gln Gln Arg Pro Gly Val Pro Ala Gly Pro Arg Pro Leu Asp Gly Tyr
 65                  70                  75                  80 ctc gga gtg gcg gac cac aag ccc ctg aaa atg cac tgc agg gac tgt      288
Leu Gly Val Ala Asp His Lys Pro Leu Lys Met His Cys Arg Asp Cys
                 85                  90                  95 gcc ctg gtg acc agc tca ggg cat ctg ctg cac agt cgg caa ggc tcc      336
Ala Leu Val Thr Ser Ser Gly His Leu Leu His Ser Arg Gln Gly Ser
            100                 105                 110 cag att gac cag aca gag tgt gtc atc cgc atg aat gac gcc ccc aca      384
Gln Ile Asp Gln Thr Glu Cys Val Ile Arg Met Asn Asp Ala Pro Thr
        115                 120                 125 cgc ggc tat ggg cgt gac gtg ggc aat cgc acc agc ctg agg gtc atc      432
Arg Gly Tyr Gly Arg Asp Val Gly Asn Arg Thr Ser Leu Arg Val Ile
    130                 135                 140 gcg cat tcc agc atc cag agg atc ctc cgc aac cgc cat gac ctg ctc      480
Ala His Ser Ser Ile Gln Arg Ile Leu Arg Asn Arg His Asp Leu Leu
145                 150                 155                 160 aac gtg agc cag ggc acc gtg ttc atc ttc tgg ggc ccc agc agc tac      528
Asn Val Ser Gln Gly Thr Val Phe Ile Phe Trp Gly Pro Ser Ser Tyr
                165                 170                 175 atg cgg cgg gac ggc aag ggc cag gtc tac aac aac ctg cat ctc ctg      576
Met Arg Arg Asp Gly Lys Gly Gln Val Tyr Asn Asn Leu His Leu Leu
            180                 185                 190 agc cag gtg ctg ccc cgg ctg aag gcc ttc atg att act cgc cac aag      624
Ser Gln Val Leu Pro Arg Leu Lys Ala Phe Met Ile Thr Arg His Lys
        195                 200                 205 atg ctg cag ttt gat gag ctc ttc aag cag gag act ggc aaa gac agg      672
Met Leu Gln Phe Asp Glu Leu Phe Lys Gln Glu Thr Gly Lys Asp Arg
    210                 215                 220 aag ata tcc aac act tgg ctc agc act ggc tgg ttt aca atg aca att      720
Lys Ile Ser Asn Thr Trp Leu Ser Thr Gly Trp Phe Thr Met Thr Ile
225                 230                 235                 240 gca ctg gag ctc tgt gac agg atc aat gtt tat ggc atg gtg ccc cca      768
Ala Leu Glu Leu Cys Asp Arg Ile Asn Val Tyr Gly Met Val Pro Pro
                245                 250                 255 gac ttc tgc agg gat ccc aat cac cct tca gta cct tat cat tat tat      816
Asp Phe Cys Arg Asp Pro Asn His Pro Ser Val Pro Tyr His Tyr Tyr
            260                 265                 270 gaa cct ttt gga cct gat gaa tgt aca atg tac ctc tcc cat gag cga      864
Glu Pro Phe Gly Pro Asp Glu Cys Thr Met Tyr Leu Ser His Glu Arg
        275                 280                 285 gga cgc aag ggc agt cat cac cgc ttt atc aca gag aaa cga gtc ttt      912
Gly Arg Lys Gly Ser His His Arg Phe Ile Thr Glu Lys Arg Val Phe
    290                 295                 300 aag aac tgg gca cgg aca ttc aat att cac ttt ttt caa cca gac tgg      960
Lys Asn Trp Ala Arg Thr Phe Asn Ile His Phe Phe Gln Pro Asp Trp
305                 310                 315                 320 aaa cca gaa tca ctt gct ata aat cat cct gag aat aaa cct gtg ttc     1008
Lys Pro Glu Ser Leu Ala Ile Asn His Pro Glu Asn Lys Pro Val Phe
                325                 330                 335 taa                                                                 1011

<210> SEQ ID NO 14
<211> LENGTH: 336
<212> TYPE: PRT
<213> ORGANISM: Homo sapiens
```

<400> SEQUENCE: 14

```
Met Lys Thr Leu Met Arg His Gly Leu Ala Val Cys Leu Ala Leu Thr
1               5                   10                  15

Thr Met Cys Thr Ser Leu Leu Leu Val Tyr Ser Ser Leu Gly Gly Gln
            20                  25                  30

Lys Glu Arg Pro Pro Gln Gln Gln Gln Gln Gln Gln Gln Gln Gln Gln
        35                  40                  45

Gln Ala Ser Ala Thr Gly Ser Ser Gln Pro Ala Ala Glu Ser Ser Thr
50                  55                  60

Gln Gln Arg Pro Gly Val Pro Ala Gly Pro Arg Pro Leu Asp Gly Tyr
65                  70                  75                  80

Leu Gly Val Ala Asp His Lys Pro Leu Lys Met His Cys Arg Asp Cys
                85                  90                  95

Ala Leu Val Thr Ser Ser Gly His Leu Leu His Ser Arg Gln Gly Ser
            100                 105                 110

Gln Ile Asp Gln Thr Glu Cys Val Ile Arg Met Asn Asp Ala Pro Thr
        115                 120                 125

Arg Gly Tyr Gly Arg Asp Val Gly Asn Arg Thr Ser Leu Arg Val Ile
130                 135                 140

Ala His Ser Ser Ile Gln Arg Ile Leu Arg Asn Arg His Asp Leu Leu
145                 150                 155                 160

Asn Val Ser Gln Gly Thr Val Phe Ile Phe Trp Gly Pro Ser Ser Tyr
                165                 170                 175

Met Arg Arg Asp Gly Lys Gly Gln Val Tyr Asn Asn Leu His Leu Leu
            180                 185                 190

Ser Gln Val Leu Pro Arg Leu Lys Ala Phe Met Ile Thr Arg His Lys
        195                 200                 205

Met Leu Gln Phe Asp Glu Leu Phe Lys Gln Glu Thr Gly Lys Asp Arg
210                 215                 220

Lys Ile Ser Asn Thr Trp Leu Ser Thr Gly Trp Phe Thr Met Thr Ile
225                 230                 235                 240

Ala Leu Glu Leu Cys Asp Arg Ile Asn Val Tyr Gly Met Val Pro Pro
                245                 250                 255

Asp Phe Cys Arg Asp Pro Asn His Pro Ser Val Pro Tyr His Tyr Tyr
            260                 265                 270

Glu Pro Phe Gly Pro Asp Glu Cys Thr Met Tyr Leu Ser His Glu Arg
        275                 280                 285

Gly Arg Lys Gly Ser His His Arg Phe Ile Thr Glu Lys Arg Val Phe
290                 295                 300

Lys Asn Trp Ala Arg Thr Phe Asn Ile His Phe Phe Gln Pro Asp Trp
305                 310                 315                 320

Lys Pro Glu Ser Leu Ala Ile Asn His Pro Glu Asn Lys Pro Val Phe
                325                 330                 335
```

<210> SEQ ID NO 15
<211> LENGTH: 1002
<212> TYPE: DNA
<213> ORGANISM: Homo sapiens
<220> FEATURE:
<221> NAME/KEY: CDS
<222> LOCATION: (1)..(1002)

<400> SEQUENCE: 15

```
atg gct tgc tcg agg ccc ccc agc cag tgt gaa ccc aca tcc ctg ccc      48
Met Ala Cys Ser Arg Pro Pro Ser Gln Cys Glu Pro Thr Ser Leu Pro
```

```
       1               5                  10                 15
cca ggg cca cct gca gga cgc cga cac cta ccc ctc agc aga cgc cgg    96
Pro Gly Pro Pro Ala Gly Arg Arg His Leu Pro Leu Ser Arg Arg Arg
            20                  25                  30 aga gaa atg agt agc aac aaa gag cag cgg tca gca gtg ttc gtg atc   144
Arg Glu Met Ser Ser Asn Lys Glu Gln Arg Ser Ala Val Phe Val Ile
        35                  40                  45 ctc ttt gcc ctc atc acc atc ctc atc ctc tac agc tcc aac agt gcc   192
Leu Phe Ala Leu Ile Thr Ile Leu Ile Leu Tyr Ser Ser Asn Ser Ala
    50                  55                  60 aat gag gtc ttc cat tac ggc tcc ctg cgg ggc cgt agc cgc cga cct   240
Asn Glu Val Phe His Tyr Gly Ser Leu Arg Gly Arg Ser Arg Arg Pro
65                  70                  75                  80 gtc aac ctc aag aag tgg agc atc act gac ggc tat gtc ccc att ctc   288
Val Asn Leu Lys Lys Trp Ser Ile Thr Asp Gly Tyr Val Pro Ile Leu
                85                  90                  95 ggc aac aag aca ctg ccc tct cgg tgc cac cag tgt gtg att gtc agc   336
Gly Asn Lys Thr Leu Pro Ser Arg Cys His Gln Cys Val Ile Val Ser
            100                 105                 110 agc tcc agc cac ctg ctg ggc acc aag ctg ggc cct gag atc gag cgg   384
Ser Ser Ser His Leu Leu Gly Thr Lys Leu Gly Pro Glu Ile Glu Arg
        115                 120                 125 gct gag tgt aca atc cgc atg aat gat gca ccc acc act ggc tac tca   432
Ala Glu Cys Thr Ile Arg Met Asn Asp Ala Pro Thr Thr Gly Tyr Ser
    130                 135                 140 gct gat gtg ggc aac aag acc acc tac cgc gtc gtg gcc cat tcc agt   480
Ala Asp Val Gly Asn Lys Thr Thr Tyr Arg Val Val Ala His Ser Ser
145                 150                 155                 160 gtg ttc cgc gtg ctg agg agg ccc cag gag ttt gtc aac cgg acc cct   528
Val Phe Arg Val Leu Arg Arg Pro Gln Glu Phe Val Asn Arg Thr Pro
                165                 170                 175 gaa acc gtg ttc atc ttc tgg ggg ccc ccg agc aag atg cag aag ccc   576
Glu Thr Val Phe Ile Phe Trp Gly Pro Pro Ser Lys Met Gln Lys Pro
            180                 185                 190 cag ggc agc ctc gtg cgt gtg atc cag cga gcg ggc ctg gtg ttc ccc   624
Gln Gly Ser Leu Val Arg Val Ile Gln Arg Ala Gly Leu Val Phe Pro
        195                 200                 205 aac atg gaa gca tat gcc gtc tct ccc ggc cgc atg cgg caa ttt gac   672
Asn Met Glu Ala Tyr Ala Val Ser Pro Gly Arg Met Arg Gln Phe Asp
    210                 215                 220 gac ctc ttc cgg ggt gag acg ggc aag gac agg gag aag tct cat tcg   720
Asp Leu Phe Arg Gly Glu Thr Gly Lys Asp Arg Glu Lys Ser His Ser
225                 230                 235                 240 tgg ttg agc aca ggc tgg ttt acc atg gtg atc gcg gtg gag ttg tgt   768
Trp Leu Ser Thr Gly Trp Phe Thr Met Val Ile Ala Val Glu Leu Cys
                245                 250                 255 gac cac gtg cat gtc tat ggc atg gtc ccc ccc aac tac tgc agc cag   816
Asp His Val His Val Tyr Gly Met Val Pro Pro Asn Tyr Cys Ser Gln
            260                 265                 270 cgg ccc cgc ctc cag cgc atg ccc tac cac tac tac gag ccc aag ggg   864
Arg Pro Arg Leu Gln Arg Met Pro Tyr His Tyr Tyr Glu Pro Lys Gly
        275                 280                 285 ccg gac gaa tgt gtc acc tac atc cag aat gag cac agt cgc aag ggc   912
Pro Asp Glu Cys Val Thr Tyr Ile Gln Asn Glu His Ser Arg Lys Gly
    290                 295                 300 aac cac cac cgc ttc atc acc gag aaa agg gtc ttc tca tcg tgg gcc   960
Asn His His Arg Phe Ile Thr Glu Lys Arg Val Phe Ser Ser Trp Ala
305                 310                 315                 320 cag ctg tat ggc atc acc ttc tcc cac ccc tcc tgg acc tag           1002
```

```
Gln Leu Tyr Gly Ile Thr Phe Ser His Pro Ser Trp Thr
            325                 330
```

<210> SEQ ID NO 16
<211> LENGTH: 333
<212> TYPE: PRT
<213> ORGANISM: Homo sapiens

<400> SEQUENCE: 16

```
Met Ala Cys Ser Arg Pro Pro Ser Gln Cys Glu Pro Thr Ser Leu Pro
1               5                   10                  15

Pro Gly Pro Pro Ala Gly Arg Arg His Leu Pro Leu Ser Arg Arg Arg
            20                  25                  30

Arg Glu Met Ser Ser Asn Lys Glu Gln Arg Ser Ala Val Phe Val Ile
        35                  40                  45

Leu Phe Ala Leu Ile Thr Ile Leu Ile Leu Tyr Ser Ser Asn Ser Ala
    50                  55                  60

Asn Glu Val Phe His Tyr Gly Ser Leu Arg Gly Arg Ser Arg Arg Pro
65                  70                  75                  80

Val Asn Leu Lys Lys Trp Ser Ile Thr Asp Gly Tyr Val Pro Ile Leu
                85                  90                  95

Gly Asn Lys Thr Leu Pro Ser Arg Cys His Gln Cys Val Ile Val Ser
            100                 105                 110

Ser Ser Ser His Leu Leu Gly Thr Lys Leu Gly Pro Glu Ile Glu Arg
        115                 120                 125

Ala Glu Cys Thr Ile Arg Met Asn Asp Ala Pro Thr Thr Gly Tyr Ser
    130                 135                 140

Ala Asp Val Gly Asn Lys Thr Thr Tyr Arg Val Val Ala His Ser Ser
145                 150                 155                 160

Val Phe Arg Val Leu Arg Arg Pro Gln Glu Phe Val Asn Arg Thr Pro
                165                 170                 175

Glu Thr Val Phe Ile Phe Trp Gly Pro Pro Ser Lys Met Gln Lys Pro
            180                 185                 190

Gln Gly Ser Leu Val Arg Val Ile Gln Arg Ala Gly Leu Val Phe Pro
        195                 200                 205

Asn Met Glu Ala Tyr Ala Val Ser Pro Gly Arg Met Arg Gln Phe Asp
    210                 215                 220

Asp Leu Phe Arg Gly Glu Thr Gly Lys Asp Arg Glu Lys Ser His Ser
225                 230                 235                 240

Trp Leu Ser Thr Gly Trp Phe Thr Met Val Ile Ala Val Glu Leu Cys
                245                 250                 255

Asp His Val His Val Tyr Gly Met Val Pro Pro Asn Tyr Cys Ser Gln
            260                 265                 270

Arg Pro Arg Leu Gln Arg Met Pro Tyr His Tyr Tyr Glu Pro Lys Gly
        275                 280                 285

Pro Asp Glu Cys Val Thr Tyr Ile Gln Asn Glu His Ser Arg Lys Gly
    290                 295                 300

Asn His His Arg Phe Ile Thr Glu Lys Arg Val Phe Ser Ser Trp Ala
305                 310                 315                 320

Gln Leu Tyr Gly Ile Thr Phe Ser His Pro Ser Trp Thr
                325                 330
```

<210> SEQ ID NO 17
<211> LENGTH: 1023
<212> TYPE: DNA
<213> ORGANISM: Homo sapiens

```
<220> FEATURE:
<221> NAME/KEY: CDS
<222> LOCATION: (1)..(1023)

<400> SEQUENCE: 17 atg gtg acc ctg cgg aag agg acc ctg aaa gtg ctc acc ttc ctc gtg      48
Met Val Thr Leu Arg Lys Arg Thr Leu Lys Val Leu Thr Phe Leu Val
1               5                   10                  15 ctc ttc atc ttc ctc acc tcc ttc ttc ctg aac tac tcc cac acc atg      96
Leu Phe Ile Phe Leu Thr Ser Phe Phe Leu Asn Tyr Ser His Thr Met
                20                  25                  30 gtg gcc acc acc tgg ttc ccc aag cag atg gtc ctg gag ctc tcc gag     144
Val Ala Thr Thr Trp Phe Pro Lys Gln Met Val Leu Glu Leu Ser Glu
            35                  40                  45 aac ctg aag aga ctg atc aag cac agg cct tgc acc tgc acc cac tgc     192
Asn Leu Lys Arg Leu Ile Lys His Arg Pro Cys Thr Cys Thr His Cys
        50                  55                  60 atc ggg cag cgc aag ctc tcg gcc tgg ttc gat gag agg ttc aac cag     240
Ile Gly Gln Arg Lys Leu Ser Ala Trp Phe Asp Glu Arg Phe Asn Gln
65                  70                  75                  80 acc atg cag ccg ctg ctg acc gcc cag aac gcg ctc ttg gag gac gac     288
Thr Met Gln Pro Leu Leu Thr Ala Gln Asn Ala Leu Leu Glu Asp Asp
                85                  90                  95 acc tac cga tgg tgg ctg agg ctc cag cgg gag aag aag ccc aat aac     336
Thr Tyr Arg Trp Trp Leu Arg Leu Gln Arg Glu Lys Lys Pro Asn Asn
            100                 105                 110 ttg aat gac acc atc aag gag ctg ttc aga gtg gtg cct ggg aat gtg     384
Leu Asn Asp Thr Ile Lys Glu Leu Phe Arg Val Val Pro Gly Asn Val
        115                 120                 125 gac cct atg ctg gag aag agg tcg gtg ggc tgc cgg cgc tgc gcc gtt     432
Asp Pro Met Leu Glu Lys Arg Ser Val Gly Cys Arg Arg Cys Ala Val
130                 135                 140 gtg ggc aac tcg ggc aac ctg agg gag tct tct tat ggg cct gag ata     480
Val Gly Asn Ser Gly Asn Leu Arg Glu Ser Ser Tyr Gly Pro Glu Ile
145                 150                 155                 160 gac agt cac gac ttt gtc ctc agg atg aac aag gcg ccc acg gca ggg     528
Asp Ser His Asp Phe Val Leu Arg Met Asn Lys Ala Pro Thr Ala Gly
                165                 170                 175 ttt gaa gct gat gtt ggg acc aag acc acc cac cat ctg gtg tac cct     576
Phe Glu Ala Asp Val Gly Thr Lys Thr Thr His His Leu Val Tyr Pro
            180                 185                 190 gag agc ttc cgg gag ctg gga gat aat gtc agc atg atc ctg gtg ccc     624
Glu Ser Phe Arg Glu Leu Gly Asp Asn Val Ser Met Ile Leu Val Pro
        195                 200                 205 ttc aag acc atc gac ttg gag tgg gtg gtg agc gcc atc acc acg ggc     672
Phe Lys Thr Ile Asp Leu Glu Trp Val Val Ser Ala Ile Thr Thr Gly
210                 215                 220 acc att tcc cac acc tac atc ccg gtt cct gca aag atc aga gtg aaa     720
Thr Ile Ser His Thr Tyr Ile Pro Val Pro Ala Lys Ile Arg Val Lys
225                 230                 235                 240 cag gat aag atc ctg atc tac cac cca gcc ttc atc aag tat gtc ttt     768
Gln Asp Lys Ile Leu Ile Tyr His Pro Ala Phe Ile Lys Tyr Val Phe
                245                 250                 255 gac aac tgg ctg caa ggg cac ggg cga tac cca tct acc ggc atc ctc     816
Asp Asn Trp Leu Gln Gly His Gly Arg Tyr Pro Ser Thr Gly Ile Leu
            260                 265                 270 tcg gtc atc ttc tca atg cat gtc tgc gat gag gtg gac ttg tac ggc     864
Ser Val Ile Phe Ser Met His Val Cys Asp Glu Val Asp Leu Tyr Gly
        275                 280                 285 ttc ggg gca gac agc aaa ggg aac tgg cac cac tac tgg gag aac aac     912
```

```
                    Phe Gly Ala Asp Ser Lys Gly Asn Trp His His Tyr Trp Glu Asn Asn
                        290                 295                 300 cca tcc gcg ggg gct ttt cgc aag acg ggg gtg cac gat gca gac ttt          960
Pro Ser Ala Gly Ala Phe Arg Lys Thr Gly Val His Asp Ala Asp Phe
305                 310                 315                 320 gag tct aac gtg acg gcc acc ttg gcc tcc atc aat aaa atc cgg atc         1008
Glu Ser Asn Val Thr Ala Thr Leu Ala Ser Ile Asn Lys Ile Arg Ile
                325                 330                 335 ttc aag ggg aga tga                                                     1023
Phe Lys Gly Arg
            340

<210> SEQ ID NO 18
<211> LENGTH: 340
<212> TYPE: PRT
<213> ORGANISM: Homo sapiens

<400> SEQUENCE: 18

Met Val Thr Leu Arg Lys Arg Thr Leu Lys Val Leu Thr Phe Leu Val
1               5                   10                  15

Leu Phe Ile Phe Leu Thr Ser Phe Phe Leu Asn Tyr Ser His Thr Met
                20                  25                  30

Val Ala Thr Thr Trp Phe Pro Lys Gln Met Val Leu Glu Leu Ser Glu
            35                  40                  45

Asn Leu Lys Arg Leu Ile Lys His Arg Pro Cys Thr Cys Thr His Cys
50                  55                  60

Ile Gly Gln Arg Lys Leu Ser Ala Trp Phe Asp Glu Arg Phe Asn Gln
65                  70                  75                  80

Thr Met Gln Pro Leu Leu Thr Ala Gln Asn Ala Leu Leu Glu Asp Asp
                85                  90                  95

Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
130                 135                 140

Val Gly Asn Ser Gly Asn Leu Arg Glu Ser Ser Tyr Gly Pro Glu Ile
145                 150                 155                 160

Asp Ser His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Ile Thr Thr Gly
210                 215                 220

Thr Ile Ser His Thr Tyr Ile Pro Val Pro Ala Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
290                 295                 300
```

| | | | | | | | | | | | | |
|---|---|---|---|---|---|---|---|---|---|---|---|---|
| Pro | Ser | Ala | Gly | Ala | Phe | Arg | Lys | Thr | Gly | Val | His | Asp | Ala | Asp | Phe |
| 305 | | | | 310 | | | | | 315 | | | | 320 | | |
| Glu | Ser | Asn | Val | Thr | Ala | Thr | Leu | Ala | Ser | Ile | Asn | Lys | Ile | Arg | Ile |
| | | | | 325 | | | | | 330 | | | | | 335 | |
| Phe | Lys | Gly | Arg | | | | | | | | | | | | |
| | | | 340 | | | | | | | | | | | | |

```
<210> SEQ ID NO 19
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 19
```

| | | | | | | | | | | | | | | | | |
|---|---|---|---|---|---|---|---|---|---|---|---|---|---|---|---|---|
| atg | aag | tgc | tcc | ctg | cgg | gtg | tgg | ttc | ctc | tcc | gtg | gcc | ttc | ctg | ctg | 48 |
| Met | Lys | Cys | Ser | Leu | Arg | Val | Trp | Phe | Leu | Ser | Val | Ala | Phe | Leu | Leu | |
| 1 | | | | 5 | | | | | 10 | | | | | 15 | | |
| gtg | ttc | atc | atg | tcc | ctg | ctc | ttc | acc | tac | tcg | cac | cac | agc | atg | gcc | 96 |
| Val | Phe | Ile | Met | Ser | Leu | Leu | Phe | Thr | Tyr | Ser | His | His | Ser | Met | Ala | |
| | | | 20 | | | | | 25 | | | | | 30 | | | |
| acg | ctc | ccc | tac | ctg | gac | tca | ggg | gcc | ctg | gat | ggg | acg | cac | cgg | gtg | 144 |
| Thr | Leu | Pro | Tyr | Leu | Asp | Ser | Gly | Ala | Leu | Asp | Gly | Thr | His | Arg | Val | |
| | | 35 | | | | | 40 | | | | | 45 | | | | |
| aag | ctg | gtg | ccc | ggc | tat | gcc | ggc | ctg | cag | cgc | ctc | agc | aag | gag | agg | 192 |
| Lys | Leu | Val | Pro | Gly | Tyr | Ala | Gly | Leu | Gln | Arg | Leu | Ser | Lys | Glu | Arg | |
| | 50 | | | | | 55 | | | | | 60 | | | | | |
| ctc | tcg | ggc | aag | agc | tgt | gcc | tgt | cgc | cgc | tgc | atg | ggc | gat | gcc | ggt | 240 |
| Leu | Ser | Gly | Lys | Ser | Cys | Ala | Cys | Arg | Arg | Cys | Met | Gly | Asp | Ala | Gly | |
| 65 | | | | | 70 | | | | | 75 | | | | | 80 | |
| gcc | tcc | gac | tgg | ttt | gac | agc | cac | ttt | gac | ggt | aac | att | tcc | ccc | gtc | 288 |
| Ala | Ser | Asp | Trp | Phe | Asp | Ser | His | Phe | Asp | Gly | Asn | Ile | Ser | Pro | Val | |
| | | | | 85 | | | | | 90 | | | | | 95 | | |
| tgg | acc | cga | gag | aac | atg | gat | ctt | cca | ccg | gac | gtc | cag | agg | tgg | tgg | 336 |
| Trp | Thr | Arg | Glu | Asn | Met | Asp | Leu | Pro | Pro | Asp | Val | Gln | Arg | Trp | Trp | |
| | | | 100 | | | | | 105 | | | | | 110 | | | |
| atg | atg | ctg | cag | ccc | cag | ttc | aag | tca | cac | aac | acc | aat | gag | gtg | ctg | 384 |
| Met | Met | Leu | Gln | Pro | Gln | Phe | Lys | Ser | His | Asn | Thr | Asn | Glu | Val | Leu | |
| | | 115 | | | | | 120 | | | | | 125 | | | | |
| gag | aag | ctg | ttc | cag | ata | gtg | cct | ggc | gag | aac | ccc | tac | cgc | ttc | cgg | 432 |
| Glu | Lys | Leu | Phe | Gln | Ile | Val | Pro | Gly | Glu | Asn | Pro | Tyr | Arg | Phe | Arg | |
| | 130 | | | | | 135 | | | | | 140 | | | | | |
| gac | ccc | cac | cag | tgc | cgg | cgc | tgt | gcc | gtg | gtg | ggg | aac | tcg | ggc | aac | 480 |
| Asp | Pro | His | Gln | Cys | Arg | Arg | Cys | Ala | Val | Val | Gly | Asn | Ser | Gly | Asn | |
| 145 | | | | | 150 | | | | | 155 | | | | | 160 | |
| ctg | cgg | ggc | tct | ggc | tat | ggg | cag | gac | gtg | gac | ggg | cac | aac | ttc | atc | 528 |
| Leu | Arg | Gly | Ser | Gly | Tyr | Gly | Gln | Asp | Val | Asp | Gly | His | Asn | Phe | Ile | |
| | | | 165 | | | | | 170 | | | | | 175 | | | |
| atg | agg | atg | aat | cag | gcg | cca | acc | gtg | ggc | ttt | gag | cag | gat | gtt | ggc | 576 |
| Met | Arg | Met | Asn | Gln | Ala | Pro | Thr | Val | Gly | Phe | Glu | Gln | Asp | Val | Gly | |
| | | | | 180 | | | | | 185 | | | | | 190 | | |
| agc | cga | acc | acc | cac | cat | ttc | atg | tac | cct | gag | agt | gcc | aag | aac | ctg | 624 |
| Ser | Arg | Thr | Thr | His | His | Phe | Met | Tyr | Pro | Glu | Ser | Ala | Lys | Asn | Leu | |
| | | | 195 | | | | | 200 | | | | | 205 | | | |
| ccc | gcc | aac | gtc | agc | ttc | gtg | ctg | gtg | ccc | ttc | aag | gtc | ctg | gac | ctt | 672 |
| Pro | Ala | Asn | Val | Ser | Phe | Val | Leu | Val | Pro | Phe | Lys | Val | Leu | Asp | Leu | |
| | | 210 | | | | | 215 | | | | | 220 | | | | |
| ctg | tgg | atc | gcc | agc | gcc | ttg | tcc | acg | ggg | cag | atc | cga | ttc | acc | tac | 720 |
| Leu | Trp | Ile | Ala | Ser | Ala | Leu | Ser | Thr | Gly | Gln | Ile | Arg | Phe | Thr | Tyr | |

```
                225                 230                 235                 240
gcc cca gtg aag tcc ttc ctt cga gtg gat aaa gaa aag gtc cag atc          768
Ala Pro Val Lys Ser Phe Leu Arg Val Asp Lys Glu Lys Val Gln Ile
                    245                 250                 255 tac aac cca gcc ttc ttc aag tat atc cac gac agg tgg aca gag cat          816
Tyr Asn Pro Ala Phe Phe Lys Tyr Ile His Asp Arg Trp Thr Glu His
        260                 265                 270 cac ggg cgg tac cct tcc acg ggg atg ctg gtg ctt ttc ttt gcc ctg          864
His Gly Arg Tyr Pro Ser Thr Gly Met Leu Val Leu Phe Phe Ala Leu
            275                 280                 285 cat gtg tgt gat gag gtg aac gtg tac ggg ttc ggg gcc gac agc cgg          912
His Val Cys Asp Glu Val Asn Val Tyr Gly Phe Gly Ala Asp Ser Arg
                290                 295                 300 ggc aac tgg cac cac tac tgg gag aac aac cgg tac gcg ggc gag ttc          960
Gly Asn Trp His His Tyr Trp Glu Asn Asn Arg Tyr Ala Gly Glu Phe
305                 310                 315                 320 cgg aag act ggc gtg cac gac gcg gac ttc gag gcc cac atc atc gac         1008
Arg Lys Thr Gly Val His Asp Ala Asp Phe Glu Ala His Ile Ile Asp
                    325                 330                 335 atg ctg gcc aag gcc agc aag atc gaa gtc tac cgg ggc aac tga             1053
Met Leu Ala Lys Ala Ser Lys Ile Glu Val Tyr Arg Gly Asn
                340                 345                 350

<210> SEQ ID NO 20
<211> LENGTH: 350
<212> TYPE: PRT
<213> ORGANISM: Homo sapiens

<400> SEQUENCE: 20

Met Lys Cys Ser Leu Arg Val Trp Phe Leu Ser Val Ala Phe Leu Leu
1               5                   10                  15

Val Phe Ile Met Ser Leu Leu Phe Thr Tyr Ser His His Ser Met Ala
                20                  25                  30

Thr Leu Pro Tyr Leu Asp Ser Gly Ala Leu Asp Gly Thr His Arg Val
            35                  40                  45

Lys Leu Val Pro Gly Tyr Ala Gly Leu Gln Arg Leu Ser Lys Glu Arg
        50                  55                  60

Leu Ser Gly Lys Ser Cys Ala Cys Arg Arg Cys Met Gly Asp Ala Gly
65                  70                  75                  80

Ala Ser Asp Trp Phe Asp Ser His Phe Asp Gly Asn Ile Ser Pro Val
                85                  90                  95

Trp Thr Arg Glu Asn Met Asp Leu Pro Pro Asp Val Gln Arg Trp Trp
            100                 105                 110

Met Met Leu Gln Pro Gln Phe Lys Ser His Asn Thr Asn Glu Val Leu
        115                 120                 125

Glu Lys Leu Phe Gln Ile Val Pro Gly Glu Asn Pro Tyr Arg Phe Arg
    130                 135                 140

Asp Pro His Gln Cys Arg Arg Cys Ala Val Val Gly Asn Ser Gly Asn
145                 150                 155                 160

Leu Arg Gly Ser Gly Tyr Gly Gln Asp Val Asp Gly His Asn Phe Ile
                165                 170                 175

Met Arg Met Asn Gln Ala Pro Thr Val Gly Phe Glu Gln Asp Val Gly
            180                 185                 190

Ser Arg Thr Thr His His Phe Met Tyr Pro Glu Ser Ala Lys Asn Leu
        195                 200                 205

Pro Ala Asn Val Ser Phe Val Leu Val Pro Phe Lys Val Leu Asp Leu
    210                 215                 220
```

```
Leu Trp Ile Ala Ser Ala Leu Ser Thr Gly Gln Ile Arg Phe Thr Tyr
225                 230                 235                 240

Ala Pro Val Lys Ser Phe Leu Arg Val Asp Lys Glu Lys Val Gln Ile
            245                 250                 255

Tyr Asn Pro Ala Phe Phe Lys Tyr Ile His Asp Arg Trp Thr Glu His
        260                 265                 270

His Gly Arg Tyr Pro Ser Thr Gly Met Leu Val Leu Phe Phe Ala Leu
    275                 280                 285

His Val Cys Asp Glu Val Asn Val Tyr Gly Phe Gly Ala Asp Ser Arg
290                 295                 300

Gly Asn Trp His His Tyr Trp Glu Asn Asn Arg Tyr Ala Gly Glu Phe
305                 310                 315                 320

Arg Lys Thr Gly Val His Asp Ala Asp Phe Glu Ala His Ile Ile Asp
                325                 330                 335

Met Leu Ala Lys Ala Ser Lys Ile Glu Val Tyr Arg Gly Asn
            340                 345                 350

<210> SEQ ID NO 21
<211> LENGTH: 1335
<212> TYPE: DNA
<213> ORGANISM: Homo sapiens
<220> FEATURE:
<221> NAME/KEY: CDS
<222> LOCATION: (1)..(1335)

<400> SEQUENCE: 21 atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg aag cta cac tta      96
Phe Leu Val Leu Gly Phe Leu Tyr Tyr Ser Ala Trp Lys Leu His Leu
                20                  25                  30 ctc cag tgg gag gag gac tcc agt aag tat agt cac tct agc tca ccc     144
Leu Gln Trp Glu Glu Asp Ser Ser Lys Tyr Ser His Ser Ser Ser Pro
            35                  40                  45 cag gag aag cct gtt gca gat tca gtg gtt ctt tcc ttt gac tcc gct     192
Gln Glu Lys Pro Val Ala Asp Ser Val Val Leu Ser Phe Asp Ser Ala
        50                  55                  60 gga caa aca cta ggc tca gag tat gat cgg ttg ggc ttc ctc ctg aat     240
Gly Gln Thr Leu Gly Ser Glu Tyr Asp Arg Leu Gly Phe Leu Leu Asn
65                  70                  75                  80 ctg gac tct aaa ctc tca ccg agg act ctc tgc acg gtg gtt ttt ggc     288
Leu Asp Ser Lys Leu Ser Pro Arg Thr Leu Cys Thr Val Val Phe Gly
                85                  90                  95 ctt gac tgc ata ttg gaa tca cct gga gag cct aaa aaa tta ctg atg     336
Leu Asp Cys Ile Leu Glu Ser Pro Gly Glu Pro Lys Lys Leu Leu Met
                100                 105                 110 cct gca tcc cac cct cta gag att ttg aag tca ctg agc gag gac gca     384
Pro Ala Ser His Pro Leu Glu Ile Leu Lys Ser Leu Ser Glu Asp Ala
            115                 120                 125 gcc ttt gca tta gga ttt tta aag ctg ccc agg cct gct gaa tta gcc     432
Ala Phe Ala Leu Gly Phe Leu Lys Leu Pro Arg Pro Ala Glu Leu Ala
        130                 135                 140 acc aag tac gca aac ttt tca gag gga gct tgc aag cct ggc tat gct     480
Thr Lys Tyr Ala Asn Phe Ser Glu Gly Ala Cys Lys Pro Gly Tyr Ala
145                 150                 155                 160 tca gcc ttg atg acg gcc atc ttc ccc cgg ttc tcc aag cca gca ccc     528
Ser Ala Leu Met Thr Ala Ile Phe Pro Arg Phe Ser Lys Pro Ala Pro
                165                 170                 175
```

```
atg ttc ctg gat gac tcc ttt cgc aag tgg gct aga atc cgg gag ttc      576
Met Phe Leu Asp Asp Ser Phe Arg Lys Trp Ala Arg Ile Arg Glu Phe
        180                 185                 190 gtg ccg cct ttt ggg atc aaa ggt caa gac aat ctg atc aaa gcc atc      624
Val Pro Pro Phe Gly Ile Lys Gly Gln Asp Asn Leu Ile Lys Ala Ile
    195                 200                 205 ttg tca gtc acc aaa gag tac cgc ctg acc cct gcc ttg gac agc ctc      672
Leu Ser Val Thr Lys Glu Tyr Arg Leu Thr Pro Ala Leu Asp Ser Leu
210                 215                 220 cgc tgc cgc cgc tgc atc atc gtg ggc aat gga ggt gtt ctt gcc aac      720
Arg Cys Arg Arg Cys Ile Ile Val Gly Asn Gly Gly Val Leu Ala Asn
225                 230                 235                 240 aag tct ctg ggg tca cga att gac gac tat gac att gtg gtg aga ctg      768
Lys Ser Leu Gly Ser Arg Ile Asp Asp Tyr Asp Ile Val Val Arg Leu
                245                 250                 255 aat tca gca cca gtg aaa ggc ttt gag aag gac gtg ggc agc aaa acg      816
Asn Ser Ala Pro Val Lys Gly Phe Glu Lys Asp Val Gly Ser Lys Thr
            260                 265                 270 aca ctg cgc atc acc tac ccc gag ggc gcc atg cag cgg cct gag cag      864
Thr Leu Arg Ile Thr Tyr Pro Glu Gly Ala Met Gln Arg Pro Glu Gln
        275                 280                 285 tac gag cgc gat tct ctc ttt gtc ctc gcc ggc ttc aag tgg cag gac      912
Tyr Glu Arg Asp Ser Leu Phe Val Leu Ala Gly Phe Lys Trp Gln Asp
    290                 295                 300 ttt aag tgg ttg aaa tac atc gtc tac aag gag aga gtg agt gca tcg      960
Phe Lys Trp Leu Lys Tyr Ile Val Tyr Lys Glu Arg Val Ser Ala Ser
305                 310                 315                 320 gat ggc ttc tgg aaa tct gtg gcc act cga gtg ccc aag gag ccc cct     1008
Asp Gly Phe Trp Lys Ser Val Ala Thr Arg Val Pro Lys Glu Pro Pro
                325                 330                 335 gag att cga atc ctc aac cca tat ttc atc cag gag gcc gcc ttc acc     1056
Glu Ile Arg Ile Leu Asn Pro Tyr Phe Ile Gln Glu Ala Ala Phe Thr
            340                 345                 350 ctc att ggc ctg ccc ttc aac aat ggc ctc atg ggc cgg ggg aac atc     1104
Leu Ile Gly Leu Pro Phe Asn Asn Gly Leu Met Gly Arg Gly Asn Ile
        355                 360                 365 cct acc ctt gga agt gtg gca gtg acc atg gca cta cac ggc tgt gac     1152
Pro Thr Leu Gly Ser Val Ala Val Thr Met Ala Leu His Gly Cys Asp
    370                 375                 380 gag gtg gca gtc gca gga ttt ggc tat gac atg agc aca ccc aac gca     1200
Glu Val Ala Val Ala Gly Phe Gly Tyr Asp Met Ser Thr Pro Asn Ala
385                 390                 395                 400 ccc ctg cac tac tat gag acc gtt cgc atg gca gcc atc aaa gag tcc     1248
Pro Leu His Tyr Tyr Glu Thr Val Arg Met Ala Ala Ile Lys Glu Ser
                405                 410                 415 tgg acg cac aat atc cag cga gag aaa gag ttt ctg cgg aag ctg gtg     1296
Trp Thr His Asn Ile Gln Arg Glu Lys Glu Phe Leu Arg Lys Leu Val
            420                 425                 430 aaa gct cgc gtc atc act gat cta agc agt ggc atc tga                 1335
Lys Ala Arg Val Ile Thr Asp Leu Ser Ser Gly Ile
        435                 440

<210> SEQ ID NO 22
<211> LENGTH: 444
<212> TYPE: PRT
<213> ORGANISM: Homo sapiens

<400> SEQUENCE: 22

Met Gly Leu Leu Val Phe Val Arg Asn Leu Leu Leu Ala Leu Cys Leu
1               5                   10                  15
```

```
Phe Leu Val Leu Gly Phe Leu Tyr Tyr Ser Ala Trp Lys Leu His Leu
             20                  25                  30

Leu Gln Trp Glu Glu Asp Ser Ser Lys Tyr Ser His Ser Ser Ser Pro
         35                  40                  45

Gln Glu Lys Pro Val Ala Asp Ser Val Val Leu Ser Phe Asp Ser Ala
 50                  55                  60

Gly Gln Thr Leu Gly Ser Glu Tyr Asp Arg Leu Gly Phe Leu Leu Asn
 65                  70                  75                  80

Leu Asp Ser Lys Leu Ser Pro Arg Thr Leu Cys Thr Val Val Phe Gly
                 85                  90                  95

Leu Asp Cys Ile Leu Glu Ser Pro Gly Glu Pro Lys Lys Leu Leu Met
                100                 105                 110

Pro Ala Ser His Pro Leu Glu Ile Leu Lys Ser Leu Ser Glu Asp Ala
             115                 120                 125

Ala Phe Ala Leu Gly Phe Leu Lys Leu Pro Arg Pro Ala Glu Leu Ala
 130                 135                 140

Thr Lys Tyr Ala Asn Phe Ser Glu Gly Ala Cys Lys Pro Gly Tyr Ala
145                 150                 155                 160

Ser Ala Leu Met Thr Ala Ile Phe Pro Arg Phe Ser Lys Pro Ala Pro
                165                 170                 175

Met Phe Leu Asp Asp Ser Phe Arg Lys Trp Ala Arg Ile Arg Glu Phe
                180                 185                 190

Val Pro Pro Phe Gly Ile Lys Gly Gln Asp Asn Leu Ile Lys Ala Ile
            195                 200                 205

Leu Ser Val Thr Lys Glu Tyr Arg Leu Thr Pro Ala Leu Asp Ser Leu
    210                 215                 220

Arg Cys Arg Arg Cys Ile Ile Val Gly Asn Gly Gly Val Leu Ala Asn
225                 230                 235                 240

Lys Ser Leu Gly Ser Arg Ile Asp Asp Tyr Asp Ile Val Val Arg Leu
                245                 250                 255

Asn Ser Ala Pro Val Lys Gly Phe Glu Lys Asp Val Gly Ser Lys Thr
            260                 265                 270

Thr Leu Arg Ile Thr Tyr Pro Glu Gly Ala Met Gln Arg Pro Glu Gln
    275                 280                 285

Tyr Glu Arg Asp Ser Leu Phe Val Leu Ala Gly Phe Lys Trp Gln Asp
290                 295                 300

Phe Lys Trp Leu Lys Tyr Ile Val Tyr Lys Glu Arg Val Ser Ala Ser
305                 310                 315                 320

Asp Gly Phe Trp Lys Ser Val Ala Thr Arg Val Pro Lys Glu Pro Pro
                325                 330                 335

Glu Ile Arg Ile Leu Asn Pro Tyr Phe Ile Gln Glu Ala Ala Phe Thr
            340                 345                 350

Leu Ile Gly Leu Pro Phe Asn Asn Gly Leu Met Gly Arg Gly Asn Ile
    355                 360                 365

Pro Thr Leu Gly Ser Val Ala Val Thr Met Ala Leu His Gly Cys Asp
370                 375                 380

Glu Val Ala Val Ala Gly Phe Gly Tyr Asp Met Ser Thr Pro Asn Ala
385                 390                 395                 400

Pro Leu His Tyr Tyr Glu Thr Val Arg Met Ala Ala Ile Lys Glu Ser
                405                 410                 415

Trp Thr His Asn Ile Gln Arg Glu Lys Glu Phe Leu Arg Lys Leu Val
            420                 425                 430
```

```
Lys Ala Arg Val Ile Thr Asp Leu Ser Ser Gly Ile
            435                 440
```

<210> SEQ ID NO 23
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 23

```
atg gtc agc aag tcc cgc tgg aag ctc ctg gcc atg ttg gct ctg gtc      48
Met Val Ser Lys Ser Arg Trp Lys Leu Leu Ala Met Leu Ala Leu Val
1               5                   10                  15 ctg gtc gtc atg gtg tgg tat tcc atc tcc cgg gaa gac agt ttt tat      96
Leu Val Val Met Val Trp Tyr Ser Ile Ser Arg Glu Asp Ser Phe Tyr
            20                  25                  30 ttt ccc atc cca gag aag aag gag ccg tgc ctc cag ggt gag gca gag     144
Phe Pro Ile Pro Glu Lys Lys Glu Pro Cys Leu Gln Gly Glu Ala Glu
        35                  40                  45 agc aag gcc tct aag ctc ttt ggc aac tac tcc cgg gat cag ccc atc     192
Ser Lys Ala Ser Lys Leu Phe Gly Asn Tyr Ser Arg Asp Gln Pro Ile
    50                  55                  60 ttc ctg cgg ctt gag gat tat ttc tgg gtc aag acg cca tct gct tac     240
Phe Leu Arg Leu Glu Asp Tyr Phe Trp Val Lys Thr Pro Ser Ala Tyr
65                  70                  75                  80 gag ctg ccc tat ggg acc aag ggg agt gag gat ctc ctc ctc cgg gtg     288
Glu Leu Pro Tyr Gly Thr Lys Gly Ser Glu Asp Leu Leu Leu Arg Val
                85                  90                  95 cta gcc atc acc agc tcc tcc atc ccc aag aac atc cag agc ctc agg     336
Leu Ala Ile Thr Ser Ser Ser Ile Pro Lys Asn Ile Gln Ser Leu Arg
            100                 105                 110 tgc cgc cgc tgt gtg gtc gtg ggg aac ggg cac cgg ctg cgg aac agc     384
Cys Arg Arg Cys Val Val Val Gly Asn Gly His Arg Leu Arg Asn Ser
        115                 120                 125 tca ctg gga gat gcc atc aac aag tac gat gtg gtc atc aga ttg aac     432
Ser Leu Gly Asp Ala Ile Asn Lys Tyr Asp Val Val Ile Arg Leu Asn
    130                 135                 140 aat gcc cca gtg gct ggc tat gag ggt gac gtg ggc tcc aag acc acc     480
Asn Ala Pro Val Ala Gly Tyr Glu Gly Asp Val Gly Ser Lys Thr Thr
145                 150                 155                 160 atg cgt ctc ttc tac cct gaa tct gcc cac ttc gac ccc aaa gta gaa     528
Met Arg Leu Phe Tyr Pro Glu Ser Ala His Phe Asp Pro Lys Val Glu
                165                 170                 175 aac aac cca gac aca ctc ctc gtc ctg gta gct ttc aag gca atg gac     576
Asn Asn Pro Asp Thr Leu Leu Val Leu Val Ala Phe Lys Ala Met Asp
            180                 185                 190 ttc cac tgg att gag acc atc ctg agt gat aag aag cgg gtg cga aag     624
Phe His Trp Ile Glu Thr Ile Leu Ser Asp Lys Lys Arg Val Arg Lys
        195                 200                 205 ggt ttc tgg aaa cag cct ccc ctc atc tgg gat gtc aat cct aaa cag     672
Gly Phe Trp Lys Gln Pro Pro Leu Ile Trp Asp Val Asn Pro Lys Gln
    210                 215                 220 att cgg att ctc aac ccc ttc ttc atg gag att gca gct gac aaa ctg     720
Ile Arg Ile Leu Asn Pro Phe Phe Met Glu Ile Ala Ala Asp Lys Leu
225                 230                 235                 240 ctg agc ctg cca atg caa cag cca cgg aag att aag cag aag ccc acc     768
Leu Ser Leu Pro Met Gln Gln Pro Arg Lys Ile Lys Gln Lys Pro Thr
                245                 250                 255 acg ggc ctg ttg gcc atc acg ctg gcc ctc cac ctc tgt gac ttg gtg     816
Thr Gly Leu Leu Ala Ile Thr Leu Ala Leu His Leu Cys Asp Leu Val
```

```
          Thr Gly Leu Leu Ala Ile Thr Leu Ala Leu His Leu Cys Asp Leu Val
                      260                 265                 270 cac att gcc ggc ttt ggc tac cca gac gcc tac aac aag aag cag acc        864
His Ile Ala Gly Phe Gly Tyr Pro Asp Ala Tyr Asn Lys Lys Gln Thr
        275                 280                 285 att cac tac tat gag cag atc acg ctc aag tcc atg gcg ggg tca ggc        912
Ile His Tyr Tyr Glu Gln Ile Thr Leu Lys Ser Met Ala Gly Ser Gly
290                 295                 300 cat aat gtc tcc caa gag gcc ctg gcc att aag cgg atg ctg gag atg        960
His Asn Val Ser Gln Glu Ala Leu Ala Ile Lys Arg Met Leu Glu Met
305                 310                 315                 320 gga gct atc aag aac ctc acg tcc ttc tga                                990
Gly Ala Ile Lys Asn Leu Thr Ser Phe
                325

<210> SEQ ID NO 24
<211> LENGTH: 329
<212> TYPE: PRT
<213> ORGANISM: Homo sapiens

<400> SEQUENCE: 24

Met Val Ser Lys Ser Arg Trp Lys Leu Leu Ala Met Leu Ala Leu Val
1               5                   10                  15

Leu Val Val Met Val Trp Tyr Ser Ile Ser Arg Glu Asp Ser Phe Tyr
                20                  25                  30

Phe Pro Ile Pro Glu Lys Lys Glu Pro Cys Leu Gln Gly Glu Ala Glu
            35                  40                  45

Ser Lys Ala Ser Lys Leu Phe Gly Asn Tyr Ser Arg Asp Gln Pro Ile
    50                  55                  60

Phe Leu Arg Leu Glu Asp Tyr Phe Trp Val Lys Thr Pro Ser Ala Tyr
65                  70                  75                  80

Glu Leu Pro Tyr Gly Thr Lys Gly Ser Glu Asp Leu Leu Arg Val
                85                  90                  95

Leu Ala Ile Thr Ser Ser Ser Ile Pro Lys Asn Ile Gln Ser Leu Arg
                100                 105                 110

Cys Arg Arg Cys Val Val Val Gly Asn Gly His Arg Leu Arg Asn Ser
            115                 120                 125

Ser Leu Gly Asp Ala Ile Asn Lys Tyr Asp Val Val Ile Arg Leu Asn
    130                 135                 140

Asn Ala Pro Val Ala Gly Tyr Glu Gly Asp Val Gly Ser Lys Thr Thr
145                 150                 155                 160

Met Arg Leu Phe Tyr Pro Glu Ser Ala His Phe Asp Pro Lys Val Glu
                165                 170                 175

Asn Asn Pro Asp Thr Leu Leu Val Leu Val Ala Phe Lys Ala Met Asp
            180                 185                 190

Phe His Trp Ile Glu Thr Ile Leu Ser Asp Lys Lys Arg Val Arg Lys
        195                 200                 205

Gly Phe Trp Lys Gln Pro Pro Leu Ile Trp Asp Val Asn Pro Lys Gln
    210                 215                 220

Ile Arg Ile Leu Asn Pro Phe Phe Met Glu Ile Ala Ala Asp Lys Leu
225                 230                 235                 240

Leu Ser Leu Pro Met Gln Gln Pro Arg Lys Ile Lys Gln Lys Pro Thr
                245                 250                 255

Thr Gly Leu Leu Ala Ile Thr Leu Ala Leu His Leu Cys Asp Leu Val
            260                 265                 270

His Ile Ala Gly Phe Gly Tyr Pro Asp Ala Tyr Asn Lys Lys Gln Thr
```

```
                275                 280                 285
Ile His Tyr Tyr Glu Gln Ile Thr Leu Lys Ser Met Ala Gly Ser Gly
            290                 295                 300

His Asn Val Ser Gln Glu Ala Leu Ala Ile Lys Arg Met Leu Glu Met
305                 310                 315                 320

Gly Ala Ile Lys Asn Leu Thr Ser Phe
                325

<210> SEQ ID NO 25
<211> LENGTH: 1089
<212> TYPE: DNA
<213> ORGANISM: Homo sapiens
<220> FEATURE:
<221> NAME/KEY: CDS
<222> LOCATION: (1)..(1089)

<400> SEQUENCE: 25 atg aga agg ccc agc ttg tta tta aaa gac atc ctc aaa tgt aca ttg      48
Met Arg Arg Pro Ser Leu Leu Leu Lys Asp Ile Leu Lys Cys Thr Leu
1               5                   10                  15 ctt gtg ttt gga gtg tgg atc ctt tat atc ctc aag tta aat tat act      96
Leu Val Phe Gly Val Trp Ile Leu Tyr Ile Leu Lys Leu Asn Tyr Thr
                20                  25                  30 act gaa gaa tgt gac atg aaa aaa atg cat tat gtg gac cct gac cat     144
Thr Glu Glu Cys Asp Met Lys Lys Met His Tyr Val Asp Pro Asp His
            35                  40                  45 gta aag aga gct cag aaa tat gct cag caa gtc ttg cag aag gaa tgt     192
Val Lys Arg Ala Gln Lys Tyr Ala Gln Gln Val Leu Gln Lys Glu Cys
        50                  55                  60 cgt ccc aag ttt gcc aag aca tca atg gcg ctg tta ttt gag cac agg     240
Arg Pro Lys Phe Ala Lys Thr Ser Met Ala Leu Leu Phe Glu His Arg
65                  70                  75                  80 tat agc gtg gac tta ctc cct ttt gtg cag aag gcc ccc aaa gac agt     288
Tyr Ser Val Asp Leu Leu Pro Phe Val Gln Lys Ala Pro Lys Asp Ser
                85                  90                  95 gaa gct gag tcc aag tac gat cct cct ttt ggg ttc cgg aag ttc tcc     336
Glu Ala Glu Ser Lys Tyr Asp Pro Pro Phe Gly Phe Arg Lys Phe Ser
                100                 105                 110 agt aaa gtc cag acc ctc ttg gaa ctc ttg cca gag cac gac ctc cct     384
Ser Lys Val Gln Thr Leu Leu Glu Leu Leu Pro Glu His Asp Leu Pro
            115                 120                 125 gaa cac ttg aaa gcc aag acc tgt cgg cgc tgt gtg gtt att gga agc     432
Glu His Leu Lys Ala Lys Thr Cys Arg Arg Cys Val Val Ile Gly Ser
        130                 135                 140 gga gga ata ctg cac gga tta gaa ctg ggc cac acc ctg aac cag ttc     480
Gly Gly Ile Leu His Gly Leu Glu Leu Gly His Thr Leu Asn Gln Phe
145                 150                 155                 160 gat gtt gtg ata agg tta aac agt gca cca gtt gag gga tat tca gaa     528
Asp Val Val Ile Arg Leu Asn Ser Ala Pro Val Glu Gly Tyr Ser Glu
                165                 170                 175 cat gtt gga aat aaa act act ata agg atg act tat cca gag ggc gca     576
His Val Gly Asn Lys Thr Thr Ile Arg Met Thr Tyr Pro Glu Gly Ala
                180                 185                 190 cca ctg tct gac ctt gaa tat tat tcc aat gac tta ttt gtt gct gtt     624
Pro Leu Ser Asp Leu Glu Tyr Tyr Ser Asn Asp Leu Phe Val Ala Val
            195                 200                 205 tta ttt aag agt gtt gat ttc aac tgg ctt caa gca atg gta aaa aag     672
Leu Phe Lys Ser Val Asp Phe Asn Trp Leu Gln Ala Met Val Lys Lys
        210                 215                 220 gaa acc ctg cca ttc tgg gta cga ctc ttc ttt tgg aag cag gtg gca     720
```

```
Glu Thr Leu Pro Phe Trp Val Arg Leu Phe Phe Trp Lys Gln Val Ala
225                 230                 235                 240 gaa aaa atc cca ctg cag cca aaa cat ttc agg att ttg aat cca gtt        768
Glu Lys Ile Pro Leu Gln Pro Lys His Phe Arg Ile Leu Asn Pro Val
            245                 250                 255 atc atc aaa gag act gcc ttt gac atc ctt cag tac tca gag cct cag        816
Ile Ile Lys Glu Thr Ala Phe Asp Ile Leu Gln Tyr Ser Glu Pro Gln
        260                 265                 270 tca agg ttc tgg ggc cga gat aag aac gtc ccc aca atc ggt gtc att        864
Ser Arg Phe Trp Gly Arg Asp Lys Asn Val Pro Thr Ile Gly Val Ile
    275                 280                 285 gcc gtt gtc tta gcc aca cat ctg tgc gat gaa gtc agt ttg gcg ggt        912
Ala Val Val Leu Ala Thr His Leu Cys Asp Glu Val Ser Leu Ala Gly
290                 295                 300 ttt gga tat gac ctc aat caa ccc aga aca cct ttg cac tac ttc gac        960
Phe Gly Tyr Asp Leu Asn Gln Pro Arg Thr Pro Leu His Tyr Phe Asp
305                 310                 315                 320 agt caa tgc atg gct gct atg aac ttt cag acc atg cat aat gtg aca       1008
Ser Gln Cys Met Ala Ala Met Asn Phe Gln Thr Met His Asn Val Thr
            325                 330                 335 acg gaa acc aag ttc ctc tta aag ctg gtc aaa gag gga gtg gtg aaa       1056
Thr Glu Thr Lys Phe Leu Leu Lys Leu Val Lys Glu Gly Val Val Lys
        340                 345                 350 gat ctc agt gga ggc att gat cgt gaa ttt tga                           1089
Asp Leu Ser Gly Gly Ile Asp Arg Glu Phe
    355                 360

<210> SEQ ID NO 26
<211> LENGTH: 362
<212> TYPE: PRT
<213> ORGANISM: Homo sapiens

<400> SEQUENCE: 26

Met Arg Arg Pro Ser Leu Leu Lys Asp Ile Leu Lys Cys Thr Leu
1               5                   10                  15

Leu Val Phe Gly Val Trp Ile Leu Tyr Ile Leu Lys Leu Asn Tyr Thr
                20                  25                  30

Thr Glu Glu Cys Asp Met Lys Lys Met His Tyr Val Asp Pro Asp His
            35                  40                  45

Val Lys Arg Ala Gln Lys Tyr Ala Gln Gln Val Leu Gln Lys Glu Cys
        50                  55                  60

Arg Pro Lys Phe Ala Lys Thr Ser Met Ala Leu Leu Phe Glu His Arg
65                  70                  75                  80

Tyr Ser Val Asp Leu Pro Phe Val Gln Lys Ala Pro Lys Asp Ser
                85                  90                  95

Glu Ala Glu Ser Lys Tyr Asp Pro Pro Phe Gly Phe Lys Phe Ser
            100                 105                 110

Ser Lys Val Gln Thr Leu Leu Glu Leu Leu Pro Glu His Asp Leu Pro
        115                 120                 125

Glu His Leu Lys Ala Lys Thr Cys Arg Arg Cys Val Val Ile Gly Ser
    130                 135                 140

Gly Gly Ile Leu His Gly Leu Glu Leu Gly His Thr Leu Asn Gln Phe
145                 150                 155                 160

Asp Val Val Ile Arg Leu Asn Ser Ala Pro Val Glu Gly Tyr Ser Glu
                165                 170                 175

His Val Gly Asn Lys Thr Thr Ile Arg Met Thr Tyr Pro Glu Gly Ala
            180                 185                 190
```

```
Pro Leu Ser Asp Leu Glu Tyr Tyr Ser Asn Asp Leu Phe Val Ala Val
        195                 200                 205

Leu Phe Lys Ser Val Asp Phe Asn Trp Leu Gln Ala Met Val Lys Lys
210                 215                 220

Glu Thr Leu Pro Phe Trp Val Arg Leu Phe Trp Lys Gln Val Ala
225                 230                 235                 240

Glu Lys Ile Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
            260                 265                 270

Ser Arg Phe Trp Gly Arg Asp Lys Asn Val Pro Thr Ile Gly Val Ile
        275                 280                 285

Ala Val Val Leu Ala Thr His Leu Cys Asp Glu Val Ser Leu Ala Gly
    290                 295                 300

Phe Gly Tyr Asp Leu Asn Gln Pro Arg Thr Pro Leu His Tyr Phe Asp
305                 310                 315                 320

Ser Gln Cys Met Ala Ala Met Asn Phe Gln Thr Met His Asn Val Thr
                325                 330                 335

Thr Glu Thr Lys Phe Leu Leu Lys Leu Val Lys Glu Gly Val Val Lys
            340                 345                 350

Asp Leu Ser Gly Gly Ile Asp Arg Glu Phe
        355                 360

<210> SEQ ID NO 27
<211> LENGTH: 996
<212> TYPE: DNA
<213> ORGANISM: Homo sapiens
<220> FEATURE:
<221> NAME/KEY: CDS
<222> LOCATION: (1)..(996)

<400> SEQUENCE: 27 atg aga ggg tat ctt gtg gcc ata ttc ctg agt gct gtc ttc ctc tat       48
Met Arg Gly Tyr Leu Val Ala Ile Phe Leu Ser Ala Val Phe Leu Tyr
1               5                   10                  15 tat gta ctg cat tgc ata tta tgg gga acg aat gtc tat tgg gtg gca       96
Tyr Val Leu His Cys Ile Leu Trp Gly Thr Asn Val Tyr Trp Val Ala
                20                  25                  30 cct gtg gaa atg aaa cgg aga aat aag atc cag cct tgt tta tca aag      144
Pro Val Glu Met Lys Arg Arg Asn Lys Ile Gln Pro Cys Leu Ser Lys
            35                  40                  45 cca gct ttt gcc tct ctg ctg agg ttt cat cag ttt cac cct ttt ctg      192
Pro Ala Phe Ala Ser Leu Leu Arg Phe His Gln Phe His Pro Phe Leu
        50                  55                  60 tgt gcg gct gat ttt aga aag att gct tcc ttg tat ggt agc gat aag      240
Cys Ala Ala Asp Phe Arg Lys Ile Ala Ser Leu Tyr Gly Ser Asp Lys
65                  70                  75                  80 ttt gat ttg ccc tat ggg atg aga aca tca gcg gaa tat ttt cga ctt      288
Phe Asp Leu Pro Tyr Gly Met Arg Thr Ser Ala Glu Tyr Phe Arg Leu
                85                  90                  95 gct ctt tca aaa ctg cag agt tgt gat ctc ttt gat gag ttt gac aac      336
Ala Leu Ser Lys Leu Gln Ser Cys Asp Leu Phe Asp Glu Phe Asp Asn
            100                 105                 110 ata ccc tgt aaa aag tgt gtg gtt ggt aat gga gga gtt ttg aag      384
Ile Pro Cys Lys Lys Cys Val Val Val Gly Asn Gly Gly Val Leu Lys
        115                 120                 125 aat aag aca tta gga gaa aaa atc gac tcc tat gat gta ata ata aga      432
Asn Lys Thr Leu Gly Glu Lys Ile Asp Ser Tyr Asp Val Ile Ile Arg
    130                 135                 140
```

```
atg aat aat ggt cct gtt tta gga cat gaa gaa gaa gtt ggg aga agg      480
Met Asn Asn Gly Pro Val Leu Gly His Glu Glu Glu Val Gly Arg Arg
145                 150                 155                 160 aca acc ttc cga ctt ttt tat cca gaa tct gtt ttt tca gat cct att      528
Thr Thr Phe Arg Leu Phe Tyr Pro Glu Ser Val Phe Ser Asp Pro Ile
                165                 170                 175 cac aat gac cct aat acg aca gtg att ctc act gct ttt aag cca cat      576
His Asn Asp Pro Asn Thr Thr Val Ile Leu Thr Ala Phe Lys Pro His
            180                 185                 190 gat tta agg tgg ctg ttg gaa ttg ttg atg ggt gac aaa ata aac act      624
Asp Leu Arg Trp Leu Leu Glu Leu Leu Met Gly Asp Lys Ile Asn Thr
        195                 200                 205 aat ggt ttt tgg aag aaa cca gcc tta aac ctg att tat aaa cct tat      672
Asn Gly Phe Trp Lys Lys Pro Ala Leu Asn Leu Ile Tyr Lys Pro Tyr
210                 215                 220 caa atc cga ata tta gat cct ttc att atc aga aca gca gct tat gaa      720
Gln Ile Arg Ile Leu Asp Pro Phe Ile Ile Arg Thr Ala Ala Tyr Glu
225                 230                 235                 240 ctg ctt cat ttt cca aaa gtg ttt ccc aaa aat cag aaa cct aaa cac      768
Leu Leu His Phe Pro Lys Val Phe Pro Lys Asn Gln Lys Pro Lys His
                245                 250                 255 cca aca aca gga att att gcc atc aca ttg gcg ttt tac ata tgt cac      816
Pro Thr Thr Gly Ile Ile Ala Ile Thr Leu Ala Phe Tyr Ile Cys His
            260                 265                 270 gaa gtt cac cta gct ggt ttt aaa tac aac ttt tct gac ctc aag agt      864
Glu Val His Leu Ala Gly Phe Lys Tyr Asn Phe Ser Asp Leu Lys Ser
        275                 280                 285 cct ttg cac tac tat ggg aat gcc acc atg tct ttg atg aat aag aac      912
Pro Leu His Tyr Tyr Gly Asn Ala Thr Met Ser Leu Met Asn Lys Asn
290                 295                 300 gcg tat cac aat gtg act gca gag cag ctc ttt ttg aag gac att ata      960
Ala Tyr His Asn Val Thr Ala Glu Gln Leu Phe Leu Lys Asp Ile Ile
305                 310                 315                 320 gaa aaa aac ctc gta atc aac ttg act caa gat tga                      996
Glu Lys Asn Leu Val Ile Asn Leu Thr Gln Asp
                325                 330

<210> SEQ ID NO 28
<211> LENGTH: 331
<212> TYPE: PRT
<213> ORGANISM: Homo sapiens

<400> SEQUENCE: 28

Met Arg Gly Tyr Leu Val Ala Ile Phe Leu Ser Ala Val Phe Leu Tyr
1               5                   10                  15

Tyr Val Leu His Cys Ile Leu Trp Gly Thr Asn Val Tyr Trp Val Ala
                20                  25                  30

Pro Val Glu Met Lys Arg Arg Asn Lys Ile Gln Pro Cys Leu Ser Lys
            35                  40                  45

Pro Ala Phe Ala Ser Leu Leu Arg Phe His Gln Phe His Pro Phe Leu
        50                  55                  60

Cys Ala Ala Asp Phe Arg Lys Ile Ala Ser Leu Tyr Gly Ser Asp Lys
65                  70                  75                  80

Phe Asp Leu Pro Tyr Gly Met Arg Thr Ser Ala Glu Tyr Phe Arg Leu
                85                  90                  95

Ala Leu Ser Lys Leu Gln Ser Cys Asp Leu Phe Asp Glu Phe Asp Asn
            100                 105                 110

Ile Pro Cys Lys Lys Cys Val Val Val Gly Asn Gly Gly Val Leu Lys
```

```
            115                 120                 125
Asn Lys Thr Leu Gly Glu Lys Ile Asp Ser Tyr Asp Val Ile Ile Arg
    130                 135                 140

Met Asn Asn Gly Pro Val Leu Gly His Glu Glu Val Gly Arg Arg
145                 150                 155                 160

Thr Thr Phe Arg Leu Phe Tyr Pro Glu Ser Val Phe Ser Asp Pro Ile
                165                 170                 175

His Asn Asp Pro Asn Thr Thr Val Ile Leu Thr Ala Phe Lys Pro His
            180                 185                 190

Asp Leu Arg Trp Leu Leu Glu Leu Leu Met Gly Asp Lys Ile Asn Thr
        195                 200                 205

Asn Gly Phe Trp Lys Lys Pro Ala Leu Asn Leu Ile Tyr Lys Pro Tyr
    210                 215                 220

Gln Ile Arg Ile Leu Asp Pro Phe Ile Ile Arg Thr Ala Ala Tyr Glu
225                 230                 235                 240

Leu Leu His Phe Pro Lys Val Phe Pro Lys Asn Gln Lys Pro Lys His
                245                 250                 255

Pro Thr Thr Gly Ile Ile Ala Ile Thr Leu Ala Phe Tyr Ile Cys His
            260                 265                 270

Glu Val His Leu Ala Gly Phe Lys Tyr Asn Phe Ser Asp Leu Lys Ser
        275                 280                 285

Pro Leu His Tyr Tyr Gly Asn Ala Thr Met Ser Leu Met Asn Lys Asn
    290                 295                 300

Ala Tyr His Asn Val Thr Ala Glu Gln Leu Phe Leu Lys Asp Ile Ile
305                 310                 315                 320

Glu Lys Asn Leu Val Ile Asn Leu Thr Gln Asp
                325                 330

<210> SEQ ID NO 29
<211> LENGTH: 1125
<212> TYPE: DNA
<213> ORGANISM: Rattus rattus
<220> FEATURE:
<221> NAME/KEY: CDS
<222> LOCATION: (1)..(1125)

<400> SEQUENCE: 29 atg gga ctc ttg gta ttt gta cgc aac ctg ctg cta gcc ctg tgc ctc    48
Met Gly Leu Leu Val Phe Val Arg Asn Leu Leu Leu Ala Leu Cys Leu
1               5                   10                  15 ttt ctg gtc ctg gga ttt ttg tat tat tct gcc tgg aag cta cac tta    96
Phe Leu Val Leu Gly Phe Leu Tyr Tyr Ser Ala Trp Lys Leu His Leu
            20                  25                  30 ctc caa tgg gaa gac tcc aat tca ctg att ctt tcc ctt gac tcc gct   144
Leu Gln Trp Glu Asp Ser Asn Ser Leu Ile Leu Ser Leu Asp Ser Ala
        35                  40                  45 gga caa acc cta ggc aca gag tat gat agg ctg ggt ttc ctc ctg aag   192
Gly Gln Thr Leu Gly Thr Glu Tyr Asp Arg Leu Gly Phe Leu Leu Lys
50                  55                  60 ctg gac tct aaa ctg cct gca gag ctg gcc acc aag tac gct aac ttt   240
Leu Asp Ser Lys Leu Pro Ala Glu Leu Ala Thr Lys Tyr Ala Asn Phe
65                  70                  75                  80 tcc gag gga gcc tgc aaa ccc ggc tac gct tca gcc atg atg act gcc   288
Ser Glu Gly Ala Cys Lys Pro Gly Tyr Ala Ser Ala Met Met Thr Ala
                85                  90                  95 atc ttc ccc agg ttc tcc aag cca gca ccc atg ttc ctg gat gac tcc   336
Ile Phe Pro Arg Phe Ser Lys Pro Ala Pro Met Phe Leu Asp Asp Ser
            100                 105                 110
```

```
ttt cgc aaa tgg gct agg att cgg gag ttt gtg cca ccc ttt ggg atc       384
Phe Arg Lys Trp Ala Arg Ile Arg Glu Phe Val Pro Pro Phe Gly Ile
        115                 120                 125 aaa ggt caa gac aat ctg atc aaa gcc atc ttg tca gtc acc aaa gaa       432
Lys Gly Gln Asp Asn Leu Ile Lys Ala Ile Leu Ser Val Thr Lys Glu
130                 135                 140 tac cgc ctg acc cct gcc ttg gac agc ctc cac tgc cgc cgc tgc atc       480
Tyr Arg Leu Thr Pro Ala Leu Asp Ser Leu His Cys Arg Arg Cys Ile
145                 150                 155                 160 atc gta ggc aat gga ggg gtc ctc gcc aac aag tct ctg ggg tca cga       528
Ile Val Gly Asn Gly Gly Val Leu Ala Asn Lys Ser Leu Gly Ser Arg
                165                 170                 175 att gac gac tat gac att gtg atc aga ttg aac tca gca cct gtg aag       576
Ile Asp Asp Tyr Asp Ile Val Ile Arg Leu Asn Ser Ala Pro Val Lys
            180                 185                 190 ggc ttt gag aag gac gtg ggc agc aag acc acc ctg cgc atc acc tac       624
Gly Phe Glu Lys Asp Val Gly Ser Lys Thr Thr Leu Arg Ile Thr Tyr
        195                 200                 205 cct gaa ggt gcc atg cag cgg cct gag caa tat gaa cga gac tct ctc       672
Pro Glu Gly Ala Met Gln Arg Pro Glu Gln Tyr Glu Arg Asp Ser Leu
    210                 215                 220 ttt gta cta gct ggc ttc aag tgg cag gac ttc aag tgg ctg aag tac       720
Phe Val Leu Ala Gly Phe Lys Trp Gln Asp Phe Lys Trp Leu Lys Tyr
225                 230                 235                 240 atc gtc tac aag gag aga gtg agc gca tcc gat ggc ttc tgg aag tcc       768
Ile Val Tyr Lys Glu Arg Val Ser Ala Ser Asp Gly Phe Trp Lys Ser
                245                 250                 255 gtg gcc acc cga gtg ccc aag gag ccc cct gag atc cgc atc ctc aac       816
Val Ala Thr Arg Val Pro Lys Glu Pro Pro Glu Ile Arg Ile Leu Asn
            260                 265                 270 ccg tac ttc atc cag gag gct gcc ttc acg ctc atc gga ctg ccc ttc       864
Pro Tyr Phe Ile Gln Glu Ala Ala Phe Thr Leu Ile Gly Leu Pro Phe
        275                 280                 285 aac aat ggc ctc atg ggc aga ggg aac atc cca acc ctt ggc agt gtg       912
Asn Asn Gly Leu Met Gly Arg Gly Asn Ile Pro Thr Leu Gly Ser Val
    290                 295                 300 gca gtg acc atg gca ctc gat ggc tgt gat gaa gtg gca gtc gcg ggc       960
Ala Val Thr Met Ala Leu Asp Gly Cys Asp Glu Val Ala Val Ala Gly
305                 310                 315                 320 ttt ggc tat gac atg aac aca ccc aac gcc ccc ctg cac tac tat gaa      1008
Phe Gly Tyr Asp Met Asn Thr Pro Asn Ala Pro Leu His Tyr Tyr Glu
                325                 330                 335 act gtg cgc atg gca gcc atc aaa gag tcc tgg aca cac aac atc cag      1056
Thr Val Arg Met Ala Ala Ile Lys Glu Ser Trp Thr His Asn Ile Gln
            340                 345                 350 cga gag aaa gag ttt ctg cgg aag cta gtg aaa gca cgc gtc atc act      1104
Arg Glu Lys Glu Phe Leu Arg Lys Leu Val Lys Ala Arg Val Ile Thr
        355                 360                 365 gac tta agc agt ggt atc tga                                          1125
Asp Leu Ser Ser Gly Ile
        370

<210> SEQ ID NO 30
<211> LENGTH: 374
<212> TYPE: PRT
<213> ORGANISM: Rattus rattus

<400> SEQUENCE: 30

Met Gly Leu Leu Val Phe Val Arg Asn Leu Leu Leu Ala Leu Cys Leu
1               5                   10                  15
```

Phe Leu Val Leu Gly Phe Leu Tyr Tyr Ser Ala Trp Lys Leu His Leu
            20                  25                  30

Leu Gln Trp Glu Asp Ser Asn Ser Leu Ile Leu Ser Leu Asp Ser Ala
        35                  40                  45

Gly Gln Thr Leu Gly Thr Glu Tyr Asp Arg Leu Gly Phe Leu Leu Lys
    50                  55                  60

Leu Asp Ser Lys Leu Pro Ala Glu Leu Ala Thr Lys Tyr Ala Asn Phe
65                  70                  75                  80

Ser Glu Gly Ala Cys Lys Pro Gly Tyr Ala Ser Ala Met Met Thr Ala
                85                  90                  95

Ile Phe Pro Arg Phe Ser Lys Pro Ala Pro Met Phe Leu Asp Asp Ser
            100                 105                 110

Phe Arg Lys Trp Ala Arg Ile Arg Glu Phe Val Pro Pro Phe Gly Ile
        115                 120                 125

Lys Gly Gln Asp Asn Leu Ile Lys Ala Ile Leu Ser Val Thr Lys Glu
130                 135                 140

Tyr Arg Leu Thr Pro Ala Leu Asp Ser Leu His Cys Arg Arg Cys Ile
145                 150                 155                 160

Ile Val Gly Asn Gly Gly Val Leu Ala Asn Lys Ser Leu Gly Ser Arg
                165                 170                 175

Ile Asp Asp Tyr Asp Ile Val Ile Arg Leu Asn Ser Ala Pro Val Lys
            180                 185                 190

Gly Phe Glu Lys Asp Val Gly Ser Lys Thr Thr Leu Arg Ile Thr Tyr
        195                 200                 205

Pro Glu Gly Ala Met Gln Arg Pro Glu Gln Tyr Glu Arg Asp Ser Leu
210                 215                 220

Phe Val Leu Ala Gly Phe Lys Trp Gln Asp Phe Lys Trp Leu Lys Tyr
225                 230                 235                 240

Ile Val Tyr Lys Glu Arg Val Ser Ala Ser Asp Gly Phe Trp Lys Ser
                245                 250                 255

Val Ala Thr Arg Val Pro Lys Glu Pro Pro Glu Ile Arg Ile Leu Asn
            260                 265                 270

Pro Tyr Phe Ile Gln Glu Ala Ala Phe Thr Leu Ile Gly Leu Pro Phe
        275                 280                 285

Asn Asn Gly Leu Met Gly Arg Gly Asn Ile Pro Thr Leu Gly Ser Val
290                 295                 300

Ala Val Thr Met Ala Leu Asp Gly Cys Asp Glu Val Ala Val Ala Gly
305                 310                 315                 320

Phe Gly Tyr Asp Met Asn Thr Pro Asn Ala Pro Leu His Tyr Tyr Glu
                325                 330                 335

Thr Val Arg Met Ala Ala Ile Lys Glu Ser Trp Thr His Asn Ile Gln
            340                 345                 350

Arg Glu Lys Glu Phe Leu Arg Lys Leu Val Lys Ala Arg Val Ile Thr
        355                 360                 365

Asp Leu Ser Ser Gly Ile
    370

<210> SEQ ID NO 31
<211> LENGTH: 1071
<212> TYPE: DNA
<213> ORGANISM: Homo sapiens
<220> FEATURE:
<221> NAME/KEY: CDS
<222> LOCATION: (1)..(1071)

<400> SEQUENCE: 31

```
atg agc ccc tgc ggg cgg gcc cgg cga caa acg tcc aga ggg gcc atg      48
Met Ser Pro Cys Gly Arg Ala Arg Arg Gln Thr Ser Arg Gly Ala Met
 1               5                  10                  15 gct gta ctg gcg tgg aag ttc ccg cgg acc cgg ctg ccc atg gga gcc      96
Ala Val Leu Ala Trp Lys Phe Pro Arg Thr Arg Leu Pro Met Gly Ala
             20                  25                  30 agt gcc ctc tgt gtc gtg gtc ctc tgt tgg ctc tac atc ttc ccc gtc     144
Ser Ala Leu Cys Val Val Val Leu Cys Trp Leu Tyr Ile Phe Pro Val
         35                  40                  45 tac cgg ctg ccc aac gag aaa gag atc gtg cag ggg gtg ctg caa cag     192
Tyr Arg Leu Pro Asn Glu Lys Glu Ile Val Gln Gly Val Leu Gln Gln
     50                  55                  60 ggc acg gcg tgg agg agg aac cag acc gcg gcc aga gcg ttc agg aaa     240
Gly Thr Ala Trp Arg Arg Asn Gln Thr Ala Ala Arg Ala Phe Arg Lys
 65                  70                  75                  80 caa atg gaa gac tgc tgc gac cct gcc cat ctc ttt gct atg act aaa     288
Gln Met Glu Asp Cys Cys Asp Pro Ala His Leu Phe Ala Met Thr Lys
                 85                  90                  95 atg aat tcc cct atg ggg aag agc atg tgg tat gac ggg gag ttt tta     336
Met Asn Ser Pro Met Gly Lys Ser Met Trp Tyr Asp Gly Glu Phe Leu
            100                 105                 110 tac tca ttc acc att gac aat tca act tac tct ctc ttc cca cag gca     384
Tyr Ser Phe Thr Ile Asp Asn Ser Thr Tyr Ser Leu Phe Pro Gln Ala
        115                 120                 125 acc cca ttc cag ctg cca ttg aag aaa tgc gcg gtg gtg gga aat ggt     432
Thr Pro Phe Gln Leu Pro Leu Lys Lys Cys Ala Val Val Gly Asn Gly
    130                 135                 140 ggg att ctg aag aag agt ggc tgt ggc cgt caa ata gat gaa gca aat     480
Gly Ile Leu Lys Lys Ser Gly Cys Gly Arg Gln Ile Asp Glu Ala Asn
145                 150                 155                 160 ttt gtc atg cga tgc aat ctc cct cct ttg tca agt gaa tac act aag     528
Phe Val Met Arg Cys Asn Leu Pro Pro Leu Ser Ser Glu Tyr Thr Lys
                165                 170                 175 gat gtt gga tcc aaa agt cag tta gtg aca gct aat ccc agc ata att     576
Asp Val Gly Ser Lys Ser Gln Leu Val Thr Ala Asn Pro Ser Ile Ile
            180                 185                 190 cgg caa agg ttt cag aac ctt ctg tgg tcc aga aag aca ttt gtg gac     624
Arg Gln Arg Phe Gln Asn Leu Leu Trp Ser Arg Lys Thr Phe Val Asp
        195                 200                 205 aac atg aaa att tat aac cac agt tac atc tac atg cct gcc ttt tct     672
Asn Met Lys Ile Tyr Asn His Ser Tyr Ile Tyr Met Pro Ala Phe Ser
    210                 215                 220 atg aag aca gga aca gag cca tct ttg agg gtt tat tat aca ctg tca     720
Met Lys Thr Gly Thr Glu Pro Ser Leu Arg Val Tyr Tyr Thr Leu Ser
225                 230                 235                 240 gat gtt ggt gcc aat caa aca gtg ctg ttt gcc aac ccc aac ttt ctg     768
Asp Val Gly Ala Asn Gln Thr Val Leu Phe Ala Asn Pro Asn Phe Leu
                245                 250                 255 cgt agc att gga aag ttc tgg aaa agt aga gga atc cat gcc aag cgc     816
Arg Ser Ile Gly Lys Phe Trp Lys Ser Arg Gly Ile His Ala Lys Arg
            260                 265                 270 ctg tcc aca gga ctt ttt ctg gtg agc gca gct ctg ggt ctc tgt gaa     864
Leu Ser Thr Gly Leu Phe Leu Val Ser Ala Ala Leu Gly Leu Cys Glu
        275                 280                 285 gag gtg gcc atc tat ggc ttc tgg ccc ttc tct gtg aat atg cat gag     912
Glu Val Ala Ile Tyr Gly Phe Trp Pro Phe Ser Val Asn Met His Glu
    290                 295                 300 cag ccc atc agc cac cac tac tat gac aac gtc tta ccc ttt tct ggc     960
Gln Pro Ile Ser His His Tyr Tyr Asp Asn Val Leu Pro Phe Ser Gly
```

```
                    Gln Pro Ile Ser His His Tyr Tyr Asp Asn Val Leu Pro Phe Ser Gly
                    305                 310                 315                 320 ttc cat gcc atg ccc gag gaa ttt ctc caa ctc tgg tat ctt cat aaa        1008
Phe His Ala Met Pro Glu Glu Phe Leu Gln Leu Trp Tyr Leu His Lys
            325                 330                 335 atc ggt gca ctg aga atg cag ctg gac cca tgt gaa gat acc tca ctc        1056
Ile Gly Ala Leu Arg Met Gln Leu Asp Pro Cys Glu Asp Thr Ser Leu
            340                 345                 350 cag ccc act tcc tag                                                     1071
Gln Pro Thr Ser
        355

<210> SEQ ID NO 32
<211> LENGTH: 356
<212> TYPE: PRT
<213> ORGANISM: Homo sapiens

<400> SEQUENCE: 32

Met Ser Pro Cys Gly Arg Ala Arg Arg Gln Thr Ser Arg Gly Ala Met
1               5                   10                  15

Ala Val Leu Ala Trp Lys Phe Pro Arg Thr Arg Leu Pro Met Gly Ala
            20                  25                  30

Ser Ala Leu Cys Val Val Val Leu Cys Trp Leu Tyr Ile Phe Pro Val
        35                  40                  45

Tyr Arg Leu Pro Asn Glu Lys Glu Ile Val Gln Gly Val Leu Gln Gln
    50                  55                  60

Gly Thr Ala Trp Arg Arg Asn Gln Thr Ala Ala Arg Ala Phe Arg Lys
65                  70                  75                  80

Gln Met Glu Asp Cys Cys Asp Pro Ala His Leu Phe Ala Met Thr Lys
                85                  90                  95

Met Asn Ser Pro Met Gly Lys Ser Met Trp Tyr Asp Gly Glu Phe Leu
            100                 105                 110

Tyr Ser Phe Thr Ile Asp Asn Ser Thr Tyr Ser Leu Phe Pro Gln Ala
        115                 120                 125

Thr Pro Phe Gln Leu Pro Leu Lys Lys Cys Ala Val Val Gly Asn Gly
    130                 135                 140

Gly Ile Leu Lys Lys Ser Gly Cys Gly Arg Gln Ile Asp Glu Ala Asn
145                 150                 155                 160

Phe Val Met Arg Cys Asn Leu Pro Pro Leu Ser Ser Glu Tyr Thr Lys
                165                 170                 175

Asp Val Gly Ser Lys Ser Gln Leu Val Thr Ala Asn Pro Ser Ile Ile
            180                 185                 190

Arg Gln Arg Phe Gln Asn Leu Leu Trp Ser Arg Lys Thr Phe Val Asp
        195                 200                 205

Asn Met Lys Ile Tyr Asn His Ser Tyr Ile Tyr Met Pro Ala Phe Ser
    210                 215                 220

Met Lys Thr Gly Thr Glu Pro Ser Leu Arg Val Tyr Tyr Thr Leu Ser
225                 230                 235                 240

Asp Val Gly Ala Asn Gln Thr Val Leu Phe Ala Asn Pro Asn Phe Leu
                245                 250                 255

Arg Ser Ile Gly Lys Phe Trp Lys Ser Arg Gly Ile His Ala Lys Arg
            260                 265                 270

Leu Ser Thr Gly Leu Phe Leu Val Ser Ala Ala Leu Gly Leu Cys Glu
        275                 280                 285

Glu Val Ala Ile Tyr Gly Phe Trp Pro Phe Ser Val Asn Met His Glu
    290                 295                 300
```

| | | | | | | | | | | | | |
|---|---|---|---|---|---|---|---|---|---|---|---|---|
| Gln | Pro | Ile | Ser | His | His | Tyr | Tyr | Asp | Asn | Val | Leu | Pro | Phe | Ser | Gly |
| 305 | | | | 310 | | | | 315 | | | | 320 |

| Phe | His | Ala | Met | Pro | Glu | Glu | Phe | Leu | Gln | Leu | Trp | Tyr | Leu | His | Lys |
|---|---|---|---|---|---|---|---|---|---|---|---|---|---|---|---|
| | | | | 325 | | | | 330 | | | | 335 | | | |

| Ile | Gly | Ala | Leu | Arg | Met | Gln | Leu | Asp | Pro | Cys | Glu | Asp | Thr | Ser | Leu |
|---|---|---|---|---|---|---|---|---|---|---|---|---|---|---|---|
| | | | 340 | | | | 345 | | | | 350 | | | | |

Gln Pro Thr Ser
    355

<210> SEQ ID NO 33
<211> LENGTH: 1128
<212> TYPE: DNA
<213> ORGANISM: Homo sapiens
<220> FEATURE:
<221> NAME/KEY: CDS
<222> LOCATION: (1)..(1128)

<400> SEQUENCE: 33

```
atg cag ctg cag ttc cgg agc tgg atg ctg gcc gcg ctc acg ctg ctc      48
Met Gln Leu Gln Phe Arg Ser Trp Met Leu Ala Ala Leu Thr Leu Leu
1               5                   10                  15 gtg gtc ttc ctc atc ttc gca gac atc tca gag atc gaa gaa gaa atc      96
Val Val Phe Leu Ile Phe Ala Asp Ile Ser Glu Ile Glu Glu Glu Ile
                20                  25                  30 ggg aat tcg gga ggc aga ggt aca atc aga tca gct gtg aac agc tta     144
Gly Asn Ser Gly Gly Arg Gly Thr Ile Arg Ser Ala Val Asn Ser Leu
            35                  40                  45 cat agc aaa tct aat aga gct gaa gtt gta ata aac ggc tcc tca tca     192
His Ser Lys Ser Asn Arg Ala Glu Val Val Ile Asn Gly Ser Ser Ser
        50                  55                  60 cca gct gtt gtt gac aga agt aat gaa agc atc aag cac aac atc cag     240
Pro Ala Val Val Asp Arg Ser Asn Glu Ser Ile Lys His Asn Ile Gln
65                  70                  75                  80 cca gcc tcg tcc aaa tgg aga cat aac cag acg ctc tct ctg agg atc     288
Pro Ala Ser Ser Lys Trp Arg His Asn Gln Thr Leu Ser Leu Arg Ile
                85                  90                  95 agg aag cag att tta aag ttc ttg gat gct gaa aag gac att tct gtc     336
Arg Lys Gln Ile Leu Lys Phe Leu Asp Ala Glu Lys Asp Ile Ser Val
                100                 105                 110 cta aag gga acc ctg aag cct gga gat att att cat tac atc ttc gat     384
Leu Lys Gly Thr Leu Lys Pro Gly Asp Ile Ile His Tyr Ile Phe Asp
            115                 120                 125 cga gac agc acc atg aat gtg tcc cag aac ctc tac gag ctc ctc ccc     432
Arg Asp Ser Thr Met Asn Val Ser Gln Asn Leu Tyr Glu Leu Leu Pro
        130                 135                 140 agg act tcg cca ctg aag aat aag cac ttt ggg act tgt gcc atc gtg     480
Arg Thr Ser Pro Leu Lys Asn Lys His Phe Gly Thr Cys Ala Ile Val
145                 150                 155                 160 ggc aac tcg ggg gtc ttg ctg aac agc ggc tgt ggg cag gag att gac     528
Gly Asn Ser Gly Val Leu Leu Asn Ser Gly Cys Gly Gln Glu Ile Asp
                165                 170                 175 gcc cac agc ttc gtc atc agg tgc aac ctg gcc cca gta cag gag tat     576
Ala His Ser Phe Val Ile Arg Cys Asn Leu Ala Pro Val Gln Glu Tyr
            180                 185                 190 gcc cgg gat gtg ggg ctc aag aca gac ctg gta acc atg aac ccc tcg     624
Ala Arg Asp Val Gly Leu Lys Thr Asp Leu Val Thr Met Asn Pro Ser
        195                 200                 205 gtc atc cag cgg gcc ttt gag gac ttg gtc aat gcc acg tgg cgg gag     672
Val Ile Gln Arg Ala Phe Glu Asp Leu Val Asn Ala Thr Trp Arg Glu
210                 215                 220
```

```
aag ctg ctg caa cgg ctg cac agc ctc aat ggc agc atc ctg tgg atc    720
Lys Leu Leu Gln Arg Leu His Ser Leu Asn Gly Ser Ile Leu Trp Ile
225                 230                 235                 240 cct gcc ttc atg gcc cgg ggc aag gag cgt gtt gag tgg gtc aac        768
Pro Ala Phe Met Ala Arg Gly Gly Lys Glu Arg Val Glu Trp Val Asn
                245                 250                 255 gag ctt atc ctg aag cac cac gtc aac gtg cgc act gca tac ccc tcg    816
Glu Leu Ile Leu Lys His His Val Asn Val Arg Thr Ala Tyr Pro Ser
            260                 265                 270 ctg cgc ctg ctg cac gcc gtt cgc gga tac tgg ctg acc aac aaa gtc    864
Leu Arg Leu Leu His Ala Val Arg Gly Tyr Trp Leu Thr Asn Lys Val
        275                 280                 285 cac atc aaa aga ccc acc acc ggc ctc ttg atg tat acc ctg gcc aca    912
His Ile Lys Arg Pro Thr Thr Gly Leu Leu Met Tyr Thr Leu Ala Thr
    290                 295                 300 cgt ttc tgc aaa caa atc tac ctc tac ggc ttc tgg ccc ttt ccg ctg    960
Arg Phe Cys Lys Gln Ile Tyr Leu Tyr Gly Phe Trp Pro Phe Pro Leu
305                 310                 315                 320 gat cag aac cag aac cca gtc aag tac cac tat tat gac agc ctc aag   1008
Asp Gln Asn Gln Asn Pro Val Lys Tyr His Tyr Tyr Asp Ser Leu Lys
                325                 330                 335 tat ggc tac acc tcc cag gcc agc ccg cat acc atg ccc ttg gag ttt   1056
Tyr Gly Tyr Thr Ser Gln Ala Ser Pro His Thr Met Pro Leu Glu Phe
            340                 345                 350 aag gcc ctc aag agc cta cat gag cag ggg gct ttg aaa ctg act gtc   1104
Lys Ala Leu Lys Ser Leu His Glu Gln Gly Ala Leu Lys Leu Thr Val
        355                 360                 365 ggc cag tgc gat ggg gcc acg tag                                   1128
Gly Gln Cys Asp Gly Ala Thr
    370                 375

<210> SEQ ID NO 34
<211> LENGTH: 375
<212> TYPE: PRT
<213> ORGANISM: Homo sapiens

<400> SEQUENCE: 34

Met Gln Leu Gln Phe Arg Ser Trp Met Leu Ala Ala Leu Thr Leu Leu
1               5                   10                  15

Val Val Phe Leu Ile Phe Ala Asp Ile Ser Glu Ile Glu Glu Glu Ile
            20                  25                  30

Gly Asn Ser Gly Gly Arg Gly Thr Ile Arg Ser Ala Val Asn Ser Leu
        35                  40                  45

His Ser Lys Ser Asn Arg Ala Glu Val Val Ile Asn Gly Ser Ser Ser
    50                  55                  60

Pro Ala Val Val Asp Arg Ser Asn Glu Ser Ile Lys His Asn Ile Gln
65                  70                  75                  80

Pro Ala Ser Ser Lys Trp Arg His Asn Gln Thr Leu Ser Leu Arg Ile
                85                  90                  95

Arg Lys Gln Ile Leu Lys Phe Leu Asp Ala Glu Lys Asp Ile Ser Val
            100                 105                 110

Leu Lys Gly Thr Leu Lys Pro Gly Asp Ile Ile His Tyr Ile Phe Asp
        115                 120                 125

Arg Asp Ser Thr Met Asn Val Ser Gln Asn Leu Tyr Glu Leu Leu Pro
    130                 135                 140

Arg Thr Ser Pro Leu Lys Asn Lys His Phe Gly Thr Cys Ala Ile Val
145                 150                 155                 160
```

```
Gly Asn Ser Gly Val Leu Leu Asn Ser Gly Cys Gly Gln Glu Ile Asp
            165                 170                 175

Ala His Ser Phe Val Ile Arg Cys Asn Leu Ala Pro Val Gln Glu Tyr
        180                 185                 190

Ala Arg Asp Val Gly Leu Lys Thr Asp Leu Val Thr Met Asn Pro Ser
        195                 200                 205

Val Ile Gln Arg Ala Phe Glu Asp Leu Val Asn Ala Thr Trp Arg Glu
    210                 215                 220

Lys Leu Leu Gln Arg Leu His Ser Leu Asn Gly Ser Ile Leu Trp Ile
225                 230                 235                 240

Pro Ala Phe Met Ala Arg Gly Gly Lys Glu Arg Val Glu Trp Val Asn
                245                 250                 255

Glu Leu Ile Leu Lys His His Val Asn Val Arg Thr Ala Tyr Pro Ser
                260                 265                 270

Leu Arg Leu Leu His Ala Val Arg Gly Tyr Trp Leu Thr Asn Lys Val
        275                 280                 285

His Ile Lys Arg Pro Thr Thr Gly Leu Leu Met Tyr Thr Leu Ala Thr
    290                 295                 300

Arg Phe Cys Lys Gln Ile Tyr Leu Tyr Gly Phe Trp Pro Phe Pro Leu
305                 310                 315                 320

Asp Gln Asn Gln Asn Pro Val Lys Tyr His Tyr Asp Ser Leu Lys
                325                 330                 335

Tyr Gly Tyr Thr Ser Gln Ala Ser Pro His Thr Met Pro Leu Glu Phe
            340                 345                 350

Lys Ala Leu Lys Ser Leu His Glu Gln Gly Ala Leu Lys Leu Thr Val
                355                 360                 365

Gly Gln Cys Asp Gly Ala Thr
        370                 375

<210> SEQ ID NO 35
<211> LENGTH: 1143
<212> TYPE: DNA
<213> ORGANISM: Homo sapiens
<220> FEATURE:
<221> NAME/KEY: CDS
<222> LOCATION: (1)..(1143)

<400> SEQUENCE: 35 atg aga aac tgc aaa atg gcc cgg gtc gcc agt gtg ctg ggg ctg gtc      48
Met Arg Asn Cys Lys Met Ala Arg Val Ala Ser Val Leu Gly Leu Val
1               5                   10                  15 atg ctc agc gtc gcc ctg ctg att tta tcg ctc atc agc tac gtg tcc     96
Met Leu Ser Val Ala Leu Leu Ile Leu Ser Leu Ile Ser Tyr Val Ser
                20                  25                  30 ctg aaa aag gag aac atc ttc acc act ccc aag tac gcc agc ccg ggg    144
Leu Lys Lys Glu Asn Ile Phe Thr Thr Pro Lys Tyr Ala Ser Pro Gly
            35                  40                  45 gcg ccc cga atg tac atg ttc cac gcg gga ttc cgg tca caa ttt gcg    192
Ala Pro Arg Met Tyr Met Phe His Ala Gly Phe Arg Ser Gln Phe Ala
        50                  55                  60 ctg aag ttt cta gac ccg tca ttc gtg ccc att acg aat tct ctc acc    240
Leu Lys Phe Leu Asp Pro Ser Phe Val Pro Ile Thr Asn Ser Leu Thr
65                  70                  75                  80 cag gaa ctc caa gag aaa cct tct aag tgg aaa ttt aat cgg aca gcg    288
Gln Glu Leu Gln Glu Lys Pro Ser Lys Trp Lys Phe Asn Arg Thr Ala
                85                  90                  95 ttt tta cat caa agg caa gaa att ctt cag cat gtc gat gta ata aaa    336
Phe Leu His Gln Arg Gln Glu Ile Leu Gln His Val Asp Val Ile Lys
```

```
aat ttt tct ttg acc aag aat agt gtt cgg att gga caa ctg atg cac      384
Asn Phe Ser Leu Thr Lys Asn Ser Val Arg Ile Gly Gln Leu Met His
            115                 120                 125 tat gat tat tcc agc cat aaa tat gtt ttc tct att agc aat aac ttc      432
Tyr Asp Tyr Ser Ser His Lys Tyr Val Phe Ser Ile Ser Asn Asn Phe
130                 135                 140 cgg tca ctt ctt cca gat gtg tca ccc att atg aac aag cat tat aat      480
Arg Ser Leu Leu Pro Asp Val Ser Pro Ile Met Asn Lys His Tyr Asn
145                 150                 155                 160 att tgt gct gtg gtt gga aat agt ggg atc ctg aca ttt atc cag tgt      528
Ile Cys Ala Val Val Gly Asn Ser Gly Ile Leu Thr Phe Ile Gln Cys
                165                 170                 175 gga cga gaa ata gat aaa tca gat ttt gtt ttc cgt tgc aat ttc gcc      576
Gly Arg Glu Ile Asp Lys Ser Asp Phe Val Phe Arg Cys Asn Phe Ala
            180                 185                 190 cca tcg gag gct ttc caa aga gat gtt gga agg aaa acc aat ctt acc      624
Pro Ser Glu Ala Phe Gln Arg Asp Val Gly Arg Lys Thr Asn Leu Thr
        195                 200                 205 acc ttc aac ccc agc atc ctg gaa aaa tat tac aac aat ctc ttg act      672
Thr Phe Asn Pro Ser Ile Leu Glu Lys Tyr Tyr Asn Asn Leu Leu Thr
210                 215                 220 att cag gac cgt aac aac ttt ttc ctc agt tta aaa aag ctt gac ggg      720
Ile Gln Asp Arg Asn Asn Phe Phe Leu Ser Leu Lys Lys Leu Asp Gly
225                 230                 235                 240 gcc att ctt tgg atc cct gca ttt ttc ttc cac act tca gca act gtg      768
Ala Ile Leu Trp Ile Pro Ala Phe Phe Phe His Thr Ser Ala Thr Val
                245                 250                 255 acc agg aca tta gtt gac ttt ttt gtt gaa cac aga ggt cag tta aaa      816
Thr Arg Thr Leu Val Asp Phe Phe Val Glu His Arg Gly Gln Leu Lys
            260                 265                 270 gtc caa ctg gct tgg ccg gga aat ata atg caa cat gtc aac agg tac      864
Val Gln Leu Ala Trp Pro Gly Asn Ile Met Gln His Val Asn Arg Tyr
        275                 280                 285 tgg aaa aac aaa cat ttg tca cct aaa cgg ctg agc aca ggt att ctt      912
Trp Lys Asn Lys His Leu Ser Pro Lys Arg Leu Ser Thr Gly Ile Leu
290                 295                 300 atg tac acc ctt gca tca gca ata tgt gaa gag atc cac ttg tat gga      960
Met Tyr Thr Leu Ala Ser Ala Ile Cys Glu Glu Ile His Leu Tyr Gly
305                 310                 315                 320 ttt tgg ccg ttt gga ttt gac ccc aac aca agg gaa gat ctt cca tac     1008
Phe Trp Pro Phe Gly Phe Asp Pro Asn Thr Arg Glu Asp Leu Pro Tyr
                325                 330                 335 cat tac tat gac aaa aaa gga acc aaa ttt acc acc aag tgg cag gag     1056
His Tyr Tyr Asp Lys Lys Gly Thr Lys Phe Thr Thr Lys Trp Gln Glu
            340                 345                 350 tcc cac cag ctg cct gct gag ttt cag ctg ctg tac cga atg cat ggg     1104
Ser His Gln Leu Pro Ala Glu Phe Gln Leu Leu Tyr Arg Met His Gly
        355                 360                 365 gaa ggg ctc acc aag ctg act ctg tca cac tgt gcc taa                 1143
Glu Gly Leu Thr Lys Leu Thr Leu Ser His Cys Ala
370                 375                 380

<210> SEQ ID NO 36
<211> LENGTH: 380
<212> TYPE: PRT
<213> ORGANISM: Homo sapiens

<400> SEQUENCE: 36

Met Arg Asn Cys Lys Met Ala Arg Val Ala Ser Val Leu Gly Leu Val
```

```
  1               5                   10                  15
Met Leu Ser Val Ala Leu Leu Ile Leu Ser Leu Ile Ser Tyr Val Ser
             20                  25                  30
Leu Lys Lys Glu Asn Ile Phe Thr Thr Pro Lys Tyr Ala Ser Pro Gly
             35                  40                  45
Ala Pro Arg Met Tyr Met Phe His Ala Gly Phe Arg Ser Gln Phe Ala
         50                  55                  60
Leu Lys Phe Leu Asp Pro Ser Phe Val Pro Ile Thr Asn Ser Leu Thr
 65                  70                  75                  80
Gln Glu Leu Gln Glu Lys Pro Ser Lys Trp Lys Phe Asn Arg Thr Ala
                 85                  90                  95
Phe Leu His Gln Arg Gln Glu Ile Leu Gln His Val Asp Val Ile Lys
                100                 105                 110
Asn Phe Ser Leu Thr Lys Asn Ser Val Arg Ile Gly Gln Leu Met His
                115                 120                 125
Tyr Asp Tyr Ser Ser His Lys Tyr Val Phe Ser Ile Ser Asn Asn Phe
            130                 135                 140
Arg Ser Leu Leu Pro Asp Val Ser Pro Ile Met Asn Lys His Tyr Asn
145                 150                 155                 160
Ile Cys Ala Val Val Gly Asn Ser Gly Ile Leu Thr Phe Ile Gln Cys
                165                 170                 175
Gly Arg Glu Ile Asp Lys Ser Asp Phe Val Phe Arg Cys Asn Phe Ala
                180                 185                 190
Pro Ser Glu Ala Phe Gln Arg Asp Val Gly Arg Lys Thr Asn Leu Thr
            195                 200                 205
Thr Phe Asn Pro Ser Ile Leu Glu Lys Tyr Tyr Asn Asn Leu Leu Thr
210                 215                 220
Ile Gln Asp Arg Asn Asn Phe Phe Leu Ser Leu Lys Lys Leu Asp Gly
225                 230                 235                 240
Ala Ile Leu Trp Ile Pro Ala Phe Phe Phe His Thr Ser Ala Thr Val
                245                 250                 255
Thr Arg Thr Leu Val Asp Phe Phe Val Glu His Arg Gly Gln Leu Lys
            260                 265                 270
Val Gln Leu Ala Trp Pro Gly Asn Ile Met Gln His Val Asn Arg Tyr
        275                 280                 285
Trp Lys Asn Lys His Leu Ser Pro Lys Arg Leu Ser Thr Gly Ile Leu
        290                 295                 300
Met Tyr Thr Leu Ala Ser Ala Ile Cys Glu Glu Ile His Leu Tyr Gly
305                 310                 315                 320
Phe Trp Pro Phe Gly Phe Asp Pro Asn Thr Arg Glu Asp Leu Pro Tyr
                325                 330                 335
His Tyr Tyr Asp Lys Lys Gly Thr Lys Phe Thr Thr Lys Trp Gln Glu
            340                 345                 350
Ser His Gln Leu Pro Ala Glu Phe Gln Leu Leu Tyr Arg Met His Gly
            355                 360                 365
Glu Gly Leu Thr Lys Leu Thr Leu Ser His Cys Ala
            370                 375                 380

<210> SEQ ID NO 37
<211> LENGTH: 1080
<212> TYPE: DNA
<213> ORGANISM: Homo sapiens
<220> FEATURE:
<221> NAME/KEY: CDS
<222> LOCATION: (1)..(1080)
```

<400> SEQUENCE: 37

```
atg cgc tcc att agg aag agg tgg acg atc tgc aca ata agt ctg ctc      48
Met Arg Ser Ile Arg Lys Arg Trp Thr Ile Cys Thr Ile Ser Leu Leu
1               5                   10                  15 ctg atc ttt tat aag aca aaa gaa ata gca aga act gag gag cac cag      96
Leu Ile Phe Tyr Lys Thr Lys Glu Ile Ala Arg Thr Glu Glu His Gln
            20                  25                  30 gag acg caa ctc atc gga gat ggt gaa ttg tct ttg agt cgg tca ctt     144
Glu Thr Gln Leu Ile Gly Asp Gly Glu Leu Ser Leu Ser Arg Ser Leu
        35                  40                  45 gtc aat agc tct gat aaa atc att cga aag gct ggc tct tca atc ttc     192
Val Asn Ser Ser Asp Lys Ile Ile Arg Lys Ala Gly Ser Ser Ile Phe
50                  55                  60 cag cac aat gta gaa ggt tgg aaa atc aat tcc tct ttg gtc cta gag     240
Gln His Asn Val Glu Gly Trp Lys Ile Asn Ser Ser Leu Val Leu Glu
65                  70                  75                  80 ata agg aag aac ata ctt cgt ttc tta gat gca gaa cga gat gtg tca     288
Ile Arg Lys Asn Ile Leu Arg Phe Leu Asp Ala Glu Arg Asp Val Ser
                85                  90                  95 gtg gtc aag agc agt ttt aag cct ggt gat gtc ata cac tat gtg ctt     336
Val Val Lys Ser Ser Phe Lys Pro Gly Asp Val Ile His Tyr Val Leu
            100                 105                 110 gac agg cgc cgg aca cta aac att tct cat gat cta cat agc ctc cta     384
Asp Arg Arg Arg Thr Leu Asn Ile Ser His Asp Leu His Ser Leu Leu
        115                 120                 125 cct gaa gtt tca cca atg aag aat cgc agg ttt aag acc tgt gca gtt     432
Pro Glu Val Ser Pro Met Lys Asn Arg Arg Phe Lys Thr Cys Ala Val
130                 135                 140 gtt gga aat tct ggc att ctg tta gac agt gaa tgt gga aag gag att     480
Val Gly Asn Ser Gly Ile Leu Leu Asp Ser Glu Cys Gly Lys Glu Ile
145                 150                 155                 160 gac agt cac aat ttt gta ata agg tgt aat cta gct cct gtg gtg gag     528
Asp Ser His Asn Phe Val Ile Arg Cys Asn Leu Ala Pro Val Val Glu
                165                 170                 175 ttt gct gca gat gtg gga act aaa tca gat ttt att acc atg aat cca     576
Phe Ala Ala Asp Val Gly Thr Lys Ser Asp Phe Ile Thr Met Asn Pro
            180                 185                 190 tca gtt gta caa aga gca ttt gga ggc ttt cga aat gag agt gac aga     624
Ser Val Val Gln Arg Ala Phe Gly Gly Phe Arg Asn Glu Ser Asp Arg
        195                 200                 205 gaa aaa ttt gtg cat aga ctt tcc atg ctg aat gac agt gtc ctt tgg     672
Glu Lys Phe Val His Arg Leu Ser Met Leu Asn Asp Ser Val Leu Trp
210                 215                 220 att cct gct ttc atg gtc aaa gga gga gag aag cac gtg gag tgg gtt     720
Ile Pro Ala Phe Met Val Lys Gly Gly Glu Lys His Val Glu Trp Val
225                 230                 235                 240 aat gca tta atc ctt aag aat aaa ctg aaa gtg cga act gcc tat ccg     768
Asn Ala Leu Ile Leu Lys Asn Lys Leu Lys Val Arg Thr Ala Tyr Pro
                245                 250                 255 tca ttg aga ctt att cat gct gtc aga ggt tac tgg ctg acc aac aaa     816
Ser Leu Arg Leu Ile His Ala Val Arg Gly Tyr Trp Leu Thr Asn Lys
            260                 265                 270 gtt cct atc aaa aga ccc agc aca ggt ctt ctc atg tat aca ctt gcc     864
Val Pro Ile Lys Arg Pro Ser Thr Gly Leu Leu Met Tyr Thr Leu Ala
        275                 280                 285 aca aga ttc tgt gat gaa att cac ctg tat gga ttc tgg ccc ttc cct     912
Thr Arg Phe Cys Asp Glu Ile His Leu Tyr Gly Phe Trp Pro Phe Pro
290                 295                 300
```

-continued

```
aag gat tta aat gga aaa gcg gtc aaa tat cat tat tat gat gac tta      960
Lys Asp Leu Asn Gly Lys Ala Val Lys Tyr His Tyr Tyr Asp Asp Leu
305                 310                 315                 320 aaa tat agg tac ttt tcc aat gca agc cct cac aga atg cca tta gaa     1008
Lys Tyr Arg Tyr Phe Ser Asn Ala Ser Pro His Arg Met Pro Leu Glu
            325                 330                 335 ttc aaa aca tta aat gtg cta cat aat aga gga gct cta aaa ctg aca     1056
Phe Lys Thr Leu Asn Val Leu His Asn Arg Gly Ala Leu Lys Leu Thr
                340                 345                 350 aca gga aag tgt gta aag caa taa                                     1080
Thr Gly Lys Cys Val Lys Gln
            355
```

<210> SEQ ID NO 38
<211> LENGTH: 359
<212> TYPE: PRT
<213> ORGANISM: Homo sapiens

<400> SEQUENCE: 38

```
Met Arg Ser Ile Arg Lys Arg Trp Thr Ile Cys Thr Ile Ser Leu Leu
1               5                   10                  15

Leu Ile Phe Tyr Lys Thr Lys Glu Ile Ala Arg Thr Glu Glu His Gln
            20                  25                  30

Glu Thr Gln Leu Ile Gly Asp Gly Glu Leu Ser Leu Ser Arg Ser Leu
        35                  40                  45

Val Asn Ser Ser Asp Lys Ile Ile Arg Lys Ala Gly Ser Ser Ile Phe
    50                  55                  60

Gln His Asn Val Glu Gly Trp Lys Ile Asn Ser Ser Leu Val Leu Glu
65                  70                  75                  80

Ile Arg Lys Asn Ile Leu Arg Phe Leu Asp Ala Glu Arg Asp Val Ser
                85                  90                  95

Val Val Lys Ser Ser Phe Lys Pro Gly Asp Val Ile His Tyr Val Leu
            100                 105                 110

Asp Arg Arg Arg Thr Leu Asn Ile Ser His Asp Leu His Ser Leu Leu
        115                 120                 125

Pro Glu Val Ser Pro Met Lys Asn Arg Arg Phe Lys Thr Cys Ala Val
    130                 135                 140

Val Gly Asn Ser Gly Ile Leu Leu Asp Ser Glu Cys Gly Lys Glu Ile
145                 150                 155                 160

Asp Ser His Asn Phe Val Ile Arg Cys Asn Leu Ala Pro Val Val Glu
                165                 170                 175

Phe Ala Ala Asp Val Gly Thr Lys Ser Asp Phe Ile Thr Met Asn Pro
            180                 185                 190

Ser Val Val Gln Arg Ala Phe Gly Gly Phe Arg Asn Glu Ser Asp Arg
        195                 200                 205

Glu Lys Phe Val His Arg Leu Ser Met Leu Asn Asp Ser Val Leu Trp
    210                 215                 220

Ile Pro Ala Phe Met Val Lys Gly Gly Glu Lys His Val Glu Trp Val
225                 230                 235                 240

Asn Ala Leu Ile Leu Lys Asn Lys Leu Lys Val Arg Thr Ala Tyr Pro
                245                 250                 255

Ser Leu Arg Leu Ile His Ala Val Arg Gly Tyr Trp Leu Thr Asn Lys
            260                 265                 270

Val Pro Ile Lys Arg Pro Ser Thr Gly Leu Leu Met Tyr Thr Leu Ala
        275                 280                 285

Thr Arg Phe Cys Asp Glu Ile His Leu Tyr Gly Phe Trp Pro Phe Pro
```

```
                    290                 295                 300
Lys Asp Leu Asn Gly Lys Ala Val Lys Tyr His Tyr Tyr Asp Asp Leu
305                 310                 315                 320

Lys Tyr Arg Tyr Phe Ser Asn Ala Ser Pro His Arg Met Pro Leu Glu
                325                 330                 335

Phe Lys Thr Leu Asn Val Leu His Asn Arg Gly Ala Leu Lys Leu Thr
            340                 345                 350

Thr Gly Lys Cys Val Lys Gln
        355

<210> SEQ ID NO 39
<211> LENGTH: 1131
<212> TYPE: DNA
<213> ORGANISM: Homo sapiens
<220> FEATURE:
<221> NAME/KEY: CDS
<222> LOCATION: (1)..(1131)

<400> SEQUENCE: 39 atg cgc tac gcg gac ccc tcg gcc aac cgg gat ttg ttg ggg agc cga      48
Met Arg Tyr Ala Asp Pro Ser Ala Asn Arg Asp Leu Leu Gly Ser Arg
1               5                   10                  15 act ttg ctc ttc atc ttc atc tgc gcc ttt gcc ttg gtg acc ttg ctg      96
Thr Leu Leu Phe Ile Phe Ile Cys Ala Phe Ala Leu Val Thr Leu Leu
                20                  25                  30 caa cag atc ctg tat ggc agg aac tac att aag agg tac ttt gaa ttt     144
Gln Gln Ile Leu Tyr Gly Arg Asn Tyr Ile Lys Arg Tyr Phe Glu Phe
            35                  40                  45 tat gag ggg cct ttt gaa tat aac tcc aca aga tgc ctg gag ctg agg     192
Tyr Glu Gly Pro Phe Glu Tyr Asn Ser Thr Arg Cys Leu Glu Leu Arg
        50                  55                  60 cac gaa ata ttg gaa gtg aag gtg ctg tcc atg gtg aag cag tca gag     240
His Glu Ile Leu Glu Val Lys Val Leu Ser Met Val Lys Gln Ser Glu
65                  70                  75                  80 ctg ttc gac agg tgg aag agc ctc cag atg tgc aaa tgg gcg atg aac     288
Leu Phe Asp Arg Trp Lys Ser Leu Gln Met Cys Lys Trp Ala Met Asn
                85                  90                  95 atc tct gag gcc aac cag ttc aag tct act ctg tcc agg tgc tgc aac     336
Ile Ser Glu Ala Asn Gln Phe Lys Ser Thr Leu Ser Arg Cys Cys Asn
                100                 105                 110 gcc cct gcc ttt ctc ttc acc acc cag aag aac act ccc ctg ggg aca     384
Ala Pro Ala Phe Leu Phe Thr Thr Gln Lys Asn Thr Pro Leu Gly Thr
            115                 120                 125 aag ctc aag tat gag gtg gac acc agt ggc atc tac cac atc aac cag     432
Lys Leu Lys Tyr Glu Val Asp Thr Ser Gly Ile Tyr His Ile Asn Gln
        130                 135                 140 gag atc ttc cgc atg ttt ccc aag gac atg ccc tac tac cgg tcc cag     480
Glu Ile Phe Arg Met Phe Pro Lys Asp Met Pro Tyr Tyr Arg Ser Gln
145                 150                 155                 160 ttt aag aag tgt gct gta gtg ggc aac gga ggc atc ttg aag aac agc     528
Phe Lys Lys Cys Ala Val Val Gly Asn Gly Gly Ile Leu Lys Asn Ser
                165                 170                 175 cgc tgc ggg agg gag atc aac agc gcc gac ttc gtc ttc cgg tgc aac     576
Arg Cys Gly Arg Glu Ile Asn Ser Ala Asp Phe Val Phe Arg Cys Asn
                180                 185                 190 ctg ccc ccc atc tca gag aag tac acc atg gat gtg ggg gtg aag acg     624
Leu Pro Pro Ile Ser Glu Lys Tyr Thr Met Asp Val Gly Val Lys Thr
            195                 200                 205 gat gtg gtc act gtg aac ccc agc atc atc aca gag agg ttc cac aag     672
Asp Val Val Thr Val Asn Pro Ser Ile Ile Thr Glu Arg Phe His Lys
```

```
                210                 215                 220
ctg gag aag tgg cgg cgg ccg ttc tat cgc gtg ctg cag gtg tac gag        720
Leu Glu Lys Trp Arg Arg Pro Phe Tyr Arg Val Leu Gln Val Tyr Glu
225                 230                 235                 240 aac gcg tcg gtg ctg ctg cct gcc ttc tac aac acg cgc aac acc gac        768
Asn Ala Ser Val Leu Leu Pro Ala Phe Tyr Asn Thr Arg Asn Thr Asp
                245                 250                 255 gtg tcc atc cgc gtc aag tac gtg ctg gac gac ttc gaa tcg ccg caa        816
Val Ser Ile Arg Val Lys Tyr Val Leu Asp Asp Phe Glu Ser Pro Gln
            260                 265                 270 gct gtc tac tac ttc cat ccg cag tac ctg gtc aac gtg tcg cgc tac        864
Ala Val Tyr Tyr Phe His Pro Gln Tyr Leu Val Asn Val Ser Arg Tyr
        275                 280                 285 tgg ctc agc ctg ggg gtg cgc gcc aag cgc atc agc acc ggc ctc att        912
Trp Leu Ser Leu Gly Val Arg Ala Lys Arg Ile Ser Thr Gly Leu Ile
    290                 295                 300 ctg gtc act gcg gcg ctg gag ctc tgt gag gag gtg cac ctc ttt ggc        960
Leu Val Thr Ala Ala Leu Glu Leu Cys Glu Glu Val His Leu Phe Gly
305                 310                 315                 320 ttc tgg gcc ttc ccc atg aac ccc tcg ggc ctc tac atc act cac cac       1008
Phe Trp Ala Phe Pro Met Asn Pro Ser Gly Leu Tyr Ile Thr His His
                325                 330                 335 tac tat gac aac gtc aag ccg cgt ccc ggc ttc cac gcc atg ccc tct       1056
Tyr Tyr Asp Asn Val Lys Pro Arg Pro Gly Phe His Ala Met Pro Ser
            340                 345                 350 gag atc ttc aac ttc ctg cac ttg cac agc cga ggc atc ctc cgc gtg       1104
Glu Ile Phe Asn Phe Leu His Leu His Ser Arg Gly Ile Leu Arg Val
        355                 360                 365 cac acg ggc acc tgc agc tgc tgc tga                                   1131
His Thr Gly Thr Cys Ser Cys Cys
    370                 375

<210> SEQ ID NO 40
<211> LENGTH: 376
<212> TYPE: PRT
<213> ORGANISM: Homo sapiens

<400> SEQUENCE: 40

Met Arg Tyr Ala Asp Pro Ser Ala Asn Arg Asp Leu Leu Gly Ser Arg
1               5                   10                  15

Thr Leu Leu Phe Ile Phe Ile Cys Ala Phe Ala Leu Val Thr Leu Leu
            20                  25                  30

Gln Gln Ile Leu Tyr Gly Arg Asn Tyr Ile Lys Arg Tyr Phe Glu Phe
        35                  40                  45

Tyr Glu Gly Pro Phe Glu Tyr Asn Ser Thr Arg Cys Leu Glu Leu Arg
    50                  55                  60

His Glu Ile Leu Glu Val Lys Val Leu Ser Met Val Lys Gln Ser Glu
65                  70                  75                  80

Leu Phe Asp Arg Trp Lys Ser Leu Gln Met Cys Lys Trp Ala Met Asn
                85                  90                  95

Ile Ser Glu Ala Asn Gln Phe Lys Ser Thr Leu Ser Arg Cys Cys Asn
            100                 105                 110

Ala Pro Ala Phe Leu Phe Thr Thr Gln Lys Asn Thr Pro Leu Gly Thr
        115                 120                 125

Lys Leu Lys Tyr Glu Val Asp Thr Ser Gly Ile Tyr His Ile Asn Gln
    130                 135                 140

Glu Ile Phe Arg Met Phe Pro Lys Asp Met Pro Tyr Tyr Arg Ser Gln
145                 150                 155                 160
```

```
Phe Lys Lys Cys Ala Val Val Gly Asn Gly Ile Leu Lys Asn Ser
                165                 170                 175

Arg Cys Gly Arg Glu Ile Asn Ser Ala Asp Phe Val Phe Arg Cys Asn
            180                 185                 190

Leu Pro Pro Ile Ser Glu Lys Tyr Thr Met Asp Val Gly Val Lys Thr
                195                 200                 205

Asp Val Val Thr Val Asn Pro Ser Ile Ile Thr Glu Arg Phe His Lys
            210                 215                 220

Leu Glu Lys Trp Arg Arg Pro Phe Tyr Arg Val Leu Gln Val Tyr Glu
225                 230                 235                 240

Asn Ala Ser Val Leu Leu Pro Ala Phe Tyr Asn Thr Arg Asn Thr Asp
                245                 250                 255

Val Ser Ile Arg Val Lys Tyr Val Leu Asp Asp Phe Glu Ser Pro Gln
            260                 265                 270

Ala Val Tyr Tyr Phe His Pro Gln Tyr Leu Val Asn Val Ser Arg Tyr
        275                 280                 285

Trp Leu Ser Leu Gly Val Arg Ala Lys Arg Ile Ser Thr Gly Leu Ile
    290                 295                 300

Leu Val Thr Ala Ala Leu Glu Leu Cys Glu Glu Val His Leu Phe Gly
305                 310                 315                 320

Phe Trp Ala Phe Pro Met Asn Pro Ser Gly Leu Tyr Ile Thr His His
                325                 330                 335

Tyr Tyr Asp Asn Val Lys Pro Arg Pro Gly Phe His Ala Met Pro Ser
            340                 345                 350

Glu Ile Phe Asn Phe Leu His Leu His Ser Arg Gly Ile Leu Arg Val
        355                 360                 365

His Thr Gly Thr Cys Ser Cys Cys
    370                 375

<210> SEQ ID NO 41
<211> LENGTH: 1197
<212> TYPE: DNA
<213> ORGANISM: Homo sapiens
<220> FEATURE:
<221> NAME/KEY: CDS
<222> LOCATION: (1)..(1197)

<400> SEQUENCE: 41 atg cgg ccg ggg ggc gca ctg ctc gcc ctg ctc gcc agc ctg ctg ctg      48
Met Arg Pro Gly Gly Ala Leu Leu Ala Leu Leu Ala Ser Leu Leu Leu
1               5                   10                  15 ctg ctg ctg ctg cgc ctg ctc tgg tgc ccg gca gac gcg ccc ggc cgc      96
Leu Leu Leu Leu Arg Leu Leu Trp Cys Pro Ala Asp Ala Pro Gly Arg
            20                  25                  30 gcc agg att ctg gtg gag gaa agc agg gag gcc acc cac ggc acc ccc     144
Ala Arg Ile Leu Val Glu Glu Ser Arg Glu Ala Thr His Gly Thr Pro
        35                  40                  45 gca gcg ctg agg acg ctc cgg agc ccg gcg acc gcg gta ccg cgc gcc     192
Ala Ala Leu Arg Thr Leu Arg Ser Pro Ala Thr Ala Val Pro Arg Ala
    50                  55                  60 act aac agc aca tat ctg aat gag aag tcg ctc caa ctg acg gag aaa     240
Thr Asn Ser Thr Tyr Leu Asn Glu Lys Ser Leu Gln Leu Thr Glu Lys
65                  70                  75                  80 tgc aaa aat ctg caa tat ggc att gag tct ttc tct aac aaa acg aaa     288
Cys Lys Asn Leu Gln Tyr Gly Ile Glu Ser Phe Ser Asn Lys Thr Lys
                85                  90                  95 ggg tat tca gag aac gac tac ctt cag att atc aca gat ata cag agt     336
```

-continued

```
            Gly Tyr Ser Glu Asn Asp Tyr Leu Gln Ile Ile Thr Asp Ile Gln Ser
                            100                 105                 110 tgt cca tgg aaa cgg caa gca gaa gaa tat gca aat ttt aga gcc aaa       384
Cys Pro Trp Lys Arg Gln Ala Glu Glu Tyr Ala Asn Phe Arg Ala Lys
            115                 120                 125 ctt gct tcc tgc tgt gat gct gtt caa aac ttt gtt gtt tct cag aat       432
Leu Ala Ser Cys Cys Asp Ala Val Gln Asn Phe Val Val Ser Gln Asn
        130                 135                 140 aac act cca gtt ggg act aat atg agt tac gag gtg gaa agc aaa aaa       480
Asn Thr Pro Val Gly Thr Asn Met Ser Tyr Glu Val Glu Ser Lys Lys
145                 150                 155                 160 gaa atc cca att aag aag aac att ttt cat atg ttt cca gtg tcc cag       528
Glu Ile Pro Ile Lys Lys Asn Ile Phe His Met Phe Pro Val Ser Gln
                165                 170                 175 cct ttt gtg gac tac cct tat aat cag tgt gca gtg gtc gga aat ggg       576
Pro Phe Val Asp Tyr Pro Tyr Asn Gln Cys Ala Val Val Gly Asn Gly
            180                 185                 190 gga att ctg aat aag tct ctc tgt gga act gaa ata gat aaa tcc gac       624
Gly Ile Leu Asn Lys Ser Leu Cys Gly Thr Glu Ile Asp Lys Ser Asp
        195                 200                 205 ttc gtt ttt agg tgt aac cta ccc cca acc aca gga gat gtt agt aaa       672
Phe Val Phe Arg Cys Asn Leu Pro Pro Thr Thr Gly Asp Val Ser Lys
210                 215                 220 gat gtt ggc agt aaa aca aat ctt gtg act ata aat cca agc atc ata       720
Asp Val Gly Ser Lys Thr Asn Leu Val Thr Ile Asn Pro Ser Ile Ile
225                 230                 235                 240 act ctg aaa tat ggg aac tta aag gaa aaa aaa gcc cta ttt ctg gag       768
Thr Leu Lys Tyr Gly Asn Leu Lys Glu Lys Lys Ala Leu Phe Leu Glu
                245                 250                 255 gac att gca acc tat gga gat gca ttt ttt ctt ctg cca gca ttt tcc       816
Asp Ile Ala Thr Tyr Gly Asp Ala Phe Phe Leu Leu Pro Ala Phe Ser
            260                 265                 270 ttc agg gcc aac acg ggt acc tct ttc aaa gta tac tac acg ctc gaa       864
Phe Arg Ala Asn Thr Gly Thr Ser Phe Lys Val Tyr Tyr Thr Leu Glu
        275                 280                 285 gag tct aaa gca aga caa aag gtt cta ttt ttc cat ccc aag tac ctg       912
Glu Ser Lys Ala Arg Gln Lys Val Leu Phe Phe His Pro Lys Tyr Leu
290                 295                 300 aaa gat ctg gcc ctt ttc tgg aga act aaa ggt gtg act gca tac cgc       960
Lys Asp Leu Ala Leu Phe Trp Arg Thr Lys Gly Val Thr Ala Tyr Arg
305                 310                 315                 320 ttg tcc acc ggc ttg atg atc aca agt gtt gca gtg gaa ctg tgt aaa      1008
Leu Ser Thr Gly Leu Met Ile Thr Ser Val Ala Val Glu Leu Cys Lys
                325                 330                 335 aat gtg aag ctg tat gga ttc tgg ccc ttc tct aaa act gta gaa gac      1056
Asn Val Lys Leu Tyr Gly Phe Trp Pro Phe Ser Lys Thr Val Glu Asp
            340                 345                 350 ata cct gtc agc cat cac tat tat gac aac aag cta cct aaa cat ggt      1104
Ile Pro Val Ser His His Tyr Tyr Asp Asn Lys Leu Pro Lys His Gly
        355                 360                 365 ttc cat cag atg ccc aaa gaa tac agc cag atc ctc caa ctt cac atg      1152
Phe His Gln Met Pro Lys Glu Tyr Ser Gln Ile Leu Gln Leu His Met
370                 375                 380 aaa gga atc ctc aaa ctg caa ttt agc aaa tgt gaa gtc gcc taa          1197
Lys Gly Ile Leu Lys Leu Gln Phe Ser Lys Cys Glu Val Ala
385                 390                 395

<210> SEQ ID NO 42
<211> LENGTH: 398
<212> TYPE: PRT
```

<213> ORGANISM: Homo sapiens

<400> SEQUENCE: 42

```
Met Arg Pro Gly Gly Ala Leu Leu Ala Leu Leu Ala Ser Leu Leu Leu
1               5                   10                  15

Leu Leu Leu Leu Arg Leu Leu Trp Cys Pro Ala Asp Ala Pro Gly Arg
            20                  25                  30

Ala Arg Ile Leu Val Glu Glu Ser Arg Glu Ala Thr His Gly Thr Pro
        35                  40                  45

Ala Ala Leu Arg Thr Leu Arg Ser Pro Ala Thr Ala Val Pro Arg Ala
    50                  55                  60

Thr Asn Ser Thr Tyr Leu Asn Glu Lys Ser Leu Gln Leu Thr Glu Lys
65                  70                  75                  80

Cys Lys Asn Leu Gln Tyr Gly Ile Glu Ser Phe Ser Asn Lys Thr Lys
                85                  90                  95

Gly Tyr Ser Glu Asn Asp Tyr Leu Gln Ile Ile Thr Asp Ile Gln Ser
            100                 105                 110

Cys Pro Trp Lys Arg Gln Ala Glu Glu Tyr Ala Asn Phe Arg Ala Lys
        115                 120                 125

Leu Ala Ser Cys Cys Asp Ala Val Gln Asn Phe Val Val Ser Gln Asn
    130                 135                 140

Asn Thr Pro Val Gly Thr Asn Met Ser Tyr Glu Val Glu Ser Lys Lys
145                 150                 155                 160

Glu Ile Pro Ile Lys Lys Asn Ile Phe His Met Phe Pro Val Ser Gln
                165                 170                 175

Pro Phe Val Asp Tyr Pro Tyr Asn Gln Cys Ala Val Val Gly Asn Gly
            180                 185                 190

Gly Ile Leu Asn Lys Ser Leu Cys Gly Thr Glu Ile Asp Lys Ser Asp
        195                 200                 205

Phe Val Phe Arg Cys Asn Leu Pro Pro Thr Thr Gly Asp Val Ser Lys
    210                 215                 220

Asp Val Gly Ser Lys Thr Asn Leu Val Thr Ile Asn Pro Ser Ile Ile
225                 230                 235                 240

Thr Leu Lys Tyr Gly Asn Leu Lys Glu Lys Lys Ala Leu Phe Leu Glu
                245                 250                 255

Asp Ile Ala Thr Tyr Gly Asp Ala Phe Phe Leu Leu Pro Ala Phe Ser
            260                 265                 270

Phe Arg Ala Asn Thr Gly Thr Ser Phe Lys Val Tyr Tyr Thr Leu Glu
        275                 280                 285

Glu Ser Lys Ala Arg Gln Lys Val Leu Phe Phe His Pro Lys Tyr Leu
    290                 295                 300

Lys Asp Leu Ala Leu Phe Trp Arg Thr Lys Gly Val Thr Ala Tyr Arg
305                 310                 315                 320

Leu Ser Thr Gly Leu Met Ile Thr Ser Val Ala Val Glu Leu Cys Lys
                325                 330                 335

Asn Val Lys Leu Tyr Gly Phe Trp Pro Phe Ser Lys Thr Val Glu Asp
            340                 345                 350

Ile Pro Val Ser His His Tyr Tyr Asp Asn Lys Leu Pro Lys His Gly
        355                 360                 365

Phe His Gln Met Pro Lys Glu Tyr Ser Gln Ile Leu Gln Leu His Met
    370                 375                 380

Lys Gly Ile Leu Lys Leu Gln Phe Ser Lys Cys Glu Val Ala
385                 390                 395
```

-continued

```
<210> SEQ ID NO 43
<211> LENGTH: 951
<212> TYPE: DNA
<213> ORGANISM: Artificial sequence
<220> FEATURE:
<223> OTHER INFORMATION: Nucleotides 268-1218 of SEQ ID NO : 1
<220> FEATURE:
<221> NAME/KEY: CDS
<222> LOCATION: (1)..(951)

<400> SEQUENCE: 43 gag gcc tcc ttc cag gtg tgg aac aag gac agc tct tcc aaa aac ctt      48
Glu Ala Ser Phe Gln Val Trp Asn Lys Asp Ser Ser Ser Lys Asn Leu
1               5                   10                  15 atc cct agg ctg caa aag atc tgg aag aat tac cta agc atg aac aag      96
Ile Pro Arg Leu Gln Lys Ile Trp Lys Asn Tyr Leu Ser Met Asn Lys
            20                  25                  30 tac aaa gtg tcc tac aag ggg cca gga cca ggc atc aag ttc agt gca     144
Tyr Lys Val Ser Tyr Lys Gly Pro Gly Pro Gly Ile Lys Phe Ser Ala
        35                  40                  45 gag gcc ctg cgc tgc cac ctc cgg gac cat gtg aat gta tcc atg gta     192
Glu Ala Leu Arg Cys His Leu Arg Asp His Val Asn Val Ser Met Val
    50                  55                  60 gag gtc aca gat ttt ccc ttc aat acc tct gaa tgg gag ggt tat ctg     240
Glu Val Thr Asp Phe Pro Phe Asn Thr Ser Glu Trp Glu Gly Tyr Leu
65                  70                  75                  80 ccc aag gag agc att agg acc aag gct ggg cct tgg ggc agg tgt gct     288
Pro Lys Glu Ser Ile Arg Thr Lys Ala Gly Pro Trp Gly Arg Cys Ala
                85                  90                  95 gtt gtg tcg tca gcg gga tct ctg aag tcc tcc caa cta ggc aga gaa     336
Val Val Ser Ser Ala Gly Ser Leu Lys Ser Ser Gln Leu Gly Arg Glu
            100                 105                 110 atc gat gat cat gac gca gtc ctg agg ttt aat ggg gca ccc aca gcc     384
Ile Asp Asp His Asp Ala Val Leu Arg Phe Asn Gly Ala Pro Thr Ala
        115                 120                 125 aac ttc caa caa gat gtg ggc aca aaa act acc att cgc ctg atg aac     432
Asn Phe Gln Gln Asp Val Gly Thr Lys Thr Thr Ile Arg Leu Met Asn
    130                 135                 140 tct cag ttg gtt acc aca gag aag cgc ttc ctc aaa gac agt ttg tac     480
Ser Gln Leu Val Thr Thr Glu Lys Arg Phe Leu Lys Asp Ser Leu Tyr
145                 150                 155                 160 aat gaa gga atc cta att gta tgg gac cca tct gta tac cac tca gat     528
Asn Glu Gly Ile Leu Ile Val Trp Asp Pro Ser Val Tyr His Ser Asp
                165                 170                 175 atc cca aag tgg tac cag aat ccg gat tat aat ttc ttt aac aac tac     576
Ile Pro Lys Trp Tyr Gln Asn Pro Asp Tyr Asn Phe Phe Asn Asn Tyr
            180                 185                 190 aag act tat cgt aag ctg cac ccc aat cag ccc ttt tac atc ctc aag     624
Lys Thr Tyr Arg Lys Leu His Pro Asn Gln Pro Phe Tyr Ile Leu Lys
        195                 200                 205 ccc cag atg cct tgg gag cta tgg gac att ctt caa gaa atc tcc cca     672
Pro Gln Met Pro Trp Glu Leu Trp Asp Ile Leu Gln Glu Ile Ser Pro
    210                 215                 220 gaa gag att cag cca aac ccc cca tcc tct ggg atg ctt ggt atc atc     720
Glu Glu Ile Gln Pro Asn Pro Pro Ser Ser Gly Met Leu Gly Ile Ile
225                 230                 235                 240 atc atg atg acg ctg tgt gac cag gtg gat att tat gag ttc ctc cca     768
Ile Met Met Thr Leu Cys Asp Gln Val Asp Ile Tyr Glu Phe Leu Pro
                245                 250                 255 tcc aag cgc aag act gac gtg tgc tac tac tac cag aag ttc ttc gat     816
Ser Lys Arg Lys Thr Asp Val Cys Tyr Tyr Tyr Gln Lys Phe Phe Asp
```

```
                    260                 265                 270
agt gcc tgc acg atg ggt gcc tac cac ccg ctg ctc tat gag aag aat      864
Ser Ala Cys Thr Met Gly Ala Tyr His Pro Leu Leu Tyr Glu Lys Asn
        275                 280                 285 ttg gtg aag cat ctc aac cag ggc aca gat gag gac atc tac ctg ctt      912
Leu Val Lys His Leu Asn Gln Gly Thr Asp Glu Asp Ile Tyr Leu Leu
    290                 295                 300 gga aaa gcc aca ctg cct ggc ttc cgg acc att cac tgc                  951
Gly Lys Ala Thr Leu Pro Gly Phe Arg Thr Ile His Cys
305                 310                 315
```

<210> SEQ ID NO 44
<211> LENGTH: 317
<212> TYPE: PRT
<213> ORGANISM: Artificial sequence
<220> FEATURE:
<223> OTHER INFORMATION: Synthetic Construct

<400> SEQUENCE: 44

```
Glu Ala Ser Phe Gln Val Trp Asn Lys Asp Ser Ser Lys Asn Leu
1               5                   10                  15

Ile Pro Arg Leu Gln Lys Ile Trp Lys Asn Tyr Leu Ser Met Asn Lys
            20                  25                  30

Tyr Lys Val Ser Tyr Lys Gly Pro Gly Pro Gly Ile Lys Phe Ser Ala
                35                  40                  45

Glu Ala Leu Arg Cys His Leu Arg Asp His Val Asn Val Ser Met Val
    50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
                85                  90                  95

Val Val Ser Ser Ala Gly Ser Leu Lys Ser Ser Gln Leu Gly Arg Glu
            100                 105                 110

Ile Asp Asp His Asp Ala Val Leu Arg Phe Asn Gly Ala Pro Thr Ala
        115                 120                 125

Asn Phe Gln Gln Asp Val Gly Thr Lys Thr Thr Ile Arg Leu Met Asn
130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
                165                 170                 175

Ile Pro Lys Trp Tyr Gln Asn Pro Asp Tyr Asn Phe Phe Asn Asn Tyr
            180                 185                 190

Lys Thr Tyr Arg Lys Leu His Pro Asn Gln Pro Phe Tyr Ile Leu Lys
        195                 200                 205

Pro Gln Met Pro Trp Glu Leu Trp Asp Ile Leu Gln Glu Ile Ser Pro
    210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
                245                 250                 255

Ser Lys Arg Lys Thr Asp Val Cys Tyr Tyr Tyr Gln Lys Phe Phe Asp
            260                 265                 270

Ser Ala Cys Thr Met Gly Ala Tyr His Pro Leu Leu Tyr Glu Lys Asn
        275                 280                 285

Leu Val Lys His Leu Asn Gln Gly Thr Asp Glu Asp Ile Tyr Leu Leu
```

```
                290              295               300
Gly Lys Ala Thr Leu Pro Gly Phe Arg Thr Ile His Cys
305              310               315
```

<210> SEQ ID NO 45
<211> LENGTH: 27
<212> TYPE: DNA
<213> ORGANISM: Artificial sequence
<220> FEATURE:
<223> OTHER INFORMATION: Nucleotides 1-27 of SEQ ID NO : 1
<220> FEATURE:
<221> NAME/KEY: CDS
<222> LOCATION: (1)..(27)

<400> SEQUENCE: 45

```
atg att cac acc aac ctg aag aaa aag                          27
Met Ile His Thr Asn Leu Lys Lys Lys
1               5
```

<210> SEQ ID NO 46
<211> LENGTH: 9
<212> TYPE: PRT
<213> ORGANISM: Artificial sequence
<220> FEATURE:
<223> OTHER INFORMATION: Synthetic Construct

<400> SEQUENCE: 46

```
Met Ile His Thr Asn Leu Lys Lys Lys
1               5
```

<210> SEQ ID NO 47
<211> LENGTH: 30
<212> TYPE: DNA
<213> ORGANISM: Artificial sequence
<220> FEATURE:
<223> OTHER INFORMATION: Nucleotides 1-30 of SEQ ID NO : 3
<220> FEATURE:
<221> NAME/KEY: CDS
<222> LOCATION: (1)..(30)

<400> SEQUENCE: 47

```
atg aaa cca cac ttg aag caa tgg aga caa                      30
Met Lys Pro His Leu Lys Gln Trp Arg Gln
1               5                   10
```

<210> SEQ ID NO 48
<211> LENGTH: 10
<212> TYPE: PRT
<213> ORGANISM: Artificial sequence
<220> FEATURE:
<223> OTHER INFORMATION: Synthetic Construct

<400> SEQUENCE: 48

```
Met Lys Pro His Leu Lys Gln Trp Arg Gln
1               5                   10
```

<210> SEQ ID NO 49
<211> LENGTH: 42
<212> TYPE: DNA
<213> ORGANISM: Artificial sequence
<220> FEATURE:
<223> OTHER INFORMATION: Nucleotides 1-42 of SEQ ID NO : 5
<220> FEATURE:
<221> NAME/KEY: CDS
<222> LOCATION: (1)..(42)

<400> SEQUENCE: 49

```
atg agg tcc tgc ctg tgg aga tgc agg cac ctg agc caa ggc       42
```

```
Met Arg Ser Cys Leu Trp Arg Cys Arg His Leu Ser Gln Gly
1               5                   10
```

<210> SEQ ID NO 50
<211> LENGTH: 14
<212> TYPE: PRT
<213> ORGANISM: Artificial sequence
<220> FEATURE:
<223> OTHER INFORMATION: Synthetic Construct

<400> SEQUENCE: 50

```
Met Arg Ser Cys Leu Trp Arg Cys Arg His Leu Ser Gln Gly
1               5                   10
```

<210> SEQ ID NO 51
<211> LENGTH: 21
<212> TYPE: DNA
<213> ORGANISM: Artificial sequence
<220> FEATURE:
<223> OTHER INFORMATION: Nucleotides 1-21 of SEQ ID NO : 7
<220> FEATURE:
<221> NAME/KEY: CDS
<222> LOCATION: (1)..(21)

<400> SEQUENCE: 51

```
atg ggg ctc ccg cgc ggg tcg                                      21
Met Gly Leu Pro Arg Gly Ser
1               5
```

<210> SEQ ID NO 52
<211> LENGTH: 7
<212> TYPE: PRT
<213> ORGANISM: Artificial sequence
<220> FEATURE:
<223> OTHER INFORMATION: Synthetic Construct

<400> SEQUENCE: 52

```
Met Gly Leu Pro Arg Gly Ser
1               5
```

<210> SEQ ID NO 53
<211> LENGTH: 24
<212> TYPE: DNA
<213> ORGANISM: Artificial
<220> FEATURE:
<223> OTHER INFORMATION: Nucleotides 1-24 of SEQ ID NO : 9
<220> FEATURE:
<221> NAME/KEY: CDS
<222> LOCATION: (1)..(24)

<400> SEQUENCE: 53

```
atg gcc tgc atc ctg aag aga aag                                  24
Met Ala Cys Ile Leu Lys Arg Lys
1               5
```

<210> SEQ ID NO 54
<211> LENGTH: 8
<212> TYPE: PRT
<213> ORGANISM: Artificial
<220> FEATURE:
<223> OTHER INFORMATION: Synthetic Construct

<400> SEQUENCE: 54

```
Met Ala Cys Ile Leu Lys Arg Lys
1               5
```

<210> SEQ ID NO 55
<211> LENGTH: 18

```
<212> TYPE: DNA
<213> ORGANISM: Artificial
<220> FEATURE:
<223> OTHER INFORMATION: Nucleotides 1-18 of SEQ ID NO : 11
<220> FEATURE:
<221> NAME/KEY: CDS
<222> LOCATION: (1)..(18)

<400> SEQUENCE: 55 atg aag gct ccg ggt cgg                                              18
Met Lys Ala Pro Gly Arg
1               5

<210> SEQ ID NO 56
<211> LENGTH: 6
<212> TYPE: PRT
<213> ORGANISM: Artificial
<220> FEATURE:
<223> OTHER INFORMATION: Synthetic Construct

<400> SEQUENCE: 56

Met Lys Ala Pro Gly Arg
1               5

<210> SEQ ID NO 57
<211> LENGTH: 24
<212> TYPE: DNA
<213> ORGANISM: Artificial
<220> FEATURE:
<223> OTHER INFORMATION: Nucleotides 1-24 of SEQ ID NO : 13
<220> FEATURE:
<221> NAME/KEY: CDS
<222> LOCATION: (1)..(21)

<400> SEQUENCE: 57 atg aag acc ctg atg cgc cat ggt                                      24
Met Lys Thr Leu Met Arg His
1               5

<210> SEQ ID NO 58
<211> LENGTH: 7
<212> TYPE: PRT
<213> ORGANISM: Artificial
<220> FEATURE:
<223> OTHER INFORMATION: Synthetic Construct

<400> SEQUENCE: 58

Met Lys Thr Leu Met Arg His
1               5

<210> SEQ ID NO 59
<211> LENGTH: 129
<212> TYPE: DNA
<213> ORGANISM: Artificial
<220> FEATURE:
<223> OTHER INFORMATION: Nucleotides 1-129 of SED ID NO : 15
<220> FEATURE:
<221> NAME/KEY: CDS
<222> LOCATION: (1)..(129)

<400> SEQUENCE: 59 atg gct tgc tcg agg ccc ccc agc cag tgt gaa ccc aca tcc ctg ccc      48
Met Ala Cys Ser Arg Pro Pro Ser Gln Cys Glu Pro Thr Ser Leu Pro
1               5                   10                  15 cca ggg cca cct gca gga cgc cga cac cta ccc ctc agc aga cgc cgg      96
Pro Gly Pro Pro Ala Gly Arg Arg His Leu Pro Leu Ser Arg Arg Arg
            20                  25                  30 aga gaa atg agt agc aac aaa gag cag cgg tca                          129
```

Arg Glu Met Ser Ser Asn Lys Glu Gln Arg Ser
        35                  40

<210> SEQ ID NO 60
<211> LENGTH: 43
<212> TYPE: PRT
<213> ORGANISM: Artificial
<220> FEATURE:
<223> OTHER INFORMATION: Synthetic Construct

<400> SEQUENCE: 60

Met Ala Cys Ser Arg Pro Pro Ser Gln Cys Glu Pro Thr Ser Leu Pro
1               5                   10                  15

Pro Gly Pro Pro Ala Gly Arg Arg His Leu Pro Leu Ser Arg Arg Arg
            20                  25                  30

Arg Glu Met Ser Ser Asn Lys Glu Gln Arg Ser
        35                  40

<210> SEQ ID NO 61
<211> LENGTH: 39
<212> TYPE: DNA
<213> ORGANISM: Artificial
<220> FEATURE:
<223> OTHER INFORMATION: Nucleotides 1-39 of SEQ ID NO : 17
<220> FEATURE:
<221> NAME/KEY: CDS
<222> LOCATION: (1)..(30)

<400> SEQUENCE: 61 atg gtg acc ctg cgg aag agg acc ctg aaa gtgctcacc          39
Met Val Thr Leu Arg Lys Arg Thr Leu Lys
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic Construct

<400> SEQUENCE: 62

Met Val Thr Leu Arg Lys Arg Thr Leu Lys
1               5                   10

<210> SEQ ID NO 63
<211> LENGTH: 18
<212> TYPE: DNA
<213> ORGANISM: Artificial
<220> FEATURE:
<223> OTHER INFORMATION: Nucleotides 1-18 of SEQ ID NO : 19
<220> FEATURE:
<221> NAME/KEY: CDS
<222> LOCATION: (1)..(18)

<400> SEQUENCE: 63 atg aag tgc tcc ctg cgg                                    18
Met Lys Cys Ser Leu Arg
1               5

<210> SEQ ID NO 64
<211> LENGTH: 6
<212> TYPE: PRT
<213> ORGANISM: Artificial
<220> FEATURE:
<223> OTHER INFORMATION: Synthetic Construct

<400> SEQUENCE: 64

```
Met Lys Cys Ser Leu Arg
1               5

<210> SEQ ID NO 65
<211> LENGTH: 24
<212> TYPE: DNA
<213> ORGANISM: Artificial
<220> FEATURE:
<223> OTHER INFORMATION: Nucleotides 1-24 of SEQ ID NO : 21
<220> FEATURE:
<221> NAME/KEY: CDS
<222> LOCATION: (1)..(24)

<400> SEQUENCE: 65 atg gga ctc ttg gta ttt gtg cgc                                  24
Met Gly Leu Leu Val Phe Val Arg
1               5

<210> SEQ ID NO 66
<211> LENGTH: 8
<212> TYPE: PRT
<213> ORGANISM: Artificial
<220> FEATURE:
<223> OTHER INFORMATION: Synthetic Construct

<400> SEQUENCE: 66

Met Gly Leu Leu Val Phe Val Arg
1               5

<210> SEQ ID NO 67
<211> LENGTH: 24
<212> TYPE: DNA
<213> ORGANISM: Artificial
<220> FEATURE:
<223> OTHER INFORMATION: Nucleotides 1-24 of SEQ ID NO : 23
<220> FEATURE:
<221> NAME/KEY: CDS
<222> LOCATION: (1)..(24)

<400> SEQUENCE: 67 atg gtc agc aag tcc cgc tgg aag                                  24
Met Val Ser Lys Ser Arg Trp Lys
1               5

<210> SEQ ID NO 68
<211> LENGTH: 8
<212> TYPE: PRT
<213> ORGANISM: Artificial
<220> FEATURE:
<223> OTHER INFORMATION: Synthetic Construct

<400> SEQUENCE: 68

Met Val Ser Lys Ser Arg Trp Lys
1               5

<210> SEQ ID NO 69
<211> LENGTH: 15
<212> TYPE: DNA
<213> ORGANISM: Artificial
<220> FEATURE:
<223> OTHER INFORMATION: Nucleotides 1-15 of SEQ ID NO : 25
<220> FEATURE:
<221> NAME/KEY: CDS
<222> LOCATION: (1)..(15)

<400> SEQUENCE: 69 atg aga agg ccc agc                                              15
Met Arg Arg Pro Ser
1               5
```

```
<210> SEQ ID NO 70
<211> LENGTH: 5
<212> TYPE: PRT
<213> ORGANISM: Artificial
<220> FEATURE:
<223> OTHER INFORMATION: Synthetic Construct

<400> SEQUENCE: 70

Met Arg Arg Pro Ser
1               5

<210> SEQ ID NO 71
<211> LENGTH: 12
<212> TYPE: DNA
<213> ORGANISM: Artificial
<220> FEATURE:
<223> OTHER INFORMATION: Nucleotides 1-12 of SEQ ID NO : 27
<220> FEATURE:
<221> NAME/KEY: CDS
<222> LOCATION: (1)..(12)

<400> SEQUENCE: 71 atg aga ggg tat                                              12
Met Arg Gly Tyr
1

<210> SEQ ID NO 72
<211> LENGTH: 4
<212> TYPE: PRT
<213> ORGANISM: Artificial
<220> FEATURE:
<223> OTHER INFORMATION: Synthetic Construct

<400> SEQUENCE: 72

Met Arg Gly Tyr
1

<210> SEQ ID NO 73
<211> LENGTH: 24
<212> TYPE: DNA
<213> ORGANISM: Artificial
<220> FEATURE:
<223> OTHER INFORMATION: Nucleotides 1-24 of SEQ ID NO : 29
<220> FEATURE:
<221> NAME/KEY: CDS
<222> LOCATION: (1)..(24)

<400> SEQUENCE: 73 atg gga ctc ttg gta ttt gta cgc                              24
Met Gly Leu Leu Val Phe Val Arg
1               5

<210> SEQ ID NO 74
<211> LENGTH: 8
<212> TYPE: PRT
<213> ORGANISM: Artificial
<220> FEATURE:
<223> OTHER INFORMATION: Synthetic Construct

<400> SEQUENCE: 74

Met Gly Leu Leu Val Phe Val Arg
1               5

<210> SEQ ID NO 75
<211> LENGTH: 87
<212> TYPE: DNA
<213> ORGANISM: Artificial
```

```
<220> FEATURE:
<223> OTHER INFORMATION: Nucleotides 1-87 of SEQ ID NO : 31
<220> FEATURE:
<221> NAME/KEY: CDS
<222> LOCATION: (1)..(87)

<400> SEQUENCE: 75 atg agc ccc tgc ggg cgg gcc cgg cga caa acg tcc aga ggg gcc atg        48
Met Ser Pro Cys Gly Arg Ala Arg Arg Gln Thr Ser Arg Gly Ala Met
1               5                   10                  15 gct gta ctg gcg tgg aag ttc ccg cgg acc cgg ctg ccc                    87
Ala Val Leu Ala Trp Lys Phe Pro Arg Thr Arg Leu Pro
            20                  25

<210> SEQ ID NO 76
<211> LENGTH: 29
<212> TYPE: PRT
<213> ORGANISM: Artificial
<220> FEATURE:
<223> OTHER INFORMATION: Synthetic Construct

<400> SEQUENCE: 76

Met Ser Pro Cys Gly Arg Ala Arg Arg Gln Thr Ser Arg Gly Ala Met
1               5                   10                  15

Ala Val Leu Ala Trp Lys Phe Pro Arg Thr Arg Leu Pro
            20                  25

<210> SEQ ID NO 77
<211> LENGTH: 18
<212> TYPE: DNA
<213> ORGANISM: Artificial
<220> FEATURE:
<223> OTHER INFORMATION: Nucleotides 1-18 of SEQ ID NO : 33
<220> FEATURE:
<221> NAME/KEY: CDS
<222> LOCATION: (1)..(18)

<400> SEQUENCE: 77 atg cag ctg cag ttc cgg                                                18
Met Gln Leu Gln Phe Arg
1               5

<210> SEQ ID NO 78
<211> LENGTH: 6
<212> TYPE: PRT
<213> ORGANISM: Artificial
<220> FEATURE:
<223> OTHER INFORMATION: Synthetic Construct

<400> SEQUENCE: 78

Met Gln Leu Gln Phe Arg
1               5

<210> SEQ ID NO 79
<211> LENGTH: 27
<212> TYPE: DNA
<213> ORGANISM: Artificial
<220> FEATURE:
<223> OTHER INFORMATION: Nucleotides 1-27 of SEQ ID NO : 35
<220> FEATURE:
<221> NAME/KEY: CDS
<222> LOCATION: (1)..(27)

<400> SEQUENCE: 79 atg aga aac tgc aaa atg gcc cgg gtc                                    27
Met Arg Asn Cys Lys Met Ala Arg Val
1               5
```

```
<210> SEQ ID NO 80
<211> LENGTH: 9
<212> TYPE: PRT
<213> ORGANISM: Artificial
<220> FEATURE:
<223> OTHER INFORMATION: Synthetic Construct

<400> SEQUENCE: 80

Met Arg Asn Cys Lys Met Ala Arg Val
1               5

<210> SEQ ID NO 81
<211> LENGTH: 21
<212> TYPE: DNA
<213> ORGANISM: Artificial
<220> FEATURE:
<223> OTHER INFORMATION: Nucleotides 1-21 of SEQ ID NO : 37
<220> FEATURE:
<221> NAME/KEY: CDS
<222> LOCATION: (1)..(21)

<400> SEQUENCE: 81 atg cgc tcc att agg aag agg                                    21
Met Arg Ser Ile Arg Lys Arg
1               5

<210> SEQ ID NO 82
<211> LENGTH: 7
<212> TYPE: PRT
<213> ORGANISM: Artificial
<220> FEATURE:
<223> OTHER INFORMATION: Synthetic Construct

<400> SEQUENCE: 82

Met Arg Ser Ile Arg Lys Arg
1               5

<210> SEQ ID NO 83
<211> LENGTH: 51
<212> TYPE: DNA
<213> ORGANISM: Artificial
<220> FEATURE:
<223> OTHER INFORMATION: Nucleotides 1-51 of SEQ ID NO : 39
<220> FEATURE:
<221> NAME/KEY: CDS
<222> LOCATION: (1)..(51)

<400> SEQUENCE: 83 atg cgc tac gcg gac ccc tcg gcc aac cgg gat ttg ttg ggg agc cga    48
Met Arg Tyr Ala Asp Pro Ser Ala Asn Arg Asp Leu Leu Gly Ser Arg
1               5                   10                  15 act                                                                51
Thr

<210> SEQ ID NO 84
<211> LENGTH: 17
<212> TYPE: PRT
<213> ORGANISM: Artificial
<220> FEATURE:
<223> OTHER INFORMATION: Synthetic Construct

<400> SEQUENCE: 84

Met Arg Tyr Ala Asp Pro Ser Ala Asn Arg Asp Leu Leu Gly Ser Arg
1               5                   10                  15

Thr
```

```
<210> SEQ ID NO 85
<211> LENGTH: 9
<212> TYPE: DNA
<213> ORGANISM: Artificial
<220> FEATURE:
<223> OTHER INFORMATION: Nucleotides 1-9 of SEQ ID NO : 41
<220> FEATURE:
<221> NAME/KEY: CDS
<222> LOCATION: (1)..(9)

<400> SEQUENCE: 85 atg cgg ccg                                                              9
Met Arg Pro
1

<210> SEQ ID NO 86
<211> LENGTH: 3
<212> TYPE: PRT
<213> ORGANISM: Artificial
<220> FEATURE:
<223> OTHER INFORMATION: amino acid 1-3 of SEQ ID NO : 42

<400> SEQUENCE: 86

Met Arg Pro
1

<210> SEQ ID NO 87
<211> LENGTH: 51
<212> TYPE: DNA
<213> ORGANISM: Artificial
<220> FEATURE:
<223> OTHER INFORMATION: Nucleotides 28-78 of SEQ ID NO : 1
<220> FEATURE:
<221> NAME/KEY: CDS
<222> LOCATION: (1)..(51)

<400> SEQUENCE: 87 ttc agc tgc tgc gtc ctg gtc ttt ctt ctg ttt gca gtc atc tgt gtg        48
Phe Ser Cys Cys Val Leu Val Phe Leu Leu Phe Ala Val Ile Cys Val
1               5                   10                  15 tgg                                                                      51
Trp

<210> SEQ ID NO 88
<211> LENGTH: 17
<212> TYPE: PRT
<213> ORGANISM: Artificial
<220> FEATURE:
<223> OTHER INFORMATION: Synthetic Construct

<400> SEQUENCE: 88

Phe Ser Cys Cys Val Leu Val Phe Leu Leu Phe Ala Val Ile Cys Val
1               5                   10                  15

Trp

<210> SEQ ID NO 89
<211> LENGTH: 60
<212> TYPE: DNA
<213> ORGANISM: Artificial
<220> FEATURE:
<223> OTHER INFORMATION: Nucleotides 31-90 of SEQ ID NO : 3
<220> FEATURE:
<221> NAME/KEY: CDS
<222> LOCATION: (1)..(60)

<400> SEQUENCE: 89 cga atg ctt ttc gga ata ttc gct tgg ggg ctc ctc ttt ttg ctg att        48
Arg Met Leu Phe Gly Ile Phe Ala Trp Gly Leu Leu Phe Leu Leu Ile
```

```
                1               5                   10                  15
ttc atc tac ttc                                                                     60
Phe Ile Tyr Phe
            20

<210> SEQ ID NO 90
<211> LENGTH: 20
<212> TYPE: PRT
<213> ORGANISM: Artificial
<220> FEATURE:
<223> OTHER INFORMATION: Synthetic Construct

<400> SEQUENCE: 90

Arg Met Leu Phe Gly Ile Phe Ala Trp Gly Leu Leu Phe Leu Leu Ile
1               5                   10                  15

Phe Ile Tyr Phe
            20

<210> SEQ ID NO 91
<211> LENGTH: 63
<212> TYPE: DNA
<213> ORGANISM: Artificial
<220> FEATURE:
<223> OTHER INFORMATION: Nucleotides 43-105 of SEQ ID NO : 5
<220> FEATURE:
<221> NAME/KEY: CDS
<222> LOCATION: (1)..(63)

<400> SEQUENCE: 91 gtc cag tgg tcc ttg ctt ctg gct gtc ctg gtc ttc ttt ctc ttc gcc     48
Val Gln Trp Ser Leu Leu Leu Ala Val Leu Val Phe Phe Leu Phe Ala
1               5                   10                  15 ttg ccc tct ttt att                                                 63
Leu Pro Ser Phe Ile
            20

<210> SEQ ID NO 92
<211> LENGTH: 21
<212> TYPE: PRT
<213> ORGANISM: Artificial
<220> FEATURE:
<223> OTHER INFORMATION: Synthetic Construct

<400> SEQUENCE: 92

Val Gln Trp Ser Leu Leu Leu Ala Val Leu Val Phe Phe Leu Phe Ala
1               5                   10                  15

Leu Pro Ser Phe Ile
            20

<210> SEQ ID NO 93
<211> LENGTH: 63
<212> TYPE: DNA
<213> ORGANISM: Artificial
<220> FEATURE:
<223> OTHER INFORMATION: Nucleotides 22-84 of SEQ ID NO : 7
<220> FEATURE:
<221> NAME/KEY: CDS
<222> LOCATION: (1)..(63)

<400> SEQUENCE: 93 ttc ttc tgg gtg ctg ctc ctg ctc acg gct gcc tgc tcg ggg ctc ctc     48
Phe Phe Trp Val Leu Leu Leu Leu Thr Ala Ala Cys Ser Gly Leu Leu
1               5                   10                  15 ttt gcc ctg tac ttc                                                 63
Phe Ala Leu Tyr Phe
            20
```

```
<210> SEQ ID NO 94
<211> LENGTH: 21
<212> TYPE: PRT
<213> ORGANISM: Artificial
<220> FEATURE:
<223> OTHER INFORMATION: Synthetic Construct

<400> SEQUENCE: 94

Phe Phe Trp Val Leu Leu Leu Thr Ala Ala Cys Ser Gly Leu Leu
1               5                   10                  15

Phe Ala Leu Tyr Phe
            20

<210> SEQ ID NO 95
<211> LENGTH: 60
<212> TYPE: DNA
<213> ORGANISM: Artificial
<220> FEATURE:
<223> OTHER INFORMATION: Nucleotides 25-84 of SEQ ID NO : 9
<220> FEATURE:
<221> NAME/KEY: CDS
<222> LOCATION: (1)..(60)

<400> SEQUENCE: 95 tct gtg att gct gtg agc ttc ata gca gcg ttc ctt ttc ctg ctg gtt    48
Ser Val Ile Ala Val Ser Phe Ile Ala Ala Phe Leu Phe Leu Leu Val
1               5                   10                  15 gtg cgt ctt gta                                                    60
Val Arg Leu Val
            20

<210> SEQ ID NO 96
<211> LENGTH: 20
<212> TYPE: PRT
<213> ORGANISM: Artificial
<220> FEATURE:
<223> OTHER INFORMATION: Synthetic Construct

<400> SEQUENCE: 96

Ser Val Ile Ala Val Ser Phe Ile Ala Ala Phe Leu Phe Leu Leu Val
1               5                   10                  15

Val Arg Leu Val
            20

<210> SEQ ID NO 97
<211> LENGTH: 63
<212> TYPE: DNA
<213> ORGANISM: Artificial
<220> FEATURE:
<223> OTHER INFORMATION: Nucleotides 19-81 of SEQ ID NO : 11
<220> FEATURE:
<221> NAME/KEY: CDS
<222> LOCATION: (1)..(63)

<400> SEQUENCE: 97 ctc gtg ctc atc atc ctg tgc tcc gtg gtc ttc tct gcc gtc tac atc    48
Leu Val Leu Ile Ile Leu Cys Ser Val Val Phe Ser Ala Val Tyr Ile
1               5                   10                  15 ctc ctg tgc tgc tgg                                                63
Leu Leu Cys Cys Trp
            20

<210> SEQ ID NO 98
<211> LENGTH: 21
<212> TYPE: PRT
```

```
<213> ORGANISM: Artificial
<220> FEATURE:
<223> OTHER INFORMATION: Synthetic Construct

<400> SEQUENCE: 98

Leu Val Leu Ile Ile Leu Cys Ser Val Val Phe Ser Ala Val Tyr Ile
1               5                   10                  15

Leu Leu Cys Cys Trp
            20

<210> SEQ ID NO 99
<211> LENGTH: 63
<212> TYPE: DNA
<213> ORGANISM: Artificial
<220> FEATURE:
<223> OTHER INFORMATION: Nucleotides 25-87 of SEQ ID NO : 13
<220> FEATURE:
<221> NAME/KEY: CDS
<222> LOCATION: (1)..(63)

<400> SEQUENCE: 99 ctg gca gtg tgt tta gcg ctc acc acc atg tgc acc agc ttg ttg cta      48
Leu Ala Val Cys Leu Ala Leu Thr Thr Met Cys Thr Ser Leu Leu Leu
1               5                   10                  15 gtg tac agc agc ctc                                                   63
Val Tyr Ser Ser Leu
            20

<210> SEQ ID NO 100
<211> LENGTH: 21
<212> TYPE: PRT
<213> ORGANISM: Artificial
<220> FEATURE:
<223> OTHER INFORMATION: Synthetic Construct

<400> SEQUENCE: 100

Leu Ala Val Cys Leu Ala Leu Thr Thr Met Cys Thr Ser Leu Leu Leu
1               5                   10                  15

Val Tyr Ser Ser Leu
            20

<210> SEQ ID NO 101
<211> LENGTH: 48
<212> TYPE: DNA
<213> ORGANISM: Artificial
<220> FEATURE:
<223> OTHER INFORMATION: Nucleotides 130-177 of SEQ ID NO : 15
<220> FEATURE:
<221> NAME/KEY: CDS
<222> LOCATION: (1)..(48)

<400> SEQUENCE: 101 gca gtg ttc gtg atc ctc ttt gcc ctc atc acc atc ctc atc ctc tac      48
Ala Val Phe Val Ile Leu Phe Ala Leu Ile Thr Ile Leu Ile Leu Tyr
1               5                   10                  15

<210> SEQ ID NO 102
<211> LENGTH: 16
<212> TYPE: PRT
<213> ORGANISM: Artificial
<220> FEATURE:
<223> OTHER INFORMATION: Synthetic Construct

<400> SEQUENCE: 102

Ala Val Phe Val Ile Leu Phe Ala Leu Ile Thr Ile Leu Ile Leu Tyr
1               5                   10                  15
```

<210> SEQ ID NO 103
<211> LENGTH: 63
<212> TYPE: DNA
<213> ORGANISM: Artificial
<220> FEATURE:
<223> OTHER INFORMATION: Nucleotides 40-102 of SEQ ID NO : 17
<220> FEATURE:
<221> NAME/KEY: CDS
<222> LOCATION: (1)..(63)

<400> SEQUENCE: 103 ttc ctc gtg ctc ttc atc ttc ctc acc tcc ttc ttc ctg aac tac tcc    48
Phe Leu Val Leu Phe Ile Phe Leu Thr Ser Phe Phe Leu Asn Tyr Ser
1               5                   10                  15 cac acc atg gtg gcc                                                63
His Thr Met Val Ala
            20

<210> SEQ ID NO 104
<211> LENGTH: 21
<212> TYPE: PRT
<213> ORGANISM: Artificial
<220> FEATURE:
<223> OTHER INFORMATION: Synthetic Construct

<400> SEQUENCE: 104

Phe Leu Val Leu Phe Ile Phe Leu Thr Ser Phe Phe Leu Asn Tyr Ser
1               5                   10                  15

His Thr Met Val Ala
            20

<210> SEQ ID NO 105
<211> LENGTH: 63
<212> TYPE: DNA
<213> ORGANISM: Artificial
<220> FEATURE:
<223> OTHER INFORMATION: Nucleotides 19-81 of SEQ ID NO : 19
<220> FEATURE:
<221> NAME/KEY: CDS
<222> LOCATION: (1)..(63)

<400> SEQUENCE: 105 gtg tgg ttc ctc tcc gtg gcc ttc ctg ctg gtg ttc atc atg tcc ctg    48
Val Trp Phe Leu Ser Val Ala Phe Leu Leu Val Phe Ile Met Ser Leu
1               5                   10                  15 ctc ttc acc tac tcg                                                63
Leu Phe Thr Tyr Ser
            20

<210> SEQ ID NO 106
<211> LENGTH: 21
<212> TYPE: PRT
<213> ORGANISM: Artificial
<220> FEATURE:
<223> OTHER INFORMATION: Synthetic Construct

<400> SEQUENCE: 106

Val Trp Phe Leu Ser Val Ala Phe Leu Leu Val Phe Ile Met Ser Leu
1               5                   10                  15

Leu Phe Thr Tyr Ser
            20

<210> SEQ ID NO 107
<211> LENGTH: 60
<212> TYPE: DNA
<213> ORGANISM: Artificial

```
<220> FEATURE:
<223> OTHER INFORMATION: Nucleotides 25-84 of SEQ ID NO : 21
<220> FEATURE:
<221> NAME/KEY: CDS
<222> LOCATION: (1)..(60)

<400> SEQUENCE: 107 aat ctg ctg cta gcc ctc tgc ctc ttt ctg gta ctg gga ttt ttg tat      48
Asn Leu Leu Leu Ala Leu Cys Leu Phe Leu Val Leu Gly Phe Leu Tyr
1               5                   10                  15 tat tct gcg tgg                                                       60
Tyr Ser Ala Trp
            20

<210> SEQ ID NO 108
<211> LENGTH: 20
<212> TYPE: PRT
<213> ORGANISM: Artificial
<220> FEATURE:
<223> OTHER INFORMATION: Synthetic Construct

<400> SEQUENCE: 108

Asn Leu Leu Leu Ala Leu Cys Leu Phe Leu Val Leu Gly Phe Leu Tyr
1               5                   10                  15

Tyr Ser Ala Trp
            20

<210> SEQ ID NO 109
<211> LENGTH: 54
<212> TYPE: DNA
<213> ORGANISM: Artificial
<220> FEATURE:
<223> OTHER INFORMATION: nucleotides 25-78 of SEQ ID NO : 23
<220> FEATURE:
<221> NAME/KEY: CDS
<222> LOCATION: (1)..(54)

<400> SEQUENCE: 109 ctc ctg gcc atg ttg gct ctg gtc ctg gtc gtc atg gtg tgg tat tcc      48
Leu Leu Ala Met Leu Ala Leu Val Leu Val Val Met Val Trp Tyr Ser
1               5                   10                  15 atc tcc                                                               54
Ile Ser <210> SEQ ID NO 110
<211> LENGTH: 18
<212> TYPE: PRT
<213> ORGANISM: Artificial
<220> FEATURE:
<223> OTHER INFORMATION: Synthetic Construct

<400> SEQUENCE: 110

Leu Leu Ala Met Leu Ala Leu Val Leu Val Val Met Val Trp Tyr Ser
1               5                   10                  15

Ile Ser

<210> SEQ ID NO 111
<211> LENGTH: 63
<212> TYPE: DNA
<213> ORGANISM: Artificial
<220> FEATURE:
<223> OTHER INFORMATION: nucleotides 16-78 of SEQ ID NO : 25
<220> FEATURE:
<221> NAME/KEY: CDS
<222> LOCATION: (1)..(63)

<400> SEQUENCE: 111
```

```
ttg tta tta aaa gac atc ctc aaa tgt aca ttg ctt gtg ttt gga gtg      48
Leu Leu Leu Lys Asp Ile Leu Lys Cys Thr Leu Leu Val Phe Gly Val
1               5                   10                  15 tgg atc ctt tat atc                                                  63
Trp Ile Leu Tyr Ile
            20
```

<210> SEQ ID NO 112
<211> LENGTH: 21
<212> TYPE: PRT
<213> ORGANISM: Artificial
<220> FEATURE:
<223> OTHER INFORMATION: Synthetic Construct

<400> SEQUENCE: 112

```
Leu Leu Leu Lys Asp Ile Leu Lys Cys Thr Leu Leu Val Phe Gly Val
1               5                   10                  15

Trp Ile Leu Tyr Ile
            20
```

<210> SEQ ID NO 113
<211> LENGTH: 63
<212> TYPE: DNA
<213> ORGANISM: Artificial
<220> FEATURE:
<223> OTHER INFORMATION: Nucleotides 13-75 of SEQ ID NO : 27
<220> FEATURE:
<221> NAME/KEY: CDS
<222> LOCATION: (1)..(63)

<400> SEQUENCE: 113

```
ctt gtg gcc ata ttc ctg agt gct gtc ttc ctc tat tat gta ctg cat      48
Leu Val Ala Ile Phe Leu Ser Ala Val Phe Leu Tyr Tyr Val Leu His
1               5                   10                  15 tgc ata tta tgg gga                                                  63
Cys Ile Leu Trp Gly
            20
```

<210> SEQ ID NO 114
<211> LENGTH: 21
<212> TYPE: PRT
<213> ORGANISM: Artificial
<220> FEATURE:
<223> OTHER INFORMATION: Synthetic Construct

<400> SEQUENCE: 114

```
Leu Val Ala Ile Phe Leu Ser Ala Val Phe Leu Tyr Tyr Val Leu His
1               5                   10                  15

Cys Ile Leu Trp Gly
            20
```

<210> SEQ ID NO 115
<211> LENGTH: 60
<212> TYPE: DNA
<213> ORGANISM: Artificial
<220> FEATURE:
<223> OTHER INFORMATION: Nucleotides 25-84 of SEQ ID NO : 29
<220> FEATURE:
<221> NAME/KEY: CDS
<222> LOCATION: (1)..(60)

<400> SEQUENCE: 115

```
aac ctg ctg cta gcc ctc tgc ctc ttt ctg gtc ctg gga ttt tgt tat      48
Asn Leu Leu Leu Ala Leu Cys Leu Phe Leu Val Leu Gly Phe Leu Tyr
1               5                   10                  15
```

-continued

```
tat tct gcc tgg                                              60
Tyr Ser Ala Trp
        20

<210> SEQ ID NO 116
<211> LENGTH: 20
<212> TYPE: PRT
<213> ORGANISM: Artificial
<220> FEATURE:
<223> OTHER INFORMATION: Synthetic Construct

<400> SEQUENCE: 116

Asn Leu Leu Leu Ala Leu Cys Leu Phe Leu Val Leu Gly Phe Leu Tyr
1               5                   10                  15

Tyr Ser Ala Trp
        20

<210> SEQ ID NO 117
<211> LENGTH: 57
<212> TYPE: DNA
<213> ORGANISM: Artificial
<220> FEATURE:
<223> OTHER INFORMATION: Nucleotides 88-144 of SEQ ID NO : 31
<220> FEATURE:
<221> NAME/KEY: CDS
<222> LOCATION: (1)..(57)

<400> SEQUENCE: 117 atg gga gcc agt gcc ctc tgt gtc gtg gtc ctc tgt tgg ctc tac atc    48
Met Gly Ala Ser Ala Leu Cys Val Val Val Leu Cys Trp Leu Tyr Ile
1               5                   10                  15 ttc ccc gtc                                                  57
Phe Pro Val

<210> SEQ ID NO 118
<211> LENGTH: 19
<212> TYPE: PRT
<213> ORGANISM: Artificial
<220> FEATURE:
<223> OTHER INFORMATION: Synthetic Construct

<400> SEQUENCE: 118

Met Gly Ala Ser Ala Leu Cys Val Val Val Leu Cys Trp Leu Tyr Ile
1               5                   10                  15

Phe Pro Val

<210> SEQ ID NO 119
<211> LENGTH: 51
<212> TYPE: DNA
<213> ORGANISM: Artificial
<220> FEATURE:
<223> OTHER INFORMATION: Nucleotides 19-69 of SEQ ID NO : 33
<220> FEATURE:
<221> NAME/KEY: CDS
<222> LOCATION: (1)..(51)

<400> SEQUENCE: 119 agc tgg atg ctg gcc gcg ctc acg ctg ctc gtg gtc ttc ctc atc ttc    48
Ser Trp Met Leu Ala Ala Leu Thr Leu Leu Val Val Phe Leu Ile Phe
1               5                   10                  15 gca                                                          51
Ala

<210> SEQ ID NO 120
<211> LENGTH: 17
<212> TYPE: PRT
```

```
<213> ORGANISM: Artificial
<220> FEATURE:
<223> OTHER INFORMATION: Synthetic Construct

<400> SEQUENCE: 120

Ser Trp Met Leu Ala Ala Leu Thr Leu Leu Val Val Phe Leu Ile Phe
1               5                   10                  15

Ala

<210> SEQ ID NO 121
<211> LENGTH: 72
<212> TYPE: DNA
<213> ORGANISM: Artificial
<220> FEATURE:
<223> OTHER INFORMATION: Nucleotides 28-99 of SEQ ID NO : 35
<220> FEATURE:
<221> NAME/KEY: CDS
<222> LOCATION: (1)..(72)

<400> SEQUENCE: 121 gcc agt gtg ctg ggg ctg gtc atg ctc agc gtc gcc ctg ctg att tta      48
Ala Ser Val Leu Gly Leu Val Met Leu Ser Val Ala Leu Leu Ile Leu
1               5                   10                  15 tcg ctc atc agc tac gtg tcc ctg                                      72
Ser Leu Ile Ser Tyr Val Ser Leu
            20

<210> SEQ ID NO 122
<211> LENGTH: 24
<212> TYPE: PRT
<213> ORGANISM: Artificial
<220> FEATURE:
<223> OTHER INFORMATION: Synthetic Construct

<400> SEQUENCE: 122

Ala Ser Val Leu Gly Leu Val Met Leu Ser Val Ala Leu Leu Ile Leu
1               5                   10                  15

Ser Leu Ile Ser Tyr Val Ser Leu
            20

<210> SEQ ID NO 123
<211> LENGTH: 39
<212> TYPE: DNA
<213> ORGANISM: Artificial
<220> FEATURE:
<223> OTHER INFORMATION: Nucleotides 22-60 of SEQ ID NO : 37
<220> FEATURE:
<221> NAME/KEY: CDS
<222> LOCATION: (1)..(39)

<400> SEQUENCE: 123 tgg acg atc tgc aca ata agt ctg ctc ctg atc ttt tat                  39
Trp Thr Ile Cys Thr Ile Ser Leu Leu Leu Ile Phe Tyr
1               5                   10

<210> SEQ ID NO 124
<211> LENGTH: 13
<212> TYPE: PRT
<213> ORGANISM: Artificial
<220> FEATURE:
<223> OTHER INFORMATION: Synthetic Construct

<400> SEQUENCE: 124

Trp Thr Ile Cys Thr Ile Ser Leu Leu Leu Ile Phe Tyr
1               5                   10
```

<210> SEQ ID NO 125
<211> LENGTH: 63
<212> TYPE: DNA
<213> ORGANISM: Artificial
<220> FEATURE:
<223> OTHER INFORMATION: Nucleotides 52-114 of SEQ ID NO : 39
<220> FEATURE:
<221> NAME/KEY: CDS
<222> LOCATION: (1)..(63)

<400> SEQUENCE: 125

```
ttg ctc ttc atc ttc atc tgc gcc ttt gcc ttg gtg acc ttg ctg caa      48
Leu Leu Phe Ile Phe Ile Cys Ala Phe Ala Leu Val Thr Leu Leu Gln
1               5                   10                  15 cag atc ctg tat ggc                                                  63
Gln Ile Leu Tyr Gly
            20
```

<210> SEQ ID NO 126
<211> LENGTH: 21
<212> TYPE: PRT
<213> ORGANISM: Artificial
<220> FEATURE:
<223> OTHER INFORMATION: Synthetic Construct

<400> SEQUENCE: 126

```
Leu Leu Phe Ile Phe Ile Cys Ala Phe Ala Leu Val Thr Leu Leu Gln
1               5                   10                  15

Gln Ile Leu Tyr Gly
            20
```

<210> SEQ ID NO 127
<211> LENGTH: 63
<212> TYPE: DNA
<213> ORGANISM: Artificial
<220> FEATURE:
<223> OTHER INFORMATION: Nucleotides 10-72 of SEQ ID NO : 41
<220> FEATURE:
<221> NAME/KEY: CDS
<222> LOCATION: (1)..(63)

<400> SEQUENCE: 127

```
ggg ggc gca ctg ctc gcc ctg ctc gcc agc ctg ctg ctg ctg ctg          48
Gly Gly Ala Leu Leu Ala Leu Leu Ala Ser Leu Leu Leu Leu Leu
1               5                   10                  15 ctg cgc ctg ctc tgg                                                  63
Leu Arg Leu Leu Trp
            20
```

<210> SEQ ID NO 128
<211> LENGTH: 21
<212> TYPE: PRT
<213> ORGANISM: Artificial
<220> FEATURE:
<223> OTHER INFORMATION: Synthetic Construct

<400> SEQUENCE: 128

```
Gly Gly Ala Leu Leu Ala Leu Leu Ala Ser Leu Leu Leu Leu Leu
1               5                   10                  15

Leu Arg Leu Leu Trp
            20
```

<210> SEQ ID NO 129
<211> LENGTH: 117
<212> TYPE: DNA
<213> ORGANISM: Artificial
<220> FEATURE:

<223> OTHER INFORMATION: Nucleotides 106-222 of SEQ ID NO : 5
<220> FEATURE:
<221> NAME/KEY: CDS
<222> LOCATION: (1)..(117)

<400> SEQUENCE: 129

```
aag gag cct caa aca aag cct tcc agg cat caa cgc aca gag aac att      48
Lys Glu Pro Gln Thr Lys Pro Ser Arg His Gln Arg Thr Glu Asn Ile
1               5                   10                  15 aaa gaa agg tct cta cag tcc ctg gca aag cct aag tcc cag gca ccc      96
Lys Glu Arg Ser Leu Gln Ser Leu Ala Lys Pro Lys Ser Gln Ala Pro
            20                  25                  30 aca agg gca agg agg aca acc                                         117
Thr Arg Ala Arg Arg Thr Thr
        35
```

<210> SEQ ID NO 130
<211> LENGTH: 39
<212> TYPE: PRT
<213> ORGANISM: Artificial
<220> FEATURE:
<223> OTHER INFORMATION: Synthetic Construct

<400> SEQUENCE: 130

```
Lys Glu Pro Gln Thr Lys Pro Ser Arg His Gln Arg Thr Glu Asn Ile
1               5                   10                  15

Lys Glu Arg Ser Leu Gln Ser Leu Ala Lys Pro Lys Ser Gln Ala Pro
            20                  25                  30

Thr Arg Ala Arg Arg Thr Thr
        35
```

<210> SEQ ID NO 131
<211> LENGTH: 114
<212> TYPE: DNA
<213> ORGANISM: Artificial
<220> FEATURE:
<223> OTHER INFORMATION: Nucleotides 109-222 of SEQ ID NO : 5
<220> FEATURE:
<221> NAME/KEY: CDS
<222> LOCATION: (1)..(114)

<400> SEQUENCE: 131

```
gag cct caa aca aag cct tcc agg cat caa cgc aca gag aac att aaa      48
Glu Pro Gln Thr Lys Pro Ser Arg His Gln Arg Thr Glu Asn Ile Lys
1               5                   10                  15 gaa agg tct cta cag tcc ctg gca aag cct aag tcc cag gca ccc aca      96
Glu Arg Ser Leu Gln Ser Leu Ala Lys Pro Lys Ser Gln Ala Pro Thr
            20                  25                  30 agg gca agg agg aca acc                                             114
Arg Ala Arg Arg Thr Thr
        35
```

<210> SEQ ID NO 132
<211> LENGTH: 38
<212> TYPE: PRT
<213> ORGANISM: Artificial
<220> FEATURE:
<223> OTHER INFORMATION: Synthetic Construct

<400> SEQUENCE: 132

```
Glu Pro Gln Thr Lys Pro Ser Arg His Gln Arg Thr Glu Asn Ile Lys
1               5                   10                  15

Glu Arg Ser Leu Gln Ser Leu Ala Lys Pro Lys Ser Gln Ala Pro Thr
            20                  25                  30
```

```
Arg Ala Arg Arg Thr Thr
        35

<210> SEQ ID NO 133
<211> LENGTH: 315
<212> TYPE: DNA
<213> ORGANISM: Artificial
<220> FEATURE:
<223> OTHER INFORMATION: Nucleotides 106-420 of SEQ ID NO : 5
<220> FEATURE:
<221> NAME/KEY: CDS
<222> LOCATION: (1)..(315)

<400> SEQUENCE: 133 aag gag cct caa aca aag cct tcc agg cat caa cgc aca gag aac att         48
Lys Glu Pro Gln Thr Lys Pro Ser Arg His Gln Arg Thr Glu Asn Ile
1               5                   10                  15 aaa gaa agg tct cta cag tcc ctg gca aag cct aag tcc cag gca ccc         96
Lys Glu Arg Ser Leu Gln Ser Leu Ala Lys Pro Lys Ser Gln Ala Pro
            20                  25                  30 aca agg gca agg agg aca acc atc tat gca gag cca gtg cca gag aac        144
Thr Arg Ala Arg Arg Thr Thr Ile Tyr Ala Glu Pro Val Pro Glu Asn
        35                  40                  45 aat gcc ctc aac aca caa acc cag ccc aag gcc cac acc acc gga gac        192
Asn Ala Leu Asn Thr Gln Thr Gln Pro Lys Ala His Thr Thr Gly Asp
    50                  55                  60 aga gga aag gag gcc aac cag gca ccg ccg gag gag cag gac aag gtg        240
Arg Gly Lys Glu Ala Asn Gln Ala Pro Pro Glu Glu Gln Asp Lys Val
65                  70                  75                  80 ccc cac aca gca cag agg gca gca tgg aag agc cca gaa aaa gag aaa        288
Pro His Thr Ala Gln Arg Ala Ala Trp Lys Ser Pro Glu Lys Glu Lys
                85                  90                  95 acc atg gtg aac aca ctg tca ccc aga                                    315
Thr Met Val Asn Thr Leu Ser Pro Arg
            100                 105

<210> SEQ ID NO 134
<211> LENGTH: 105
<212> TYPE: PRT
<213> ORGANISM: Artificial
<220> FEATURE:
<223> OTHER INFORMATION: Synthetic Construct

<400> SEQUENCE: 134

Lys Glu Pro Gln Thr Lys Pro Ser Arg His Gln Arg Thr Glu Asn Ile
1               5                   10                  15

Lys Glu Arg Ser Leu Gln Ser Leu Ala Lys Pro Lys Ser Gln Ala Pro
            20                  25                  30

Thr Arg Ala Arg Arg Thr Thr Ile Tyr Ala Glu Pro Val Pro Glu Asn
        35                  40                  45

Asn Ala Leu Asn Thr Gln Thr Gln Pro Lys Ala His Thr Thr Gly Asp
    50                  55                  60

Arg Gly Lys Glu Ala Asn Gln Ala Pro Pro Glu Glu Gln Asp Lys Val
65                  70                  75                  80

Pro His Thr Ala Gln Arg Ala Ala Trp Lys Ser Pro Glu Lys Glu Lys
                85                  90                  95

Thr Met Val Asn Thr Leu Ser Pro Arg
            100                 105

<210> SEQ ID NO 135
<211> LENGTH: 669
<212> TYPE: DNA
```

<213> ORGANISM: Artificial
<220> FEATURE:
<223> OTHER INFORMATION: Nucleotides 106-774 of SEQ ID NO : 5
<220> FEATURE:
<221> NAME/KEY: CDS
<222> LOCATION: (1)..(669)

<400> SEQUENCE: 135

```
aag gag cct caa aca aag cct tcc agg cat caa cgc aca gag aac att      48
Lys Glu Pro Gln Thr Lys Pro Ser Arg His Gln Arg Thr Glu Asn Ile
1               5                   10                  15 aaa gaa agg tct cta cag tcc ctg gca aag cct aag tcc cag gca ccc      96
Lys Glu Arg Ser Leu Gln Ser Leu Ala Lys Pro Lys Ser Gln Ala Pro
            20                  25                  30 aca agg gca agg agg aca acc atc tat gca gag cca gtg cca gag aac     144
Thr Arg Ala Arg Arg Thr Thr Ile Tyr Ala Glu Pro Val Pro Glu Asn
        35                  40                  45 aat gcc ctc aac aca caa acc cag ccc aag gcc cac acc acc gga gac     192
Asn Ala Leu Asn Thr Gln Thr Gln Pro Lys Ala His Thr Thr Gly Asp
    50                  55                  60 aga gga aag gag gcc aac cag gca ccg ccg gag gag cag gac aag gtg     240
Arg Gly Lys Glu Ala Asn Gln Ala Pro Pro Glu Glu Gln Asp Lys Val
65                  70                  75                  80 ccc cac aca gca cag agg gca gca tgg aag agc cca gaa aaa gag aaa     288
Pro His Thr Ala Gln Arg Ala Ala Trp Lys Ser Pro Glu Lys Glu Lys
                85                  90                  95 acc atg gtg aac aca ctg tca ccc aga ggg caa gat gca ggg atg gcc     336
Thr Met Val Asn Thr Leu Ser Pro Arg Gly Gln Asp Ala Gly Met Ala
            100                 105                 110 tct ggc agg aca gag gca caa tca tgg aag agc cag gac aca aag acg     384
Ser Gly Arg Thr Glu Ala Gln Ser Trp Lys Ser Gln Asp Thr Lys Thr
        115                 120                 125 acc caa gga aat ggg ggc cag acc agg aag ctg acg gcc tcc agg acg     432
Thr Gln Gly Asn Gly Gly Gln Thr Arg Lys Leu Thr Ala Ser Arg Thr
    130                 135                 140 gtg tca gag aag cac cag ggc aaa gcg caa acc aca gcc aag acg ctc     480
Val Ser Glu Lys His Gln Gly Lys Ala Ala Thr Thr Ala Lys Thr Leu
145                 150                 155                 160 att ccc aaa agt cag cac aga atg ctg gct ccc aca gga gca gtg tca     528
Ile Pro Lys Ser Gln His Arg Met Leu Ala Pro Thr Gly Ala Val Ser
                165                 170                 175 aca agg acg aga cag aaa gga gtg acc aca gca gtc atc cca cct aag     576
Thr Arg Thr Arg Gln Lys Gly Val Thr Thr Ala Val Ile Pro Pro Lys
            180                 185                 190 gag aag aaa cct cag gcc acc cca ccc cct gcc cct ttc cag agc ccc     624
Glu Lys Lys Pro Gln Ala Thr Pro Pro Pro Ala Pro Phe Gln Ser Pro
        195                 200                 205 acg acg cag aga aac caa aga ctg aag gcc gcc aac ttc aaa tct         669
Thr Thr Gln Arg Asn Gln Arg Leu Lys Ala Ala Asn Phe Lys Ser
    210                 215                 220
```

<210> SEQ ID NO 136
<211> LENGTH: 223
<212> TYPE: PRT
<213> ORGANISM: Artificial
<220> FEATURE:
<223> OTHER INFORMATION: Synthetic Construct

<400> SEQUENCE: 136

```
Lys Glu Pro Gln Thr Lys Pro Ser Arg His Gln Arg Thr Glu Asn Ile
1               5                   10                  15

Lys Glu Arg Ser Leu Gln Ser Leu Ala Lys Pro Lys Ser Gln Ala Pro
```

```
                 20                  25                  30

Thr Arg Ala Arg Arg Thr Thr Ile Tyr Ala Glu Pro Val Pro Glu Asn
             35                  40                  45

Asn Ala Leu Asn Thr Gln Thr Gln Pro Lys Ala His Thr Thr Gly Asp
         50                  55                  60

Arg Gly Lys Glu Ala Asn Gln Ala Pro Pro Glu Gln Asp Lys Val
 65                  70                  75                  80

Pro His Thr Ala Gln Arg Ala Ala Trp Lys Ser Pro Glu Lys Glu Lys
                 85                  90                  95

Thr Met Val Asn Thr Leu Ser Pro Arg Gly Gln Asp Ala Gly Met Ala
            100                 105                 110

Ser Gly Arg Thr Glu Ala Gln Ser Trp Lys Ser Gln Asp Thr Lys Thr
        115                 120                 125

Thr Gln Gly Asn Gly Gly Gln Thr Arg Lys Leu Thr Ala Ser Arg Thr
    130                 135                 140

Val Ser Glu Lys His Gln Gly Lys Ala Ala Thr Thr Ala Lys Thr Leu
145                 150                 155                 160

Ile Pro Lys Ser Gln His Arg Met Leu Ala Pro Thr Gly Ala Val Ser
                165                 170                 175

Thr Arg Thr Arg Gln Lys Gly Val Thr Thr Ala Val Ile Pro Pro Lys
            180                 185                 190

Glu Lys Lys Pro Gln Ala Thr Pro Pro Ala Pro Phe Gln Ser Pro
        195                 200                 205

Thr Thr Gln Arg Asn Gln Arg Leu Lys Ala Ala Asn Phe Lys Ser
    210                 215                 220

<210> SEQ ID NO 137
<211> LENGTH: 54
<212> TYPE: DNA
<213> ORGANISM: Artificial
<220> FEATURE:
<223> OTHER INFORMATION: Nucleotides 85-138 of SEQ ID NO : 21
<220> FEATURE:
<221> NAME/KEY: CDS
<222> LOCATION: (1)..(54)

<400> SEQUENCE: 137 aag cta cac tta ctc cag tgg gag gag gac tcc agt aag tat agt cac    48
Lys Leu His Leu Leu Gln Trp Glu Glu Asp Ser Ser Lys Tyr Ser His
1               5                  10                  15 tct agc                                                              54
Ser Ser

<210> SEQ ID NO 138
<211> LENGTH: 18
<212> TYPE: PRT
<213> ORGANISM: Artificial
<220> FEATURE:
<223> OTHER INFORMATION: Synthetic Construct

<400> SEQUENCE: 138

Lys Leu His Leu Leu Gln Trp Glu Glu Asp Ser Ser Lys Tyr Ser His
1               5                  10                  15

Ser Ser

<210> SEQ ID NO 139
<211> LENGTH: 54
<212> TYPE: DNA
<213> ORGANISM: Artificial
<220> FEATURE:
```

<223> OTHER INFORMATION: Nucleotides 85-138 of SEQ ID NO : 29
<220> FEATURE:
<221> NAME/KEY: CDS
<222> LOCATION: (1)..(54)

<400> SEQUENCE: 139

```
aag cta cac tta ctc caa tgg gaa gac tcc aat tca ctg att ctt tcc      48
Lys Leu His Leu Leu Gln Trp Glu Asp Ser Asn Ser Leu Ile Leu Ser
1               5                  10                  15 ctt gac                                                              54
Leu Asp
```

<210> SEQ ID NO 140
<211> LENGTH: 18
<212> TYPE: PRT
<213> ORGANISM: Artificial
<220> FEATURE:
<223> OTHER INFORMATION: Synthetic Construct

<400> SEQUENCE: 140

```
Lys Leu His Leu Leu Gln Trp Glu Asp Ser Asn Ser Leu Ile Leu Ser
1               5                  10                  15

Leu Asp
```

<210> SEQ ID NO 141
<211> LENGTH: 168
<212> TYPE: DNA
<213> ORGANISM: Artificial
<220> FEATURE:
<223> OTHER INFORMATION: Nucleotides 70-237 of SEQ ID NO : 33
<220> FEATURE:
<221> NAME/KEY: CDS
<222> LOCATION: (1)..(168)

<400> SEQUENCE: 141

```
gac atc tca gag atc gaa gaa gaa atc ggg aat tcg gga ggc aga ggt      48
Asp Ile Ser Glu Ile Glu Glu Glu Ile Gly Asn Ser Gly Gly Arg Gly
1               5                  10                  15 aca atc aga tca gct gtg aac agc tta cat agc aaa tct aat aga gct      96
Thr Ile Arg Ser Ala Val Asn Ser Leu His Ser Lys Ser Asn Arg Ala
            20                  25                  30 gaa gtt gta ata aac ggc tcc tca tca cca gct gtt gtt gac aga agt     144
Glu Val Val Ile Asn Gly Ser Ser Ser Pro Ala Val Val Asp Arg Ser
        35                  40                  45 aat gaa agc atc aag cac aac atc                                     168
Asn Glu Ser Ile Lys His Asn Ile
    50                  55
```

<210> SEQ ID NO 142
<211> LENGTH: 56
<212> TYPE: PRT
<213> ORGANISM: Artificial
<220> FEATURE:
<223> OTHER INFORMATION: Synthetic Construct

<400> SEQUENCE: 142

```
Asp Ile Ser Glu Ile Glu Glu Glu Ile Gly Asn Ser Gly Gly Arg Gly
1               5                  10                  15

Thr Ile Arg Ser Ala Val Asn Ser Leu His Ser Lys Ser Asn Arg Ala
            20                  25                  30

Glu Val Val Ile Asn Gly Ser Ser Ser Pro Ala Val Val Asp Arg Ser
        35                  40                  45

Asn Glu Ser Ile Lys His Asn Ile
    50                  55
```

<210> SEQ ID NO 143
<211> LENGTH: 141
<212> TYPE: DNA
<213> ORGANISM: Artificial
<220> FEATURE:
<223> OTHER INFORMATION: Nucleotides 61-201 of SEQ ID NO : 37
<220> FEATURE:
<221> NAME/KEY: CDS
<222> LOCATION: (1)..(141)

<400> SEQUENCE: 143

```
aag aca aaa gaa ata gca aga act gag gag cac cag gag acg caa ctc      48
Lys Thr Lys Glu Ile Ala Arg Thr Glu Glu His Gln Glu Thr Gln Leu
1               5                  10                  15 atc gga gat ggt gaa ttg tct ttg agt cgg tca ctt gtc aat agc tct      96
Ile Gly Asp Gly Glu Leu Ser Leu Ser Arg Ser Leu Val Asn Ser Ser
            20                  25                  30 gat aaa atc att cga aag gct ggc tct tca atc ttc cag cac aat         141
Asp Lys Ile Ile Arg Lys Ala Gly Ser Ser Ile Phe Gln His Asn
        35                  40                  45
```

<210> SEQ ID NO 144
<211> LENGTH: 47
<212> TYPE: PRT
<213> ORGANISM: Artificial
<220> FEATURE:
<223> OTHER INFORMATION: Synthetic Construct

<400> SEQUENCE: 144

```
Lys Thr Lys Glu Ile Ala Arg Thr Glu Glu His Gln Glu Thr Gln Leu
1               5                  10                  15

Ile Gly Asp Gly Glu Leu Ser Leu Ser Arg Ser Leu Val Asn Ser Ser
            20                  25                  30

Asp Lys Ile Ile Arg Lys Ala Gly Ser Ser Ile Phe Gln His Asn
        35                  40                  45
```

<210> SEQ ID NO 145
<211> LENGTH: 222
<212> TYPE: DNA
<213> ORGANISM: Artificial
<220> FEATURE:
<223> OTHER INFORMATION: Nucleotides 1-222 of SEQ ID NO : 5
<220> FEATURE:
<221> NAME/KEY: CDS
<222> LOCATION: (1)..(222)

<400> SEQUENCE: 145

```
atg agg tcc tgc ctg tgg aga tgc agg cac ctg agc caa ggc gtc cag      48
Met Arg Ser Cys Leu Trp Arg Cys Arg His Leu Ser Gln Gly Val Gln
1               5                  10                  15 tgg tcc ttg ctt ctg gct gtc ctg gtc ttc ttt ctc ttc gcc ttg ccc      96
Trp Ser Leu Leu Leu Ala Val Leu Val Phe Phe Leu Phe Ala Leu Pro
            20                  25                  30 tct ttt att aag gag cct caa aca aag cct tcc agg cat caa cgc aca     144
Ser Phe Ile Lys Glu Pro Gln Thr Lys Pro Ser Arg His Gln Arg Thr
        35                  40                  45 gag aac att aaa gaa agg tct cta cag tcc ctg gca aag cct aag tcc     192
Glu Asn Ile Lys Glu Arg Ser Leu Gln Ser Leu Ala Lys Pro Lys Ser
    50                  55                  60 cag gca ccc aca agg gca agg agg aca acc                             222
Gln Ala Pro Thr Arg Ala Arg Arg Thr Thr
65                  70
```

<210> SEQ ID NO 146
<211> LENGTH: 74
<212> TYPE: PRT
<213> ORGANISM: Artificial
<220> FEATURE:
<223> OTHER INFORMATION: Synthetic Construct

<400> SEQUENCE: 146

```
Met Arg Ser Cys Leu Trp Arg Cys Arg His Leu Ser Gln Gly Val Gln
1               5                   10                  15

Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
        35                  40                  45

Glu Asn Ile Lys Glu Arg Ser Leu Gln Ser Leu Ala Lys Pro Lys Ser
    50                  55                  60

Gln Ala Pro Thr Arg Ala Arg Arg Thr Thr
65                  70
```

<210> SEQ ID NO 147
<211> LENGTH: 420
<212> TYPE: DNA
<213> ORGANISM: Artificial
<220> FEATURE:
<223> OTHER INFORMATION: Nucleotides 1-420 of SEQ ID NO : 5
<220> FEATURE:
<221> NAME/KEY: CDS
<222> LOCATION: (1)..(420)

<400> SEQUENCE: 147

```
atg agg tcc tgc ctg tgg aga tgc agg cac ctg agc caa ggc gtc cag      48
Met Arg Ser Cys Leu Trp Arg Cys Arg His Leu Ser Gln Gly Val Gln
1               5                   10                  15 tgg tcc ttg ctt ctg gct gtc ctg gtc ttc ttt ctc ttc gcc ttg ccc      96
Trp Ser Leu Leu Leu Ala Val Leu Val Phe Phe Leu Phe Ala Leu Pro
            20                  25                  30 tct ttt att aag gag cct caa aca aag cct tcc agg cat caa cgc aca     144
Ser Phe Ile Lys Glu Pro Gln Thr Lys Pro Ser Arg His Gln Arg Thr
        35                  40                  45 gag aac att aaa gaa agg tct cta cag tcc ctg gca aag cct aag tcc     192
Glu Asn Ile Lys Glu Arg Ser Leu Gln Ser Leu Ala Lys Pro Lys Ser
    50                  55                  60 cag gca ccc aca agg gca agg agg aca acc atc tat gca gag cca gtg     240
Gln Ala Pro Thr Arg Ala Arg Arg Thr Thr Ile Tyr Ala Glu Pro Val
65                  70                  75                  80 cca gag aac aat gcc ctc aac aca caa acc cag ccc aag gcc cac acc     288
Pro Glu Asn Asn Ala Leu Asn Thr Gln Thr Gln Pro Lys Ala His Thr
                85                  90                  95 acc gga gac aga gga aag gag gcc aac cag gca ccg ccg gag gag cag     336
Thr Gly Asp Arg Gly Lys Glu Ala Asn Gln Ala Pro Pro Glu Glu Gln
            100                 105                 110 gac aag gtg ccc cac aca gca cag agg gca gca tgg aag agc cca gaa     384
Asp Lys Val Pro His Thr Ala Gln Arg Ala Ala Trp Lys Ser Pro Glu
        115                 120                 125 aaa gag aaa acc atg gtg aac aca ctg tca ccc aga                     420
Lys Glu Lys Thr Met Val Asn Thr Leu Ser Pro Arg
    130                 135                 140
```

<210> SEQ ID NO 148
<211> LENGTH: 140
<212> TYPE: PRT
<213> ORGANISM: Artificial
<220> FEATURE:

<223> OTHER INFORMATION: Synthetic Construct

<400> SEQUENCE: 148

| Met | Arg | Ser | Cys | Leu | Trp | Arg | Cys | Arg | His | Leu | Ser | Gln | Gly | Val | Gln |
|---|---|---|---|---|---|---|---|---|---|---|---|---|---|---|---|
| 1 | | | | 5 | | | | | 10 | | | | | 15 | |

| Trp | Ser | Leu | Leu | Leu | Ala | Val | Leu | Val | Phe | Phe | Leu | Phe | Ala | Leu | Pro |
|---|---|---|---|---|---|---|---|---|---|---|---|---|---|---|---|
| | | | 20 | | | | | 25 | | | | | 30 | | |

| Ser | Phe | Ile | Lys | Glu | Pro | Gln | Thr | Lys | Pro | Ser | Arg | His | Gln | Arg | Thr |
|---|---|---|---|---|---|---|---|---|---|---|---|---|---|---|---|
| | | | 35 | | | | | 40 | | | | | 45 | | |

| Glu | Asn | Ile | Lys | Glu | Arg | Ser | Leu | Gln | Ser | Leu | Ala | Lys | Pro | Lys | Ser |
|---|---|---|---|---|---|---|---|---|---|---|---|---|---|---|---|
| | 50 | | | | | 55 | | | | | 60 | | | | |

| Gln | Ala | Pro | Thr | Arg | Ala | Arg | Arg | Thr | Thr | Ile | Tyr | Ala | Glu | Pro | Val |
|---|---|---|---|---|---|---|---|---|---|---|---|---|---|---|---|
| 65 | | | | | 70 | | | | | 75 | | | | | 80 |

| Pro | Glu | Asn | Asn | Ala | Leu | Asn | Thr | Gln | Thr | Gln | Pro | Lys | Ala | His | Thr |
|---|---|---|---|---|---|---|---|---|---|---|---|---|---|---|---|
| | | | | 85 | | | | | 90 | | | | | 95 | |

| Thr | Gly | Asp | Arg | Gly | Lys | Glu | Ala | Asn | Gln | Ala | Pro | Pro | Glu | Glu | Gln |
|---|---|---|---|---|---|---|---|---|---|---|---|---|---|---|---|
| | | | 100 | | | | | 105 | | | | | 110 | | |

| Asp | Lys | Val | Pro | His | Thr | Ala | Gln | Arg | Ala | Ala | Trp | Lys | Ser | Pro | Glu |
|---|---|---|---|---|---|---|---|---|---|---|---|---|---|---|---|
| | | 115 | | | | | 120 | | | | | 125 | | | |

| Lys | Glu | Lys | Thr | Met | Val | Asn | Thr | Leu | Ser | Pro | Arg |
|---|---|---|---|---|---|---|---|---|---|---|---|
| 130 | | | | | 135 | | | | | 140 | |

<210> SEQ ID NO 149
<211> LENGTH: 774
<212> TYPE: DNA
<213> ORGANISM: Artificial
<220> FEATURE:
<223> OTHER INFORMATION: Nucleotides 1-774 of SEQ ID NO : 5
<220> FEATURE:
<221> NAME/KEY: CDS
<222> LOCATION: (1)..(774)

<400> SEQUENCE: 149

```
atg agg tcc tgc ctg tgg aga tgc agg cac ctg agc caa ggc gtc cag      48
Met Arg Ser Cys Leu Trp Arg Cys Arg His Leu Ser Gln Gly Val Gln
1               5                   10                  15 tgg tcc ttg ctt ctg gct gtc ctg gtc ttc ttt ctc ttc gcc ttg ccc      96
Trp Ser Leu Leu Leu Ala Val Leu Val Phe Phe Leu Phe Ala Leu Pro
            20                  25                  30 tct ttt att aag gag cct caa aca aag cct tcc agg cat caa cgc aca     144
Ser Phe Ile Lys Glu Pro Gln Thr Lys Pro Ser Arg His Gln Arg Thr
        35                  40                  45 gag aac att aaa gaa agg tct cta cag tcc ctg gca aag cct aag tcc     192
Glu Asn Ile Lys Glu Arg Ser Leu Gln Ser Leu Ala Lys Pro Lys Ser
    50                  55                  60 cag gca ccc aca agg gca agg agg aca acc atc tat gca gag cca gtg     240
Gln Ala Pro Thr Arg Ala Arg Arg Thr Thr Ile Tyr Ala Glu Pro Val
65                  70                  75                  80 cca gag aac aat gcc ctc aac aca caa acc cag ccc aag gcc cac acc     288
Pro Glu Asn Asn Ala Leu Asn Thr Gln Thr Gln Pro Lys Ala His Thr
                85                  90                  95 acc gga gac aga gga aag gag gcc aac cag gca ccg ccg gag gag cag     336
Thr Gly Asp Arg Gly Lys Glu Ala Asn Gln Ala Pro Pro Glu Glu Gln
            100                 105                 110 gac aag gtg ccc cac aca gca cag agg gca gca tgg aag agc cca gaa     384
Asp Lys Val Pro His Thr Ala Gln Arg Ala Ala Trp Lys Ser Pro Glu
        115                 120                 125 aaa gag aaa acc atg gtg aac aca ctg tca ccc aga ggg caa gat gca     432
Lys Glu Lys Thr Met Val Asn Thr Leu Ser Pro Arg Gly Gln Asp Ala
    130                 135                 140
```

```
ggg atg gcc tct ggc agg aca gag gca caa tca tgg aag agc cag gac    480
Gly Met Ala Ser Gly Arg Thr Glu Ala Gln Ser Trp Lys Ser Gln Asp
145             150                 155                 160 aca aag acg acc caa gga aat ggc ggc cag acc agg aag ctg acg gcc    528
Thr Lys Thr Thr Gln Gly Asn Gly Gly Gln Thr Arg Lys Leu Thr Ala
                165                 170                 175 tcc agg acg gtg tca gag aag cac cag ggc aaa gcg gca acc aca gcc    576
Ser Arg Thr Val Ser Glu Lys His Gln Gly Lys Ala Ala Thr Thr Ala
            180                 185                 190 aag acg ctc att ccc aaa agt cag cac aga atg ctg gct ccc aca gga    624
Lys Thr Leu Ile Pro Lys Ser Gln His Arg Met Leu Ala Pro Thr Gly
        195                 200                 205 gca gtg tca aca agg acg aga cag aaa gga gtg acc aca gca gtc atc    672
Ala Val Ser Thr Arg Thr Arg Gln Lys Gly Val Thr Thr Ala Val Ile
    210                 215                 220 cca cct aag gag aag aaa cct cag gcc acc cca ccc cct gcc cct ttc    720
Pro Pro Lys Glu Lys Lys Pro Gln Ala Thr Pro Pro Pro Ala Pro Phe
225                 230                 235                 240 cag agc ccc acg acg cag aga aac caa aga ctg aag gcc gcc aac ttc    768
Gln Ser Pro Thr Thr Gln Arg Asn Gln Arg Leu Lys Ala Ala Asn Phe
                245                 250                 255 aaa tct                                                             774
Lys Ser

<210> SEQ ID NO 150
<211> LENGTH: 258
<212> TYPE: PRT
<213> ORGANISM: Artificial
<220> FEATURE:
<223> OTHER INFORMATION: Synthetic Construct

<400> SEQUENCE: 150

Met Arg Ser Cys Leu Trp Arg Cys Arg His Leu Ser Gln Gly Val Gln
1               5                   10                  15

Trp Ser Leu Leu Leu Ala Val Leu Val Phe Leu Phe Ala Leu Pro
            20                  25                  30

Ser Phe Ile Lys Glu Pro Gln Thr Lys Pro Ser Arg His Gln Arg Thr
        35                  40                  45

Glu Asn Ile Lys Glu Arg Ser Leu Gln Ser Leu Ala Lys Pro Lys Ser
    50                  55                  60

Gln Ala Pro Thr Arg Ala Arg Arg Thr Thr Ile Tyr Ala Glu Pro Val
65                  70                  75                  80

Pro Glu Asn Asn Ala Leu Asn Thr Gln Thr Gln Pro Lys Ala His Thr
                85                  90                  95

Thr Gly Asp Arg Gly Lys Glu Ala Asn Gln Ala Pro Glu Glu Gln
            100                 105                 110

Asp Lys Val Pro His Thr Ala Gln Arg Ala Ala Trp Lys Ser Pro Glu
        115                 120                 125

Lys Glu Lys Thr Met Val Asn Thr Leu Ser Pro Arg Gly Gln Asp Ala
    130                 135                 140

Gly Met Ala Ser Gly Arg Thr Glu Ala Gln Ser Trp Lys Ser Gln Asp
145                 150                 155                 160

Thr Lys Thr Thr Gln Gly Asn Gly Gly Gln Thr Arg Lys Leu Thr Ala
                165                 170                 175

Ser Arg Thr Val Ser Glu Lys His Gln Gly Lys Ala Ala Thr Thr Ala
            180                 185                 190

Lys Thr Leu Ile Pro Lys Ser Gln His Arg Met Leu Ala Pro Thr Gly
```

```
            195                 200                 205
Ala Val Ser Thr Arg Thr Arg Gln Lys Gly Val Thr Thr Ala Val Ile
        210                 215                 220

Pro Pro Lys Glu Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
                245                 250                 255

Lys Ser

<210> SEQ ID NO 151
<211> LENGTH: 138
<212> TYPE: DNA
<213> ORGANISM: Artificial
<220> FEATURE:
<223> OTHER INFORMATION: Nucleotides 1-138 of SEQ ID NO : 21,
<220> FEATURE:
<221> NAME/KEY: CDS
<222> LOCATION: (1)..(138)

<400> SEQUENCE: 151 atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg aag cta cac tta      96
Phe Leu Val Leu Gly Phe Leu Tyr Tyr Ser Ala Trp Lys Leu His Leu
            20                  25                  30 ctc cag tgg gag gag gac tcc agt aag tat agt cac tct agc              138
Leu Gln Trp Glu Glu Asp Ser Ser Lys Tyr Ser His Ser Ser
        35                  40                  45

<210> SEQ ID NO 152
<211> LENGTH: 46
<212> TYPE: PRT
<213> ORGANISM: Artificial
<220> FEATURE:
<223> OTHER INFORMATION: Synthetic Construct

<400> SEQUENCE: 152

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Ser Lys Tyr Ser His Ser Ser
        35                  40                  45

<210> SEQ ID NO 153
<211> LENGTH: 138
<212> TYPE: DNA
<213> ORGANISM: Artificial
<220> FEATURE:
<223> OTHER INFORMATION: Nucleotides 1-138 of SEQ ID NO : 29
<220> FEATURE:
<221> NAME/KEY: CDS
<222> LOCATION: (1)..(138)

<400> SEQUENCE: 153 atg gga ctc ttg gta ttt gta cgc aac ctg ctg cta gcc ctc tgc ctc      48
Met Gly Leu Leu Val Phe Val Arg Asn Leu Leu Leu Ala Leu Cys Leu
1               5                   10                  15 ttt ctg gtc ctg gga ttt ttg tat tat tct gcc tgg aag cta cac tta      96
Phe Leu Val Leu Gly Phe Leu Tyr Tyr Ser Ala Trp Lys Leu His Leu
            20                  25                  30 ctc caa tgg gaa gac tcc aat tca ctg att ctt tcc ctt gac             138
```

-continued

Leu Gln Trp Glu Asp Ser Asn Ser Leu Ile Leu Ser Leu Asp
          35                  40                  45

<210> SEQ ID NO 154
<211> LENGTH: 46
<212> TYPE: PRT
<213> ORGANISM: Artificial
<220> FEATURE:
<223> OTHER INFORMATION: Synthetic Construct

<400> SEQUENCE: 154

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Asp Ser Asn Ser Leu Ile Leu Ser Leu Asp
          35                  40                  45

<210> SEQ ID NO 155
<211> LENGTH: 237
<212> TYPE: DNA
<213> ORGANISM: Artificial
<220> FEATURE:
<223> OTHER INFORMATION: Nucleotides 1-237 of SEQ ID NO : 33
<220> FEATURE:
<221> NAME/KEY: CDS
<222> LOCATION: (1)..(237)

<400> SEQUENCE: 155 atg cag ctg cag ttc cgg agc tgg atg ctg gcc gcg ctc acg ctg ctc      48
Met Gln Leu Gln Phe Arg Ser Trp Met Leu Ala Ala Leu Thr Leu Leu
1               5                   10                  15 gtg gtc ttc ctc atc ttc gca gac atc tca gag atc gaa gaa gaa atc      96
Val Val Phe Leu Ile Phe Ala Asp Ile Ser Glu Ile Glu Glu Glu Ile
            20                  25                  30 ggg aat tcg gga ggc aga ggt aca atc aga tca gct gtg aac agc tta     144
Gly Asn Ser Gly Gly Arg Gly Thr Ile Arg Ser Ala Val Asn Ser Leu
        35                  40                  45 cat agc aaa tct aat aga gct gaa gtt gta ata aac ggc tcc tca tca     192
His Ser Lys Ser Asn Arg Ala Glu Val Val Ile Asn Gly Ser Ser Ser
    50                  55                  60 cca gct gtt gtt gac aga agt aat gaa agc atc aag cac aac atc         237
Pro Ala Val Val Asp Arg Ser Asn Glu Ser Ile Lys His Asn Ile
65                  70                  75

<210> SEQ ID NO 156
<211> LENGTH: 79
<212> TYPE: PRT
<213> ORGANISM: Artificial
<220> FEATURE:
<223> OTHER INFORMATION: Synthetic Construct

<400> SEQUENCE: 156

Met Gln Leu Gln Phe Arg Ser Trp Met Leu Ala Ala Leu Thr Leu Leu
1               5                   10                  15

Val Val Phe Leu Ile Phe Ala Asp Ile Ser Glu Ile Glu Glu Glu Ile
            20                  25                  30

Gly Asn Ser Gly Gly Arg Gly Thr Ile Arg Ser Ala Val Asn Ser Leu
        35                  40                  45

His Ser Lys Ser Asn Arg Ala Glu Val Val Ile Asn Gly Ser Ser Ser
    50                  55                  60

Pro Ala Val Val Asp Arg Ser Asn Glu Ser Ile Lys His Asn Ile
65                  70                  75

<210> SEQ ID NO 157
<211> LENGTH: 201
<212> TYPE: DNA
<213> ORGANISM: Artificial
<220> FEATURE:
<223> OTHER INFORMATION: Nucleotides 1-201 of SEQ ID NO : 37
<220> FEATURE:
<221> NAME/KEY: CDS
<222> LOCATION: (1)..(201)

<400> SEQUENCE: 157

```
atg cgc tcc att agg aag agg tgg acg atc tgc aca ata agt ctg ctc      48
Met Arg Ser Ile Arg Lys Arg Trp Thr Ile Cys Thr Ile Ser Leu Leu
1               5                   10                  15 ctg atc ttt tat aag aca aaa gaa ata gca aga act gag gag cac cag      96
Leu Ile Phe Tyr Lys Thr Lys Glu Ile Ala Arg Thr Glu Glu His Gln
            20                  25                  30 gag acg caa ctc atc gga gat ggt gaa ttg tct ttg agt cgg tca ctt     144
Glu Thr Gln Leu Ile Gly Asp Gly Glu Leu Ser Leu Ser Arg Ser Leu
        35                  40                  45 gtc aat agc tct gat aaa atc att cga aag gct ggc tct tca atc ttc     192
Val Asn Ser Ser Asp Lys Ile Ile Arg Lys Ala Gly Ser Ser Ile Phe
    50                  55                  60 cag cac aat                                                         201
Gln His Asn
65
```

<210> SEQ ID NO 158
<211> LENGTH: 67
<212> TYPE: PRT
<213> ORGANISM: Artificial
<220> FEATURE:
<223> OTHER INFORMATION: Synthetic Construct

<400> SEQUENCE: 158

```
Met Arg Ser Ile Arg Lys Arg Trp Thr Ile Cys Thr Ile Ser Leu Leu
1               5                   10                  15

Leu Ile Phe Tyr Lys Thr Lys Glu Ile Ala Arg Thr Glu Glu His Gln
            20                  25                  30

Glu Thr Gln Leu Ile Gly Asp Gly Glu Leu Ser Leu Ser Arg Ser Leu
        35                  40                  45

Val Asn Ser Ser Asp Lys Ile Ile Arg Lys Ala Gly Ser Ser Ile Phe
    50                  55                  60

Gln His Asn
65
```

<210> SEQ ID NO 159
<211> LENGTH: 198
<212> TYPE: DNA
<213> ORGANISM: Artificial
<220> FEATURE:
<223> OTHER INFORMATION: Fusion of the nucleotide sequence SEQ ID NO:
      161 with the nucleotide sequence SEQ ID NO: 131
<220> FEATURE:
<221> NAME/KEY: CDS
<222> LOCATION: (1)..(198)

<400> SEQUENCE: 159

```
atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg gag cct caa aca      96
Phe Leu Val Leu Gly Phe Leu Tyr Tyr Ser Ala Trp Glu Pro Gln Thr
```

```
aag cct tcc agg cat caa cgc aca gag aac att aaa gaa agg tct cta    144
Lys Pro Ser Arg His Gln Arg Thr Glu Asn Ile Lys Glu Arg Ser Leu
         35                  40                  45 cag tcc ctg gca aag cct aag tcc cag gca ccc aca agg gca agg agg    192
Gln Ser Leu Ala Lys Pro Lys Ser Gln Ala Pro Thr Arg Ala Arg Arg
 50                  55                  60 aca acc                                                             198
Thr Thr
 65

<210> SEQ ID NO 160
<211> LENGTH: 66
<212> TYPE: PRT
<213> ORGANISM: Artificial
<220> FEATURE:
<223> OTHER INFORMATION: Synthetic Construct

<400> SEQUENCE: 160

Met Gly Leu Leu Val Phe Val Arg Asn Leu Leu Ala Leu Cys Leu
 1               5                  10                  15

Phe Leu Val Leu Gly Phe Leu Tyr Tyr Ser Ala Trp Glu Pro Gln Thr
             20                  25                  30

Lys Pro Ser Arg His Gln Arg Thr Glu Asn Ile Lys Glu Arg Ser Leu
         35                  40                  45

Gln Ser Leu Ala Lys Pro Lys Ser Gln Ala Pro Thr Arg Ala Arg Arg
 50                  55                  60

Thr Thr
 65

<210> SEQ ID NO 161
<211> LENGTH: 1179
<212> TYPE: DNA
<213> ORGANISM: Artificial
<220> FEATURE:
<223> OTHER INFORMATION: Fusion of the nucleotide sequence SEQ ID NO:
      145 with the nucleotide sequence SEQ ID NO: 43
<220> FEATURE:
<221> NAME/KEY: CDS
<222> LOCATION: (1)..(1179)

<400> SEQUENCE: 161 atg agg tcc tgc ctg tgg aga tgc agg cac ctg agc caa ggc gtc cag     48
Met Arg Ser Cys Leu Trp Arg Cys Arg His Leu Ser Gln Gly Val Gln
 1               5                  10                  15 tgg tcc ttg ctt ctg gct gtc ctg gtc ttc ttt ctc ttc gcc ttg ccc     96
Trp Ser Leu Leu Leu Ala Val Leu Val Phe Phe Leu Phe Ala Leu Pro
             20                  25                  30 tct ttt att aag gag cct caa aca aag cct tcc agg cat caa cgc aca    144
Ser Phe Ile Lys Glu Pro Gln Thr Lys Pro Ser Arg His Gln Arg Thr
         35                  40                  45 gag aac att aaa gaa agg tct cta cag tcc ctg gca aag cct aag tcc    192
Glu Asn Ile Lys Glu Arg Ser Leu Gln Ser Leu Ala Lys Pro Lys Ser
 50                  55                  60 cag gca ccc aca agg gca agg agg aca acc gga tcc gag gcc tcc ttc    240
Gln Ala Pro Thr Arg Ala Arg Arg Thr Thr Gly Ser Glu Ala Ser Phe
 65                  70                  75                  80 cag gtg tgg aac aag gac agc tct tcc aaa aac ctt atc cct agg ctg    288
Gln Val Trp Asn Lys Asp Ser Ser Ser Lys Asn Leu Ile Pro Arg Leu
                 85                  90                  95 caa aag atc tgg aag aat tac cta agc atg aac aag tac aaa gtg tcc    336
Gln Lys Ile Trp Lys Asn Tyr Leu Ser Met Asn Lys Tyr Lys Val Ser
```

```
                100                 105                 110
tac aag ggg cca gga cca ggc atc aag ttc agt gca gag gcc ctg cgc    384
Tyr Lys Gly Pro Gly Pro Gly Ile Lys Phe Ser Ala Glu Ala Leu Arg
        115                 120                 125 tgc cac ctc cgg gac cat gtg aat gta tcc atg gta gag gtc aca gat    432
Cys His Leu Arg Asp His Val Asn Val Ser Met Val Glu Val Thr Asp
130                 135                 140 ttt ccc ttc aat acc tct gaa tgg gag ggt tat ctg ccc aag gag agc    480
Phe Pro Phe Asn Thr Ser Glu Trp Glu Gly Tyr Leu Pro Lys Glu Ser
145                 150                 155                 160 att agg acc aag gct ggg cct tgg ggc agg tgt gct gtt gtg tcg tca    528
Ile Arg Thr Lys Ala Gly Pro Trp Gly Arg Cys Ala Val Val Ser Ser
            165                 170                 175 gcg gga tct ctg aag tcc tcc caa cta ggc aga gaa atc gat gat cat    576
Ala Gly Ser Leu Lys Ser Ser Gln Leu Gly Arg Glu Ile Asp Asp His
        180                 185                 190 gac gca gtc ctg agg ttt aat ggg gca ccc aca gcc aac ttc caa caa    624
Asp Ala Val Leu Arg Phe Asn Gly Ala Pro Thr Ala Asn Phe Gln Gln
    195                 200                 205 gat gtg ggc aca aaa act acc att cgc ctg atg aac tct cag ttg gtt    672
Asp Val Gly Thr Lys Thr Thr Ile Arg Leu Met Asn Ser Gln Leu Val
210                 215                 220 acc aca gag aag cgc ttc ctc aaa gac agt ttg tac aat gaa gga atc    720
Thr Thr Glu Lys Arg Phe Leu Lys Asp Ser Leu Tyr Asn Glu Gly Ile
225                 230                 235                 240 cta att gta tgg gac cca tct gta tac cac tca gat atc cca aag tgg    768
Leu Ile Val Trp Asp Pro Ser Val Tyr His Ser Asp Ile Pro Lys Trp
            245                 250                 255 tac cag aat ccg gat tat aat ttc ttt aac aac tac aag act tat cgt    816
Tyr Gln Asn Pro Asp Tyr Asn Phe Phe Asn Asn Tyr Lys Thr Tyr Arg
        260                 265                 270 aag ctg cac ccc aat cag ccc ttt tac atc ctc aag ccc cag atg cct    864
Lys Leu His Pro Asn Gln Pro Phe Tyr Ile Leu Lys Pro Gln Met Pro
    275                 280                 285 tgg gag cta tgg gac att ctt caa gaa atc tcc cca gaa gag att cag    912
Trp Glu Leu Trp Asp Ile Leu Gln Glu Ile Ser Pro Glu Glu Ile Gln
290                 295                 300 cca aac ccc cca tcc tct ggg atg ctt ggt atc atc atc atg atg acg    960
Pro Asn Pro Pro Ser Ser Gly Met Leu Gly Ile Ile Ile Met Met Thr
305                 310                 315                 320 ctg tgt gac cag gtg gat att tat gag ttc ctc cca tcc aag cgc aag   1008
Leu Cys Asp Gln Val Asp Ile Tyr Glu Phe Leu Pro Ser Lys Arg Lys
            325                 330                 335 act gac gtg tgc tac tac tac cag aag ttc ttc gat agt gcc tgc acg   1056
Thr Asp Val Cys Tyr Tyr Tyr Gln Lys Phe Phe Asp Ser Ala Cys Thr
        340                 345                 350 atg ggt gcc tac cac ccg ctg ctc tat gag aag aat ttg gtg aag cat   1104
Met Gly Ala Tyr His Pro Leu Leu Tyr Glu Lys Asn Leu Val Lys His
    355                 360                 365 ctc aac cag ggc aca gat gag gac atc tac ctg ctt gga aaa gcc aca   1152
Leu Asn Gln Gly Thr Asp Glu Asp Ile Tyr Leu Leu Gly Lys Ala Thr
370                 375                 380 ctg cct ggc ttc cgg acc att cac tgc                                1179
Leu Pro Gly Phe Arg Thr Ile His Cys
385                 390

<210> SEQ ID NO 162
<211> LENGTH: 393
<212> TYPE: PRT
<213> ORGANISM: Artificial
```

```
<220> FEATURE:
<223> OTHER INFORMATION: Synthetic Construct

<400> SEQUENCE: 162

Met Arg Ser Cys Leu Trp Arg Cys Arg His Leu Ser Gln Gly Val Gln
1               5                   10                  15

Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
            35                  40                  45

Glu Asn Ile Lys Glu Arg Ser Leu Gln Ser Leu Ala Lys Pro Lys Ser
50                  55                  60

Gln Ala Pro Thr Arg Ala Arg Arg Thr Thr Gly Ser Glu Ala Ser Phe
65                  70                  75                  80

Gln Val Trp Asn Lys Asp Ser Ser Lys Asn Leu Ile Pro Arg Leu
                85                  90                  95

Gln Lys Ile Trp Lys Asn Tyr Leu Ser Met Asn Lys Tyr Lys Val Ser
            100                 105                 110

Tyr Lys Gly Pro Gly Pro Gly Ile Lys Phe Ser Ala Glu Ala Leu Arg
            115                 120                 125

Cys His Leu Arg Asp His Val Asn Val Ser Met Val Glu Val Thr Asp
        130                 135                 140

Phe Pro Phe Asn Thr Ser Glu Trp Glu Gly Tyr Leu Pro Lys Glu Ser
145                 150                 155                 160

Ile Arg Thr Lys Ala Gly Pro Trp Gly Arg Cys Ala Val Val Ser Ser
                165                 170                 175

Ala Gly Ser Leu Lys Ser Ser Gln Leu Gly Arg Glu Ile Asp Asp His
            180                 185                 190

Asp Ala Val Leu Arg Phe Asn Gly Ala Pro Thr Ala Asn Phe Gln Gln
        195                 200                 205

Asp Val Gly Thr Lys Thr Thr Ile Arg Leu Met Asn Ser Gln Leu Val
        210                 215                 220

Thr Thr Glu Lys Arg Phe Leu Lys Asp Ser Leu Tyr Asn Glu Gly Ile
225                 230                 235                 240

Leu Ile Val Trp Asp Pro Ser Val Tyr His Ser Asp Ile Pro Lys Trp
                245                 250                 255

Tyr Gln Asn Pro Asp Tyr Asn Phe Phe Asn Asn Tyr Lys Thr Tyr Arg
            260                 265                 270

Lys Leu His Pro Asn Gln Pro Phe Tyr Ile Leu Lys Pro Gln Met Pro
        275                 280                 285

Trp Glu Leu Trp Asp Ile Leu Gln Glu Ile Ser Pro Glu Glu Ile Gln
        290                 295                 300

Pro Asn Pro Pro Ser Ser Gly Met Leu Gly Ile Ile Ile Met Met Thr
305                 310                 315                 320

Leu Cys Asp Gln Val Asp Ile Tyr Glu Phe Leu Pro Ser Lys Arg Lys
                325                 330                 335

Thr Asp Val Cys Tyr Tyr Tyr Gln Lys Phe Phe Asp Ser Ala Cys Thr
            340                 345                 350

Met Gly Ala Tyr His Pro Leu Leu Tyr Glu Lys Asn Leu Val Lys His
        355                 360                 365

Leu Asn Gln Gly Thr Asp Glu Asp Ile Tyr Leu Leu Gly Lys Ala Thr
        370                 375                 380

Leu Pro Gly Phe Arg Thr Ile His Cys
385                 390
```

<210> SEQ ID NO 163
<211> LENGTH: 1377
<212> TYPE: DNA
<213> ORGANISM: Artificial
<220> FEATURE:
<223> OTHER INFORMATION: Fusion of the nucleotide sequence SEQ ID NO: 147 with the nucleotide sequence SEQ ID NO: 43
<220> FEATURE:
<221> NAME/KEY: CDS
<222> LOCATION: (1)..(1377)

<400> SEQUENCE: 163

```
atg agg tcc tgc ctg tgg aga tgc agg cac ctg agc caa ggc gtc cag        48
Met Arg Ser Cys Leu Trp Arg Cys Arg His Leu Ser Gln Gly Val Gln
1               5                   10                  15 tgg tcc ttg ctt ctg gct gtc ctg gtc ttc ttt ctc ttc gcc ttg ccc        96
Trp Ser Leu Leu Leu Ala Val Leu Val Phe Phe Leu Phe Ala Leu Pro
                20                  25                  30 tct ttt att aag gag cct caa aca aag cct tcc agg cat caa cgc aca       144
Ser Phe Ile Lys Glu Pro Gln Thr Lys Pro Ser Arg His Gln Arg Thr
        35                  40                  45 gag aac att aaa gaa agg tct cta cag tcc ctg gca aag cct aag tcc       192
Glu Asn Ile Lys Glu Arg Ser Leu Gln Ser Leu Ala Lys Pro Lys Ser
    50                  55                  60 cag gca ccc aca agg gca agg agg aca acc atc tat gca gag cca gtg       240
Gln Ala Pro Thr Arg Ala Arg Arg Thr Thr Ile Tyr Ala Glu Pro Val
65                  70                  75                  80 cca gag aac aat gcc ctc aac aca caa acc cag ccc aag gcc cac acc       288
Pro Glu Asn Asn Ala Leu Asn Thr Gln Thr Gln Pro Lys Ala His Thr
                85                  90                  95 acc gga gac aga gga aag gag gcc aac cag gca ccg ccg gag gag cag       336
Thr Gly Asp Arg Gly Lys Glu Ala Asn Gln Ala Pro Pro Glu Glu Gln
            100                 105                 110 gac aag gtg ccc cac aca gca cag agg gca gca tgg aag agc cca gaa       384
Asp Lys Val Pro His Thr Ala Gln Arg Ala Ala Trp Lys Ser Pro Glu
        115                 120                 125 aaa gag aaa acc atg gtg aac aca ctg tca ccc aga gga tcc gag gcc       432
Lys Glu Lys Thr Met Val Asn Thr Leu Ser Pro Arg Gly Ser Glu Ala
    130                 135                 140 tcc ttc cag gtg tgg aac aag gac agc tct tcc aaa aac ctt atc cct       480
Ser Phe Gln Val Trp Asn Lys Asp Ser Ser Ser Lys Asn Leu Ile Pro
145                 150                 155                 160 agg ctg caa aag atc tgg aag aat tac cta agc atg aac aag tac aaa       528
Arg Leu Gln Lys Ile Trp Lys Asn Tyr Leu Ser Met Asn Lys Tyr Lys
                165                 170                 175 gtg tcc tac aag ggg cca gga cca ggc atc aag ttc agt gca gag gcc       576
Val Ser Tyr Lys Gly Pro Gly Pro Gly Ile Lys Phe Ser Ala Glu Ala
            180                 185                 190 ctg cgc tgc cac ctc cgg gac cat gtg aat gta tcc atg gta gag gtc       624
Leu Arg Cys His Leu Arg Asp His Val Asn Val Ser Met Val Glu Val
        195                 200                 205 aca gat ttt ccc ttc aat acc tct gaa tgg gag ggt tat ctg ccc aag       672
Thr Asp Phe Pro Phe Asn Thr Ser Glu Trp Glu Gly Tyr Leu Pro Lys
    210                 215                 220 gag agc att agg acc aag gct ggg cct tgg ggc agg tgt gct gtt gtg       720
Glu Ser Ile Arg Thr Lys Ala Gly Pro Trp Gly Arg Cys Ala Val Val
225                 230                 235                 240 tcg tca gcg gga tct ctg aag tcc tcc caa cta ggc aga gaa atc gat       768
Ser Ser Ala Gly Ser Leu Lys Ser Ser Gln Leu Gly Arg Glu Ile Asp
                245                 250                 255
```

```
gat cat gac gca gtc ctg agg ttt aat ggg gca ccc aca gcc aac ttc     816
Asp His Asp Ala Val Leu Arg Phe Asn Gly Ala Pro Thr Ala Asn Phe
            260                 265                 270 caa caa gat gtg ggc aca aaa act acc att cgc ctg atg aac tct cag     864
Gln Gln Asp Val Gly Thr Lys Thr Thr Ile Arg Leu Met Asn Ser Gln
            275                 280                 285 ttg gtt acc aca gag aag cgc ttc ctc aaa gac agt ttg tac aat gaa     912
Leu Val Thr Thr Glu Lys Arg Phe Leu Lys Asp Ser Leu Tyr Asn Glu
        290                 295                 300 gga atc cta att gta tgg gac cca tct gta tac cac tca gat atc cca     960
Gly Ile Leu Ile Val Trp Asp Pro Ser Val Tyr His Ser Asp Ile Pro
305                 310                 315                 320 aag tgg tac cag aat ccg gat tat aat ttc ttt aac aac tac aag act    1008
Lys Trp Tyr Gln Asn Pro Asp Tyr Asn Phe Phe Asn Asn Tyr Lys Thr
                325                 330                 335 tat cgt aag ctg cac ccc aat cag ccc ttt tac atc ctc aag ccc cag    1056
Tyr Arg Lys Leu His Pro Asn Gln Pro Phe Tyr Ile Leu Lys Pro Gln
            340                 345                 350 atg cct tgg gag cta tgg gac att ctt caa gaa atc tcc cca gaa gag    1104
Met Pro Trp Glu Leu Trp Asp Ile Leu Gln Glu Ile Ser Pro Glu Glu
            355                 360                 365 att cag cca aac ccc cca tcc tct ggg atg ctt ggt atc atc atc atg    1152
Ile Gln Pro Asn Pro Pro Ser Ser Gly Met Leu Gly Ile Ile Ile Met
370                 375                 380 atg acg ctg tgt gac cag gtg gat att tat gag ttc ctc cca tcc aag    1200
Met Thr Leu Cys Asp Gln Val Asp Ile Tyr Glu Phe Leu Pro Ser Lys
385                 390                 395                 400 cgc aag act gac gtg tgc tac tac tac cag aag ttc ttc gat agt gcc    1248
Arg Lys Thr Asp Val Cys Tyr Tyr Tyr Gln Lys Phe Phe Asp Ser Ala
            405                 410                 415 tgc acg atg ggt gcc tac cac ccg ctc ctc tat gag aag aat ttg gtg    1296
Cys Thr Met Gly Ala Tyr His Pro Leu Leu Tyr Glu Lys Asn Leu Val
            420                 425                 430 aag cat ctc aac cag ggc aca gat gag gac atc tac ctg ctt gga aaa    1344
Lys His Leu Asn Gln Gly Thr Asp Glu Asp Ile Tyr Leu Leu Gly Lys
            435                 440                 445 gcc aca ctg cct ggc ttc cgg acc att cac tgc                        1377
Ala Thr Leu Pro Gly Phe Arg Thr Ile His Cys
    450                 455

<210> SEQ ID NO 164
<211> LENGTH: 459
<212> TYPE: PRT
<213> ORGANISM: Artificial
<220> FEATURE:
<223> OTHER INFORMATION: Synthetic Construct

<400> SEQUENCE: 164

Met Arg Ser Cys Leu Trp Arg Cys Arg His Leu Ser Gln Gly Val Gln
1               5                   10                  15

Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
        35                  40                  45

Glu Asn Ile Lys Glu Arg Ser Leu Gln Ser Leu Ala Lys Pro Lys Ser
    50                  55                  60

Gln Ala Pro Thr Arg Ala Arg Arg Thr Thr Ile Tyr Ala Glu Pro Val
65                  70                  75                  80

Pro Glu Asn Asn Ala Leu Asn Thr Gln Thr Gln Pro Lys Ala His Thr
            85                  90                  95
```

```
Thr Gly Asp Arg Gly Lys Glu Ala Asn Gln Ala Pro Glu Glu Gln
            100                 105                 110

Asp Lys Val Pro His Thr Ala Gln Arg Ala Ala Trp Lys Ser Pro Glu
            115                 120                 125

Lys Glu Lys Thr Met Val Asn Thr Leu Ser Pro Arg Gly Ser Glu Ala
            130                 135                 140

Ser Phe Gln Val Trp Asn Lys Asp Ser Ser Lys Asn Leu Ile Pro
145                 150                 155                 160

Arg Leu Gln Lys Ile Trp Lys Asn Tyr Leu Ser Met Asn Lys Tyr Lys
                165                 170                 175

Val Ser Tyr Lys Gly Pro Gly Pro Gly Ile Lys Phe Ser Ala Glu Ala
            180                 185                 190

Leu Arg Cys His Leu Arg Asp His Val Asn Val Ser Met Val Glu Val
            195                 200                 205

Thr Asp Phe Pro Phe Asn Thr Ser Glu Trp Glu Gly Tyr Leu Pro Lys
            210                 215                 220

Glu Ser Ile Arg Thr Lys Ala Gly Pro Trp Gly Arg Cys Ala Val Val
225                 230                 235                 240

Ser Ser Ala Gly Ser Leu Lys Ser Ser Gln Leu Gly Arg Glu Ile Asp
                245                 250                 255

Asp His Asp Ala Val Leu Arg Phe Asn Gly Ala Pro Thr Ala Asn Phe
            260                 265                 270

Gln Gln Asp Val Gly Thr Lys Thr Thr Ile Arg Leu Met Asn Ser Gln
            275                 280                 285

Leu Val Thr Thr Glu Lys Arg Phe Leu Lys Asp Ser Leu Tyr Asn Glu
            290                 295                 300

Gly Ile Leu Ile Val Trp Asp Pro Ser Val Tyr His Ser Asp Ile Pro
305                 310                 315                 320

Lys Trp Tyr Gln Asn Pro Asp Tyr Asn Phe Phe Asn Tyr Lys Thr
                325                 330                 335

Tyr Arg Lys Leu His Pro Asn Gln Pro Phe Tyr Ile Leu Lys Pro Gln
            340                 345                 350

Met Pro Trp Glu Leu Trp Asp Ile Leu Gln Glu Ile Ser Pro Glu Glu
            355                 360                 365

Ile Gln Pro Asn Pro Pro Ser Ser Gly Met Leu Gly Ile Ile Ile Met
370                 375                 380

Met Thr Leu Cys Asp Gln Val Asp Ile Tyr Glu Phe Leu Pro Ser Lys
385                 390                 395                 400

Arg Lys Thr Asp Val Cys Tyr Tyr Tyr Gln Lys Phe Phe Asp Ser Ala
                405                 410                 415

Cys Thr Met Gly Ala Tyr His Pro Leu Leu Tyr Glu Lys Asn Leu Val
            420                 425                 430

Lys His Leu Asn Gln Gly Thr Asp Glu Asp Ile Tyr Leu Leu Gly Lys
            435                 440                 445

Ala Thr Leu Pro Gly Phe Arg Thr Ile His Cys
            450                 455

<210> SEQ ID NO 165
<211> LENGTH: 1731
<212> TYPE: DNA
<213> ORGANISM: Artificial
<220> FEATURE:
<223> OTHER INFORMATION: Fusion of the nucleotide sequence SEQ ID NO:
      149 with the nucleotide sequence SEQ ID NO : 43
<220> FEATURE:
```

<221> NAME/KEY: CDS
<222> LOCATION: (1)..(1731)

<400> SEQUENCE: 165

| | | | | | | | | | | | | | | | | |
|---|---|---|---|---|---|---|---|---|---|---|---|---|---|---|---|---|
| atg | agg | tcc | tgc | ctg | tgg | aga | tgc | agg | cac | ctg | agc | caa | ggc | gtc | cag | 48 |
| Met | Arg | Ser | Cys | Leu | Trp | Arg | Cys | Arg | His | Leu | Ser | Gln | Gly | Val | Gln | |
| 1 | | | | 5 | | | | | 10 | | | | | 15 | | |
| tgg | tcc | ttg | ctt | ctg | gct | gtc | ctg | gtc | ttc | ttt | ctc | ttc | gcc | ttg | ccc | 96 |
| Trp | Ser | Leu | Leu | Leu | Ala | Val | Leu | Val | Phe | Phe | Leu | Phe | Ala | Leu | Pro | |
| | | | 20 | | | | | 25 | | | | | 30 | | | |
| tct | ttt | att | aag | gag | cct | caa | aca | aag | cct | tcc | agg | cat | caa | cgc | aca | 144 |
| Ser | Phe | Ile | Lys | Glu | Pro | Gln | Thr | Lys | Pro | Ser | Arg | His | Gln | Arg | Thr | |
| | | | 35 | | | | | 40 | | | | | 45 | | | |
| gag | aac | att | aaa | gaa | agg | tct | cta | cag | tcc | ctg | gca | aag | cct | aag | tcc | 192 |
| Glu | Asn | Ile | Lys | Glu | Arg | Ser | Leu | Gln | Ser | Leu | Ala | Lys | Pro | Lys | Ser | |
| | 50 | | | | | 55 | | | | | 60 | | | | | |
| cag | gca | ccc | aca | agg | gca | agg | agg | aca | acc | atc | tat | gca | gag | cca | gtg | 240 |
| Gln | Ala | Pro | Thr | Arg | Ala | Arg | Arg | Thr | Thr | Ile | Tyr | Ala | Glu | Pro | Val | |
| 65 | | | | | 70 | | | | | 75 | | | | | 80 | |
| cca | gag | aac | aat | gcc | ctc | aac | aca | caa | acc | cag | ccc | aag | gcc | cac | acc | 288 |
| Pro | Glu | Asn | Asn | Ala | Leu | Asn | Thr | Gln | Thr | Gln | Pro | Lys | Ala | His | Thr | |
| | | | | 85 | | | | | 90 | | | | | 95 | | |
| acc | gga | gac | aga | gga | aag | gag | gcc | aac | cag | gca | ccg | ccg | gag | gag | cag | 336 |
| Thr | Gly | Asp | Arg | Gly | Lys | Glu | Ala | Asn | Gln | Ala | Pro | Pro | Glu | Glu | Gln | |
| | | | 100 | | | | | 105 | | | | | 110 | | | |
| gac | aag | gtg | ccc | cac | aca | gca | cag | agg | gca | gca | tgg | aag | agc | cca | gaa | 384 |
| Asp | Lys | Val | Pro | His | Thr | Ala | Gln | Arg | Ala | Ala | Trp | Lys | Ser | Pro | Glu | |
| | | | 115 | | | | | 120 | | | | | 125 | | | |
| aaa | gag | aaa | acc | atg | gtg | aac | aca | ctg | tca | ccc | aga | ggg | caa | gat | gca | 432 |
| Lys | Glu | Lys | Thr | Met | Val | Asn | Thr | Leu | Ser | Pro | Arg | Gly | Gln | Asp | Ala | |
| | 130 | | | | | 135 | | | | | 140 | | | | | |
| ggg | atg | gcc | tct | ggc | agg | aca | gag | gca | caa | tca | tgg | aag | agc | cag | gac | 480 |
| Gly | Met | Ala | Ser | Gly | Arg | Thr | Glu | Ala | Gln | Ser | Trp | Lys | Ser | Gln | Asp | |
| 145 | | | | | 150 | | | | | 155 | | | | | 160 | |
| aca | aag | acg | acc | caa | gga | aat | ggg | ggc | cag | acc | agg | aag | ctg | acg | gcc | 528 |
| Thr | Lys | Thr | Thr | Gln | Gly | Asn | Gly | Gly | Gln | Thr | Arg | Lys | Leu | Thr | Ala | |
| | | | | 165 | | | | | 170 | | | | | 175 | | |
| tcc | agg | acg | gtg | tca | gag | aag | cac | cag | ggc | aaa | gcg | gca | acc | aca | gcc | 576 |
| Ser | Arg | Thr | Val | Ser | Glu | Lys | His | Gln | Gly | Lys | Ala | Ala | Thr | Thr | Ala | |
| | | | 180 | | | | | 185 | | | | | 190 | | | |
| aag | acg | ctc | att | ccc | aaa | agt | cag | cac | aga | atg | ctg | gct | ccc | aca | gga | 624 |
| Lys | Thr | Leu | Ile | Pro | Lys | Ser | Gln | His | Arg | Met | Leu | Ala | Pro | Thr | Gly | |
| | | | 195 | | | | | 200 | | | | | 205 | | | |
| gca | gtg | tca | aca | agg | acg | aga | cag | aaa | gga | gtg | acc | aca | gca | gtc | atc | 672 |
| Ala | Val | Ser | Thr | Arg | Thr | Arg | Gln | Lys | Gly | Val | Thr | Thr | Ala | Val | Ile | |
| | 210 | | | | | 215 | | | | | 220 | | | | | |
| cca | cct | aag | gag | aag | aaa | cct | cag | gcc | acc | cca | ccc | cct | gcc | cct | ttc | 720 |
| Pro | Pro | Lys | Glu | Lys | Lys | Pro | Gln | Ala | Thr | Pro | Pro | Pro | Ala | Pro | Phe | |
| 225 | | | | | 230 | | | | | 235 | | | | | 240 | |
| cag | agc | ccc | acg | acg | cag | aga | aac | caa | aga | ctg | aag | gcc | gcc | aac | ttc | 768 |
| Gln | Ser | Pro | Thr | Thr | Gln | Arg | Asn | Gln | Arg | Leu | Lys | Ala | Ala | Asn | Phe | |
| | | | | 245 | | | | | 250 | | | | | 255 | | |
| aaa | tct | tct | aga | gag | gcc | tcc | ttc | cag | gtg | tgg | aac | aag | gac | agc | tct | 816 |
| Lys | Ser | Ser | Arg | Glu | Ala | Ser | Phe | Gln | Val | Trp | Asn | Lys | Asp | Ser | Ser | |
| | | | 260 | | | | | 265 | | | | | 270 | | | |
| tcc | aaa | aac | ctt | atc | cct | agg | ctg | caa | aag | atc | tgg | aag | aat | tac | cta | 864 |
| Ser | Lys | Asn | Leu | Ile | Pro | Arg | Leu | Gln | Lys | Ile | Trp | Lys | Asn | Tyr | Leu | |
| | | | | 275 | | | | | 280 | | | | | 285 | | |
| agc | atg | aac | aag | tac | aaa | gtg | tcc | tac | aag | ggg | cca | gga | cca | ggc | atc | 912 |
| Ser | Met | Asn | Lys | Tyr | Lys | Val | Ser | Tyr | Lys | Gly | Pro | Gly | Pro | Gly | Ile | |

```
                290                 295                 300
aag ttc agt gca gag gcc ctg cgc tgc cac ctc cgg gac cat gtg aat        960
Lys Phe Ser Ala Glu Ala Leu Arg Cys His Leu Arg Asp His Val Asn
305                 310                 315                 320 gta tcc atg gta gag gtc aca gat ttt ccc ttc aat acc tct gaa tgg       1008
Val Ser Met Val Glu Val Thr Asp Phe Pro Phe Asn Thr Ser Glu Trp
                325                 330                 335 gag ggt tat ctg ccc aag gag agc att agg acc aag gct ggg cct tgg       1056
Glu Gly Tyr Leu Pro Lys Glu Ser Ile Arg Thr Lys Ala Gly Pro Trp
            340                 345                 350 ggc agg tgt gct gtt gtg tcg tca gcg gga tct ctg aag tcc tcc caa       1104
Gly Arg Cys Ala Val Val Ser Ser Ala Gly Ser Leu Lys Ser Ser Gln
        355                 360                 365 cta gga aga gaa atc gat gat cat gac gca gtc ctg agg ttt aat ggg       1152
Leu Gly Arg Glu Ile Asp Asp His Asp Ala Val Leu Arg Phe Asn Gly
    370                 375                 380 gca ccc aca gcc aac ttc caa caa gat gtg ggc aca aaa act acc att       1200
Ala Pro Thr Ala Asn Phe Gln Gln Asp Val Gly Thr Lys Thr Thr Ile
385                 390                 395                 400 cgc ctg atg aac tct cag ttg gtt acc aca gag aag cgc ttc ctc aaa       1248
Arg Leu Met Asn Ser Gln Leu Val Thr Thr Glu Lys Arg Phe Leu Lys
                405                 410                 415 gac agt ttg tac aat gaa gga atc cta att gta tgg gac cca tct gta       1296
Asp Ser Leu Tyr Asn Glu Gly Ile Leu Ile Val Trp Asp Pro Ser Val
            420                 425                 430 tac cac tca gat atc cca aag tgg tac cag aat ccg gat tat aat ttc       1344
Tyr His Ser Asp Ile Pro Lys Trp Tyr Gln Asn Pro Asp Tyr Asn Phe
        435                 440                 445 ttt aac aac tac aag act tat cgt aag ctg cac ccc aat cag ccc ttt       1392
Phe Asn Asn Tyr Lys Thr Tyr Arg Lys Leu His Pro Asn Gln Pro Phe
    450                 455                 460 tac atc ctc aag ccc cag atg cct tgg gag cta tgg gac att ctt caa       1440
Tyr Ile Leu Lys Pro Gln Met Pro Trp Glu Leu Trp Asp Ile Leu Gln
465                 470                 475                 480 gaa atc tcc cca gaa gag att cag cca aac ccc cca tcc tct ggg atg       1488
Glu Ile Ser Pro Glu Glu Ile Gln Pro Asn Pro Pro Ser Ser Gly Met
                485                 490                 495 ctt ggt atc atc atc atg atg acg ctg tgt gac cag gtg gat att tat       1536
Leu Gly Ile Ile Ile Met Met Thr Leu Cys Asp Gln Val Asp Ile Tyr
            500                 505                 510 gag ttc ctc cca tcc aag cgc aag act gac gtg tgc tac tac tac cag       1584
Glu Phe Leu Pro Ser Lys Arg Lys Thr Asp Val Cys Tyr Tyr Tyr Gln
        515                 520                 525 aag ttc ttc gat agt gcc tgc acg atg ggt gcc tac cac ccg ctg ctc       1632
Lys Phe Phe Asp Ser Ala Cys Thr Met Gly Ala Tyr His Pro Leu Leu
    530                 535                 540 tat gag aag aat ttg gtg aag cat ctc aac cag ggc aca gat gag gac       1680
Tyr Glu Lys Asn Leu Val Lys His Leu Asn Gln Gly Thr Asp Glu Asp
545                 550                 555                 560 atc tac ctg ctt gga aaa gcc aca ctg cct ggc ttc cgg acc att cac       1728
Ile Tyr Leu Leu Gly Lys Ala Thr Leu Pro Gly Phe Arg Thr Ile His
                565                 570                 575 tgc                                                                    1731
Cys

<210> SEQ ID NO 166
<211> LENGTH: 577
<212> TYPE: PRT
<213> ORGANISM: Artificial
<220> FEATURE:
```

<223> OTHER INFORMATION: Synthetic Construct

<400> SEQUENCE: 166

```
Met Arg Ser Cys Leu Trp Arg Cys Arg His Leu Ser Gln Gly Val Gln
1               5                   10                  15

Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
        35                  40                  45

Glu Asn Ile Lys Glu Arg Ser Leu Gln Ser Leu Ala Lys Pro Lys Ser
    50                  55                  60

Gln Ala Pro Thr Arg Ala Arg Arg Thr Thr Ile Tyr Ala Glu Pro Val
65                  70                  75                  80

Pro Glu Asn Asn Ala Leu Asn Thr Gln Thr Gln Pro Lys Ala His Thr
                85                  90                  95

Thr Gly Asp Arg Gly Lys Glu Ala Asn Gln Ala Pro Glu Glu Gln
            100                 105                 110

Asp Lys Val Pro His Thr Ala Gln Arg Ala Ala Trp Lys Ser Pro Glu
            115                 120                 125

Lys Glu Lys Thr Met Val Asn Thr Leu Ser Pro Arg Gly Gln Asp Ala
    130                 135                 140

Gly Met Ala Ser Gly Arg Thr Glu Ala Gln Ser Trp Lys Ser Gln Asp
145                 150                 155                 160

Thr Lys Thr Thr Gln Gly Asn Gly Gln Thr Arg Lys Leu Thr Ala
                165                 170                 175

Ser Arg Thr Val Ser Glu Lys His Gln Gly Lys Ala Ala Thr Thr Ala
            180                 185                 190

Lys Thr Leu Ile Pro Lys Ser Gln His Arg Met Leu Ala Pro Thr Gly
    195                 200                 205

Ala Val Ser Thr Arg Thr Arg Gln Lys Gly Val Thr Thr Ala Val Ile
    210                 215                 220

Pro Pro Lys Glu Lys Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
                245                 250                 255

Lys Ser Ser Arg Glu Ala Ser Phe Gln Val Trp Asn Lys Asp Ser Ser
            260                 265                 270

Ser Lys Asn Leu Ile Pro Arg Leu Gln Lys Ile Trp Lys Asn Tyr Leu
        275                 280                 285

Ser Met Asn Lys Tyr Lys Val Ser Tyr Lys Gly Pro Gly Pro Gly Ile
    290                 295                 300

Lys Phe Ser Ala Glu Ala Leu Arg Cys His Leu Arg Asp His Val Asn
305                 310                 315                 320

Val Ser Met Val Glu Val Thr Asp Phe Pro Phe Asn Thr Ser Glu Trp
                325                 330                 335

Glu Gly Tyr Leu Pro Lys Glu Ser Ile Arg Thr Lys Ala Gly Pro Trp
            340                 345                 350

Gly Arg Cys Ala Val Val Ser Ser Ala Gly Ser Leu Lys Ser Ser Gln
        355                 360                 365

Leu Gly Arg Glu Ile Asp Asp His Asp Ala Val Leu Arg Phe Asn Gly
    370                 375                 380

Ala Pro Thr Ala Asn Phe Gln Gln Asp Val Gly Thr Lys Thr Thr Ile
385                 390                 395                 400
```

```
Arg Leu Met Asn Ser Gln Leu Val Thr Thr Glu Lys Arg Phe Leu Lys
            405                 410                 415

Asp Ser Leu Tyr Asn Glu Gly Ile Leu Ile Val Trp Asp Pro Ser Val
        420                 425                 430

Tyr His Ser Asp Ile Pro Lys Trp Tyr Gln Asn Pro Asp Tyr Asn Phe
            435                 440                 445

Phe Asn Asn Tyr Lys Thr Tyr Arg Lys Leu His Pro Asn Gln Pro Phe
    450                 455                 460

Tyr Ile Leu Lys Pro Gln Met Pro Trp Glu Leu Trp Asp Ile Leu Gln
465                 470                 475                 480

Glu Ile Ser Pro Glu Glu Ile Gln Pro Asn Pro Pro Ser Ser Gly Met
                485                 490                 495

Leu Gly Ile Ile Ile Met Met Thr Leu Cys Asp Gln Val Asp Ile Tyr
            500                 505                 510

Glu Phe Leu Pro Ser Lys Arg Lys Thr Asp Val Cys Tyr Tyr Tyr Gln
        515                 520                 525

Lys Phe Phe Asp Ser Ala Cys Thr Met Gly Ala Tyr His Pro Leu Leu
    530                 535                 540

Tyr Glu Lys Asn Leu Val Lys His Leu Asn Gln Gly Thr Asp Glu Asp
545                 550                 555                 560

Ile Tyr Leu Leu Gly Lys Ala Thr Leu Pro Gly Phe Arg Thr Ile His
                565                 570                 575

Cys

<210> SEQ ID NO 167
<211> LENGTH: 1095
<212> TYPE: DNA
<213> ORGANISM: Artificial
<220> FEATURE:
<223> OTHER INFORMATION: Fusion of the nucleotide sequence SEQ ID NO:
      151 with the nucleotide sequence SEQ ID NO : 43
<220> FEATURE:
<221> NAME/KEY: CDS
<222> LOCATION: (1)..(1095)

<400> SEQUENCE: 167 atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg aag cta cac tta      96
Phe Leu Val Leu Gly Phe Leu Tyr Tyr Ser Ala Trp Lys Leu His Leu
            20                  25                  30 ctc cag tgg gag gag gac tcc agt aag tat agt cac tct agc gga tcc     144
Leu Gln Trp Glu Glu Asp Ser Ser Lys Tyr Ser His Ser Ser Gly Ser
        35                  40                  45 gag gcc tcc ttc cag gtg tgg aac aag gac agc tct tcc aaa aac ctt     192
Glu Ala Ser Phe Gln Val Trp Asn Lys Asp Ser Ser Ser Lys Asn Leu
    50                  55                  60 atc cct agg ctg caa aag atc tgg aag aat tac cta agc atg aac aag     240
Ile Pro Arg Leu Gln Lys Ile Trp Lys Asn Tyr Leu Ser Met Asn Lys
65                  70                  75                  80 tac aaa gtg tcc tac aag ggg cca gga cca ggc atc aag ttc agt gca     288
Tyr Lys Val Ser Tyr Lys Gly Pro Gly Pro Gly Ile Lys Phe Ser Ala
                85                  90                  95 gag gcc ctg cgc tgc cac ctc cgg gac cat gtg aat gta tcc atg gta     336
Glu Ala Leu Arg Cys His Leu Arg Asp His Val Asn Val Ser Met Val
            100                 105                 110 gag gtc aca gat ttt ccc ttc aat acc tct gaa tgg gag ggt tat ctg     384
Glu Val Thr Asp Phe Pro Phe Asn Thr Ser Glu Trp Glu Gly Tyr Leu
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |
| ccc | aag | gag | agc | att | agg | acc | aag | gct | ggg | cct | tgg | ggc | agg | tgt | gct | 432 |
| Pro | Lys | Glu | Ser | Ile | Arg | Thr | Lys | Ala | Gly | Pro | Trp | Gly | Arg | Cys | Ala |
|  | 130 |  |  |  |  | 135 |  |  |  |  | 140 |  |  |  |  |
| gtt | gtg | tcg | tca | gcg | gga | tct | ctg | aag | tcc | tcc | caa | cta | ggc | aga | gaa | 480 |
| Val | Val | Ser | Ser | Ala | Gly | Ser | Leu | Lys | Ser | Ser | Gln | Leu | Gly | Arg | Glu |
| 145 |  |  |  |  | 150 |  |  |  |  | 155 |  |  |  |  | 160 |
| atc | gat | gat | cat | gac | gca | gtc | ctg | agg | ttt | aat | ggg | gca | ccc | aca | gcc | 528 |
| Ile | Asp | Asp | His | Asp | Ala | Val | Leu | Arg | Phe | Asn | Gly | Ala | Pro | Thr | Ala |
|  |  |  |  | 165 |  |  |  |  | 170 |  |  |  |  | 175 |  |
| aac | ttc | caa | caa | gat | gtg | ggc | aca | aaa | act | acc | att | cgc | ctg | atg | aac | 576 |
| Asn | Phe | Gln | Gln | Asp | Val | Gly | Thr | Lys | Thr | Thr | Ile | Arg | Leu | Met | Asn |
|  |  |  | 180 |  |  |  |  | 185 |  |  |  |  | 190 |  |  |
| tct | cag | ttg | gtt | acc | aca | gag | aag | cgc | ttc | ctc | aaa | gac | agt | ttg | tac | 624 |
| Ser | Gln | Leu | Val | Thr | Thr | Glu | Lys | Arg | Phe | Leu | Lys | Asp | Ser | Leu | Tyr |
|  |  | 195 |  |  |  |  | 200 |  |  |  |  | 205 |  |  |  |
| aat | gaa | gga | atc | cta | att | gta | tgg | gac | cca | tct | gta | tac | cac | tca | gat | 672 |
| Asn | Glu | Gly | Ile | Leu | Ile | Val | Trp | Asp | Pro | Ser | Val | Tyr | His | Ser | Asp |
|  | 210 |  |  |  |  | 215 |  |  |  |  | 220 |  |  |  |  |
| atc | cca | aag | tgg | tac | cag | aat | ccg | gat | tat | aat | ttc | ttt | aac | aac | tac | 720 |
| Ile | Pro | Lys | Trp | Tyr | Gln | Asn | Pro | Asp | Tyr | Asn | Phe | Phe | Asn | Asn | Tyr |
| 225 |  |  |  |  | 230 |  |  |  |  | 235 |  |  |  |  | 240 |
| aag | act | tat | cgt | aag | ctg | cac | ccc | aat | cag | ccc | ttt | tac | atc | ctc | aag | 768 |
| Lys | Thr | Tyr | Arg | Lys | Leu | His | Pro | Asn | Gln | Pro | Phe | Tyr | Ile | Leu | Lys |
|  |  |  |  | 245 |  |  |  |  | 250 |  |  |  |  | 255 |  |
| ccc | cag | atg | cct | tgg | gag | cta | tgg | gac | att | ctt | caa | gaa | atc | tcc | cca | 816 |
| Pro | Gln | Met | Pro | Trp | Glu | Leu | Trp | Asp | Ile | Leu | Gln | Glu | Ile | Ser | Pro |
|  |  | 260 |  |  |  |  | 265 |  |  |  |  | 270 |  |  |  |
| gaa | gag | att | cag | cca | aac | ccc | cca | tcc | tct | ggg | atg | ctt | ggt | atc | atc | 864 |
| Glu | Glu | Ile | Gln | Pro | Asn | Pro | Pro | Ser | Ser | Gly | Met | Leu | Gly | Ile | Ile |
|  |  | 275 |  |  |  |  | 280 |  |  |  |  | 285 |  |  |  |
| atc | atg | atg | acg | ctg | tgt | gac | cag | gtg | gat | att | tat | gag | ttc | ctc | cca | 912 |
| Ile | Met | Met | Thr | Leu | Cys | Asp | Gln | Val | Asp | Ile | Tyr | Glu | Phe | Leu | Pro |
|  | 290 |  |  |  |  | 295 |  |  |  |  | 300 |  |  |  |  |
| tcc | aag | cgc | aag | act | gac | gtg | tgc | tac | tac | tac | cag | aag | ttc | ttc | gat | 960 |
| Ser | Lys | Arg | Lys | Thr | Asp | Val | Cys | Tyr | Tyr | Tyr | Gln | Lys | Phe | Phe | Asp |
| 305 |  |  |  |  | 310 |  |  |  |  | 315 |  |  |  |  | 320 |
| agt | gcc | tgc | acg | atg | ggt | gcc | tac | cac | ccg | ctg | ctc | tat | gag | aag | aat | 1008 |
| Ser | Ala | Cys | Thr | Met | Gly | Ala | Tyr | His | Pro | Leu | Leu | Tyr | Glu | Lys | Asn |
|  |  |  |  | 325 |  |  |  |  | 330 |  |  |  |  | 335 |  |
| ttg | gtg | aag | cat | ctc | aac | cag | ggc | aca | gat | gag | gac | atc | tac | ctg | ctt | 1056 |
| Leu | Val | Lys | His | Leu | Asn | Gln | Gly | Thr | Asp | Glu | Asp | Ile | Tyr | Leu | Leu |
|  |  |  | 340 |  |  |  |  | 345 |  |  |  |  | 350 |  |  |
| gga | aaa | gcc | aca | ctg | cct | ggc | ttc | cgg | acc | att | cac | tgc |  |  |  | 1095 |
| Gly | Lys | Ala | Thr | Leu | Pro | Gly | Phe | Arg | Thr | Ile | His | Cys |  |  |  |
|  |  | 355 |  |  |  |  | 360 |  |  |  |  | 365 |  |  |  |

<210> SEQ ID NO 168
<211> LENGTH: 365
<212> TYPE: PRT
<213> ORGANISM: Artificial
<220> FEATURE:
<223> OTHER INFORMATION: Synthetic Construct

<400> SEQUENCE: 168

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Ser Lys Tyr Ser His Ser Ser Gly Ser

```
                35                  40                  45
Glu Ala Ser Phe Gln Val Trp Asn Lys Asp Ser Ser Lys Asn Leu
 50                  55                  60

Ile Pro Arg Leu Gln Lys Ile Trp Lys Asn Tyr Leu Ser Met Asn Lys
 65                  70                  75                  80

Tyr Lys Val Ser Tyr Lys Gly Pro Gly Pro Gly Ile Lys Phe Ser Ala
                 85                  90                  95

Glu Ala Leu Arg Cys His Leu Arg Asp His Val Asn Val Ser Met Val
                100                 105                 110

Glu Val Thr Asp Phe Pro Phe Asn Thr Ser Glu Trp Glu Gly Tyr Leu
                115                 120                 125

Pro Lys Glu Ser Ile Arg Thr Lys Ala Gly Pro Trp Gly Arg Cys Ala
130                 135                 140

Val Val Ser Ser Ala Gly Ser Leu Lys Ser Ser Gln Leu Gly Arg Glu
145                 150                 155                 160

Ile Asp Asp His Asp Ala Val Leu Arg Phe Asn Gly Ala Pro Thr Ala
                165                 170                 175

Asn Phe Gln Gln Asp Val Gly Thr Lys Thr Thr Ile Arg Leu Met Asn
                180                 185                 190

Ser Gln Leu Val Thr Thr Glu Lys Arg Phe Leu Lys Asp Ser Leu Tyr
                195                 200                 205

Asn Glu Gly Ile Leu Ile Val Trp Asp Pro Ser Val Tyr His Ser Asp
210                 215                 220

Ile Pro Lys Trp Tyr Gln Asn Pro Asp Tyr Asn Phe Phe Asn Asn Tyr
225                 230                 235                 240

Lys Thr Tyr Arg Lys Leu His Pro Asn Gln Pro Phe Tyr Ile Leu Lys
                245                 250                 255

Pro Gln Met Pro Trp Glu Leu Trp Asp Ile Leu Gln Glu Ile Ser Pro
                260                 265                 270

Glu Glu Ile Gln Pro Asn Pro Pro Ser Ser Gly Met Leu Gly Ile Ile
                275                 280                 285

Ile Met Met Thr Leu Cys Asp Gln Val Asp Ile Tyr Glu Phe Leu Pro
290                 295                 300

Ser Lys Arg Lys Thr Asp Val Cys Tyr Tyr Tyr Gln Lys Phe Phe Asp
305                 310                 315                 320

Ser Ala Cys Thr Met Gly Ala Tyr His Pro Leu Leu Tyr Glu Lys Asn
                325                 330                 335

Leu Val Lys His Leu Asn Gln Gly Thr Asp Glu Asp Ile Tyr Leu Leu
                340                 345                 350

Gly Lys Ala Thr Leu Pro Gly Phe Arg Thr Ile His Cys
                355                 360                 365

<210> SEQ ID NO 169
<211> LENGTH: 1095
<212> TYPE: DNA
<213> ORGANISM: Artificial
<220> FEATURE:
<223> OTHER INFORMATION: Fusion of the nucleotide sequence SEQ ID NO:
      153 with the nucleotide sequence SEQ ID NO : 43
<220> FEATURE:
<221> NAME/KEY: CDS
<222> LOCATION: (1)..(1095)

<400> SEQUENCE: 169 atg gga ctc ttg gta ttt gta cgc aac ctg ctg cta gcc ctc tgc ctc   48
Met Gly Leu Leu Val Phe Val Arg Asn Leu Leu Leu Ala Leu Cys Leu
 1               5                  10                  15
```

| | | | | | | | | | | | | | | | | |
|---|---|---|---|---|---|---|---|---|---|---|---|---|---|---|---|---|
| ttt | ctg | gtc | ctg | gga | ttt | ttg | tat | tat | tct | gcc | tgg | aag | cta | cac | tta | 96 |
| Phe | Leu | Val | Leu | Gly | Phe | Leu | Tyr | Tyr | Ser | Ala | Trp | Lys | Leu | His | Leu | |
| | | 20 | | | | | 25 | | | | | 30 | | | | |
| ctc | caa | tgg | gaa | gac | tcc | aat | tca | ctg | att | ctt | tcc | ctt | gac | tct | aga | 144 |
| Leu | Gln | Trp | Glu | Asp | Ser | Asn | Ser | Leu | Ile | Leu | Ser | Leu | Asp | Ser | Arg | |
| | | 35 | | | | | 40 | | | | | 45 | | | | |
| gag | gcc | tcc | ttc | cag | gtg | tgg | aac | aag | gac | agc | tct | tcc | aaa | aac | ctt | 192 |
| Glu | Ala | Ser | Phe | Gln | Val | Trp | Asn | Lys | Asp | Ser | Ser | Ser | Lys | Asn | Leu | |
| 50 | | | | | 55 | | | | | 60 | | | | | | |
| atc | cct | agg | ctg | caa | aag | atc | tgg | aag | aat | tac | cta | agc | atg | aac | aag | 240 |
| Ile | Pro | Arg | Leu | Gln | Lys | Ile | Trp | Lys | Asn | Tyr | Leu | Ser | Met | Asn | Lys | |
| 65 | | | | 70 | | | | | 75 | | | | | 80 | | |
| tac | aaa | gtg | tcc | tac | aag | ggg | cca | gga | cca | ggc | atc | aag | ttc | agt | gca | 288 |
| Tyr | Lys | Val | Ser | Tyr | Lys | Gly | Pro | Gly | Pro | Gly | Ile | Lys | Phe | Ser | Ala | |
| | | | | 85 | | | | | 90 | | | | | 95 | | |
| gag | gcc | ctg | cgc | tgc | cac | ctc | cgg | gac | cat | gtg | aat | gta | tcc | atg | gta | 336 |
| Glu | Ala | Leu | Arg | Cys | His | Leu | Arg | Asp | His | Val | Asn | Val | Ser | Met | Val | |
| | | | | 100 | | | | | 105 | | | | | 110 | | |
| gag | gtc | aca | gat | ttt | ccc | ttc | aat | acc | tct | gaa | tgg | gag | ggt | tat | ctg | 384 |
| Glu | Val | Thr | Asp | Phe | Pro | Phe | Asn | Thr | Ser | Glu | Trp | Glu | Gly | Tyr | Leu | |
| | | 115 | | | | | 120 | | | | | 125 | | | | |
| ccc | aag | gag | agc | att | agg | acc | aag | gct | ggg | cct | tgg | ggc | agg | tgt | gct | 432 |
| Pro | Lys | Glu | Ser | Ile | Arg | Thr | Lys | Ala | Gly | Pro | Trp | Gly | Arg | Cys | Ala | |
| | | 130 | | | | | 135 | | | | | 140 | | | | |
| gtt | gtg | tcg | tca | gcg | gga | tct | ctg | aag | tcc | tcc | caa | cta | ggc | aga | gaa | 480 |
| Val | Val | Ser | Ser | Ala | Gly | Ser | Leu | Lys | Ser | Ser | Gln | Leu | Gly | Arg | Glu | |
| 145 | | | | | 150 | | | | | 155 | | | | | 160 | |
| atc | gat | gat | cat | gac | gca | gtc | ctg | agg | ttt | aat | ggg | gca | ccc | aca | gcc | 528 |
| Ile | Asp | Asp | His | Asp | Ala | Val | Leu | Arg | Phe | Asn | Gly | Ala | Pro | Thr | Ala | |
| | | | | 165 | | | | | 170 | | | | | 175 | | |
| aac | ttc | caa | caa | gat | gtg | ggc | aca | aaa | act | acc | att | cgc | ctg | atg | aac | 576 |
| Asn | Phe | Gln | Gln | Asp | Val | Gly | Thr | Lys | Thr | Thr | Ile | Arg | Leu | Met | Asn | |
| | | | | 180 | | | | | 185 | | | | | 190 | | |
| tct | cag | ttg | gtt | acc | aca | gag | aag | cgc | ttc | ctc | aaa | gac | agt | ttg | tac | 624 |
| Ser | Gln | Leu | Val | Thr | Thr | Glu | Lys | Arg | Phe | Leu | Lys | Asp | Ser | Leu | Tyr | |
| | | 195 | | | | | 200 | | | | | 205 | | | | |
| aat | gaa | gga | atc | cta | att | gta | tgg | gac | cca | tct | gta | tac | cac | tca | gat | 672 |
| Asn | Glu | Gly | Ile | Leu | Ile | Val | Trp | Asp | Pro | Ser | Val | Tyr | His | Ser | Asp | |
| 210 | | | | | 215 | | | | | 220 | | | | | | |
| atc | cca | aag | tgg | tac | cag | aat | ccg | gat | tat | aat | ttc | ttt | aac | aac | tac | 720 |
| Ile | Pro | Lys | Trp | Tyr | Gln | Asn | Pro | Asp | Tyr | Asn | Phe | Phe | Asn | Asn | Tyr | |
| 225 | | | | 230 | | | | | 235 | | | | | 240 | | |
| aag | act | tat | cgt | aag | ctg | cac | ccc | aat | cag | ccc | ttt | tac | atc | ctc | aag | 768 |
| Lys | Thr | Tyr | Arg | Lys | Leu | His | Pro | Asn | Gln | Pro | Phe | Tyr | Ile | Leu | Lys | |
| | | | | 245 | | | | | 250 | | | | | 255 | | |
| ccc | cag | atg | cct | tgg | gag | cta | tgg | gac | att | ctt | caa | gaa | atc | tcc | cca | 816 |
| Pro | Gln | Met | Pro | Trp | Glu | Leu | Trp | Asp | Ile | Leu | Gln | Glu | Ile | Ser | Pro | |
| | | | | 260 | | | | | 265 | | | | | 270 | | |
| gaa | gag | att | cag | cca | aac | ccc | cca | tcc | tct | ggg | atg | ctt | ggt | atc | atc | 864 |
| Glu | Glu | Ile | Gln | Pro | Asn | Pro | Pro | Ser | Ser | Gly | Met | Leu | Gly | Ile | Ile | |
| | | | 275 | | | | | 280 | | | | | 285 | | | |
| atc | atg | atg | acg | ctg | tgt | gac | cag | gtg | gat | att | tat | gag | ttc | ctc | cca | 912 |
| Ile | Met | Met | Thr | Leu | Cys | Asp | Gln | Val | Asp | Ile | Tyr | Glu | Phe | Leu | Pro | |
| | | 290 | | | | | 295 | | | | | 300 | | | | |
| tcc | aag | cgc | aag | act | gac | gtg | tgc | tac | tac | tac | cag | aag | ttc | ttc | gat | 960 |
| Ser | Lys | Arg | Lys | Thr | Asp | Val | Cys | Tyr | Tyr | Tyr | Gln | Lys | Phe | Phe | Asp | |
| 305 | | | | 310 | | | | | 315 | | | | | 320 | | |
| agt | gcc | tgc | acg | atg | ggt | gcc | tac | cac | ccg | ctg | ctc | tat | gag | aag | aat | 1008 |
| Ser | Ala | Cys | Thr | Met | Gly | Ala | Tyr | His | Pro | Leu | Leu | Tyr | Glu | Lys | Asn | |

```
                    325                 330                 335
ttg gtg aag cat ctc aac cag ggc aca gat gag gac atc tac ctg ctt    1056
Leu Val Lys His Leu Asn Gln Gly Thr Asp Glu Asp Ile Tyr Leu Leu
        340                 345                 350 gga aaa gcc aca ctg cct ggc ttc cgg acc att cac tgc                1095
Gly Lys Ala Thr Leu Pro Gly Phe Arg Thr Ile His Cys
        355                 360                 365

<210> SEQ ID NO 170
<211> LENGTH: 365
<212> TYPE: PRT
<213> ORGANISM: Artificial
<220> FEATURE:
<223> OTHER INFORMATION: Synthetic Construct

<400> SEQUENCE: 170

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Asp Ser Asn Ser Leu Ile Leu Ser Leu Asp Ser Arg
        35                  40                  45

Glu Ala Ser Phe Gln Val Trp Asn Lys Asp Ser Ser Lys Asn Leu
    50                  55                  60

Ile Pro Arg Leu Gln Lys Ile Trp Lys Asn Tyr Leu Ser Met Asn Lys
65                  70                  75                  80

Tyr Lys Val Ser Tyr Lys Gly Pro Gly Pro Gly Ile Lys Phe Ser Ala
                85                  90                  95

Glu Ala Leu Arg Cys His Leu Arg Asp His Val Asn Val Ser Met Val
            100                 105                 110

Glu Val Thr Asp Phe Pro Phe Asn Thr Ser Glu Trp Glu Gly Tyr Leu
        115                 120                 125

Pro Lys Glu Ser Ile Arg Thr Lys Ala Gly Pro Trp Gly Arg Cys Ala
    130                 135                 140

Val Val Ser Ser Ala Gly Ser Leu Lys Ser Ser Gln Leu Gly Arg Glu
145                 150                 155                 160

Ile Asp Asp His Asp Ala Val Leu Arg Phe Asn Gly Ala Pro Thr Ala
                165                 170                 175

Asn Phe Gln Gln Asp Val Gly Thr Lys Thr Thr Ile Arg Leu Met Asn
            180                 185                 190

Ser Gln Leu Val Thr Thr Glu Lys Arg Phe Leu Lys Asp Ser Leu Tyr
        195                 200                 205

Asn Glu Gly Ile Leu Ile Val Trp Asp Pro Ser Val Tyr His Ser Asp
    210                 215                 220

Ile Pro Lys Trp Tyr Gln Asn Pro Asp Tyr Asn Phe Phe Asn Asn Tyr
225                 230                 235                 240

Lys Thr Tyr Arg Lys Leu His Pro Asn Gln Pro Phe Tyr Ile Leu Lys
                245                 250                 255

Pro Gln Met Pro Trp Glu Leu Trp Asp Ile Leu Gln Glu Ile Ser Pro
            260                 265                 270

Glu Glu Ile Gln Pro Asn Pro Pro Ser Ser Gly Met Leu Gly Ile Ile
        275                 280                 285

Ile Met Met Thr Leu Cys Asp Gln Val Asp Ile Tyr Glu Phe Leu Pro
    290                 295                 300

Ser Lys Arg Lys Thr Asp Val Cys Tyr Tyr Gln Lys Phe Phe Asp
305                 310                 315                 320
```

```
Ser Ala Cys Thr Met Gly Ala Tyr His Pro Leu Leu Tyr Glu Lys Asn
            325                 330                 335

Leu Val Lys His Leu Asn Gln Gly Thr Asp Glu Asp Ile Tyr Leu Leu
            340                 345                 350

Gly Lys Ala Thr Leu Pro Gly Phe Arg Thr Ile His Cys
            355                 360                 365

<210> SEQ ID NO 171
<211> LENGTH: 1194
<212> TYPE: DNA
<213> ORGANISM: Artificial
<220> FEATURE:
<223> OTHER INFORMATION: Fusion of the nucleotide sequence SEQ ID NO:
      155 with the nucleotide sequence SEQ ID NO : 43
<220> FEATURE:
<221> NAME/KEY: CDS
<222> LOCATION: (1)..(1194)

<400> SEQUENCE: 171
```

| | | | | | | | | | | | | | | | | |
|---|---|---|---|---|---|---|---|---|---|---|---|---|---|---|---|---|
| atg | cag | ctg | cag | ttc | cgg | agc | tgg | atg | ctg | gcc | gcg | ctc | acg | ctg | ctc | 48 |
| Met | Gln | Leu | Gln | Phe | Arg | Ser | Trp | Met | Leu | Ala | Ala | Leu | Thr | Leu | Leu | |
| 1 | | | | 5 | | | | | 10 | | | | | 15 | | |
| gtg | gtc | ttc | ctc | atc | ttc | gca | gac | atc | tca | gag | atc | gaa | gaa | gaa | atc | 96 |
| Val | Val | Phe | Leu | Ile | Phe | Ala | Asp | Ile | Ser | Glu | Ile | Glu | Glu | Glu | Ile | |
| | | | 20 | | | | | 25 | | | | | 30 | | | |
| ggg | aat | tcg | gga | ggc | aga | ggt | aca | atc | aga | tca | gct | gtg | aac | agc | tta | 144 |
| Gly | Asn | Ser | Gly | Gly | Arg | Gly | Thr | Ile | Arg | Ser | Ala | Val | Asn | Ser | Leu | |
| | | | | 35 | | | | | 40 | | | | | 45 | | |
| cat | agc | aaa | tct | aat | aga | gct | gaa | gtt | gta | ata | aac | ggc | tcc | tca | tca | 192 |
| His | Ser | Lys | Ser | Asn | Arg | Ala | Glu | Val | Val | Ile | Asn | Gly | Ser | Ser | Ser | |
| | 50 | | | | | 55 | | | | | 60 | | | | | |
| cca | gct | gtt | gtt | gac | aga | agt | aat | gaa | agc | atc | aag | cac | aac | atc | aag | 240 |
| Pro | Ala | Val | Val | Asp | Arg | Ser | Asn | Glu | Ser | Ile | Lys | His | Asn | Ile | Lys | |
| 65 | | | | | 70 | | | | | 75 | | | | | 80 | |
| ctt | gag | gcc | tcc | ttc | cag | gtg | tgg | aac | aag | gac | agc | tct | tcc | aaa | aac | 288 |
| Leu | Glu | Ala | Ser | Phe | Gln | Val | Trp | Asn | Lys | Asp | Ser | Ser | Ser | Lys | Asn | |
| | | | | 85 | | | | | 90 | | | | | 95 | | |
| ctt | atc | cct | agg | ctg | caa | aag | atc | tgg | aag | aat | tac | cta | agc | atg | aac | 336 |
| Leu | Ile | Pro | Arg | Leu | Gln | Lys | Ile | Trp | Lys | Asn | Tyr | Leu | Ser | Met | Asn | |
| | | | 100 | | | | | 105 | | | | | 110 | | | |
| aag | tac | aaa | gtg | tcc | tac | aag | ggg | cca | gga | cca | ggc | atc | aag | ttc | agt | 384 |
| Lys | Tyr | Lys | Val | Ser | Tyr | Lys | Gly | Pro | Gly | Pro | Gly | Ile | Lys | Phe | Ser | |
| | | | | 115 | | | | | 120 | | | | | 125 | | |
| gca | gag | gcc | ctg | cgc | tgc | cac | ctc | cgg | gac | cat | gtg | aat | gta | tcc | atg | 432 |
| Ala | Glu | Ala | Leu | Arg | Cys | His | Leu | Arg | Asp | His | Val | Asn | Val | Ser | Met | |
| | 130 | | | | | 135 | | | | | 140 | | | | | |
| gta | gag | gtc | aca | gat | ttt | ccc | ttc | aat | acc | tct | gaa | tgg | gag | ggt | tat | 480 |
| Val | Glu | Val | Thr | Asp | Phe | Pro | Phe | Asn | Thr | Ser | Glu | Trp | Glu | Gly | Tyr | |
| 145 | | | | | 150 | | | | | 155 | | | | | 160 | |
| ctg | ccc | aag | gag | agc | att | agg | acc | aag | gct | ggg | cct | tgg | ggc | agg | tgt | 528 |
| Leu | Pro | Lys | Glu | Ser | Ile | Arg | Thr | Lys | Ala | Gly | Pro | Trp | Gly | Arg | Cys | |
| | | | | 165 | | | | | 170 | | | | | 175 | | |
| gct | gtt | gtg | tcg | tca | gcg | gga | tct | ctg | aag | tcc | tcc | caa | cta | ggc | aga | 576 |
| Ala | Val | Val | Ser | Ser | Ala | Gly | Ser | Leu | Lys | Ser | Ser | Gln | Leu | Gly | Arg | |
| | | | 180 | | | | | 185 | | | | | 190 | | | |
| gaa | atc | gat | gat | cat | gac | gca | gtc | ctg | agg | ttt | aat | ggg | gca | ccc | aca | 624 |
| Glu | Ile | Asp | Asp | His | Asp | Ala | Val | Leu | Arg | Phe | Asn | Gly | Ala | Pro | Thr | |
| | | | 195 | | | | | 200 | | | | | 205 | | | |
| gcc | aac | ttc | caa | caa | gat | gtg | ggc | aca | aaa | act | acc | att | cgc | ctg | atg | 672 |
| Ala | Asn | Phe | Gln | Gln | Asp | Val | Gly | Thr | Lys | Thr | Thr | Ile | Arg | Leu | Met | |
| | 210 | | | | | 215 | | | | | 220 | | | | | |

```
aac tct cag ttg gtt acc aca gag aag cgc ttc ctc aaa gac agt ttg       720
Asn Ser Gln Leu Val Thr Thr Glu Lys Arg Phe Leu Lys Asp Ser Leu
225                 230                 235                 240 tac aat gaa gga atc cta att gta tgg gac cca tct gta tac cac tca       768
Tyr Asn Glu Gly Ile Leu Ile Val Trp Asp Pro Ser Val Tyr His Ser
                245                 250                 255 gat atc cca aag tgg tac cag aat ccg gat tat aat ttc ttt aac aac       816
Asp Ile Pro Lys Trp Tyr Gln Asn Pro Asp Tyr Asn Phe Phe Asn Asn
            260                 265                 270 tac aag act tat cgt aag ctg cac ccc aat cag ccc ttt tac atc ctc       864
Tyr Lys Thr Tyr Arg Lys Leu His Pro Asn Gln Pro Phe Tyr Ile Leu
        275                 280                 285 aag ccc cag atg cct tgg gag cta tgg gac att ctt caa gaa atc tcc       912
Lys Pro Gln Met Pro Trp Glu Leu Trp Asp Ile Leu Gln Glu Ile Ser
    290                 295                 300 cca gaa gag att cag cca aac ccc cca tcc tct ggg atg ctt ggt atc       960
Pro Glu Glu Ile Gln Pro Asn Pro Pro Ser Ser Gly Met Leu Gly Ile
305                 310                 315                 320 atc atc atg atg acg ctg tgt gac cag gtg gat att tat gag ttc ctc      1008
Ile Ile Met Met Thr Leu Cys Asp Gln Val Asp Ile Tyr Glu Phe Leu
                325                 330                 335 cca tcc aag cgc aag act gac gtg tgc tac tac tac cag aag ttc ttc      1056
Pro Ser Lys Arg Lys Thr Asp Val Cys Tyr Tyr Tyr Gln Lys Phe Phe
            340                 345                 350 gat agt gcc tgc acg atg ggt gcc tac cac ccg ctg ctc tat gag aag      1104
Asp Ser Ala Cys Thr Met Gly Ala Tyr His Pro Leu Leu Tyr Glu Lys
        355                 360                 365 aat ttg gtg aag cat ctc aac cag ggc aca gat gag gac atc tac ctg      1152
Asn Leu Val Lys His Leu Asn Gln Gly Thr Asp Glu Asp Ile Tyr Leu
    370                 375                 380 ctt gga aaa gcc aca ctg cct ggc ttc cgg acc att cac tgc              1194
Leu Gly Lys Ala Thr Leu Pro Gly Phe Arg Thr Ile His Cys
385                 390                 395

<210> SEQ ID NO 172
<211> LENGTH: 398
<212> TYPE: PRT
<213> ORGANISM: Artificial
<220> FEATURE:
<223> OTHER INFORMATION: Synthetic Construct

<400> SEQUENCE: 172

Met Gln Leu Gln Phe Arg Ser Trp Met Leu Ala Ala Leu Thr Leu Leu
1               5                   10                  15

Val Val Phe Leu Ile Phe Ala Asp Ile Ser Glu Ile Glu Glu Ile
                20                  25                  30

Gly Asn Ser Gly Gly Arg Gly Thr Ile Arg Ser Ala Val Asn Ser Leu
            35                  40                  45

His Ser Lys Ser Asn Arg Ala Glu Val Val Ile Asn Gly Ser Ser Ser
        50                  55                  60

Pro Ala Val Val Asp Arg Ser Asn Glu Ser Ile Lys His Asn Ile Lys
65                  70                  75                  80

Leu Glu Ala Ser Phe Gln Val Trp Asn Lys Asp Ser Ser Lys Asn
                85                  90                  95

Leu Ile Pro Arg Leu Gln Lys Ile Trp Lys Asn Tyr Leu Ser Met Asn
            100                 105                 110

Lys Tyr Lys Val Ser Tyr Lys Gly Pro Gly Pro Gly Ile Lys Phe Ser
        115                 120                 125
```

```
Ala Glu Ala Leu Arg Cys His Leu Arg Asp His Val Asn Val Ser Met
130                 135                 140

Val Glu Val Thr Asp Phe Pro Phe Asn Thr Ser Glu Trp Glu Gly Tyr
145                 150                 155                 160

Leu Pro Lys Glu Ser Ile Arg Thr Lys Ala Gly Pro Trp Gly Arg Cys
            165                 170                 175

Ala Val Val Ser Ser Ala Gly Ser Leu Lys Ser Ser Gln Leu Gly Arg
            180                 185                 190

Glu Ile Asp Asp His Asp Ala Val Leu Arg Phe Asn Gly Ala Pro Thr
            195                 200                 205

Ala Asn Phe Gln Gln Asp Val Gly Thr Lys Thr Thr Ile Arg Leu Met
210                 215                 220

Asn Ser Gln Leu Val Thr Thr Glu Lys Arg Phe Leu Lys Asp Ser Leu
225                 230                 235                 240

Tyr Asn Glu Gly Ile Leu Ile Val Trp Asp Pro Ser Val Tyr His Ser
            245                 250                 255

Asp Ile Pro Lys Trp Tyr Gln Asn Pro Asp Tyr Asn Phe Phe Asn Asn
            260                 265                 270

Tyr Lys Thr Tyr Arg Lys Leu His Pro Asn Gln Pro Phe Tyr Ile Leu
            275                 280                 285

Lys Pro Gln Met Pro Trp Glu Leu Trp Asp Ile Leu Gln Glu Ile Ser
290                 295                 300

Pro Glu Glu Ile Gln Pro Asn Pro Pro Ser Ser Gly Met Leu Gly Ile
305                 310                 315                 320

Ile Ile Met Met Thr Leu Cys Asp Gln Val Asp Ile Tyr Glu Phe Leu
            325                 330                 335

Pro Ser Lys Arg Lys Thr Asp Val Cys Tyr Tyr Gln Lys Phe Phe
            340                 345                 350

Asp Ser Ala Cys Thr Met Gly Ala Tyr His Pro Leu Leu Tyr Glu Lys
            355                 360                 365

Asn Leu Val Lys His Leu Asn Gln Gly Thr Asp Glu Asp Ile Tyr Leu
            370                 375                 380

Leu Gly Lys Ala Thr Leu Pro Gly Phe Arg Thr Ile His Cys
385                 390                 395

<210> SEQ ID NO 173
<211> LENGTH: 1158
<212> TYPE: DNA
<213> ORGANISM: Artificial
<220> FEATURE:
<223> OTHER INFORMATION: Fusion of the nucleotide sequence SEQ ID NO:
      157 with the nucleotide sequence SEQ ID NO : 43
<220> FEATURE:
<221> NAME/KEY: CDS
<222> LOCATION: (1)..(1158)

<400> SEQUENCE: 173 atg cgc tcc att agg aag agg tgg acg atc tgc aca ata agt ctg ctc    48
Met Arg Ser Ile Arg Lys Arg Trp Thr Ile Cys Thr Ile Ser Leu Leu
1               5                   10                  15 ctg atc ttt tat aag aca aaa gaa ata gca aga act gag gag cac cag    96
Leu Ile Phe Tyr Lys Thr Lys Glu Ile Ala Arg Thr Glu Glu His Gln
            20                  25                  30 gag acg caa ctc atc gga gat ggt gaa ttg tct ttg agt cgg tca ctt   144
Glu Thr Gln Leu Ile Gly Asp Gly Glu Leu Ser Leu Ser Arg Ser Leu
        35                  40                  45 gtc aat agc tct gat aaa atc att cga aag gct ggc tct tca atc ttc   192
Val Asn Ser Ser Asp Lys Ile Ile Arg Lys Ala Gly Ser Ser Ile Phe
```

-continued

```
                50                  55                  60
cag cac aat aag ctt gag gcc tcc ttc cag gtg tgg aac aag gac agc    240
Gln His Asn Lys Leu Glu Ala Ser Phe Gln Val Trp Asn Lys Asp Ser
 65                  70                  75                  80 tct tcc aaa aac ctt atc cct agg ctg caa aag atc tgg aag aat tac    288
Ser Ser Lys Asn Leu Ile Pro Arg Leu Gln Lys Ile Trp Lys Asn Tyr
                 85                  90                  95 cta agc atg aac aag tac aaa gtg tcc tac aag ggg cca gga cca ggc    336
Leu Ser Met Asn Lys Tyr Lys Val Ser Tyr Lys Gly Pro Gly Pro Gly
            100                 105                 110 atc aag ttc agt gca gag gcc ctg cgc tgc cac ctc cgg gac cat gtg    384
Ile Lys Phe Ser Ala Glu Ala Leu Arg Cys His Leu Arg Asp His Val
        115                 120                 125 aat gta tcc atg gta gag gtc aca gat ttt ccc ttc aat acc tct gaa    432
Asn Val Ser Met Val Glu Val Thr Asp Phe Pro Phe Asn Thr Ser Glu
    130                 135                 140 tgg gag ggt tat ctg ccc aag gag agc att agg acc aag gct ggg cct    480
Trp Glu Gly Tyr Leu Pro Lys Glu Ser Ile Arg Thr Lys Ala Gly Pro
145                 150                 155                 160 tgg ggc agg tgt gct gtt gtg tcg tca gcg gga tct ctg aag tcc tcc    528
Trp Gly Arg Cys Ala Val Val Ser Ser Ala Gly Ser Leu Lys Ser Ser
                165                 170                 175 caa cta ggc aga gaa atc gat gat cat gac gca gtc ctg agg ttt aat    576
Gln Leu Gly Arg Glu Ile Asp Asp His Asp Ala Val Leu Arg Phe Asn
            180                 185                 190 ggg gca ccc aca gcc aac ttc caa caa gat gtg ggc aca aaa act acc    624
Gly Ala Pro Thr Ala Asn Phe Gln Gln Asp Val Gly Thr Lys Thr Thr
        195                 200                 205 att cgc ctg atg aac tct cag ttg gtt acc aca gag aag cgc ttc ctc    672
Ile Arg Leu Met Asn Ser Gln Leu Val Thr Thr Glu Lys Arg Phe Leu
    210                 215                 220 aaa gac agt ttg tac aat gaa gga atc cta att gta tgg gac cca tct    720
Lys Asp Ser Leu Tyr Asn Glu Gly Ile Leu Ile Val Trp Asp Pro Ser
225                 230                 235                 240 gta tac cac tca gat atc cca aag tgg tac cag aat ccg gat tat aat    768
Val Tyr His Ser Asp Ile Pro Lys Trp Tyr Gln Asn Pro Asp Tyr Asn
                245                 250                 255 ttc ttt aac aac tac aag act tat cgt aag ctg cac ccc aat cag ccc    816
Phe Phe Asn Asn Tyr Lys Thr Tyr Arg Lys Leu His Pro Asn Gln Pro
            260                 265                 270 ttt tac atc ctc aag ccc cag atg cct tgg gag cta tgg gac att ctt    864
Phe Tyr Ile Leu Lys Pro Gln Met Pro Trp Glu Leu Trp Asp Ile Leu
        275                 280                 285 caa gaa atc tcc cca gaa gag att cag cca aac ccc cca tcc tct ggg    912
Gln Glu Ile Ser Pro Glu Glu Ile Gln Pro Asn Pro Pro Ser Ser Gly
    290                 295                 300 atg ctt ggt atc atc atc atg atg acg ctg tgt gac cag gtg gat att    960
Met Leu Gly Ile Ile Ile Met Met Thr Leu Cys Asp Gln Val Asp Ile
305                 310                 315                 320 tat gag ttc ctc cca tcc aag cgc aag act gac gtg tgc tac tac tac   1008
Tyr Glu Phe Leu Pro Ser Lys Arg Lys Thr Asp Val Cys Tyr Tyr Tyr
                325                 330                 335 cag aag ttc ttc gat agt gcc tgc acg atg ggt gcc tac cac ccg ctg   1056
Gln Lys Phe Phe Asp Ser Ala Cys Thr Met Gly Ala Tyr His Pro Leu
            340                 345                 350 ctc tat gag aag aat ttg gtg aag cat ctc aac cag ggc aca gat gag   1104
Leu Tyr Glu Lys Asn Leu Val Lys His Leu Asn Gln Gly Thr Asp Glu
        355                 360                 365 gac atc tac ctg ctt gga aaa gcc aca ctg cct ggc ttc cgg acc att   1152
Asp Ile Tyr Leu Leu Gly Lys Ala Thr Leu Pro Gly Phe Arg Thr Ile
```

```
Asp Ile Tyr Leu Leu Gly Lys Ala Thr Leu Pro Gly Phe Arg Thr Ile
    370                 375                 380 cac tgc                                                              1158
His Cys
385
```

```
<210> SEQ ID NO 174
<211> LENGTH: 386
<212> TYPE: PRT
<213> ORGANISM: Artificial
<220> FEATURE:
<223> OTHER INFORMATION: Synthetic Construct

<400> SEQUENCE: 174

Met Arg Ser Ile Arg Lys Arg Trp Thr Ile Cys Thr Ile Ser Leu Leu
1               5                   10                  15

Leu Ile Phe Tyr Lys Thr Lys Glu Ile Ala Arg Thr Glu Glu His Gln
                20                  25                  30

Glu Thr Gln Leu Ile Gly Asp Gly Glu Leu Ser Leu Ser Arg Ser Leu
            35                  40                  45

Val Asn Ser Ser Asp Lys Ile Ile Arg Lys Ala Gly Ser Ser Ile Phe
50                  55                  60

Gln His Asn Lys Leu Glu Ala Ser Phe Gln Val Trp Asn Lys Asp Ser
65                  70                  75                  80

Ser Ser Lys Asn Leu Ile Pro Arg Leu Gln Lys Ile Trp Lys Asn Tyr
                85                  90                  95

Leu Ser Met Asn Lys Tyr Lys Val Ser Tyr Lys Gly Pro Gly Pro Gly
                100                 105                 110

Ile Lys Phe Ser Ala Glu Ala Leu Arg Cys His Leu Arg Asp His Val
            115                 120                 125

Asn Val Ser Met Val Glu Val Thr Asp Phe Pro Phe Asn Thr Ser Glu
130                 135                 140

Trp Glu Gly Tyr Leu Pro Lys Glu Ser Ile Arg Thr Lys Ala Gly Pro
145                 150                 155                 160

Trp Gly Arg Cys Ala Val Val Ser Ser Ala Gly Ser Leu Lys Ser Ser
                165                 170                 175

Gln Leu Gly Arg Glu Ile Asp Asp His Asp Ala Val Leu Arg Phe Asn
            180                 185                 190

Gly Ala Pro Thr Ala Asn Phe Gln Gln Asp Val Gly Thr Lys Thr Thr
        195                 200                 205

Ile Arg Leu Met Asn Ser Gln Leu Val Thr Thr Glu Lys Arg Phe Leu
210                 215                 220

Lys Asp Ser Leu Tyr Asn Glu Gly Ile Leu Ile Val Trp Asp Pro Ser
225                 230                 235                 240

Val Tyr His Ser Asp Ile Pro Lys Trp Tyr Gln Asn Pro Asp Tyr Asn
                245                 250                 255

Phe Phe Asn Asn Tyr Lys Thr Tyr Arg Lys Leu His Pro Asn Gln Pro
            260                 265                 270

Phe Tyr Ile Leu Lys Pro Gln Met Pro Trp Glu Leu Trp Asp Ile Leu
        275                 280                 285

Gln Glu Ile Ser Pro Glu Glu Ile Gln Pro Asn Pro Pro Ser Ser Gly
290                 295                 300

Met Leu Gly Ile Ile Ile Met Met Thr Leu Cys Asp Gln Val Asp Ile
305                 310                 315                 320

Tyr Glu Phe Leu Pro Ser Lys Arg Lys Thr Asp Val Cys Tyr Tyr Tyr
                325                 330                 335
```

```
Gln Lys Phe Phe Asp Ser Ala Cys Thr Met Gly Ala Tyr His Pro Leu
            340                 345                 350

Leu Tyr Glu Lys Asn Leu Val Lys His Leu Asn Gln Gly Thr Asp Glu
        355                 360                 365

Asp Ile Tyr Leu Leu Gly Lys Ala Thr Leu Pro Gly Phe Arg Thr Ile
370                 375                 380

His Cys
385

<210> SEQ ID NO 175
<211> LENGTH: 1155
<212> TYPE: DNA
<213> ORGANISM: Artificial
<220> FEATURE:
<223> OTHER INFORMATION: Fusion of the nucleotide sequence SEQ ID NO:
      159 with the nucleotide sequence SEQ ID NO: 43
<220> FEATURE:
<221> NAME/KEY: CDS
<222> LOCATION: (1)..(1155)

<400> SEQUENCE: 175 atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg gag cct caa aca      96
Phe Leu Val Leu Gly Phe Leu Tyr Tyr Ser Ala Trp Glu Pro Gln Thr
            20                  25                  30 aag cct tcc agg cat caa cgc aca gag aac att aaa gaa agg tct cta     144
Lys Pro Ser Arg His Gln Arg Thr Glu Asn Ile Lys Glu Arg Ser Leu
        35                  40                  45 cag tcc ctg gca aag cct aag tcc cag gca ccc aca agg gca agg agg     192
Gln Ser Leu Ala Lys Pro Lys Ser Gln Ala Pro Thr Arg Ala Arg Arg
    50                  55                  60 aca acc gga tcc gag gcc tcc ttc cag gtg tgg aac aag gac agc tct     240
Thr Thr Gly Ser Glu Ala Ser Phe Gln Val Trp Asn Lys Asp Ser Ser
65                  70                  75                  80 tcc aaa aac ctt atc cct agg ctg caa aag atc tgg aag aat tac cta     288
Ser Lys Asn Leu Ile Pro Arg Leu Gln Lys Ile Trp Lys Asn Tyr Leu
                85                  90                  95 agc atg aac aag tac aaa gtg tcc tac aag ggg cca gga cca ggc atc     336
Ser Met Asn Lys Tyr Lys Val Ser Tyr Lys Gly Pro Gly Pro Gly Ile
            100                 105                 110 aag ttc agt gca gag gcc ctg cgc tgc cac ctc cgg gac cat gtg aat     384
Lys Phe Ser Ala Glu Ala Leu Arg Cys His Leu Arg Asp His Val Asn
        115                 120                 125 gta tcc atg gta gag gtc aca gat ttt ccc ttc aat acc tct gaa tgg     432
Val Ser Met Val Glu Val Thr Asp Phe Pro Phe Asn Thr Ser Glu Trp
    130                 135                 140 gag ggt tat ctg ccc aag gag agc att agg acc aag gct ggg cct tgg     480
Glu Gly Tyr Leu Pro Lys Glu Ser Ile Arg Thr Lys Ala Gly Pro Trp
145                 150                 155                 160 ggc agg tgt gct gtt gtg tcg tca gcg gga tct ctg aag tcc tcc caa     528
Gly Arg Cys Ala Val Val Ser Ser Ala Gly Ser Leu Lys Ser Ser Gln
                165                 170                 175 cta ggc aga gaa atc gat gat cat gac gca gtc ctg agg ttt aat ggg     576
Leu Gly Arg Glu Ile Asp Asp His Asp Ala Val Leu Arg Phe Asn Gly
            180                 185                 190 gca ccc aca gcc aac ttc caa caa gat gtg ggc aca aaa act acc att     624
Ala Pro Thr Ala Asn Phe Gln Gln Asp Val Gly Thr Lys Thr Thr Ile
        195                 200                 205
```

```
cgc ctg atg aac tct cag ttg gtt acc aca gag aag cgc ttc ctc aaa    672
Arg Leu Met Asn Ser Gln Leu Val Thr Thr Glu Lys Arg Phe Leu Lys
    210             215                 220 gac agt ttg tac aat gaa gga atc cta att gta tgg gac cca tct gta    720
Asp Ser Leu Tyr Asn Glu Gly Ile Leu Ile Val Trp Asp Pro Ser Val
225                 230                 235                 240 tac cac tca gat atc cca aag tgg tac cag aat ccg gat tat aat ttc    768
Tyr His Ser Asp Ile Pro Lys Trp Tyr Gln Asn Pro Asp Tyr Asn Phe
                245                 250                 255 ttt aac aac tac aag act tat cgt aag ctg cac ccc aat cag ccc ttt    816
Phe Asn Asn Tyr Lys Thr Tyr Arg Lys Leu His Pro Asn Gln Pro Phe
            260                 265                 270 tac atc ctc aag ccc cag atg cct tgg gag cta tgg gac att ctt caa    864
Tyr Ile Leu Lys Pro Gln Met Pro Trp Glu Leu Trp Asp Ile Leu Gln
        275                 280                 285 gaa atc tcc cca gaa gag att cag cca aac ccc cca tcc tct ggg atg    912
Glu Ile Ser Pro Glu Glu Ile Gln Pro Asn Pro Pro Ser Ser Gly Met
    290                 295                 300 ctt ggt atc atc atc atg atg acg ctg tgt gac cag gtg gat att tat    960
Leu Gly Ile Ile Ile Met Met Thr Leu Cys Asp Gln Val Asp Ile Tyr
305                 310                 315                 320 gag ttc ctc cca tcc aag cgc aag act gac gtg tgc tac tac tac cag    1008
Glu Phe Leu Pro Ser Lys Arg Lys Thr Asp Val Cys Tyr Tyr Tyr Gln
                325                 330                 335 aag ttc ttc gat agt gcc tgc acg atg ggt gcc tac cac ccg ctg ctc    1056
Lys Phe Phe Asp Ser Ala Cys Thr Met Gly Ala Tyr His Pro Leu Leu
            340                 345                 350 tat gag aag aat ttg gtg aag cat ctc aac cag ggc aca gat gag gac    1104
Tyr Glu Lys Asn Leu Val Lys His Leu Asn Gln Gly Thr Asp Glu Asp
        355                 360                 365 atc tac ctg ctt gga aaa gcc aca ctg cct ggc ttc cgg acc att cac    1152
Ile Tyr Leu Leu Gly Lys Ala Thr Leu Pro Gly Phe Arg Thr Ile His
    370                 375                 380 tgc                                                                1155
Cys
385

<210> SEQ ID NO 176
<211> LENGTH: 385
<212> TYPE: PRT
<213> ORGANISM: Artificial
<220> FEATURE:
<223> OTHER INFORMATION: Synthetic Construct

<400> SEQUENCE: 176

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Glu Pro Gln Thr
            20                  25                  30

Lys Pro Ser Arg His Gln Arg Thr Glu Asn Ile Lys Glu Arg Ser Leu
        35                  40                  45

Gln Ser Leu Ala Lys Pro Lys Ser Gln Ala Pro Thr Arg Ala Arg Arg
    50                  55                  60

Thr Thr Gly Ser Glu Ala Ser Phe Gln Val Trp Asn Lys Asp Ser Ser
65                  70                  75                  80

Ser Lys Asn Leu Ile Pro Arg Leu Gln Lys Ile Trp Lys Asn Tyr Leu
                85                  90                  95

Ser Met Asn Lys Tyr Lys Val Ser Tyr Lys Gly Pro Gly Pro Gly Ile
            100                 105                 110
```

```
Lys Phe Ser Ala Glu Ala Leu Arg Cys His Leu Arg Asp His Val Asn
            115                 120                 125

Val Ser Met Val Glu Val Thr Asp Phe Pro Phe Asn Thr Ser Glu Trp
130                 135                 140

Glu Gly Tyr Leu Pro Lys Glu Ser Ile Arg Thr Lys Ala Gly Pro Trp
145                 150                 155                 160

Gly Arg Cys Ala Val Val Ser Ser Ala Gly Ser Leu Lys Ser Ser Gln
                165                 170                 175

Leu Gly Arg Glu Ile Asp Asp His Asp Ala Val Leu Arg Phe Asn Gly
            180                 185                 190

Ala Pro Thr Ala Asn Phe Gln Gln Asp Val Gly Thr Lys Thr Thr Ile
        195                 200                 205

Arg Leu Met Asn Ser Gln Leu Val Thr Thr Glu Lys Arg Phe Leu Lys
    210                 215                 220

Asp Ser Leu Tyr Asn Glu Gly Ile Leu Ile Val Trp Asp Pro Ser Val
225                 230                 235                 240

Tyr His Ser Asp Ile Pro Lys Trp Tyr Gln Asn Pro Asp Tyr Asn Phe
                245                 250                 255

Phe Asn Asn Tyr Lys Thr Tyr Arg Lys Leu His Pro Asn Gln Pro Phe
            260                 265                 270

Tyr Ile Leu Lys Pro Gln Met Pro Trp Glu Leu Trp Asp Ile Leu Gln
        275                 280                 285

Glu Ile Ser Pro Glu Glu Ile Gln Pro Asn Pro Pro Ser Ser Gly Met
    290                 295                 300

Leu Gly Ile Ile Ile Met Met Thr Leu Cys Asp Gln Val Asp Ile Tyr
305                 310                 315                 320

Glu Phe Leu Pro Ser Lys Arg Lys Thr Asp Val Cys Tyr Tyr Gln
                325                 330                 335

Lys Phe Asp Ser Ala Cys Thr Met Gly Ala Tyr His Pro Leu Leu
            340                 345                 350

Tyr Glu Lys Asn Leu Val Lys His Leu Asn Gln Gly Thr Asp Glu Asp
        355                 360                 365

Ile Tyr Leu Leu Gly Lys Ala Thr Leu Pro Gly Phe Arg Thr Ile His
370                 375                 380

Cys
385

<210> SEQ ID NO 177
<211> LENGTH: 84
<212> TYPE: DNA
<213> ORGANISM: Artificial
<220> FEATURE:
<223> OTHER INFORMATION: Fusion of the nucleotide sequence SEQ ID NO:
      65 with the nucleotide sequence SEQ ID NO : 107
<220> FEATURE:
<221> NAME/KEY: CDS
<222> LOCATION: (1)..(84)

<400> SEQUENCE: 177 atg gga ctc ttg gta ttt gtg cgc aat ctg ctg cta gcc ctc tgc ctc    48
Met Gly Leu Leu Val Phe Val Arg Asn Leu Leu Leu Ala Leu Cys Leu
1               5                   10                  15 ttt ctg gta ctg gga ttt ttg tat tat tct gcg tgg                    84
Phe Leu Val Leu Gly Phe Leu Tyr Tyr Ser Ala Trp
            20                  25

<210> SEQ ID NO 178
<211> LENGTH: 28
```

```
<212> TYPE: PRT
<213> ORGANISM: Artificial
<220> FEATURE:
<223> OTHER INFORMATION: Synthetic Construct

<400> SEQUENCE: 178

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp
            20                  25

<210> SEQ ID NO 179
<211> LENGTH: 192
<212> TYPE: DNA
<213> ORGANISM: Artificial
<220> FEATURE:
<223> OTHER INFORMATION: Fusion of the nucleotide sequence SEQ ID NO:
      65 with the nucleotide sequence SEQ ID NO : 119 and with the
      nucleotide sequence SEQ ID NO : 129
<220> FEATURE:
<221> NAME/KEY: CDS
<222> LOCATION: (1)..(192)

<400> SEQUENCE: 179 atg gga ctc ttg gta ttt gtg cgc agc tgg atg ctg gcc gcg ctc acg      48
Met Gly Leu Leu Val Phe Val Arg Ser Trp Met Leu Ala Ala Leu Thr
1               5                   10                  15 ctg ctc gtg gtc ttc ctc atc ttc gca aag gag cct caa aca aag cct      96
Leu Leu Val Val Phe Leu Ile Phe Ala Lys Glu Pro Gln Thr Lys Pro
            20                  25                  30 tcc agg cat caa cgc aca gag aac att aaa gaa agg tct cta cag tcc     144
Ser Arg His Gln Arg Thr Glu Asn Ile Lys Glu Arg Ser Leu Gln Ser
        35                  40                  45 ctg gca aag cct aag tcc cag gca ccc aca agg gca agg agg aca acc     192
Leu Ala Lys Pro Lys Ser Gln Ala Pro Thr Arg Ala Arg Arg Thr Thr
    50                  55                  60

<210> SEQ ID NO 180
<211> LENGTH: 64
<212> TYPE: PRT
<213> ORGANISM: Artificial
<220> FEATURE:
<223> OTHER INFORMATION: Synthetic Construct

<400> SEQUENCE: 180

Met Gly Leu Leu Val Phe Val Arg Ser Trp Met Leu Ala Ala Leu Thr
1               5                   10                  15

Leu Leu Val Val Phe Leu Ile Phe Ala Lys Glu Pro Gln Thr Lys Pro
            20                  25                  30

Ser Arg His Gln Arg Thr Glu Asn Ile Lys Glu Arg Ser Leu Gln Ser
        35                  40                  45

Leu Ala Lys Pro Lys Ser Gln Ala Pro Thr Arg Ala Arg Arg Thr Thr
    50                  55                  60

<210> SEQ ID NO 181
<211> LENGTH: 1143
<212> TYPE: DNA
<213> ORGANISM: Artificial
<220> FEATURE:
<223> OTHER INFORMATION: Fusion of the nucleotide sequence SEQ ID NO:
      179 with the nucleotide sequence SEQ ID NO: 43
<220> FEATURE:
<221> NAME/KEY: CDS
<222> LOCATION: (1)..(1143)

<400> SEQUENCE: 181
```

-continued

| | |
|---|---|
| atg gga ctc ttg gta ttt gtg cgc agc tgg atg ctg gcg ctc acg<br>Met Gly Leu Leu Val Phe Val Arg Ser Trp Met Leu Ala Ala Leu Thr<br>1               5                   10                  15 | 48 |
| ctg ctc gtg gtc ttc ctc atc ttc gca aag gag cct caa aca aag cct<br>Leu Leu Val Val Phe Leu Ile Phe Ala Lys Glu Pro Gln Thr Lys Pro<br>                20                  25                  30 | 96 |
| tcc agg cat caa cgc aca gag aac att aaa gaa agg tct cta cag tcc<br>Ser Arg His Gln Arg Thr Glu Asn Ile Lys Glu Arg Ser Leu Gln Ser<br>        35                  40                  45 | 144 |
| ctg gca aag cct aag tcc cag gca ccc aca agg gca agg agg aca acc<br>Leu Ala Lys Pro Lys Ser Gln Ala Pro Thr Arg Ala Arg Arg Thr Thr<br>50                  55                  60 | 192 |
| gag gcc tcc ttc cag gtg tgg aac aag gac agc tct tcc aaa aac ctt<br>Glu Ala Ser Phe Gln Val Trp Asn Lys Asp Ser Ser Ser Lys Asn Leu<br>65                  70                  75                  80 | 240 |
| atc cct agg ctg caa aag atc tgg aag aat tac cta agc atg aac aag<br>Ile Pro Arg Leu Gln Lys Ile Trp Lys Asn Tyr Leu Ser Met Asn Lys<br>                85                  90                  95 | 288 |
| tac aaa gtg tcc tac aag ggg cca gga cca ggc atc aag ttc agt gca<br>Tyr Lys Val Ser Tyr Lys Gly Pro Gly Pro Gly Ile Lys Phe Ser Ala<br>            100                 105                 110 | 336 |
| gag gcc ctg cgc tgc cac ctc cgg gac cat gtg aat gta tcc atg gta<br>Glu Ala Leu Arg Cys His Leu Arg Asp His Val Asn Val Ser Met Val<br>            115                 120                 125 | 384 |
| gag gtc aca gat ttt ccc ttc aat acc tct gaa tgg gag ggt tat ctg<br>Glu Val Thr Asp Phe Pro Phe Asn Thr Ser Glu Trp Glu Gly Tyr Leu<br>130                 135                 140 | 432 |
| ccc aag gag agc att agg acc aag gct ggg cct tgg ggc agg tgt gct<br>Pro Lys Glu Ser Ile Arg Thr Lys Ala Gly Pro Trp Gly Arg Cys Ala<br>145                 150                 155                 160 | 480 |
| gtt gtg tcg tca gcg gga tct ctg aag tcc tcc caa cta ggc aga gaa<br>Val Val Ser Ser Ala Gly Ser Leu Lys Ser Ser Gln Leu Gly Arg Glu<br>                165                 170                 175 | 528 |
| atc gat gat cat gac gca gtc ctg agg ttt aat ggg gca ccc aca gcc<br>Ile Asp Asp His Asp Ala Val Leu Arg Phe Asn Gly Ala Pro Thr Ala<br>            180                 185                 190 | 576 |
| aac ttc caa caa gat gtg ggc aca aaa act acc att cgc ctg atg aac<br>Asn Phe Gln Gln Asp Val Gly Thr Lys Thr Thr Ile Arg Leu Met Asn<br>            195                 200                 205 | 624 |
| tct cag ttg gtt acc aca gag aag cgc ttc ctc aaa gac agt ttg tac<br>Ser Gln Leu Val Thr Thr Glu Lys Arg Phe Leu Lys Asp Ser Leu Tyr<br>210                 215                 220 | 672 |
| aat gaa gga atc cta att gta tgg gac cca tct gta tac cac tca gat<br>Asn Glu Gly Ile Leu Ile Val Trp Asp Pro Ser Val Tyr His Ser Asp<br>225                 230                 235                 240 | 720 |
| atc cca aag tgg tac cag aat ccg gat tat aat ttc ttt aac aac tac<br>Ile Pro Lys Trp Tyr Gln Asn Pro Asp Tyr Asn Phe Phe Asn Asn Tyr<br>                245                 250                 255 | 768 |
| aag act tat cgt aag ctg cac ccc aat cag ccc ttt tac atc ctc aag<br>Lys Thr Tyr Arg Lys Leu His Pro Asn Gln Pro Phe Tyr Ile Leu Lys<br>            260                 265                 270 | 816 |
| ccc cag atg cct tgg gag cta tgg gac att ctt caa gaa atc tcc cca<br>Pro Gln Met Pro Trp Glu Leu Trp Asp Ile Leu Gln Glu Ile Ser Pro<br>            275                 280                 285 | 864 |
| gaa gag att cag cca aac ccc cca tcc tct ggg atg ctt ggt atc atc<br>Glu Glu Ile Gln Pro Asn Pro Pro Ser Ser Gly Met Leu Gly Ile Ile<br>290                 295                 300 | 912 |
| atc atg atg acg ctg tgt gac cag gtg gat att tat gag ttc ctc cca<br>Ile Met Met Thr Leu Cys Asp Gln Val Asp Ile Tyr Glu Phe Leu Pro | 960 |

```
                305                 310                 315                 320
tcc aag cgc aag act gac gtg tgc tac tac tac cag aag ttc ttc gat         1008
Ser Lys Arg Lys Thr Asp Val Cys Tyr Tyr Tyr Gln Lys Phe Phe Asp
                325                 330                 335 agt gcc tgc acg atg ggt gcc tac cac ccg ctg ctc tat gag aag aat         1056
Ser Ala Cys Thr Met Gly Ala Tyr His Pro Leu Leu Tyr Glu Lys Asn
            340                 345                 350 ttg gtg aag cat ctc aac cag ggc aca gat gag gac atc tac ctg ctt         1104
Leu Val Lys His Leu Asn Gln Gly Thr Asp Glu Asp Ile Tyr Leu Leu
        355                 360                 365 gga aaa gcc aca ctg cct ggc ttc cgg acc att cac tgc                     1143
Gly Lys Ala Thr Leu Pro Gly Phe Arg Thr Ile His Cys
    370                 375                 380

<210> SEQ ID NO 182
<211> LENGTH: 381
<212> TYPE: PRT
<213> ORGANISM: Artificial
<220> FEATURE:
<223> OTHER INFORMATION: Synthetic Construct

<400> SEQUENCE: 182

Met Gly Leu Leu Val Phe Val Arg Ser Trp Met Leu Ala Ala Leu Thr
1               5                   10                  15

Leu Leu Val Val Phe Leu Ile Phe Ala Lys Glu Pro Gln Thr Lys Pro
                20                  25                  30

Ser Arg His Gln Arg Thr Glu Asn Ile Lys Glu Arg Ser Leu Gln Ser
            35                  40                  45

Leu Ala Lys Pro Lys Ser Gln Ala Pro Thr Arg Ala Arg Thr Thr
        50                  55                  60

Glu Ala Ser Phe Gln Val Trp Asn Lys Asp Ser Ser Lys Asn Leu
65                  70                  75                  80

Ile Pro Arg Leu Gln Lys Ile Trp Lys Asn Tyr Leu Ser Met Asn Lys
                85                  90                  95

Tyr Lys Val Ser Tyr Lys Gly Pro Gly Pro Gly Ile Lys Phe Ser Ala
                100                 105                 110

Glu Ala Leu Arg Cys His Leu Arg Asp His Val Asn Val Ser Met Val
            115                 120                 125

Glu Val Thr Asp Phe Pro Phe Asn Thr Ser Glu Trp Glu Gly Tyr Leu
        130                 135                 140

Pro Lys Glu Ser Ile Arg Thr Lys Ala Gly Pro Trp Gly Arg Cys Ala
145                 150                 155                 160

Val Val Ser Ser Ala Gly Ser Leu Lys Ser Ser Gln Leu Gly Arg Glu
                165                 170                 175

Ile Asp Asp His Asp Ala Val Leu Arg Phe Asn Gly Ala Pro Thr Ala
            180                 185                 190

Asn Phe Gln Gln Asp Val Gly Thr Lys Thr Thr Ile Arg Leu Met Asn
        195                 200                 205

Ser Gln Leu Val Thr Thr Glu Lys Arg Phe Leu Lys Asp Ser Leu Tyr
        210                 215                 220

Asn Glu Gly Ile Leu Ile Val Trp Asp Pro Ser Val Tyr His Ser Asp
225                 230                 235                 240

Ile Pro Lys Trp Tyr Gln Asn Pro Asp Tyr Asn Phe Phe Asn Asn Tyr
                245                 250                 255

Lys Thr Tyr Arg Lys Leu His Pro Asn Gln Pro Phe Tyr Ile Leu Lys
            260                 265                 270
```

```
Pro Gln Met Pro Trp Glu Leu Trp Asp Ile Leu Gln Glu Ile Ser Pro
            275                 280                 285

Glu Glu Ile Gln Pro Asn Pro Pro Ser Ser Gly Met Leu Gly Ile Ile
290                 295                 300

Ile Met Met Thr Leu Cys Asp Gln Val Asp Ile Tyr Glu Phe Leu Pro
305                 310                 315                 320

Ser Lys Arg Lys Thr Asp Val Cys Tyr Tyr Tyr Gln Lys Phe Phe Asp
                325                 330                 335

Ser Ala Cys Thr Met Gly Ala Tyr His Pro Leu Leu Tyr Glu Lys Asn
                340                 345                 350

Leu Val Lys His Leu Asn Gln Gly Thr Asp Glu Asp Ile Tyr Leu Leu
                355                 360                 365

Gly Lys Ala Thr Leu Pro Gly Phe Arg Thr Ile His Cys
                370                 375                 380

<210> SEQ ID NO 183
<211> LENGTH: 403
<212> TYPE: PRT
<213> ORGANISM: Rattus norvegicus

<400> SEQUENCE: 183

Met Ile His Thr Asn Leu Lys Lys Lys Phe Ser Leu Phe Ile Leu Val
1               5                   10                  15

Phe Leu Leu Phe Ala Val Ile Cys Val Trp Lys Lys Gly Ser Asp Tyr
                20                  25                  30

Glu Ala Leu Thr Leu Gln Ala Lys Glu Phe Gln Met Pro Lys Ser Gln
            35                  40                  45

Glu Lys Val Ala Met Gly Ser Ala Ser Gln Val Val Phe Ser Asn Ser
50                  55                  60

Lys Gln Asp Pro Lys Glu Asp Ile Pro Ile Leu Ser Tyr His Arg Val
65                  70                  75                  80

Thr Ala Lys Val Lys Pro Gln Pro Ser Phe Gln Val Trp Asp Lys Asp
                85                  90                  95

Ser Thr Tyr Ser Lys Leu Asn Pro Arg Leu Leu Lys Ile Trp Arg Asn
            100                 105                 110

Tyr Leu Asn Met Asn Lys Tyr Lys Val Ser Tyr Lys Gly Pro Gly Pro
        115                 120                 125

Gly Val Lys Phe Ser Val Glu Ala Leu Arg Cys His Leu Arg Asp His
    130                 135                 140

Val Asn Val Ser Met Ile Glu Ala Thr Asp Phe Pro Phe Asn Thr Thr
145                 150                 155                 160

Glu Trp Glu Gly Tyr Leu Pro Lys Glu Asn Phe Arg Thr Lys Val Gly
                165                 170                 175

Pro Trp Gln Arg Cys Ala Val Val Ser Ser Ala Gly Ser Leu Lys Asn
            180                 185                 190

Ser Gln Leu Gly Arg Glu Ile Asp Asn His Asp Ala Val Leu Arg Phe
        195                 200                 205

Asn Gly Ala Pro Thr Asp Asn Phe Gln Gln Asp Val Gly Ser Lys Thr
    210                 215                 220

Thr Ile Arg Leu Met Asn Ser Gln Leu Val Thr Thr Glu Lys Arg Phe
225                 230                 235                 240

Leu Lys Asp Ser Leu Tyr Thr Glu Gly Ile Leu Ile Val Trp Asp Pro
                245                 250                 255

Ser Val Tyr His Ala Asp Ile Pro Lys Trp Tyr Gln Lys Pro Asp Tyr
            260                 265                 270
```

```
Asn Phe Phe Glu Thr Tyr Lys Ser Tyr Arg Arg Leu Asn Pro Ser Gln
        275                 280                 285

Pro Phe Tyr Ile Leu Lys Pro Gln Met Pro Trp Glu Leu Trp Asp Ile
    290                 295                 300

Ile Gln Glu Ile Ser Ala Asp Leu Ile Gln Pro Asn Pro Pro Ser Ser
305                 310                 315                 320

Gly Met Leu Gly Ile Ile Met Met Thr Leu Cys Asp Gln Val Asp
                325                 330                 335

Ile Tyr Glu Phe Leu Pro Ser Lys Arg Lys Thr Asp Val Cys Tyr Tyr
                340                 345                 350

His Gln Lys Phe Phe Asp Ser Ala Cys Thr Met Gly Ala Tyr Asp Pro
            355                 360                 365

Leu Leu Phe Glu Lys Asn Met Val Lys His Leu Asn Glu Gly Thr Asp
        370                 375                 380

Glu Asp Ile Tyr Leu Phe Gly Lys Ala Thr Leu Ser Gly Phe Arg Asn
385                 390                 395                 400

Ile Arg Cys

<210> SEQ ID NO 184
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in hST8Sia II

<400> SEQUENCE: 184

Thr Cys Ala Ile Val Gly Asn Ser Gly Val Leu Leu Asn Ser Gly Cys
1               5                   10                  15

Gly Gln Glu Ile Asp Ala His Ser Phe Val Ile Arg Cys Asn Leu Ala
            20                  25                  30

Pro Val Gln Glu Tyr Ala Arg Asp Val Gly Leu Lys Thr Pro Thr Thr
        35                  40                  45

Gly Leu Leu Met Tyr Thr Leu Ala Thr Arg Phe Cys Lys Gln Ile Tyr
    50                  55                  60

Leu Tyr Gly Phe Ala Ser Pro His Thr Met Pro Leu Glu Phe Lys Ala
65                  70                  75                  80

<210> SEQ ID NO 185
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in hST8Sia IV

<400> SEQUENCE: 185

Thr Cys Ala Val Val Gly Asn Ser Gly Ile Leu Leu Asp Ser Glu Cys
1               5                   10                  15

Gly Lys Glu Ile Asp Ser His Asn Phe Val Ile Arg Cys Asn Leu Ala
            20                  25                  30

Pro Val Val Glu Phe Ala Ala Asp Val Gly Thr Lys Ser Pro Ser Thr
        35                  40                  45

Gly Leu Leu Met Tyr Thr Leu Ala Thr Arg Phe Cys Asp Glu Ile His
    50                  55                  60

Leu Tyr Gly Phe Ala Ser Pro His Arg Met Pro Leu Glu Phe Lys Thr
65                  70                  75                  80
```

<210> SEQ ID NO 186
<211> LENGTH: 79
<212> TYPE: PRT
<213> ORGANISM: Artificial sequence
<220> FEATURE:
<223> OTHER INFORMATION: Amino acid sequence of sialylmotif L, S, and VS in hST3Gal I

<400> SEQUENCE: 186

Arg Cys Ala Trp Gly Asn Ser Gly Asn Leu Arg Glu Ser Ser Tyr Gly
1               5                   10                  15

Pro Glu Ile Asp Ser His Asp Phe Val Leu Arg Met Asn Lys Ala Pro
                20                  25                  30

Thr Ala Gly Phe Glu Ala Asp Val Gly Thr Lys Thr Pro Ser Thr Gly
            35                  40                  45

Ile Leu Ser Val Ile Phe Ser Met His Val Cys Asp Glu Val Asp Leu
        50                  55                  60

Tyr Gly Phe Thr Gly Val His Asp Ala Asp Phe Glu Ser Asn Val
65                  70                  75

<210> SEQ ID NO 187
<211> LENGTH: 79
<212> TYPE: PRT
<213> ORGANISM: Artificial sequence
<220> FEATURE:
<223> OTHER INFORMATION: Amino acid sequence of sialylmotif L, S, and VS in hST3Gal II

<400> SEQUENCE: 187

Arg Cys Ala Trp Gly Asn Ser Gly Asn Leu Arg Gly Ser Gly Tyr Gly
1               5                   10                  15

Gln Asp Val Asp Gly His Asn Phe Ile Met Arg Met Asn Gln Ala Pro
                20                  25                  30

Thr Val Gly Phe Glu Gln Asp Val Gly Ser Arg Thr Pro Ser Thr Gly
            35                  40                  45

Met Leu Val Leu Phe Phe Ala Leu His Val Cys Asp Glu Val Asn Val
        50                  55                  60

Tyr Gly Phe Thr Gly Val His Asp Ala Asp Phe Glu Ala His Ile
65                  70                  75

<210> SEQ ID NO 188
<211> LENGTH: 80
<212> TYPE: PRT
<213> ORGANISM: Artificial sequence
<220> FEATURE:
<223> OTHER INFORMATION: Amino acid sequence of sialylmotif L, S, and VS in ST6GalNac III

<400> SEQUENCE: 188

Leu Cys Ala Ile Val Ser Asn Ser Gly Gln Met Val Gly Gln Lys Val
1               5                   10                  15

Gly Asn Glu Ile Asp Arg Ser Ser Cys Ile Trp Arg Met Asn Asn Ala
                20                  25                  30

Pro Thr Lys Gly Tyr Glu Glu Asp Val Gly Arg Met Thr Leu Ser Thr
            35                  40                  45

Gly Trp Phe Thr Phe Leu Leu Ala Met Asp Ala Cys Tyr Gly Ile His
        50                  55                  60

Val Tyr Gly Phe Tyr Gly Gly His Arg Phe Ile Thr Glu Lys Lys Val
65                  70                  75                  80

<210> SEQ ID NO 189
<211> LENGTH: 80
<212> TYPE: PRT
<213> ORGANISM: Artificial sequence
<220> FEATURE:
<223> OTHER INFORMATION: Amino acid sequence of sialylmotif L, S, and VS in ST6GalNac IV

<400> SEQUENCE: 189

Ser Cys Ala Val Val Ser Ser Gly Gln Met Leu Gly Ser Gly Leu
1               5                   10                  15

Gly Ala Glu Ile Asp Ser Ala Glu Cys Val Phe Arg Met Asn Gln Ala
            20                  25                  30

Pro Thr Val Gly Phe Glu Ala Asp Val Gly Gln Arg Ser Leu Ser Thr
            35                  40                  45

Gly Trp Phe Thr Met Ile Leu Ala Leu Glu Leu Cys Glu Glu Ile Val
        50                  55                  60

Val Tyr Gly Met Arg Ser Ala His Arg Phe Ile Thr Glu Lys Ala Val
65                  70                  75                  80

<210> SEQ ID NO 190
<211> LENGTH: 80
<212> TYPE: PRT
<213> ORGANISM: Artificial sequence
<220> FEATURE:
<223> OTHER INFORMATION: Amino acid sequence of sialylmotif L, S, and VS in ST6GalNac V

<400> SEQUENCE: 190

Asp Cys Ala Leu Val Thr Ser Ser Gly His Leu Leu His Ser Arg Gln
1               5                   10                  15

Gly Ser Gln Ile Asp Gln Thr Glu Cys Val Ile Arg Met Asn Asp Ala
            20                  25                  30

Pro Thr Arg Gly Tyr Gly Arg Asp Val Gly Asn Arg Thr Leu Ser Thr
            35                  40                  45

Gly Trp Phe Thr Met Thr Ile Ala Leu Glu Leu Cys Asp Arg Ile Asn
        50                  55                  60

Val Tyr Gly Met Gly Ser His His Arg Phe Ile Thr Glu Lys Arg Val
65                  70                  75                  80

<210> SEQ ID NO 191
<211> LENGTH: 80
<212> TYPE: PRT
<213> ORGANISM: Artificial sequence
<220> FEATURE:
<223> OTHER INFORMATION: Amino acid sequence of sialylmotif L, S, and VS in ST6GalNac VI

<400> SEQUENCE: 191

Gln Cys Val Ile Val Ser Ser Ser His Leu Leu Gly Thr Lys Leu
1               5                   10                  15

Gly Pro Glu Ile Glu Arg Ala Glu Cys Thr Ile Arg Met Asn Asp Ala
            20                  25                  30

Pro Thr Thr Gly Tyr Ser Ala Asp Val Gly Asn Lys Thr Leu Ser Thr
            35                  40                  45

Gly Trp Phe Thr Met Val Ile Ala Val Glu Leu Cys Asp His Val His
        50                  55                  60

Val Tyr Gly Met Gly Asn His His Arg Phe Ile Thr Glu Lys Arg Val
65                  70                  75                  80

<210> SEQ ID NO 192

```
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in ST8Sia III

<400> SEQUENCE: 192

Ile Cys Ala Val Val Gly Asn Ser Gly Ile Leu Thr Phe Ile Gln Cys
1               5                   10                  15

Gly Arg Glu Ile Asp Lys Ser Asp Phe Val Phe Arg Cys Asn Phe Ala
            20                  25                  30

Pro Ser Glu Ala Phe Gln Arg Asp Val Gly Arg Lys Thr Leu Ser Thr
        35                  40                  45

Gly Ile Leu Met Tyr Thr Leu Ala Ser Ala Ile Cys Glu Glu Ile His
    50                  55                  60

Leu Tyr Gly Phe Gln Glu Ser His Gln Leu Pro Ala Glu Phe Gln Leu
65                  70                  75                  80

<210> SEQ ID NO 193
<211> LENGTH: 81
<212> TYPE: PRT
<213> ORGANISM: Artificial sequence
<220> FEATURE:
<223> OTHER INFORMATION: Amino acid sequence of sialylmotif L, S, and VS
      in ST8Sia I

<400> SEQUENCE: 193

Lys Cys Ala Val Val Gly Asn Gly Gly Ile Leu Lys Lys Ser Gly Cys
1               5                   10                  15

Gly Arg Gln Ile Asp Glu Ala Asn Phe Val Met Arg Cys Asn Leu Pro
            20                  25                  30

Pro Leu Ser Ser Glu Tyr Thr Lys Asp Val Gly Ser Lys Ser Leu Ser
        35                  40                  45

Thr Gly Leu Phe Leu Val Ser Ala Ala Leu Gly Leu Cys Glu Glu Val
    50                  55                  60

Ala Leu Tyr Gly Phe Ser Gly Phe His Ala Met Pro Glu Glu Phe Leu
65                  70                  75                  80

Gln

<210> SEQ ID NO 194
<211> LENGTH: 81
<212> TYPE: PRT
<213> ORGANISM: Artificial sequence
<220> FEATURE:
<223> OTHER INFORMATION: Amino acid sequence of sialylmotif L, S, and VS
      in ST8Sia VI

<400> SEQUENCE: 194

Gln Cys Ala Val Val Gly Asn Gly Gly Ile Leu Asn Lys Ser Leu Cys
1               5                   10                  15

Gly Thr Glu Ile Asp Lys Ser Asp Phe Val Phe Arg Cys Asn Leu Pro
            20                  25                  30

Pro Thr Thr Gly Asp Val Ser Lys Asp Val Gly Ser Lys Thr Leu Ser
        35                  40                  45

Thr Gly Leu Met Ile Thr Ser Val Ala Val Glu Leu Cys Lys Asn Val
    50                  55                  60

Lys Leu Tyr Gly Phe His Gly Phe His Gln Met Pro Lys Glu Tyr Ser
65                  70                  75                  80

Gln
```

<210> SEQ ID NO 195
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in ST8Sia V

<400> SEQUENCE: 195

Lys Cys Ala Trp Gly Asn Gly Gly Ile Leu Lys Asn Ser Arg Cys Gly
1               5                   10                  15

Arg Glu Ile Asn Ser Ala Asp Phe Val Phe Arg Cys Asn Leu Pro Pro
            20                  25                  30

Ile Ser Glu Lys Tyr Thr Met Asp Val Gly Val Lys Thr Leu Ser Thr
        35                  40                  45

Gly Leu Ile Leu Val Thr Ala Ala Leu Glu Leu Cys Glu Glu Val His
    50                  55                  60

Leu Phe Gly Phe Pro Gly Gly His Ala Met Pro Ser Glu Ile Phe Asn
65                  70                  75                  80

<210> SEQ ID NO 196
<211> LENGTH: 79
<212> TYPE: PRT
<213> ORGANISM: Artificial sequence
<220> FEATURE:
<223> OTHER INFORMATION: Amino acid sequence of sialylmotif L, S, and VS
      in ST3Gal III

<400> SEQUENCE: 196

Arg Cys Ile Ile Val Gly Asn Gly Gly Val Leu Ala Asn Lys Ser Leu
1               5                   10                  15

Gly Ser Arg Ile Asp Asp Tyr Asp Ile Trp Arg Leu Asn Ser Ala Pro
            20                  25                  30

Val Lys Gly Phe Glu Lys Asp Val Gly Ser Lys Thr Pro Thr Leu Gly
        35                  40                  45

Ser Val Ala Val Thr Met Ala Leu His Gly Cys Asp Glu Val Ala Val
    50                  55                  60

Ala Gly Phe Ser Trp Thr His Asn Ile Gln Arg Glu Lys Glu Phe
65                  70                  75

<210> SEQ ID NO 197
<211> LENGTH: 79
<212> TYPE: PRT
<213> ORGANISM: Artificial sequence
<220> FEATURE:
<223> OTHER INFORMATION: Amino acid sequence of sialylmotif L, S, and VS
      in ST3Gal V

<400> SEQUENCE: 197

Arg Cys Val Val Ile Gly Ser Gly Gly Ile Leu His Gly Leu Glu Leu
1               5                   10                  15

Gly His Thr Leu Asn Gln Phe Asp Val Val Ile Arg Leu Asn Ser Ala
            20                  25                  30

Pro Val Glu Gly Tyr Ser Glu His Val Gly Asn Lys Thr Pro Thr Ile
        35                  40                  45

Gly Val Ile Ala Trp Leu Ala Thr His Leu Cys Asp Glu Val Ser Leu
    50                  55                  60

Ala Gly Phe Gln Thr Met His Asn Val Thr Thr Glu Thr Lys Phe
65                  70                  75

<210> SEQ ID NO 198
<211> LENTH: 79
<212> TYPE: PRT
<213> ORGANISM: Artificial sequence
<220> FEATURE:
<223> OTHER INFORMATION: Amino acid sequence of sialylmotif L, S, and VS in ST3Gal IV

<400> SEQUENCE: 198

```
Arg Cys Val Val Val Gly Asn Gly His Arg Leu Arg Asn Ser Ser Leu
1               5                   10                  15

Gly Asp Ala Ile Asn Lys Tyr Asp Trp Ile Arg Leu Asn Asn Ala Pro
                20                  25                  30

Val Ala Gly Tyr Glu Gly Asp Val Gly Ser Lys Thr Pro Thr Thr Gly
            35                  40                  45

Leu Leu Ala Ile Thr Leu Ala Leu His Leu Cys Asp Leu Val His Ile
    50                  55                  60

Ala Gly Phe Gly Ser Gly His Asn Val Ser Gln Glu Ala Leu Ala
65                  70                  75
```

<210> SEQ ID NO 199
<211> LENGTH: 79
<212> TYPE: PRT
<213> ORGANISM: Artificial sequence
<220> FEATURE:
<223> OTHER INFORMATION: Amino acid sequence of sialylmotif L, S, and VS in ST3Gal VI

<400> SEQUENCE: 199

```
Lys Cys Trp Val Gly Asn Gly Gly Val Leu Lys Asn Lys Thr Leu Gly
1               5                   10                  15

Glu Lys Ile Asp Ser Tyr Asp Val Ile Arg Met Asn Asn Gly Pro
                20                  25                  30

Val Leu Gly His Glu Glu Val Gly Arg Arg Thr Pro Thr Thr Gly
            35                  40                  45

Ile Ile Ala Ile Thr Leu Ala Phe Tyr Ile Cys His Glu Val His Leu
    50                  55                  60

Ala Gly Phe Asn Ala Tyr His Asn Val Thr Ala Glu Gln Leu Phe
65                  70                  75
```

<210> SEQ ID NO 200
<211> LENGTH: 79
<212> TYPE: PRT
<213> ORGANISM: Artificial sequence
<220> FEATURE:
<223> OTHER INFORMATION: Amino acid sequence of sialylmotif L, S, and VS in ST6GalNac I

<400> SEQUENCE: 200

```
Thr Cys Ala Trp Gly Asn Gly Gly Ile Leu Asn Asn Ser His Met Gly
1               5                   10                  15

Gln Glu Ile Asp Ser His Asp Tyr Val Phe Arg Leu Ser Gly Ala Leu
                20                  25                  30

Ile Lys Gly Tyr Glu Gln Asp Val Gly Thr Arg Thr Pro Ser Thr Gly
            35                  40                  45

Ala Leu Met Leu Leu Thr Ala Leu His Thr Cys Asp Gln Val Ser Ala
    50                  55                  60

Tyr Gly Phe Tyr Ala Asn His Asp Leu Ser Leu Glu Ala Ala Leu
65                  70                  75
```

```
<210> SEQ ID NO 201
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in ST6GalNac II

<400> SEQUENCE: 201

Arg Cys Ala Val Val Gly Asn Gly Gly Ile Leu Asn Gly Ser Arg Gln
1               5                   10                  15

Gly Pro Asn Ile Asp Ala His Asp Tyr Val Phe Arg Leu Asn Gly Ala
                20                  25                  30

Val Ile Lys Gly Phe Glu Arg Asp Val Gly Thr Lys Thr Pro Ser Thr
            35                  40                  45

Gly Ala Leu Met Leu Leu Thr Ala Leu His Thr Cys Asp Gln Val Ser
        50                  55                  60

Ala Tyr Gly Phe Tyr Ala Asn His Asp Leu Ser Leu Glu Ala Ala Leu
65                  70                  75                  80

<210> SEQ ID NO 202
<211> LENGTH: 79
<212> TYPE: PRT
<213> ORGANISM: Artificial sequence
<220> FEATURE:
<223> OTHER INFORMATION: Amino acid sequence of sialylmotif L, S, and VS
      in ST6Gal I

<400> SEQUENCE: 202

Arg Cys Ala Trp Ser Ser Ala Gly Ser Leu Lys Ser Ser Gln Leu Gly
1               5                   10                  15

Arg Glu Ile Asp Asp His Asp Ala Val Leu Arg Phe Asn Gly Ala Pro
                20                  25                  30

Thr Ala Asn Phe Gln Gln Asp Val Gly Thr Lys Thr Pro Ser Ser Gly
            35                  40                  45

Met Leu Gly Ile Ile Ile Met Met Thr Leu Cys Asp Gln Val Asp Ile
        50                  55                  60

Tyr Glu Phe Gly Ala Tyr His Pro Leu Leu Tyr Glu Lys Asn Leu
65                  70                  75

<210> SEQ ID NO 203
<211> LENGTH: 80
<212> TYPE: PRT
<213> ORGANISM: Artificial sequence
<220> FEATURE:
<223> OTHER INFORMATION: Amino acid sequence of sialylmotif L, S, and VS
      in ST6GalNac II

<400> SEQUENCE: 203

Ser Cys Ala Val Val Met Ser Ala Gly Ala Ile Leu Asn Ser Ser Leu
1               5                   10                  15

Gly Glu Glu Ile Asp Ser His Asp Ala Val Leu Arg Phe Asn Ser Ala
                20                  25                  30

Pro Thr Arg Gly Tyr Glu Lys Asp Val Gly Asn Lys Thr Pro Ser Ser
            35                  40                  45

Gly Phe Ile Gly Ile Leu Ile Met Met Ser Met Cys Arg Glu Val His
        50                  55                  60

Val Tyr Glu Tyr Gly Ala Tyr His Pro Leu Leu Tyr Glu Lys Leu Leu
65                  70                  75                  80

<210> SEQ ID NO 204
```

```
<211> LENGTH: 24
<212> TYPE: DNA
<213> ORGANISM: Artificial Sequence
<220> FEATURE:
<223> OTHER INFORMATION: oligonucleotide used for the chimeric
      constructions

<400> SEQUENCE: 204
gagcccggat ccgaggcctc cttc                                          24

<210> SEQ ID NO 205
<211> LENGTH: 35
<212> TYPE: DNA
<213> ORGANISM: Artificial sequence
<220> FEATURE:
<223> OTHER INFORMATION: oligonucleotide used for the chimeric
      constructions

<400> SEQUENCE: 205
taaccctcta gattagcagt gaatggtccg gaagc                              35

<210> SEQ ID NO 206
<211> LENGTH: 30
<212> TYPE: DNA
<213> ORGANISM: Artificial sequence
<220> FEATURE:
<223> OTHER INFORMATION: oligonucleotide used for the chimeric
      constructions

<400> SEQUENCE: 206
atggactaca aagacgatga cgacaaggga                                    30

<210> SEQ ID NO 207
<211> LENGTH: 37
<212> TYPE: DNA
<213> ORGANISM: Artificial sequence
<220> FEATURE:
<223> OTHER INFORMATION: oligonucleotide used for the chimeric
      constructions

<400> SEQUENCE: 207 gagccccta agatggacta caaagacgac gatgacg                             37

<210> SEQ ID NO 208
<211> LENGTH: 36
<212> TYPE: DNA
<213> ORGANISM: Artificial sequence
<220> FEATURE:
<223> OTHER INFORMATION: oligonucleotide used for the chimeric
      constructions

<400> SEQUENCE: 208 taaggggat ccgctagagt gactatactt actgga                              36

<210> SEQ ID NO 209
<211> LENGTH: 37
<212> TYPE: DNA
<213> ORGANISM: Artificial sequence
<220> FEATURE:
<223> OTHER INFORMATION: oligonucleotide used for the chimeric
      constructions

<400> SEQUENCE: 209
gagcccctta agatggacta caaagacgac gatgacg                            37

<210> SEQ ID NO 210
<211> LENGTH: 30
```

```
<212> TYPE: DNA
<213> ORGANISM: Artificial sequence
<220> FEATURE:
<223> OTHER INFORMATION: oligonucleotide used for the chimeric
      constructions

<400> SEQUENCE: 210
taagggggat ccggttgtgg aggaacggga                                    30

<210> SEQ ID NO 211
<211> LENGTH: 33
<212> TYPE: DNA
<213> ORGANISM: Artificial sequence
<220> FEATURE:
<223> OTHER INFORMATION: oligonucleotide used for the chimeric
      constructions

<400> SEQUENCE: 211
taagggggat cctctgggtg acagtgtgtt cac                                33

<210> SEQ ID NO 212
<211> LENGTH: 26
<212> TYPE: DNA
<213> ORGANISM: Artificial sequence
<220> FEATURE:
<223> OTHER INFORMATION: oligonucleotide used for the chimeric
      constructions

<400> SEQUENCE: 212
taataaagct tgaggcctcc ttccag                                        26

<210> SEQ ID NO 213
<211> LENGTH: 26
<212> TYPE: DNA
<213> ORGANISM: Artificial sequence
<220> FEATURE:
<223> OTHER INFORMATION: oligonucleotide used for the chimeric
      constructions

<400> SEQUENCE: 213
ctattggatc cttagcagtg aatggt                                        26

<210> SEQ ID NO 214
<211> LENGTH: 30
<212> TYPE: DNA
<213> ORGANISM: Artificial sequence
<220> FEATURE:
<223> OTHER INFORMATION: oligonucleotide used for the chimeric
      constructions

<400> SEQUENCE: 214
taagggggat ccggttgtcc tccttgccct                                    30
```

The invention claimed is:

1. A polynucleotide encoding a chimeric glycosyltransferase, said chimeric glycosyltransferase containing a cytoplasmic tail (CT), a transmembrane domain (TMD), a stem region (SR) and a catalytic domain (CD), said polynucleotide consisting of a fusion of:

1) a nucleic acid sequence coding for the CT, said nucleic acid sequence selected from the group consisting of: SEQ ID NO:47, SEQ ID NO: 49, SEQ ID NO: 65, SEQ ID NO: 77, and SEQ ID NO: 81, said nucleic acid sequence coding for the CT being located upstream from 2) a nucleic acid sequence coding for the TMD, said nucleic acid sequence selected from the group consisting of: SEQ ID NO: 89, SEQ ID NO: 91, SEQ ID NO: 107, SEQ ID NO: 119, and SEQ ID NO: 123, said nucleic acid coding for the TMD being located upstream from 3) a nucleic acid sequence coding for the SR, said nucleic acid sequence selected from the group consisting of: SEQ ID NO:129, SEQ ID NO: 131, SEQ ID NO: 137, SEQ ID NO: 141, and SEQ ID NO: 143, said nucleic acid sequence coding for the SR being located upstream from 4) a nucleic acid sequence coding for the CD of a native full length glycosyltransferase, said nucleic acid sequence consisting of SEQ ID NO: 43, said chimeric glycosyltransferase having at least 30-fold higher glycosylation activity towards an acceptor substrate compared to the native full-length glycosyltransferase.

2. The polynucleotide according to claim 1, comprising SEQ ID NO: 181.

3. A vector comprising the polynucleotide according to claim 1.

4. A host cell transformed with the polynucleotide according to claim 1.

5. The polynucleotide according to claim 1, comprising SEQ ID NO: 179.

6. The polynucleotide according to claim 1, comprising the sequence selected from the group consisting of: SEQ ID NO: 161, SEQ ID NO: 167, SEQ ID NO: 171, SEQ ID NO: 173, SEQ ID NO: 175, and SEQ ID NO: 181.

7. The polynucleotide according to claim 1, further comprising a linker nucleic acid sequence encoding for at least 2 amino acids, the linker sequence being located between the nucleic acid sequence coding for the SR and the nucleic acid sequence coding for the CD.

8. The polynucleotide according to claim 7, wherein the linker nucleic acid sequence comprises a restriction enzyme site that does not exist in the nucleic acid sequence coding for the CD of the native full length glycosyltransferase.

9. The host cell according to claim 4, wherein the cell is a eukaryotic cell.

* * * * *